US010253110B2

(12) United States Patent
Bacac et al.

(10) Patent No.: US 10,253,110 B2
(45) Date of Patent: Apr. 9, 2019

(54) ANTI-FAP ANTIBODIES AND METHODS OF USE

(71) Applicant: Roche Glycart AG, Schlieren (CH)

(72) Inventors: Marina Bacac, Lausanne (CH); Anne Freimoser-Grundschober, Zurich (CH); Ralf Hosse, Cham (CH); Christian Klein, Bonstetten (CH); Ekkehard Moessner, Kreuzlingen (CH); Valeria G. Nicolini, Erlenbach (CH); Pablo Umana, Waedenswil (CH)

(73) Assignee: ROCHE GLYCART AG, Schilieren (CH)

( * ) Notice: Subject to any disclaimer, the term of this patent is extended or adjusted under 35 U.S.C. 154(b) by 0 days.

(21) Appl. No.: 14/661,839

(22) Filed: Mar. 18, 2015

(65) Prior Publication Data
US 2016/0060357 A1 Mar. 3, 2016

Related U.S. Application Data

(62) Division of application No. 13/205,743, filed on Aug. 9, 2011, now Pat. No. 9,011,847.

(30) Foreign Application Priority Data

Aug. 13, 2010 (EP) .................................... 10172842

(51) Int. Cl.
A61K 39/395 (2006.01)
C07K 16/40 (2006.01)
A61K 51/10 (2006.01)
C07K 16/30 (2006.01)
A61K 47/68 (2017.01)

(52) U.S. Cl.
CPC .......... C07K 16/40 (2013.01); A61K 47/6871 (2017.08); A61K 51/1075 (2013.01); C07K 16/30 (2013.01); C07K 2317/21 (2013.01); C07K 2317/33 (2013.01); C07K 2317/41 (2013.01); C07K 2317/55 (2013.01); C07K 2317/565 (2013.01); C07K 2317/732 (2013.01); C07K 2317/92 (2013.01)

(58) Field of Classification Search
None
See application file for complete search history.

(56) References Cited

U.S. PATENT DOCUMENTS

| 6,545,462 | B2 | 4/2003 | Schott et al. | |
| 6,602,684 | B1 | 8/2003 | Umana et al. | |
| 8,568,727 | B2* | 10/2013 | Adolf | A61K 47/48384 424/178.1 |
| 8,945,571 | B2* | 2/2015 | Mossner | A61K 47/48423 424/179.1 |
| 9,011,847 | B2 | 4/2015 | Bacac et al. | |
| 9,266,938 | B2 | 2/2016 | Ast et al. | |
| 9,346,872 | B2 | 5/2016 | Duerner et al. | |
| 9,447,159 | B2 | 9/2016 | Ast et al. | |
| 9,526,797 | B2 | 12/2016 | Gerdes et al. | |
| 2003/0143229 | A1 | 7/2003 | Park et al. | |
| 2011/0064751 | A1 | 3/2011 | Mossner et al. | |
| 2012/0184718 | A1 | 7/2012 | Bruenker et al. | |
| 2014/0370019 | A1 | 12/2014 | Bruenker et al. | |
| 2016/0060356 | A1 | 3/2016 | Bacac et al. | |
| 2016/0208017 | A1 | 7/2016 | Ast et al. | |
| 2016/0159917 | A1 | 9/2016 | Bruenker et al. | |
| 2016/0263240 | A1 | 9/2016 | Ast et al. | |
| 2017/0056522 | A1 | 2/2017 | Gerdes et al. | |
| 2017/0088631 | A1 | 3/2017 | Ast et al. | |
| 2018/0142037 | A1 | 5/2018 | Ast et al. | |

FOREIGN PATENT DOCUMENTS

| CN | 1303430 | | 1/2011 |
| WO | 99/54342 | | 10/1999 |
| WO | 99/57151 | | 11/1999 |
| WO | 01/68708 | | 9/2001 |
| WO | 07/77173 | A1 | 7/2007 |
| WO | 2011/020783 | | 2/2011 |
| WO | 2011/020783 | A2 | 2/2011 |
| WO | WO/2011/020783 | * | 2/2011 |
| WO | 2012/020006 | | 2/2012 |

OTHER PUBLICATIONS

Shields et al (JBC,vol. 277, No. 30, Jul. 2002, pp. 26733-26470) (Year: 2002).*
Baum et al., "Single-chain Fv immunoliposomes for the targeting of fibroblast activation protein-expressing tumor stromal cells" Journal of Drug Targeting 15(6):399-406 (Jul. 1, 2007).
Casset et al., "A peptide mimetic of an anti-CD4 monoclonal antibody by rational design" Biochem Bioph Res Co(307):198-205 ( 2003).
Chen et al., "Selection and analysis of an optimized anti-VEGF antibody: Crystal structure of an affinity-matured Fab in complex with antigen" J Mol Biol 293:865-881 ( 1999).
De Pascalis et. al. et al., J Immunol 169:3076-3084 ( 2002).
International Preliminary Report on Patentability for PCT/EP2011/063648, pp. 1-12 (Date of Mailing of the International Search Report Feb. 14, 2012)
Lamminmak et al., "Crystal structure of a recombinant anti-estradiol Fab fragment in complex with 17β-estradiol" Journal of Biological Chemistry 276(39):36687-36694 (Sep. 28, 2001).
Little 'Recombinant Antibodies for Immunotherapy'Cambridge University Press, ( 2009).
MacCallum et. al. et al., "Antibody-antigen interaction: contact analysis and binding site topography" J Mol Biol 262(5):732-745 (Oct. 11, 1996).

(Continued)

Primary Examiner — Laura B Goddard
Assistant Examiner — Meera Natarajan

(57) ABSTRACT

The invention provides antibodies against Fibroblast Activation Protein (FAP) and methods of using the same.

17 Claims, 38 Drawing Sheets
Specification includes a Sequence Listing.

(56) References Cited

OTHER PUBLICATIONS

Mersmann, "Human Antibody Derivatives Against the Fibroblast Protein for Tumor Stroma Targeting of Carcinomas" International Journal of Cancer 92(2):240-248 (Apr. 15, 2001).
Padian et al., "Structure of an antibody-antigen complex: crystal structure of the HyHEL-10 Fab-lysozyme compex" P Natl Acad Sci USA 86:5938-5942 ( 1989).
PCT International Search Report for PCT/EP2011/063648, pp. 1-7 (Date of mailing of the international search report Feb. 14, 2012).
Rudikoff et al., "Single amino acid substitution altering antigen-binding specificity," Proc. Nat. Acad. Sci. USA, vol. 79, pp. 1979-1983, Mar. 1982.
Vajdos et al. et al., "Comprehensive functional maps of the antigen-binding site of an anti-ErbB2 antibody obtained with shotgun scanning mutagenesis" J Mol Biol 320(2):415-428 (Jul. 5, 2002).
Written Opinion of the International Searching Authority for PCT/EP2011/063648, pp. 1-11 (Date of Mailing of the International Search Report Feb. 14, 2012).
Wu et al. et al., "Humanization of a murine monoclonal antibody by simultaneous optimization of framework and CDR residues" J Mol Biol 294(1):151-162 (Nov. 19, 1999).
Ferrara et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-mannosidase II," *Biotechnology and Bioengineering* 93(5):851-861 (2006).

\* cited by examiner

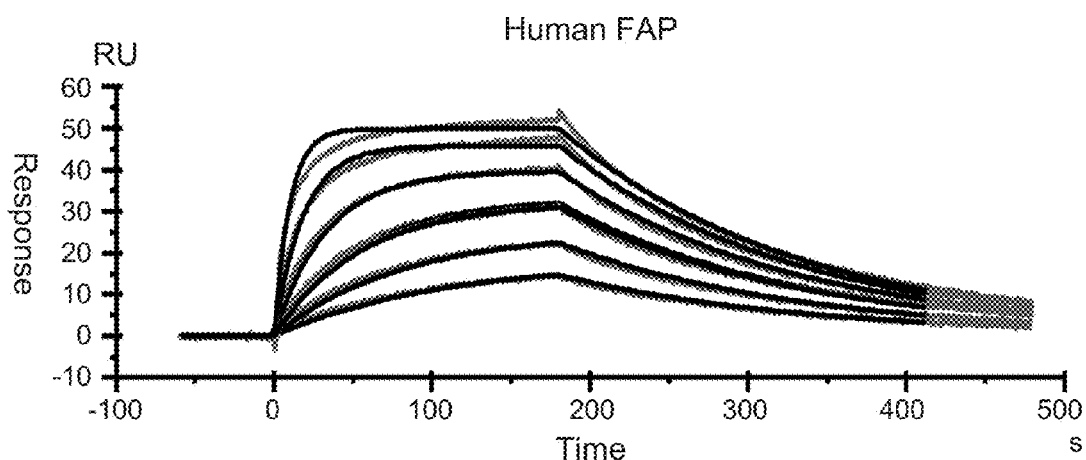
FIG. 6A1
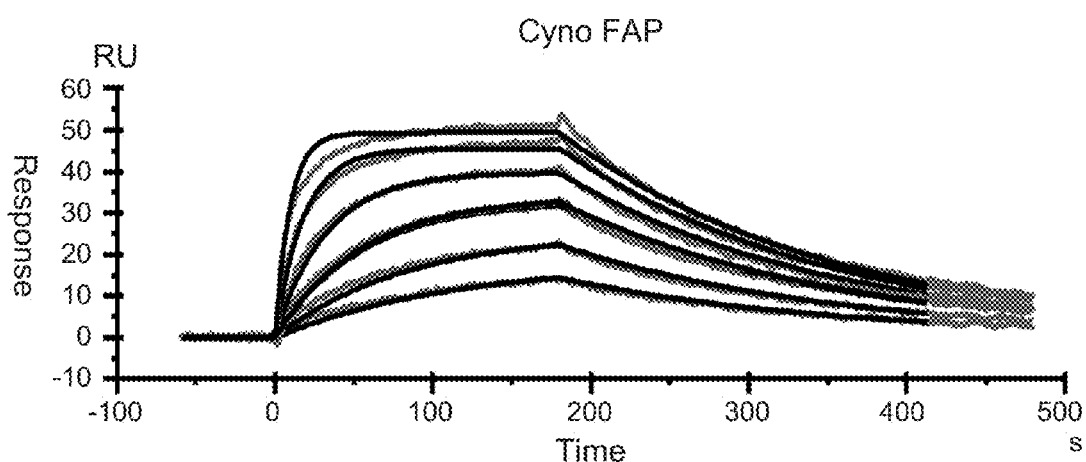
FIG. 6A2
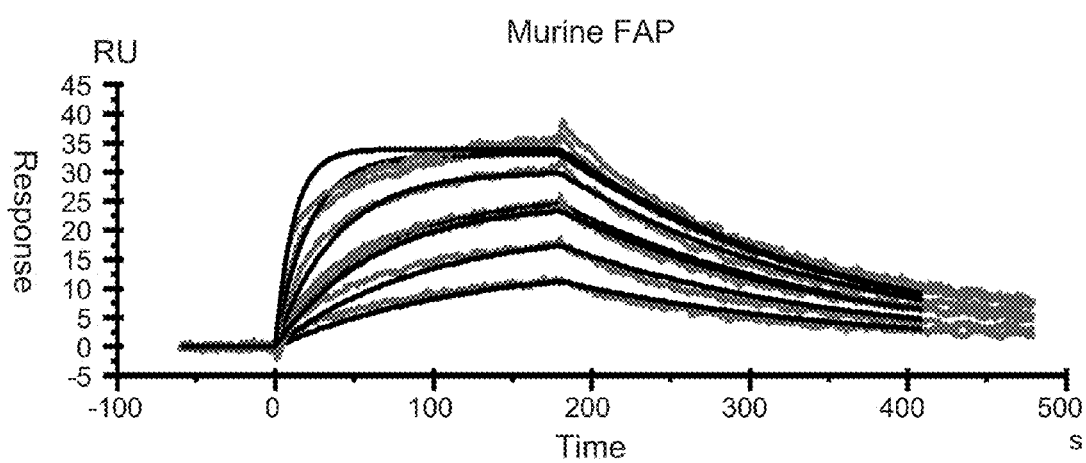
FIG. 6A3

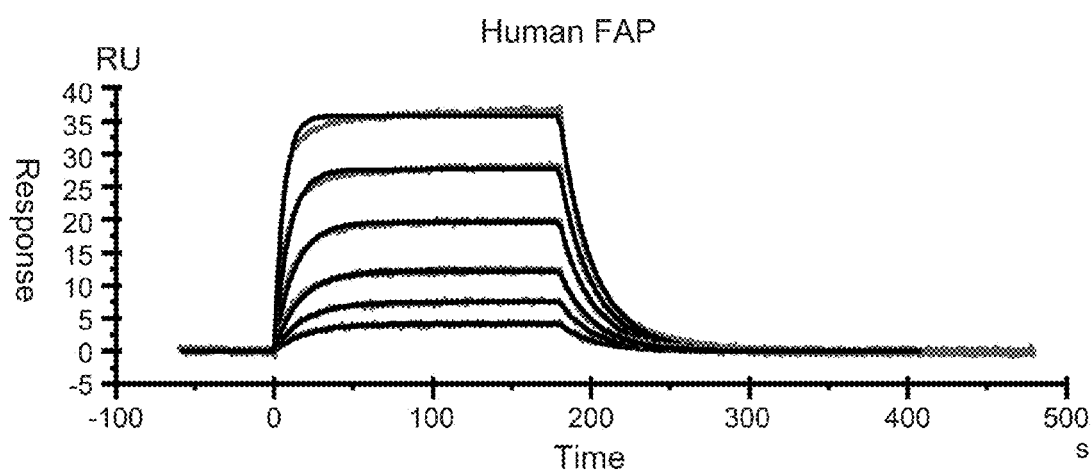
FIG. 6B1
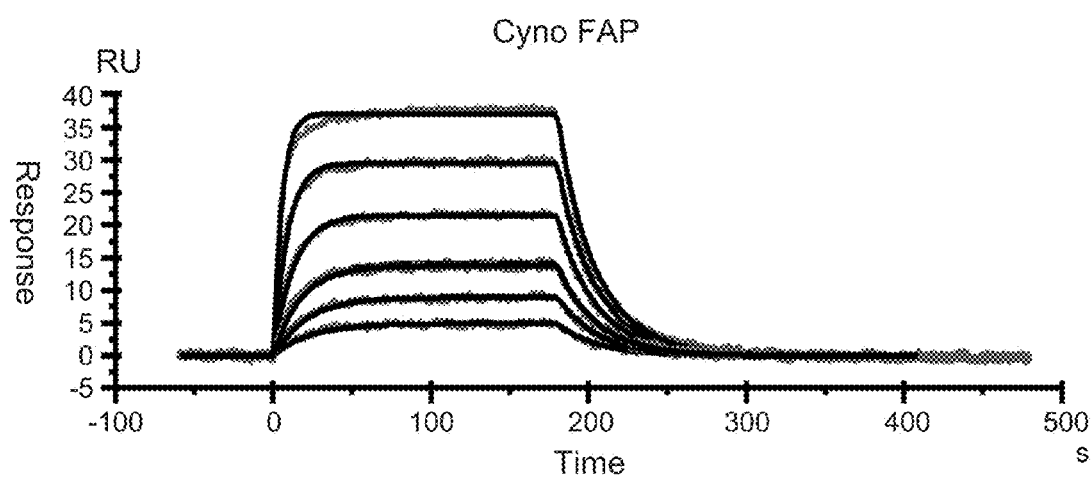
FIG. 6B2
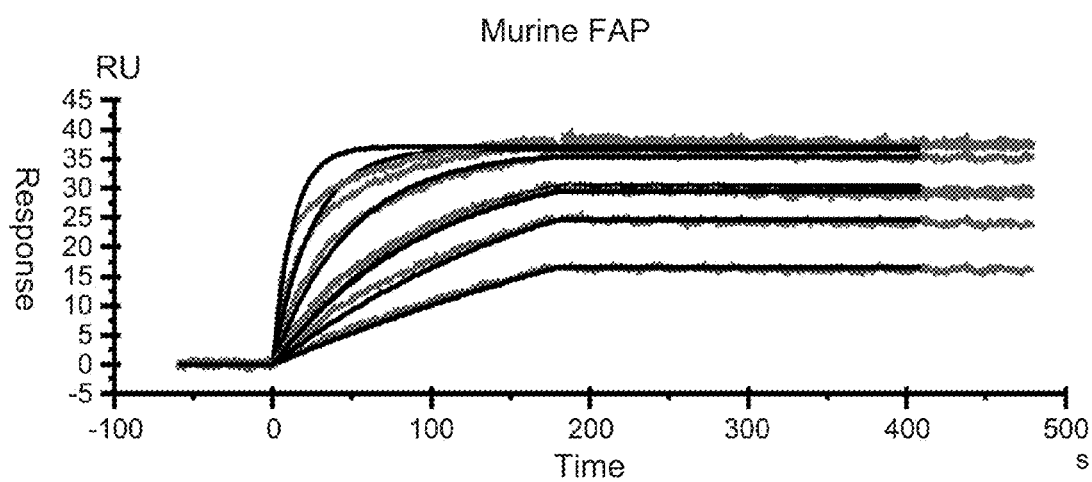
FIG. 6B3

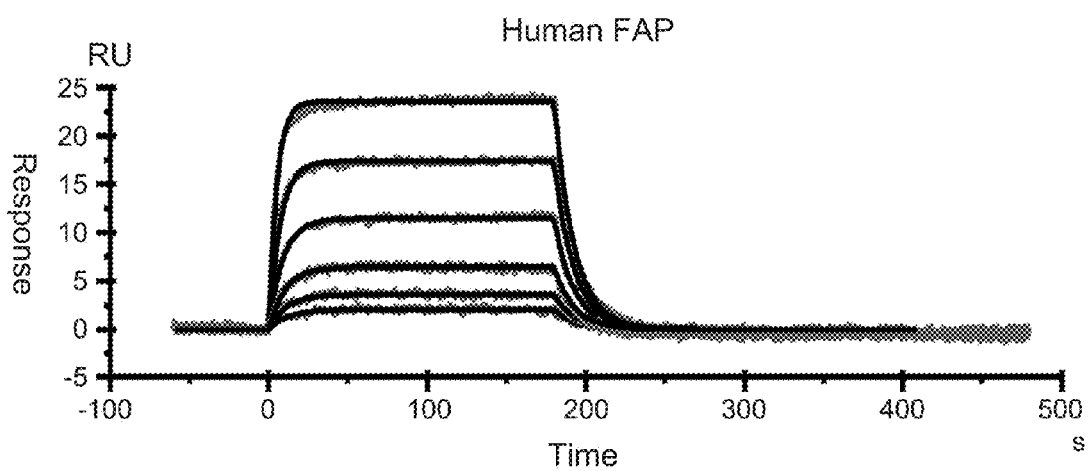
FIG. 6C1
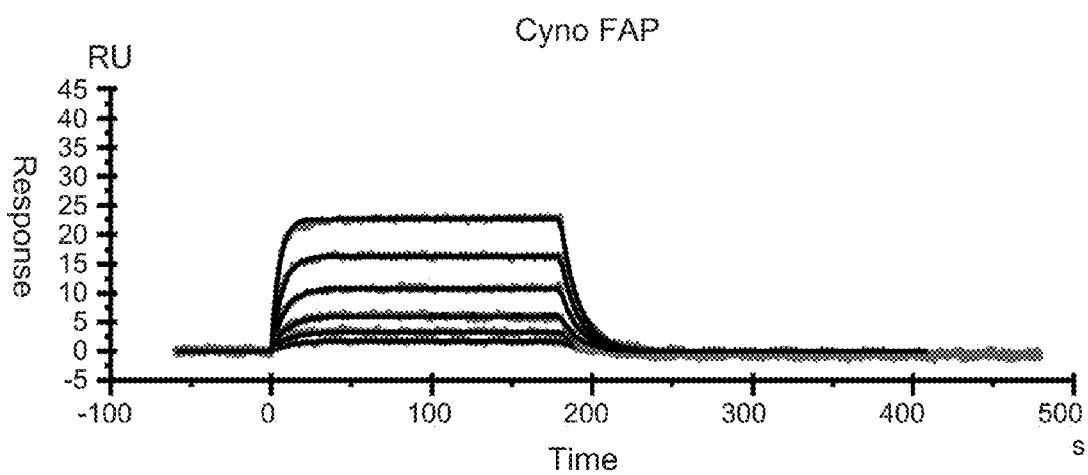
FIG. 6C2
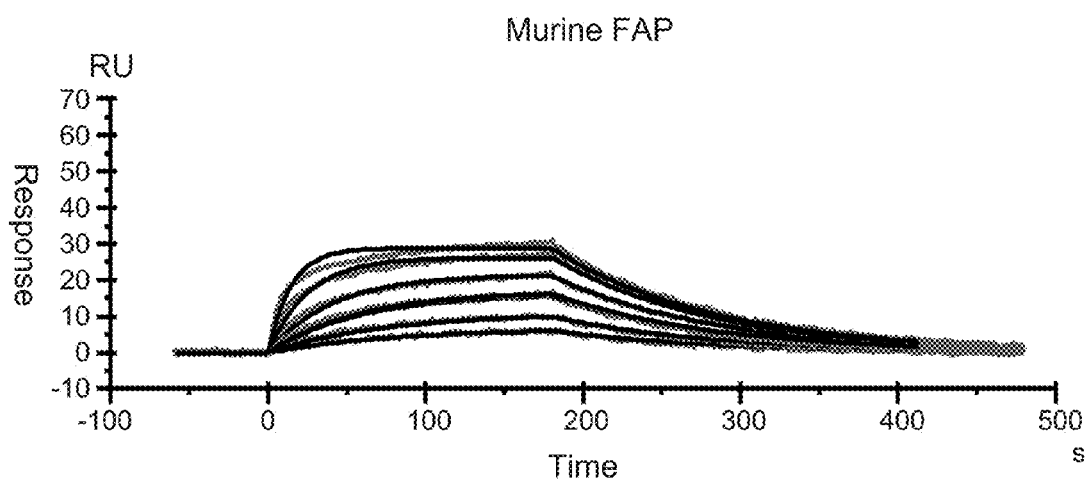
FIG. 6C3

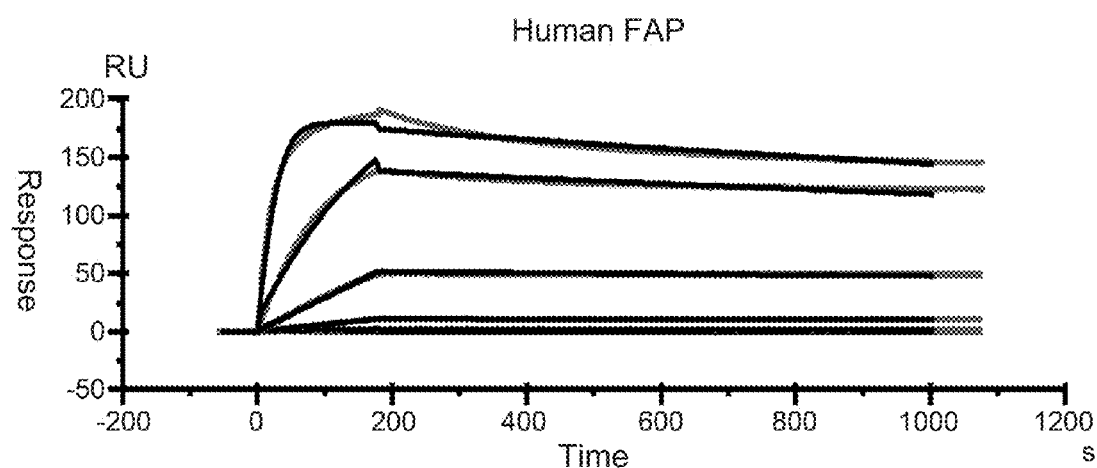
FIG. 7A1
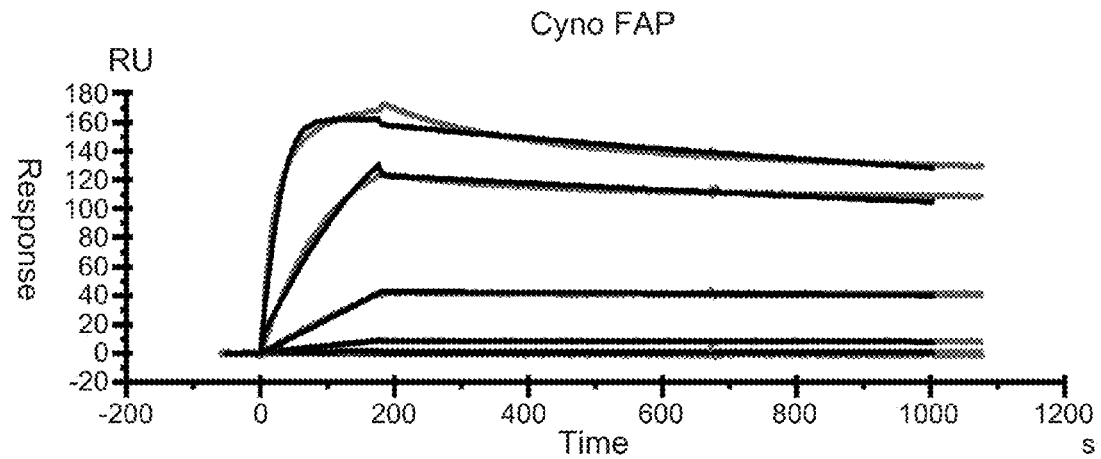
FIG. 7A2
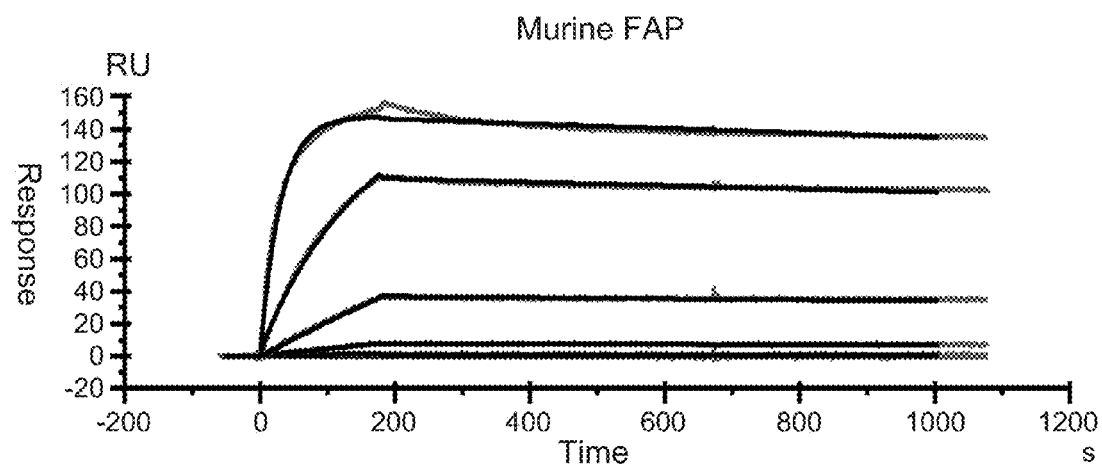
FIG. 7A3

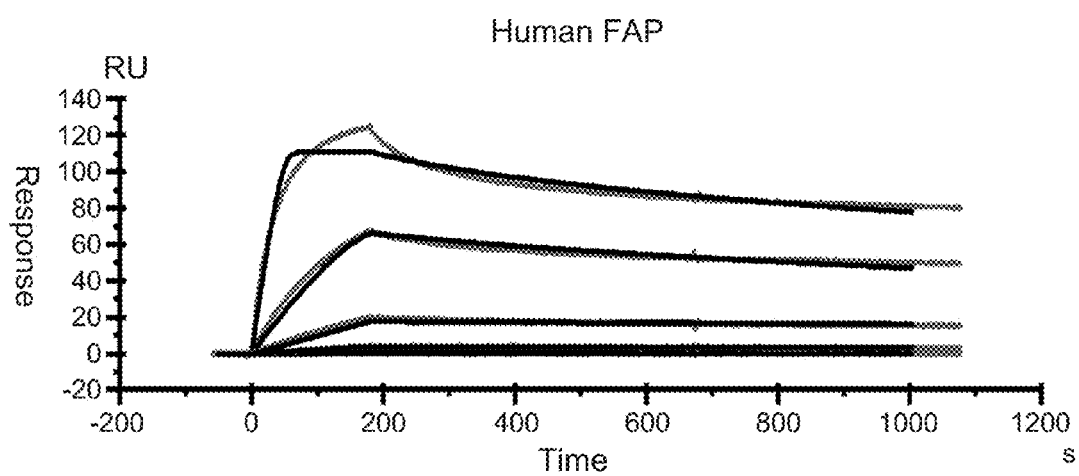
FIG. 7B1
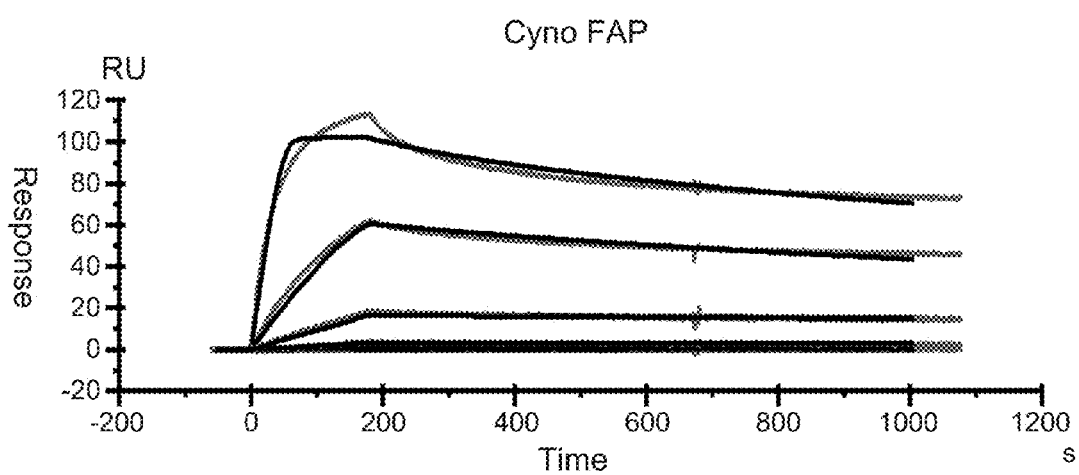
FIG. 7B2
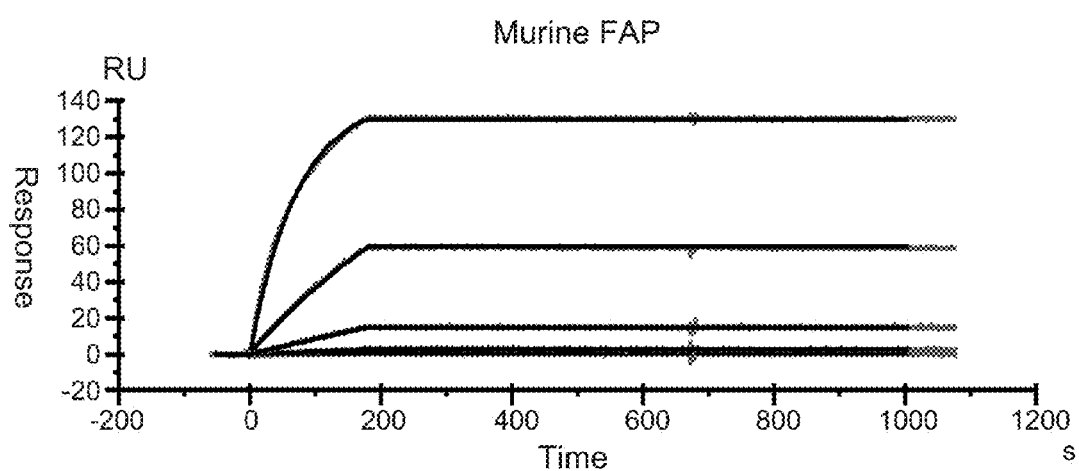
FIG. 7B3

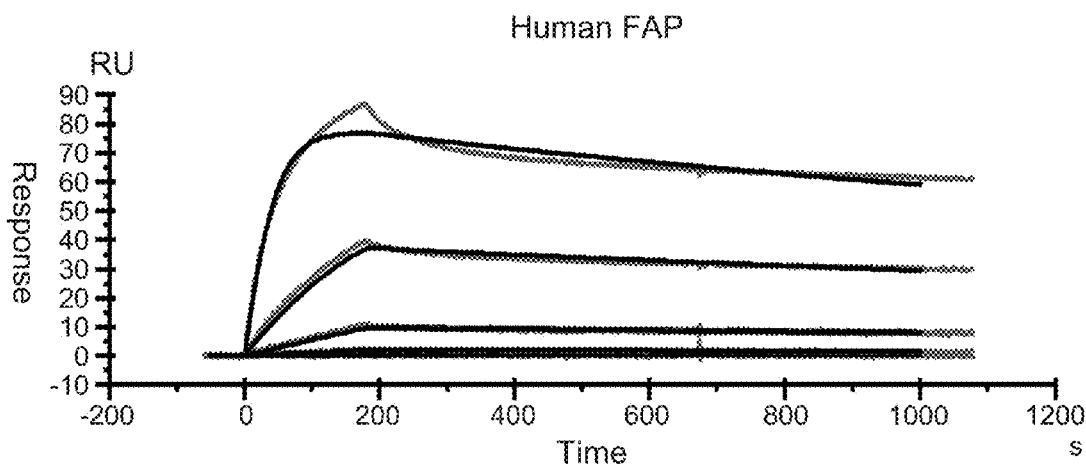
FIG. 7C1
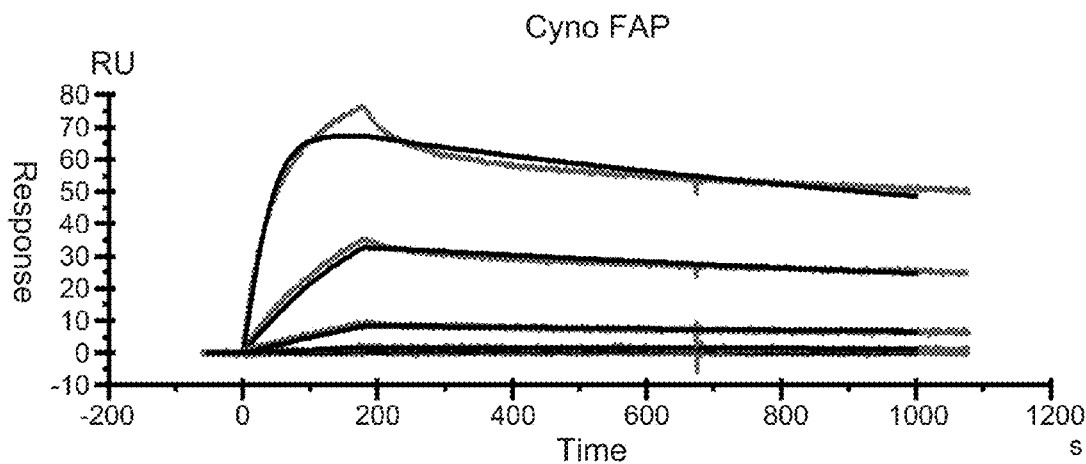
FIG. 7C2
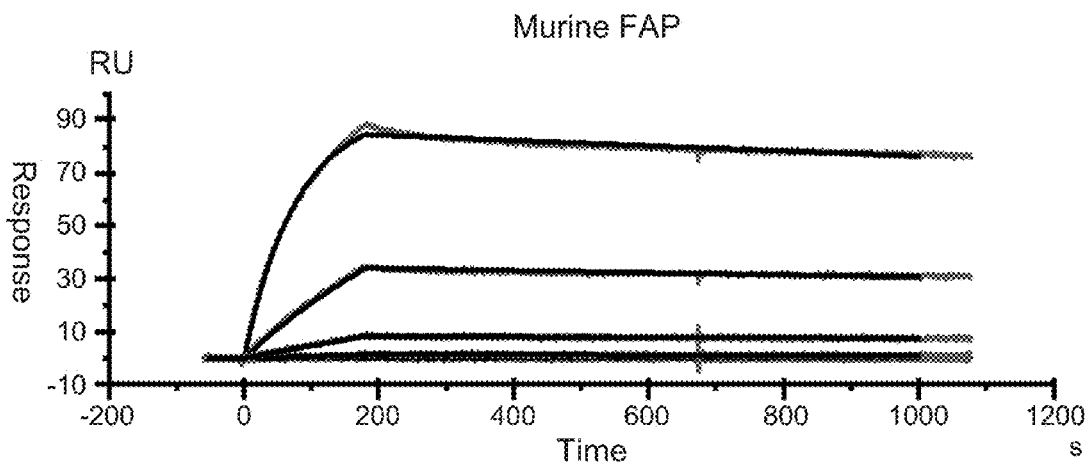
FIG. 7C3

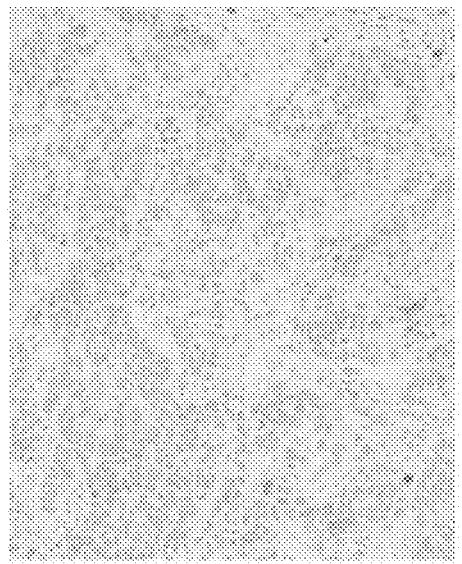
FIG. 8A2
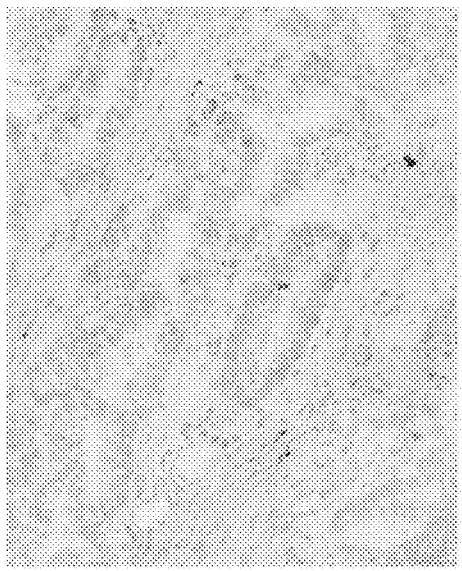
FIG. 8B2
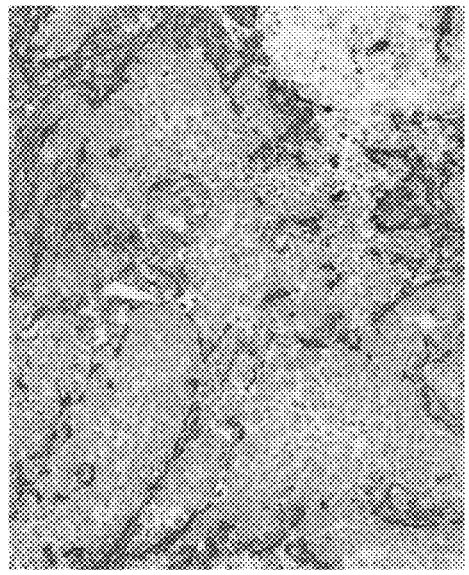
FIG. 8A1
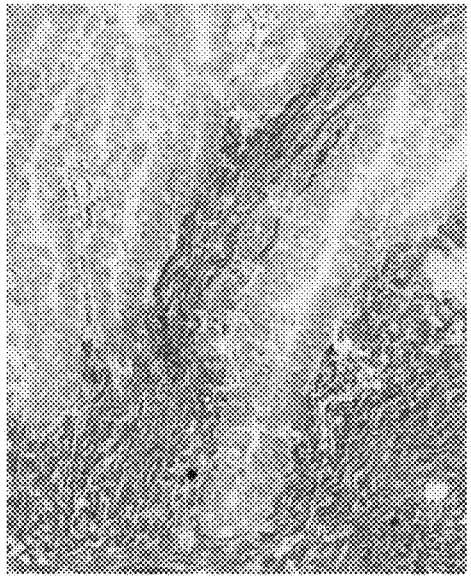
FIG. 8B1

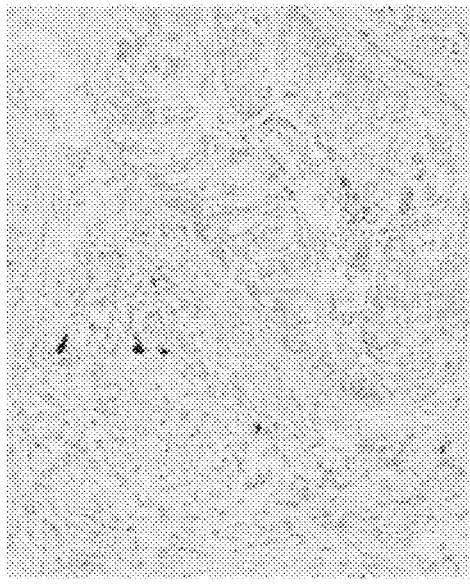
FIG. 8C2
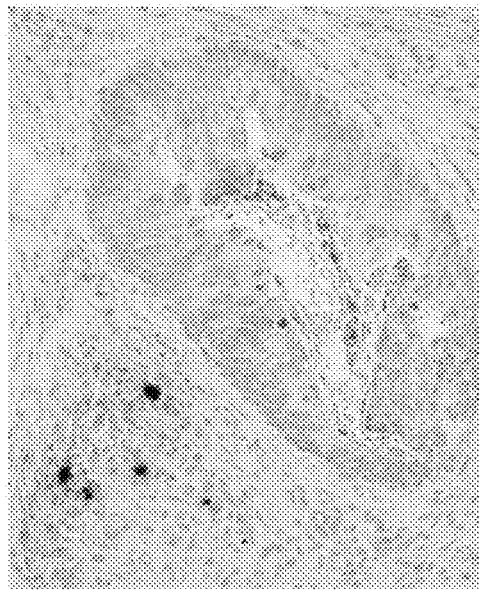
FIG. 8D2
FIG. 8C1
FIG. 8D1

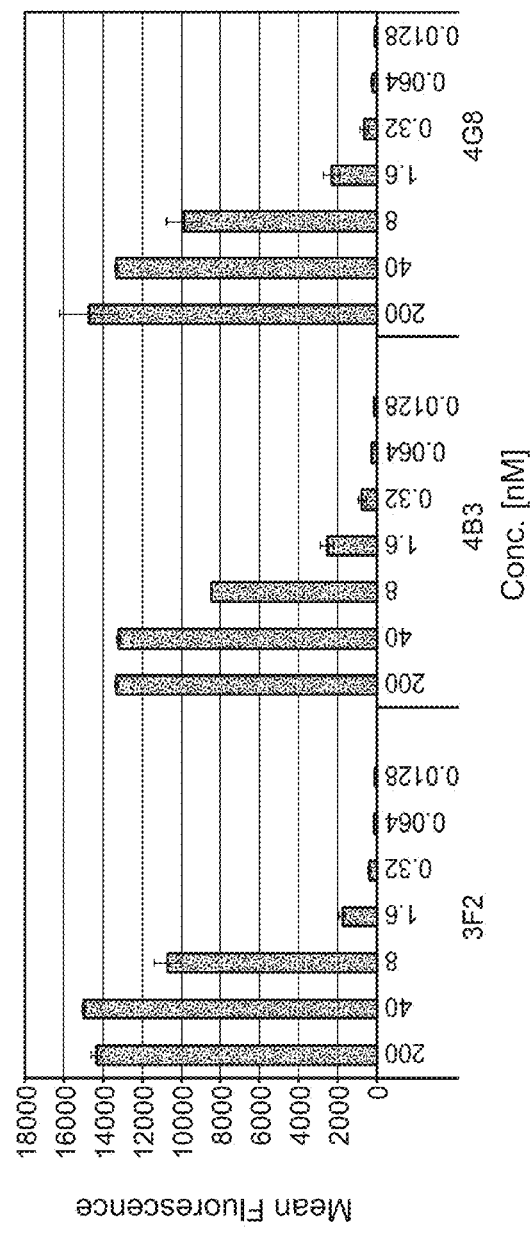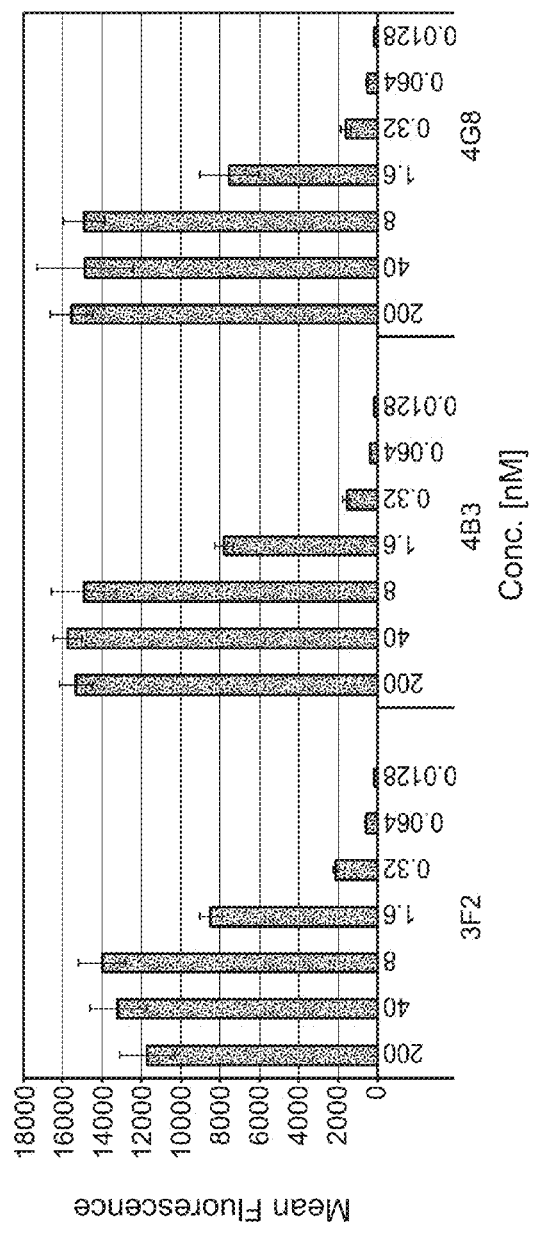
FIG. 9A
FIG. 9B

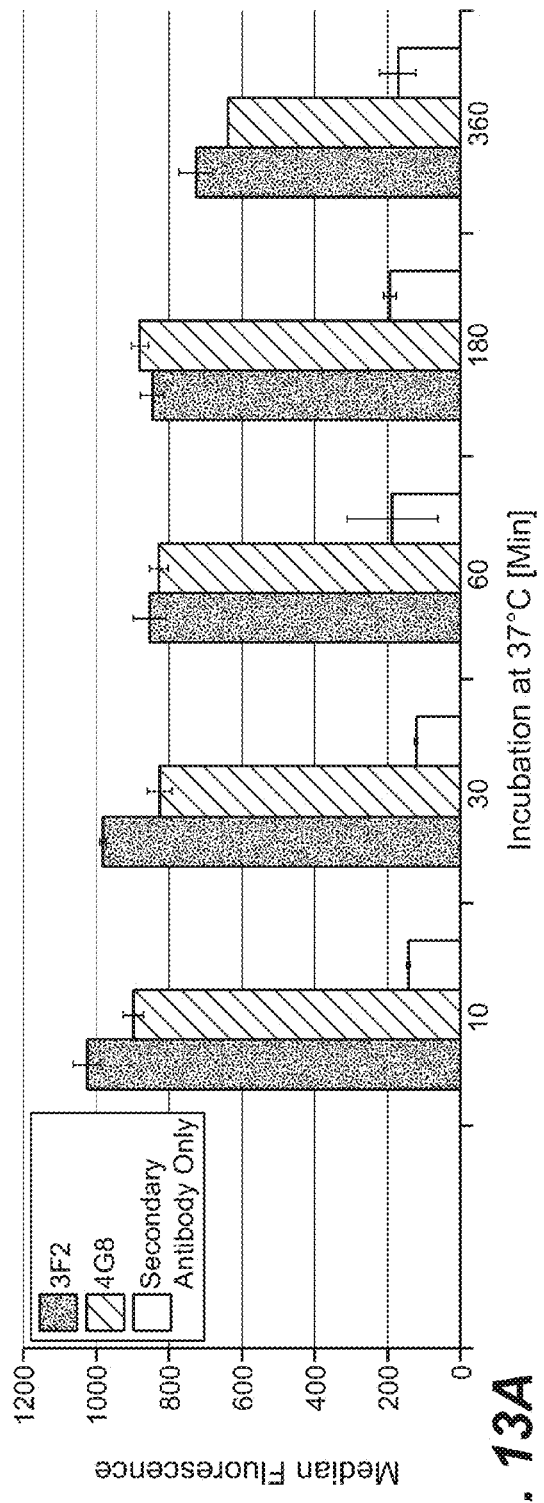
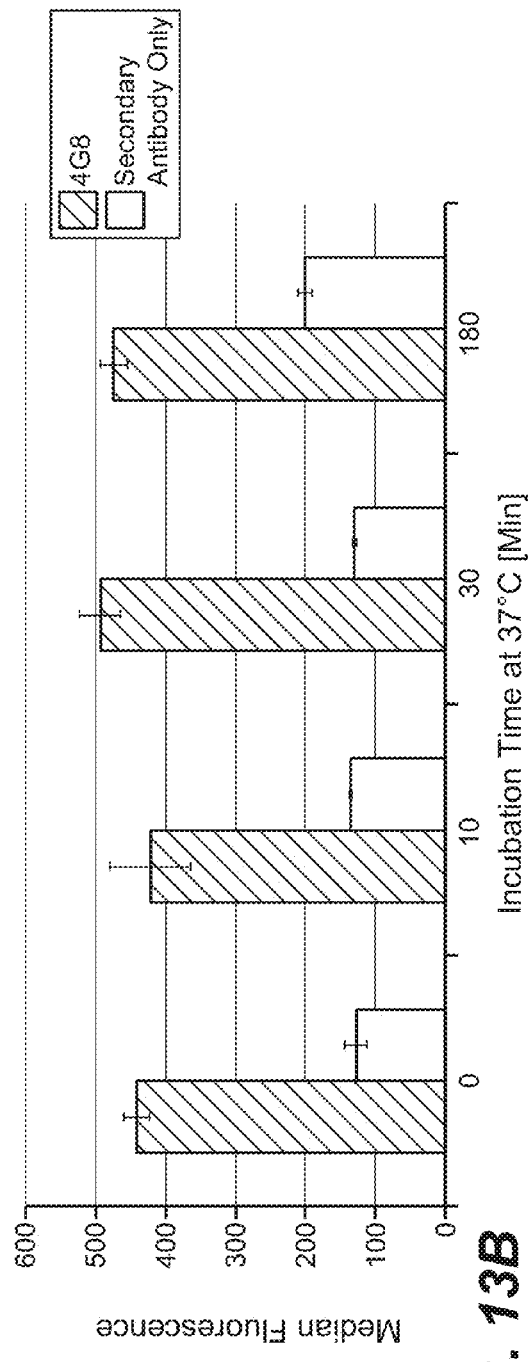
FIG. 13A
FIG. 13B

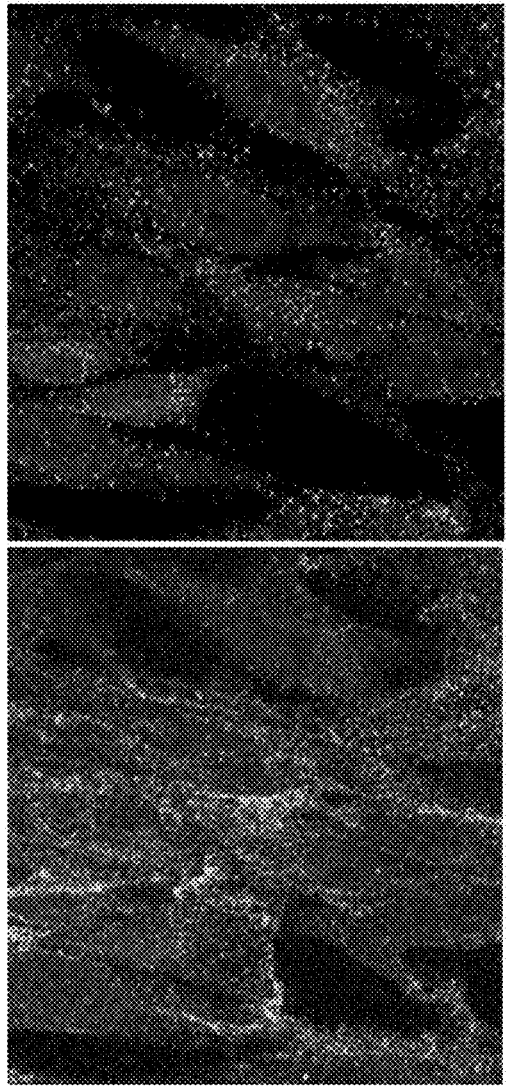
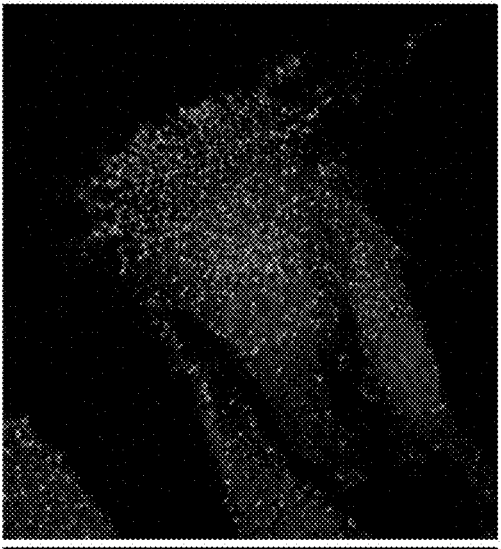
FIG. 14A1 Anti-FAP 4G8 IgG 45 Min, 4°C
FIG. 14A2 Anti-FAP 4G8 IgG 45 Min, 4°C EEA1
FIG. 14A3 GA101 45 Min, 4°C
FIG. 14A4 GA101 45 Min, 4°C EEA1

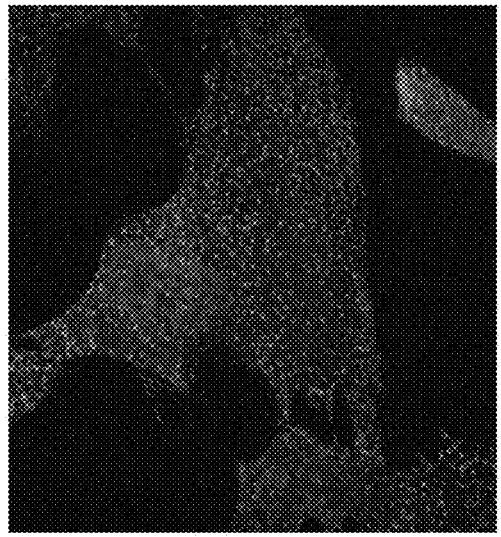
FIG. 14B1 Anti-FAP 4G8 IgG 20 Min, 37°C
FIG. 14B2 Anti-FAP 4G8 IgG 20 Min, 37°C EEA1
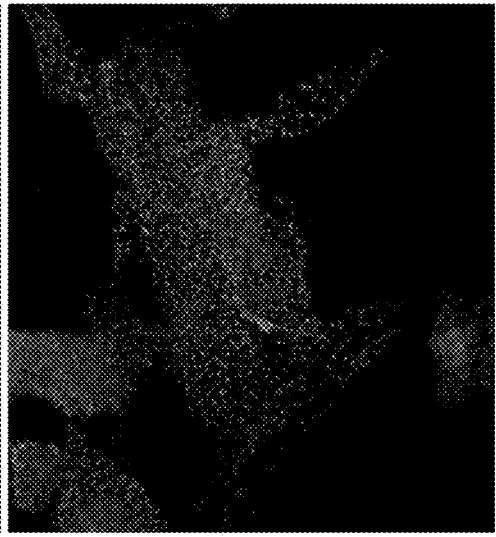
FIG. 14B3 GA101 20 Min, 37°C
FIG. 14B4 GA101 20 Min, 37°C EEA1
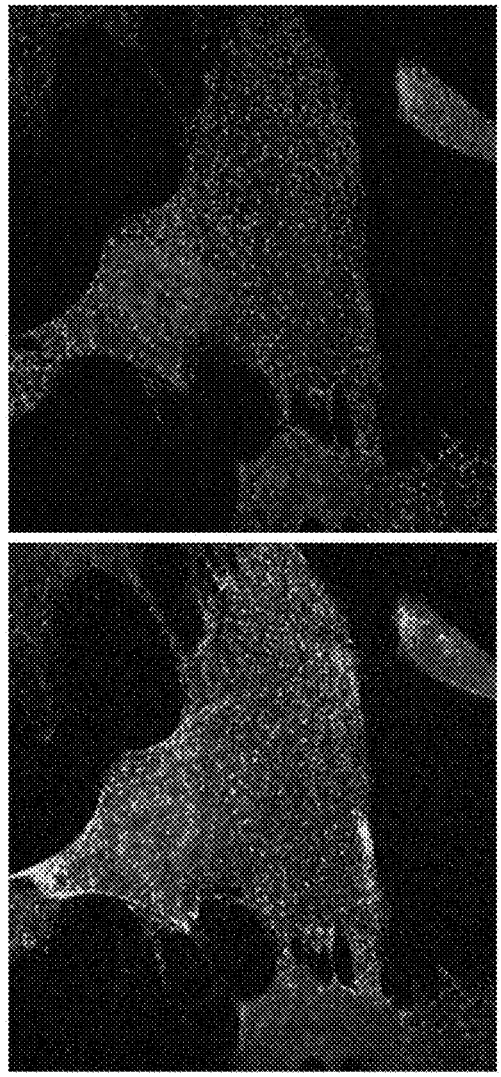

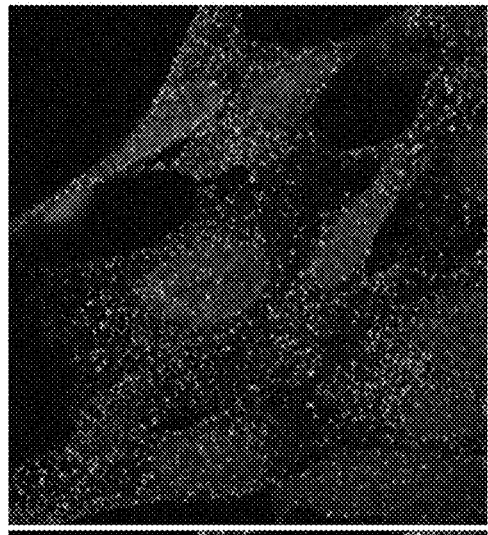
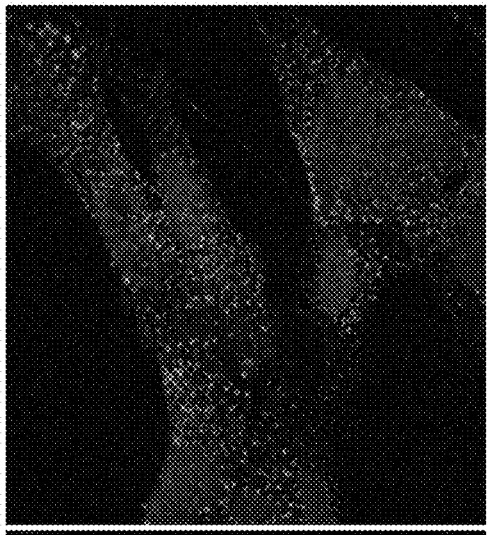
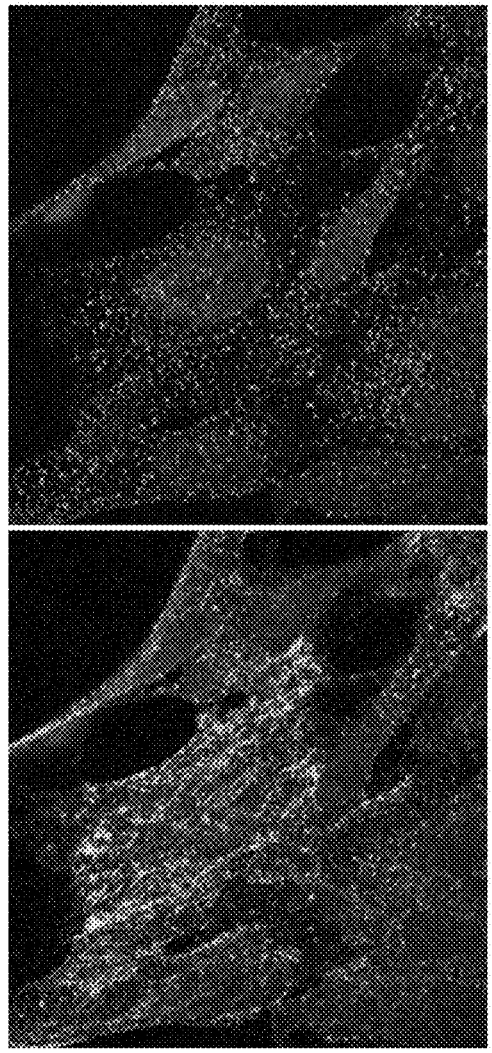
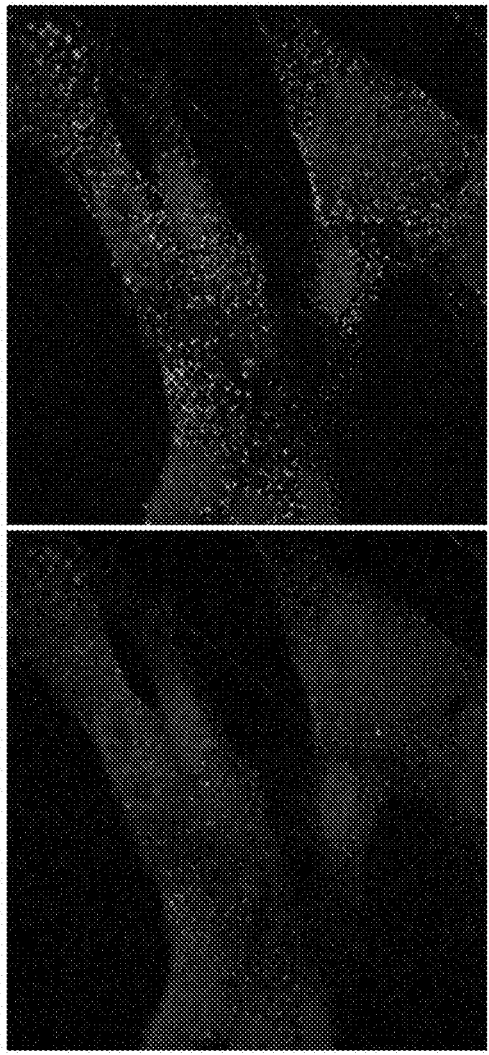
FIG. 14C1 Anti-FAP 4G8 IgG 37°C, 1H
FIG. 14C2 Anti-FAP 4G8 IgG 37°C, 1H EEA1
FIG. 14C3 GA101 37°C, 1H
FIG. 14C4 GA101 37°C, 1H EEA1

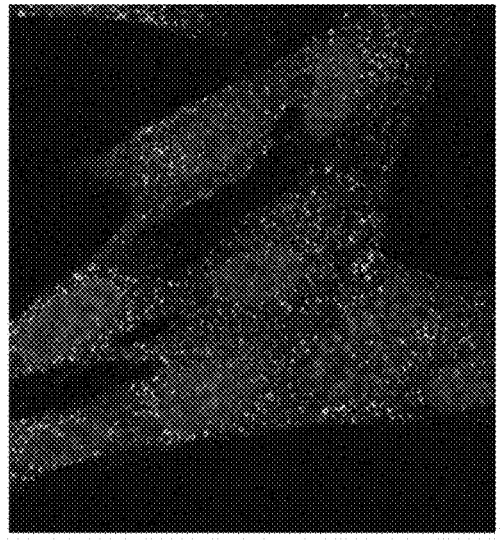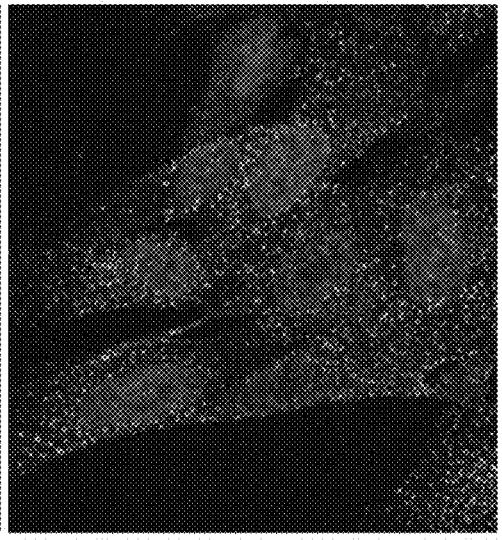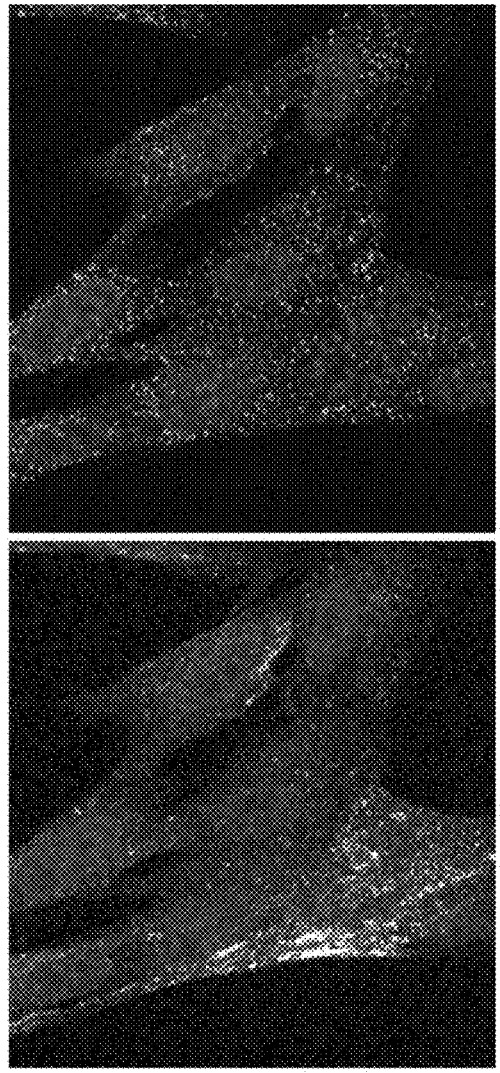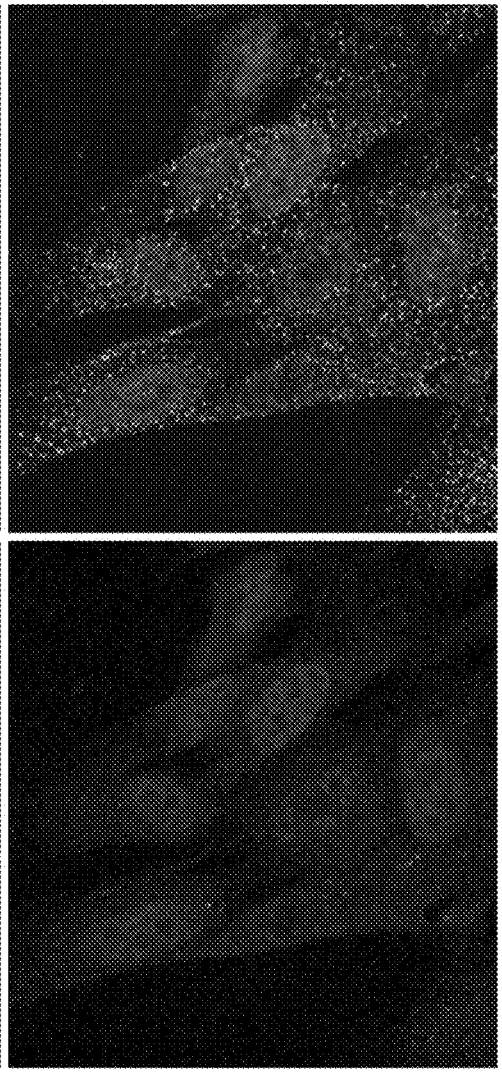
FIG. 14D1 Anti-FAP 4G8 IgG 37°C, 6 H
FIG. 14D2 Anti-FAP 4G8 IgG 37°C, 6 H EEA1
FIG. 14D3 GA101 37°C, 6 H
FIG. 14D4 GA101 37°C, 6 H EEA1

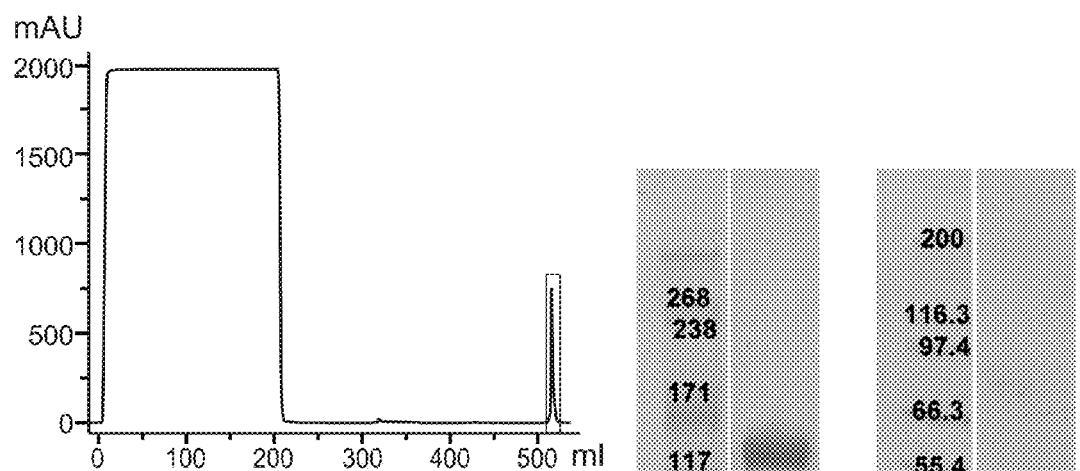
FIG. 20A
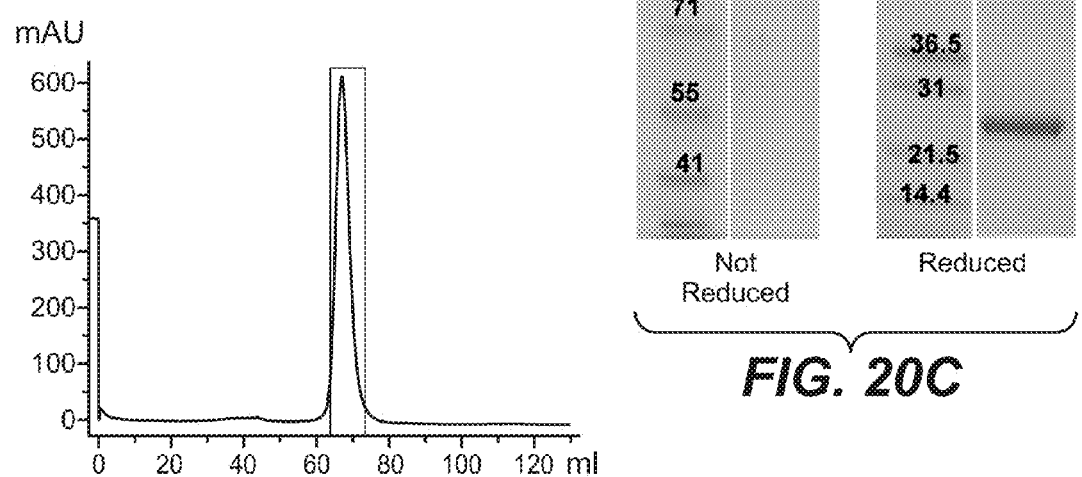
FIG. 20B
FIG. 20C
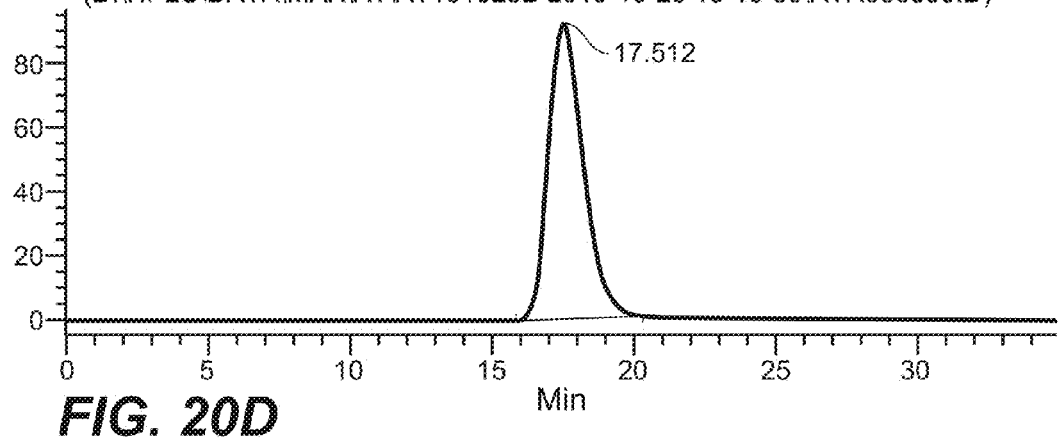
FIG. 20D

SEQUENCE LISTING

```
<160> NUMBER OF SEQ ID NOS: 352

<210> SEQ ID NO 1
<211> LENGTH: 1611
<212> TYPE: DNA
<213> ORGANISM: Artificial Sequence
<220> FEATURE:
<223> OTHER INFORMATION: Library Template for DP47-3 library

<400> SEQUENCE: 1
atgaaatacc tattgcctac ggcagccgct ggattgttat tactcgcggc ccagccggcc      60
atggccgaaa tcgtgttaac gcagtctcca ggcaccctgt ctttgtctcc aggggaaaga     120
```

| | |
|---|---|
| gccaccctct cttgcagggc cagtcagagt gttagcagca gctacttagc ctggtaccag | 180 |
| cagaaacctg gccaggctcc caggctcctc atctatggag catccagcag ggccactggc | 240 |
| atcccagaca ggttcagtgg cagtggatcc gggacagact tcactctcac catcagcaga | 300 |
| ctggagcctg aagattttgc agtgtattac tgtcagcagt atggtagctc accgctgacg | 360 |
| ttcggccagg ggaccaaagt ggaaatcaaa cgtacggtgg ctgcaccatc tgtcttcatc | 420 |
| ttcccgccat ctgatgagca gttgaaatct ggaactgcct ctgttgtgtg cctgctgaat | 480 |
| aacttctatc ccagagaggc caaagtacag tggaaggtgg ataacgccct ccaatcgggt | 540 |
| aactcccagg agagtgtcac agagcaggac agcaaggaca gcacctacag cctcagcagc | 600 |
| accctgacgc tgagcaaagc agactacgag aaacacaaag tctacgcctg cgaagtcacc | 660 |
| catcagggcc tgagctcgcc cgtcacaaag agcttcaaca ggggagagtg tggagccgca | 720 |
| gaacaaaaac tcatctcaga agaggatctg aatggagccg cagactacaa ggacgacgac | 780 |
| gacaagggtg ccgcataata aggcgcgcca attctatttc aaggagacag tcatatgaaa | 840 |
| tacctgctgc cgaccgctgc tgctggtctg ctgctcctcg ctgcccagcc ggcgatggcc | 900 |
| gaggtgcaat gctggagtc tgggggaggc ttggtacagc ctgggggtc cctgagactc | 960 |
| tcctgtgcag cctccggatt caccttagc agttatgcca tgagctgggt ccgccaggct | 1020 |
| ccagggaagg ggctggagtg ggtctcagct attagtggta gtggtggtag cacatactac | 1080 |
| gcagactccg tgaagggccg gttcaccatc tccagagaca attccaagaa cacgctgtat | 1140 |
| ctgcagatga acagcctgag agccgaggac acggccgtat attactgtgc gaaaccgttt | 1200 |
| ccgtattttg actactgggg ccaaggaacc ctggtcaccg tctcgagtgc tagcaccaaa | 1260 |
| ggcccatcgg tcttcccct ggcaccctcc tccaagagca cctctggggg cacagcggcc | 1320 |
| ctgggctgcc tggtcaagga ctacttcccc gaaccggtga cggtgtcgtg aactcaggc | 1380 |
| gccctgacca gcggcgtgca caccttcccg gctgtcctac agtcctcagg actctactcc | 1440 |
| ctcagcagcg tggtgaccgt gccctccagc agcttgggca cccagaccta catctgcaac | 1500 |
| gtgaatcaca agcccagcaa caccaaagtg gacaagaaag ttgagcccaa atcttgtgac | 1560 |
| gcggccgcaa gcactagtgc ccatcaccat caccatcacg ccgcggcata g | 1611 |

<210> SEQ ID NO 2
<211> LENGTH: 1617
<212> TYPE: DNA
<213> ORGANISM: Artificial Sequence
<220> FEATURE:
<223> OTHER INFORMATION: Library Template for DP88-3 library

<400> SEQUENCE: 2

| | |
|---|---|
| atgaaatacc tattgcctac ggcagccgct ggattgttat tactcgcggc ccagccggcc | 60 |
| atggccgata tccagatgac ccagtctcca tcctccctgt ctgcatctgt cggagaccgg | 120 |
| gtcaccatca cctgccgggc aagtcagggc attagaaatg atttaggctg gtaccagcag | 180 |
| aagccaggga aagcccctaa gcgcctgatc tatgctgcat ccagtttgca gagtggcgtc | 240 |
| ccatcaaggt tcagcggcag tggatccggg acagagttca ctctcaccat cagcagcttg | 300 |
| cagcctgaag attttgccac ctattactgc ttgcagcata tagttaccc cacgtttggc | 360 |
| cagggcacca agtcgagat caagcgtacg gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |

-continued

```
acgctgagca aagcagacta cgagaaacac aaagtctacg cctgcgaagt cacccatcag        660
ggcctgagct cgcccgtcac aaagagcttc aacaggggag agtgtggagc cgcagaacaa        720
aaactcatct cagaagagga tctgaatgga ccgcagact acaaggacga cgacgacaag         780
ggtgccgcat aataaggcgc gccaattcta tttcaaggag acagtcatat gaaatacctg        840
ctgccgaccg ctgctgctgg tctgctgctc ctcgctgccc agccggcgat ggcccaggtg        900
caattggtgc agtctgggc tgaggtgaag aagcctgggt cctcggtgaa ggtctcctgc         960
aaggcctccg gaggcacatt cagcagctac gctataagct gggtgcgaca ggcccctgga       1020
caagggctcg agtggatggg aaggatcatc cctatctttg gtacagcaaa ctacgcacag       1080
aagttccagg gcagggtcac cattactgca gacaaatcca cgagcacagc ctacatggag       1140
ctgagcagcc tgagatctga ggacaccgcc gtgtattact gtgcgagact atccccaggc       1200
ggttactatg ttatggatgc ctggggccaa gggaccaccg tgaccgtctc ctcagctagc       1260
accaaaggcc catcggtctt ccccctggca ccctcctcca agagcacctc tgggggcaca       1320
gcggccctgg gctgcctggt caaggactac ttccccgaac cggtgacggt gtcgtggaac       1380
tcaggcgccc tgaccagcgg cgtgcacacc ttcccggctg tcctacagtc ctcaggactc       1440
tactccctca gcagcgtggt gaccgtgccc tccagcagct gggcaccca gacctacatc       1500 tgcaacgtga atcacaagcc cagcaacacc aaagtggaca agaaagttga gcccaaatct       1560
tgtgacgcgg ccgcaagcac tagtgcccat caccatcacc atcacgccgc ggcatag         1617
```

<210> SEQ ID NO 3
<211> LENGTH: 5
<212> TYPE: PRT
<213> ORGANISM: Artificial Sequence
<220> FEATURE:
<223> OTHER INFORMATION: HCDR1 Kabat (1)

<400> SEQUENCE: 3

Ser Tyr Ala Met Ser
1               5

<210> SEQ ID NO 4
<211> LENGTH: 15
<212> TYPE: DNA
<213> ORGANISM: Artificial Sequence
<220> FEATURE:
<223> OTHER INFORMATION: HCDR1 Kabat (1) (DNA 1)

<400> SEQUENCE: 4
agttatgcca tgagc                                                         15

<210> SEQ ID NO 5
<211> LENGTH: 5
<212> TYPE: PRT
<213> ORGANISM: Artificial Sequence
<220> FEATURE:
<223> OTHER INFORMATION: HCDR1 Kabat (2)

<400> SEQUENCE: 5

Ser Tyr Thr Met Ser
1               5

<210> SEQ ID NO 6
<211> LENGTH: 15
<212> TYPE: DNA
<213> ORGANISM: Artificial Sequence
<220> FEATURE:

```
<223> OTHER INFORMATION: HCDR1 Kabat (2) (DNA)

<400> SEQUENCE: 6
agttatacca tgagc                                                    15

<210> SEQ ID NO 7
<211> LENGTH: 5
<212> TYPE: PRT
<213> ORGANISM: Artificial Sequence
<220> FEATURE:
<223> OTHER INFORMATION: HCDR1 Kabat (3)

<400> SEQUENCE: 7

Ser Phe Ala Met Ser
1               5

<210> SEQ ID NO 8
<211> LENGTH: 15
<212> TYPE: DNA
<213> ORGANISM: Artificial Sequence
<220> FEATURE:
<223> OTHER INFORMATION: HCDR1 Kabat (3) (DNA)

<400> SEQUENCE: 8
agttttgcca tgagc                                                    15

<210> SEQ ID NO 9
<211> LENGTH: 5
<212> TYPE: PRT
<213> ORGANISM: Artificial Sequence
<220> FEATURE:
<223> OTHER INFORMATION: HCDR1 Kabat (4)

<400> SEQUENCE: 9

Ser His Ala Met Ser
1               5

<210> SEQ ID NO 10
<211> LENGTH: 15
<212> TYPE: DNA
<213> ORGANISM: Artificial Sequence
<220> FEATURE:
<223> OTHER INFORMATION: HCDR1 Kabat (4) (DNA)

<400> SEQUENCE: 10
agtcatgcta tgagc                                                    15

<210> SEQ ID NO 11
<211> LENGTH: 5
<212> TYPE: PRT
<213> ORGANISM: Artificial Sequence
<220> FEATURE:
<223> OTHER INFORMATION: HCDR1 Kabat (5)

<400> SEQUENCE: 11

Ser Ser Ala Met Ser
1               5

<210> SEQ ID NO 12
<211> LENGTH: 15
<212> TYPE: DNA
<213> ORGANISM: Artificial Sequence
<220> FEATURE:
<223> OTHER INFORMATION: HCDR1 Kabat (5) (DNA)

<400> SEQUENCE: 12
```
agttctgcca tgagc 15

<210> SEQ ID NO 13
<211> LENGTH: 7
<212> TYPE: PRT
<213> ORGANISM: Artificial Sequence
<220> FEATURE:
<223> OTHER INFORMATION: HCDR1 Chothia (1)

<400> SEQUENCE: 13

Gly Phe Thr Phe Ser Ser Tyr
1               5

<210> SEQ ID NO 14
<211> LENGTH: 21
<212> TYPE: DNA
<213> ORGANISM: Artificial Sequence
<220> FEATURE:
<223> OTHER INFORMATION: HCDR1 Chothia (1) (DNA)

<400> SEQUENCE: 14
ggattcacct ttagcagtta t                                    21

<210> SEQ ID NO 15
<211> LENGTH: 7
<212> TYPE: PRT
<213> ORGANISM: Artificial Sequence
<220> FEATURE:
<223> OTHER INFORMATION: HCDR1 Chothia (2)

<400> SEQUENCE: 15

Gly Ser Thr Phe Ser Ser Tyr
1               5

<210> SEQ ID NO 16
<211> LENGTH: 21
<212> TYPE: DNA
<213> ORGANISM: Artificial Sequence
<220> FEATURE:
<223> OTHER INFORMATION: HCDR1 Chothia (2) (DNA)

<400> SEQUENCE: 16
ggatccacct ttagcagtta t                                    21

<210> SEQ ID NO 17
<211> LENGTH: 7
<212> TYPE: PRT
<213> ORGANISM: Artificial Sequence
<220> FEATURE:
<223> OTHER INFORMATION: HCDR1 Chothia (3)

<400> SEQUENCE: 17

Gly Phe Thr Phe Ser Ser Phe
1               5

<210> SEQ ID NO 18
<211> LENGTH: 21
<212> TYPE: DNA
<213> ORGANISM: Artificial Sequence
<220> FEATURE:
<223> OTHER INFORMATION: HCDR1 Chothia (3) (DNA)

<400> SEQUENCE: 18
ggattcacct ttagcagttt t                                    21

<210> SEQ ID NO 19

```
<211> LENGTH: 7
<212> TYPE: PRT
<213> ORGANISM: Artificial Sequence
<220> FEATURE:
<223> OTHER INFORMATION: HCDR1 Chothia (4)

<400> SEQUENCE: 19

Gly Phe Thr Phe Ser Ser His
1               5

<210> SEQ ID NO 20
<211> LENGTH: 21
<212> TYPE: DNA
<213> ORGANISM: Artificial Sequence
<220> FEATURE:
<223> OTHER INFORMATION: HCDR1 Chothia (4) (DNA)

<400> SEQUENCE: 20
ggattcacct ttagcagtca t                                             21

<210> SEQ ID NO 21
<211> LENGTH: 7
<212> TYPE: PRT
<213> ORGANISM: Artificial Sequence
<220> FEATURE:
<223> OTHER INFORMATION: HCDR1 Chothia (5)

<400> SEQUENCE: 21

Gly Phe Thr Phe Ser Ser Ser
1               5

<210> SEQ ID NO 22
<211> LENGTH: 21
<212> TYPE: DNA
<213> ORGANISM: Artificial Sequence
<220> FEATURE:
<223> OTHER INFORMATION: HCDR1 Chothia (5) (DNA)

<400> SEQUENCE: 22
ggattcacct ttagcagttc t                                             21

<210> SEQ ID NO 23
<211> LENGTH: 10
<212> TYPE: PRT
<213> ORGANISM: Artificial Sequence
<220> FEATURE:
<223> OTHER INFORMATION: HCDR1 AbM (1)

<400> SEQUENCE: 23

Gly Phe Thr Phe Ser Ser Tyr Ala Met Ser
1               5                   10

<210> SEQ ID NO 24
<211> LENGTH: 30
<212> TYPE: DNA
<213> ORGANISM: Artificial Sequence
<220> FEATURE:
<223> OTHER INFORMATION: HCDR1 AbM (1) (DNA 1)

<400> SEQUENCE: 24
ggattcacct ttagcagtta tgccatgagc                                    30

<210> SEQ ID NO 25
<211> LENGTH: 10
<212> TYPE: PRT
<213> ORGANISM: Artificial Sequence
<220> FEATURE:
```

<223> OTHER INFORMATION: HCDR1 AbM (2)

<400> SEQUENCE: 25

Gly Ser Thr Phe Ser Ser Tyr Ala Met Ser
1               5                   10

<210> SEQ ID NO 26
<211> LENGTH: 30
<212> TYPE: DNA
<213> ORGANISM: Artificial Sequence
<220> FEATURE:
<223> OTHER INFORMATION: HCDR1 AbM (2) (DNA)

<400> SEQUENCE: 26
ggatccacct ttagcagtta tgccatgagc                                      30

<210> SEQ ID NO 27
<211> LENGTH: 10
<212> TYPE: PRT
<213> ORGANISM: Artificial Sequence
<220> FEATURE:
<223> OTHER INFORMATION: HCDR1 AbM (3)

<400> SEQUENCE: 27

Gly Phe Thr Phe Ser Ser Tyr Thr Met Ser
1               5                   10

<210> SEQ ID NO 28
<211> LENGTH: 30
<212> TYPE: DNA
<213> ORGANISM: Artificial Sequence
<220> FEATURE:
<223> OTHER INFORMATION: HCDR1 AbM (3) (DNA)

<400> SEQUENCE: 28
ggattcacct ttagcagtta taccatgagc                                      30

<210> SEQ ID NO 29
<211> LENGTH: 10
<212> TYPE: PRT
<213> ORGANISM: Artificial Sequence
<220> FEATURE:
<223> OTHER INFORMATION: HCDR1 AbM (4)

<400> SEQUENCE: 29

Gly Phe Thr Phe Ser Ser Phe Ala Met Ser
1               5                   10

<210> SEQ ID NO 30
<211> LENGTH: 30
<212> TYPE: DNA
<213> ORGANISM: Artificial Sequence
<220> FEATURE:
<223> OTHER INFORMATION: HCDR1 AbM (4) (DNA)

<400> SEQUENCE: 30
ggattcacct ttagcagttt tgccatgagc                                      30

<210> SEQ ID NO 31
<211> LENGTH: 10
<212> TYPE: PRT
<213> ORGANISM: Artificial Sequence
<220> FEATURE:
<223> OTHER INFORMATION: HCDR1 AbM (5)

<400> SEQUENCE: 31

Gly Phe Thr Phe Ser Ser His Ala Met Ser
1               5                   10

<210> SEQ ID NO 32
<211> LENGTH: 30
<212> TYPE: DNA
<213> ORGANISM: Artificial Sequence
<220> FEATURE:
<223> OTHER INFORMATION: HCDR1 AbM (5) (DNA)

<400> SEQUENCE: 32
ggattcacct ttagcagtca tgctatgagc                              30

<210> SEQ ID NO 33
<211> LENGTH: 10
<212> TYPE: PRT
<213> ORGANISM: Artificial Sequence
<220> FEATURE:
<223> OTHER INFORMATION: HCDR1 AbM (6)

<400> SEQUENCE: 33

Gly Phe Thr Phe Ser Ser Ser Ala Met Ser
1               5                   10

<210> SEQ ID NO 34
<211> LENGTH: 30
<212> TYPE: DNA
<213> ORGANISM: Artificial Sequence
<220> FEATURE:
<223> OTHER INFORMATION: HCDR1 AbM (6) (DNA)

<400> SEQUENCE: 34
ggattcacct ttagcagttc tgccatgagc                              30

<210> SEQ ID NO 35
<211> LENGTH: 16
<212> TYPE: PRT
<213> ORGANISM: Artificial Sequence
<220> FEATURE:
<223> OTHER INFORMATION: HCDR2 Kabat (1)

<400> SEQUENCE: 35

Ala Ile Ser Gly Ser Gly Gly Ser Thr Tyr Tyr Ala Asp Ser Val Lys
1               5                   10                  15

<210> SEQ ID NO 36
<211> LENGTH: 48
<212> TYPE: DNA
<213> ORGANISM: Artificial Sequence
<220> FEATURE:
<223> OTHER INFORMATION: HCDR2 Kabat (1) (DNA 1)

<400> SEQUENCE: 36
gctattagtg gtagtggtgg tagcacatac tacgcagact ccgtgaag          48

<210> SEQ ID NO 37
<211> LENGTH: 16
<212> TYPE: PRT
<213> ORGANISM: Artificial Sequence
<220> FEATURE:
<223> OTHER INFORMATION: HCDR2 Kabat (2)

<400> SEQUENCE: 37

Ala Ile Gly Val Ser Thr Gly Ser Thr Tyr Tyr Ala Asp Ser Val Lys
1               5                   10                  15

-continued

```
<210> SEQ ID NO 38
<211> LENGTH: 48
<212> TYPE: DNA
<213> ORGANISM: Artificial Sequence
<220> FEATURE:
<223> OTHER INFORMATION: HCDR2 Kabat (2) (DNA)

<400> SEQUENCE: 38
gctattggtg ttagtactgg tagcacatac tacgcagact ccgtgaag            48

<210> SEQ ID NO 39
<211> LENGTH: 16
<212> TYPE: PRT
<213> ORGANISM: Artificial Sequence
<220> FEATURE:
<223> OTHER INFORMATION: HCDR2 Kabat (3)

<400> SEQUENCE: 39

Ala Ile Ser Gly Ser Ala Gly Tyr Thr Tyr Tyr Ala Asp Ser Val Lys
 1               5                  10                  15

<210> SEQ ID NO 40
<211> LENGTH: 48
<212> TYPE: DNA
<213> ORGANISM: Artificial Sequence
<220> FEATURE:
<223> OTHER INFORMATION: HCDR2 Kabat (3) (DNA)

<400> SEQUENCE: 40
gctattagtg ggagtgctgg ttatacatac tacgcagact ccgtgaag            48

<210> SEQ ID NO 41
<211> LENGTH: 15
<212> TYPE: PRT
<213> ORGANISM: Artificial Sequence
<220> FEATURE:
<223> OTHER INFORMATION: HCDR2 Kabat (4)

<400> SEQUENCE: 41

Ala Ile Ser Gly Gly Gly Arg Thr Tyr Tyr Ala Asp Ser Val Lys
 1               5                  10                  15

<210> SEQ ID NO 42
<211> LENGTH: 45
<212> TYPE: DNA
<213> ORGANISM: Artificial Sequence
<220> FEATURE:
<223> OTHER INFORMATION: HCDR2 Kabat (4) (DNA)

<400> SEQUENCE: 42
gctattagtg gtggtggtag gacatactac gcagactccg tgaag               45

<210> SEQ ID NO 43
<211> LENGTH: 16
<212> TYPE: PRT
<213> ORGANISM: Artificial Sequence
<220> FEATURE:
<223> OTHER INFORMATION: HCDR2 Kabat (5)

<400> SEQUENCE: 43

Ala Ile Ile Ser Ser Gly Gly Leu Thr Tyr Tyr Ala Asp Ser Val Lys
 1               5                  10                  15

<210> SEQ ID NO 44
<211> LENGTH: 48
<212> TYPE: DNA
<213> ORGANISM: Artificial Sequence
```

```
<220> FEATURE:
<223> OTHER INFORMATION: HCDR2 Kabat (5) (DNA)

<400> SEQUENCE: 44
gcgattatta gtagtggtgg tctcacatac tacgcagact ccgtgaag          48

<210> SEQ ID NO 45
<211> LENGTH: 16
<212> TYPE: PRT
<213> ORGANISM: Artificial Sequence
<220> FEATURE:
<223> OTHER INFORMATION: HCDR2 Kabat (6)

<400> SEQUENCE: 45

Ala Ile Ile Gly Ser Gly Ser Arg Thr Tyr Tyr Ala Asp Ser Val Lys
 1               5                  10                  15

<210> SEQ ID NO 46
<211> LENGTH: 48
<212> TYPE: DNA
<213> ORGANISM: Artificial Sequence
<220> FEATURE:
<223> OTHER INFORMATION: HCDR2 Kabat (6) (DNA)

<400> SEQUENCE: 46
gctattattg ggagtggtag tcgtacatac tacgcagact ccgtgaag          48

<210> SEQ ID NO 47
<211> LENGTH: 16
<212> TYPE: PRT
<213> ORGANISM: Artificial Sequence
<220> FEATURE:
<223> OTHER INFORMATION: HCDR2 Kabat (7)

<400> SEQUENCE: 47

Ala Ile Ile Gly Ser Gly Ala Ser Thr Tyr Tyr Ala Asp Ser Val Lys
 1               5                  10                  15

<210> SEQ ID NO 48
<211> LENGTH: 48
<212> TYPE: DNA
<213> ORGANISM: Artificial Sequence
<220> FEATURE:
<223> OTHER INFORMATION: HCDR2 Kabat (7) (DNA)

<400> SEQUENCE: 48
gctattattg gtagtggtgc tagcacatac tacgcagact ccgtgaag          48

<210> SEQ ID NO 49
<211> LENGTH: 16
<212> TYPE: PRT
<213> ORGANISM: Artificial Sequence
<220> FEATURE:
<223> OTHER INFORMATION: HCDR2 Kabat (8)

<400> SEQUENCE: 49

Ala Ile Trp Gly Gly Gly Arg Ser Thr Tyr Tyr Ala Asp Ser Val Lys
 1               5                  10                  15

<210> SEQ ID NO 50
<211> LENGTH: 48
<212> TYPE: DNA
<213> ORGANISM: Artificial Sequence
<220> FEATURE:
<223> OTHER INFORMATION: HCDR2 Kabat (8) (DNA)

<400> SEQUENCE: 50
```

```
gctatttggg gtggtggtcg tagcacatac tacgcagact ccgtgaag                    48
```

<210> SEQ ID NO 51
<211> LENGTH: 16
<212> TYPE: PRT
<213> ORGANISM: Artificial Sequence
<220> FEATURE:
<223> OTHER INFORMATION: HCDR2 Kabat (9)

<400> SEQUENCE: 51

```
Ala Ile Ile Ser Ser Gly Ala Ser Thr Tyr Tyr Ala Asp Ser Val Lys
1               5                   10                  15
```

<210> SEQ ID NO 52
<211> LENGTH: 48
<212> TYPE: DNA
<213> ORGANISM: Artificial Sequence
<220> FEATURE:
<223> OTHER INFORMATION: HCDR2 Kabat (9) (DNA)

<400> SEQUENCE: 52

```
gctattatta gtagtggggc tagcacatac tacgcagact ccgtgaag                    48
```

<210> SEQ ID NO 53
<211> LENGTH: 16
<212> TYPE: PRT
<213> ORGANISM: Artificial Sequence
<220> FEATURE:
<223> OTHER INFORMATION: HCDR2 Kabat (10)

<400> SEQUENCE: 53

```
Ala Ile Leu Ala Ser Gly Ala Ile Thr Tyr Tyr Ala Asp Ser Val Lys
1               5                   10                  15
```

<210> SEQ ID NO 54
<211> LENGTH: 48
<212> TYPE: DNA
<213> ORGANISM: Artificial Sequence
<220> FEATURE:
<223> OTHER INFORMATION: HCDR2 Kabat (10) (DNA)

<400> SEQUENCE: 54

```
gctattttgg ctagtggtgc gatcacatac tacgcagact ccgtgaag                    48
```

<210> SEQ ID NO 55
<211> LENGTH: 16
<212> TYPE: PRT
<213> ORGANISM: Artificial Sequence
<220> FEATURE:
<223> OTHER INFORMATION: HCDR2 Kabat (11)

<400> SEQUENCE: 55

```
Gly Ile Ile Gly Ser Gly Gly Ile Thr Tyr Tyr Ala Asp Ser Val Lys
1               5                   10                  15
```

<210> SEQ ID NO 56
<211> LENGTH: 48
<212> TYPE: DNA
<213> ORGANISM: Artificial Sequence
<220> FEATURE:
<223> OTHER INFORMATION: HCDR2 Kabat (11) (DNA)

<400> SEQUENCE: 56

```
ggtattattg gtagtggtgg tatcacatac tacgcagact ccgtgaag                    48
```

```
<210> SEQ ID NO 57
<211> LENGTH: 16
<212> TYPE: PRT
<213> ORGANISM: Artificial Sequence
<220> FEATURE:
<223> OTHER INFORMATION: HCDR2 Kabat (12)

<400> SEQUENCE: 57

Ala Ile Leu Gly Ser Gly Gly Ser Thr Tyr Tyr Ala Asp Ser Val Lys
 1               5                  10                  15

<210> SEQ ID NO 58
<211> LENGTH: 48
<212> TYPE: DNA
<213> ORGANISM: Artificial Sequence
<220> FEATURE:
<223> OTHER INFORMATION: HCDR2 Kabat (12) (DNA)

<400> SEQUENCE: 58
gctattcttg gtagtggtgg tagcacatac tacgcagact ccgtgaag              48

<210> SEQ ID NO 59
<211> LENGTH: 16
<212> TYPE: PRT
<213> ORGANISM: Artificial Sequence
<220> FEATURE:
<223> OTHER INFORMATION: HCDR2 Kabat (13)

<400> SEQUENCE: 59

Ala Ile Ile Gly Ser Gly Ser Asn Thr Tyr Tyr Ala Asp Ser Val Lys
 1               5                  10                  15

<210> SEQ ID NO 60
<211> LENGTH: 48
<212> TYPE: DNA
<213> ORGANISM: Artificial Sequence
<220> FEATURE:
<223> OTHER INFORMATION: HCDR2 Kabat (13) (DNA)

<400> SEQUENCE: 60
gctattattg gtagtggtag taacacatac tacgcagact ccgtgaag              48

<210> SEQ ID NO 61
<211> LENGTH: 15
<212> TYPE: PRT
<213> ORGANISM: Artificial Sequence
<220> FEATURE:
<223> OTHER INFORMATION: HCDR2 Kabat (14)

<400> SEQUENCE: 61

Ala Ile Trp Ala Ser Gly Glu Gln Tyr Tyr Ala Asp Ser Val Lys
 1               5                  10                  15

<210> SEQ ID NO 62
<211> LENGTH: 45
<212> TYPE: DNA
<213> ORGANISM: Artificial Sequence
<220> FEATURE:
<223> OTHER INFORMATION: HCDR2 Kabat (14) (DNA)

<400> SEQUENCE: 62
gctatttggg ctagtgggga gcaatactac gcagactccg tgaag                 45

<210> SEQ ID NO 63
<211> LENGTH: 16
<212> TYPE: PRT
<213> ORGANISM: Artificial Sequence
```

<220> FEATURE:
<223> OTHER INFORMATION: HCDR2 Kabat (15)

<400> SEQUENCE: 63

Ala Ile Ile Gly Ser Gly Ser Ile Thr Tyr Tyr Ala Asp Ser Val Lys
1               5                   10                  15

<210> SEQ ID NO 64
<211> LENGTH: 48
<212> TYPE: DNA
<213> ORGANISM: Artificial Sequence
<220> FEATURE:
<223> OTHER INFORMATION: HCDR2 Kabat (15) (DNA)

<400> SEQUENCE: 64
gctattattg gtagtggtag tatcacatac tacgcagact ccgtgaag        48

<210> SEQ ID NO 65
<211> LENGTH: 16
<212> TYPE: PRT
<213> ORGANISM: Artificial Sequence
<220> FEATURE:
<223> OTHER INFORMATION: HCDR2 Kabat (16)

<400> SEQUENCE: 65

Ala Ile Ile Gly Ser Gly Gly Ile Thr Tyr Tyr Ala Asp Ser Val Lys
1               5                   10                  15

<210> SEQ ID NO 66
<211> LENGTH: 48
<212> TYPE: DNA
<213> ORGANISM: Artificial Sequence
<220> FEATURE:
<223> OTHER INFORMATION: HCDR2 Kabat (16) (DNA)

<400> SEQUENCE: 66
gctattattg gtagtggtgg tatcacatac tacgcagact ccgtgaag        48

<210> SEQ ID NO 67
<211> LENGTH: 16
<212> TYPE: PRT
<213> ORGANISM: Artificial Sequence
<220> FEATURE:
<223> OTHER INFORMATION: HCDR2 Kabat (17)

<400> SEQUENCE: 67

Ala Ile Ser Thr Asn Gly Asn Tyr Thr Tyr Tyr Ala Asp Ser Val Lys
1               5                   10                  15

<210> SEQ ID NO 68
<211> LENGTH: 48
<212> TYPE: DNA
<213> ORGANISM: Artificial Sequence
<220> FEATURE:
<223> OTHER INFORMATION: HCDR2 Kabat (17) (DNA)

<400> SEQUENCE: 68
gctattagta ctaatggtaa ttatacatac tacgcagact ccgtgaag        48

<210> SEQ ID NO 69
<211> LENGTH: 7
<212> TYPE: PRT
<213> ORGANISM: Artificial Sequence
<220> FEATURE:
<223> OTHER INFORMATION: HCDR2 Chothia (1)

<400> SEQUENCE: 69

```
Ser Gly Ser Gly Gly Ser Thr
1               5

<210> SEQ ID NO 70
<211> LENGTH: 21
<212> TYPE: DNA
<213> ORGANISM: Artificial Sequence
<220> FEATURE:
<223> OTHER INFORMATION: HCDR2 Chothia (1) (DNA 1)

<400> SEQUENCE: 70
agtggtagtg gtggtagcac a                                             21

<210> SEQ ID NO 71
<211> LENGTH: 7
<212> TYPE: PRT
<213> ORGANISM: Artificial Sequence
<220> FEATURE:
<223> OTHER INFORMATION: HCDR2 Chothia (2)

<400> SEQUENCE: 71

Gly Val Ser Thr Gly Ser Thr
1               5

<210> SEQ ID NO 72
<211> LENGTH: 21
<212> TYPE: DNA
<213> ORGANISM: Artificial Sequence
<220> FEATURE:
<223> OTHER INFORMATION: HCDR2 Chothia (2) (DNA)

<400> SEQUENCE: 72
ggtgttagta ctggtagcac a                                             21

<210> SEQ ID NO 73
<211> LENGTH: 7
<212> TYPE: PRT
<213> ORGANISM: Artificial Sequence
<220> FEATURE:
<223> OTHER INFORMATION: HCDR2 Chothia (3)

<400> SEQUENCE: 73

Ser Gly Ser Ala Gly Tyr Thr
1               5

<210> SEQ ID NO 74
<211> LENGTH: 21
<212> TYPE: DNA
<213> ORGANISM: Artificial Sequence
<220> FEATURE:
<223> OTHER INFORMATION: HCDR2 Chothia (3) (DNA)

<400> SEQUENCE: 74
agtgggagtg ctggttatac a                                             21

<210> SEQ ID NO 75
<211> LENGTH: 6
<212> TYPE: PRT
<213> ORGANISM: Artificial Sequence
<220> FEATURE:
<223> OTHER INFORMATION: HCDR2 Chothia (4)

<400> SEQUENCE: 75

Ser Gly Gly Gly Arg Thr
1               5
```

<210> SEQ ID NO 76
<211> LENGTH: 18
<212> TYPE: DNA
<213> ORGANISM: Artificial Sequence
<220> FEATURE:
<223> OTHER INFORMATION: HCDR2 Chothia (4) (DNA)

<400> SEQUENCE: 76
agtggtggtg gtaggaca                                                 18

<210> SEQ ID NO 77
<211> LENGTH: 7
<212> TYPE: PRT
<213> ORGANISM: Artificial Sequence
<220> FEATURE:
<223> OTHER INFORMATION: HCDR2 Chothia (5)

<400> SEQUENCE: 77

Ile Ser Ser Gly Gly Leu Thr
1               5

<210> SEQ ID NO 78
<211> LENGTH: 21
<212> TYPE: DNA
<213> ORGANISM: Artificial Sequence
<220> FEATURE:
<223> OTHER INFORMATION: HCDR2 Chothia (5) (DNA)

<400> SEQUENCE: 78
attagtagtg gtggtctcac a                                             21

<210> SEQ ID NO 79
<211> LENGTH: 7
<212> TYPE: PRT
<213> ORGANISM: Artificial Sequence
<220> FEATURE:
<223> OTHER INFORMATION: HCDR2 Chothia (6)

<400> SEQUENCE: 79

Ile Gly Ser Gly Ser Arg Thr
1               5

<210> SEQ ID NO 80
<211> LENGTH: 21
<212> TYPE: DNA
<213> ORGANISM: Artificial Sequence
<220> FEATURE:
<223> OTHER INFORMATION: HCDR2 Chothia (6) (DNA)

<400> SEQUENCE: 80
attgggagtg gtagtcgtac a                                             21

<210> SEQ ID NO 81
<211> LENGTH: 7
<212> TYPE: PRT
<213> ORGANISM: Artificial Sequence
<220> FEATURE:
<223> OTHER INFORMATION: HCDR2 Chothia (7)

<400> SEQUENCE: 81

Ile Gly Ser Gly Ala Ser Thr
1               5

<210> SEQ ID NO 82
<211> LENGTH: 21
<212> TYPE: DNA

```
<213> ORGANISM: Artificial Sequence
<220> FEATURE:
<223> OTHER INFORMATION: HCDR2 Chothia (7) (DNA)

<400> SEQUENCE: 82
attggtagtg gtgctagcac a                                          21

<210> SEQ ID NO 83
<211> LENGTH: 7
<212> TYPE: PRT
<213> ORGANISM: Artificial Sequence
<220> FEATURE:
<223> OTHER INFORMATION: HCDR2 Chothia (8)

<400> SEQUENCE: 83

Trp Gly Gly Gly Arg Ser Thr
1               5

<210> SEQ ID NO 84
<211> LENGTH: 21
<212> TYPE: DNA
<213> ORGANISM: Artificial Sequence
<220> FEATURE:
<223> OTHER INFORMATION: HCDR2 Chothia (8) (DNA)

<400> SEQUENCE: 84
attggtagtg gtgctagcac a                                          21

<210> SEQ ID NO 85
<211> LENGTH: 7
<212> TYPE: PRT
<213> ORGANISM: Artificial Sequence
<220> FEATURE:
<223> OTHER INFORMATION: HCDR2 Chothia (9)

<400> SEQUENCE: 85

Ile Ser Ser Gly Ala Ser Thr
1               5

<210> SEQ ID NO 86
<211> LENGTH: 21
<212> TYPE: DNA
<213> ORGANISM: Artificial Sequence
<220> FEATURE:
<223> OTHER INFORMATION: HCDR2 Chothia (9) (DNA)

<400> SEQUENCE: 86
attagtagtg gggctagcac a                                          21

<210> SEQ ID NO 87
<211> LENGTH: 7
<212> TYPE: PRT
<213> ORGANISM: Artificial Sequence
<220> FEATURE:
<223> OTHER INFORMATION: HCDR2 Chothia (10)

<400> SEQUENCE: 87

Leu Ala Ser Gly Ala Ile Thr
1               5

<210> SEQ ID NO 88
<211> LENGTH: 21
<212> TYPE: DNA
<213> ORGANISM: Artificial Sequence
<220> FEATURE:
<223> OTHER INFORMATION: HCDR2 Chothia (10) (DNA)
```

```
<400> SEQUENCE: 88
ttggctagtg gtgcgatcac a                                              21

<210> SEQ ID NO 89
<211> LENGTH: 7
<212> TYPE: PRT
<213> ORGANISM: Artificial Sequence
<220> FEATURE:
<223> OTHER INFORMATION: HCDR2 Chothia (11)

<400> SEQUENCE: 89

Ile Gly Ser Gly Gly Ile Thr
1               5

<210> SEQ ID NO 90
<211> LENGTH: 21
<212> TYPE: DNA
<213> ORGANISM: Artificial Sequence
<220> FEATURE:
<223> OTHER INFORMATION: HCDR2 Chothia (11) (DNA)

<400> SEQUENCE: 90
attggtagtg gtggtatcac a                                              21

<210> SEQ ID NO 91
<211> LENGTH: 7
<212> TYPE: PRT
<213> ORGANISM: Artificial Sequence
<220> FEATURE:
<223> OTHER INFORMATION: HCDR2 Chothia (12)

<400> SEQUENCE: 91

Leu Gly Ser Gly Gly Ser Thr
1               5

<210> SEQ ID NO 92
<211> LENGTH: 21
<212> TYPE: DNA
<213> ORGANISM: Artificial Sequence
<220> FEATURE:
<223> OTHER INFORMATION: HCDR2 Chothia (12) (DNA)

<400> SEQUENCE: 92
cttggtagtg gtggtagcac a                                              21

<210> SEQ ID NO 93
<211> LENGTH: 7
<212> TYPE: PRT
<213> ORGANISM: Artificial Sequence
<220> FEATURE:
<223> OTHER INFORMATION: HCDR2 Chothia (13)

<400> SEQUENCE: 93

Ile Gly Ser Gly Ser Asn Thr
1               5

<210> SEQ ID NO 94
<211> LENGTH: 21
<212> TYPE: DNA
<213> ORGANISM: Artificial Sequence
<220> FEATURE:
<223> OTHER INFORMATION: HCDR2 Chothia (13) (DNA)

<400> SEQUENCE: 94
attggtagtg gtagtaacac a                                              21
```

<210> SEQ ID NO 95
<211> LENGTH: 6
<212> TYPE: PRT
<213> ORGANISM: Artificial Sequence
<220> FEATURE:
<223> OTHER INFORMATION: HCDR2 Chothia (14)

<400> SEQUENCE: 95

Trp Ala Ser Gly Glu Gln
1               5

<210> SEQ ID NO 96
<211> LENGTH: 18
<212> TYPE: DNA
<213> ORGANISM: Artificial Sequence
<220> FEATURE:
<223> OTHER INFORMATION: HCDR2 Chothia (14) (DNA)

<400> SEQUENCE: 96
tgggctagtg gggagcaa                                                   18

<210> SEQ ID NO 97
<211> LENGTH: 7
<212> TYPE: PRT
<213> ORGANISM: Artificial Sequence
<220> FEATURE:
<223> OTHER INFORMATION: HCDR2 Chothia (15)

<400> SEQUENCE: 97

Ile Gly Ser Gly Ser Ile Thr
1               5

<210> SEQ ID NO 98
<211> LENGTH: 21
<212> TYPE: DNA
<213> ORGANISM: Artificial Sequence
<220> FEATURE:
<223> OTHER INFORMATION: HCDR2 Chothia (15) (DNA)

<400> SEQUENCE: 98
attggtagtg gtagtatcac a                                               21

<210> SEQ ID NO 99
<211> LENGTH: 7
<212> TYPE: PRT
<213> ORGANISM: Artificial Sequence
<220> FEATURE:
<223> OTHER INFORMATION: HCDR2 Chothia (16)

<400> SEQUENCE: 99

Ser Thr Asn Gly Asn Tyr Thr
1               5

<210> SEQ ID NO 100
<211> LENGTH: 21
<212> TYPE: DNA
<213> ORGANISM: Artificial Sequence
<220> FEATURE:
<223> OTHER INFORMATION: HCDR2 Chothia (16) (DNA)

<400> SEQUENCE: 100
agtactaatg gtaattatac a                                               21

<210> SEQ ID NO 101
<211> LENGTH: 9
<212> TYPE: PRT

<213> ORGANISM: Artificial Sequence
<220> FEATURE:
<223> OTHER INFORMATION: HCDR2 AbM (1)

<400> SEQUENCE: 101

Ala Ile Ser Gly Ser Gly Gly Ser Thr
1               5

<210> SEQ ID NO 102
<211> LENGTH: 27
<212> TYPE: DNA
<213> ORGANISM: Artificial Sequence
<220> FEATURE:
<223> OTHER INFORMATION: HCDR2 AbM (1) (DNA 1)

<400> SEQUENCE: 102
gctattagtg gtagtggtgg tagcaca                                          27

<210> SEQ ID NO 103
<211> LENGTH: 9
<212> TYPE: PRT
<213> ORGANISM: Artificial Sequence
<220> FEATURE:
<223> OTHER INFORMATION: HCDR2 AbM (2)

<400> SEQUENCE: 103

Ala Ile Gly Val Ser Thr Gly Ser Thr
1               5

<210> SEQ ID NO 104
<211> LENGTH: 27
<212> TYPE: DNA
<213> ORGANISM: Artificial Sequence
<220> FEATURE:
<223> OTHER INFORMATION: HCDR2 AbM (2) (DNA)

<400> SEQUENCE: 104
gctattggtg ttagtactgg tagcaca                                          27

<210> SEQ ID NO 105
<211> LENGTH: 9
<212> TYPE: PRT
<213> ORGANISM: Artificial Sequence
<220> FEATURE:
<223> OTHER INFORMATION: HCDR2 AbM (3)

<400> SEQUENCE: 105

Ala Ile Ser Gly Ser Ala Gly Tyr Thr
1               5

<210> SEQ ID NO 106
<211> LENGTH: 27
<212> TYPE: DNA
<213> ORGANISM: Artificial Sequence
<220> FEATURE:
<223> OTHER INFORMATION: HCDR2 AbM (3) (DNA)

<400> SEQUENCE: 106
gctattagtg ggagtgctgg ttataca                                          27

<210> SEQ ID NO 107
<211> LENGTH: 8
<212> TYPE: PRT
<213> ORGANISM: Artificial Sequence
<220> FEATURE:
<223> OTHER INFORMATION: HCDR2 AbM (4)

```
<400> SEQUENCE: 107

Ala Ile Ser Gly Gly Gly Arg Thr
1               5

<210> SEQ ID NO 108
<211> LENGTH: 24
<212> TYPE: DNA
<213> ORGANISM: Artificial Sequence
<220> FEATURE:
<223> OTHER INFORMATION: HCDR2 AbM (4) (DNA)

<400> SEQUENCE: 108
gctattagtg gtggtggtag gaca                                         24

<210> SEQ ID NO 109
<211> LENGTH: 9
<212> TYPE: PRT
<213> ORGANISM: Artificial Sequence
<220> FEATURE:
<223> OTHER INFORMATION: HCDR2 AbM (5)

<400> SEQUENCE: 109

Ala Ile Ile Ser Ser Gly Gly Leu Thr
1               5

<210> SEQ ID NO 110
<211> LENGTH: 27
<212> TYPE: DNA
<213> ORGANISM: Artificial Sequence
<220> FEATURE:
<223> OTHER INFORMATION: HCDR2 AbM (5) (DNA)

<400> SEQUENCE: 110
gcgattatta gtagtggtgg tctcaca                                      27

<210> SEQ ID NO 111
<211> LENGTH: 9
<212> TYPE: PRT
<213> ORGANISM: Artificial Sequence
<220> FEATURE:
<223> OTHER INFORMATION: HCDR2 AbM (6)

<400> SEQUENCE: 111

Ala Ile Ile Gly Ser Gly Ser Arg Thr
1               5

<210> SEQ ID NO 112
<211> LENGTH: 27
<212> TYPE: DNA
<213> ORGANISM: Artificial Sequence
<220> FEATURE:
<223> OTHER INFORMATION: HCDR2 AbM (6) (DNA)

<400> SEQUENCE: 112
gctattattg ggagtggtag tcgtaca                                      27

<210> SEQ ID NO 113
<211> LENGTH: 9
<212> TYPE: PRT
<213> ORGANISM: Artificial Sequence
<220> FEATURE:
<223> OTHER INFORMATION: HCDR2 AbM (7)

<400> SEQUENCE: 113

Ala Ile Ile Gly Ser Gly Ala Ser Thr
1               5
```

<210> SEQ ID NO 114
<211> LENGTH: 27
<212> TYPE: DNA
<213> ORGANISM: Artificial Sequence
<220> FEATURE:
<223> OTHER INFORMATION: HCDR2 AbM (7) (DNA)

<400> SEQUENCE: 114
gctattattg gtagtggtgc tagcaca                                          27

<210> SEQ ID NO 115
<211> LENGTH: 9
<212> TYPE: PRT
<213> ORGANISM: Artificial Sequence
<220> FEATURE:
<223> OTHER INFORMATION: HCDR2 AbM (8)

<400> SEQUENCE: 115

Ala Ile Trp Gly Gly Gly Arg Ser Thr
1               5

<210> SEQ ID NO 116
<211> LENGTH: 27
<212> TYPE: DNA
<213> ORGANISM: Artificial Sequence
<220> FEATURE:
<223> OTHER INFORMATION: HCDR2 AbM (8) (DNA)

<400> SEQUENCE: 116
gctatttggg gtggtggtcg tagcaca                                          27

<210> SEQ ID NO 117
<211> LENGTH: 9
<212> TYPE: PRT
<213> ORGANISM: Artificial Sequence
<220> FEATURE:
<223> OTHER INFORMATION: HCDR2 AbM (9)

<400> SEQUENCE: 117

Ala Ile Ile Ser Ser Gly Ala Ser Thr
1               5

<210> SEQ ID NO 118
<211> LENGTH: 27
<212> TYPE: DNA
<213> ORGANISM: Artificial Sequence
<220> FEATURE:
<223> OTHER INFORMATION: HCDR2 AbM (9) (DNA)

<400> SEQUENCE: 118
gctattatta gtagtggggc tagcaca                                          27

<210> SEQ ID NO 119
<211> LENGTH: 9
<212> TYPE: PRT
<213> ORGANISM: Artificial Sequence
<220> FEATURE:
<223> OTHER INFORMATION: HCDR2 AbM (10)

<400> SEQUENCE: 119

Ala Ile Leu Ala Ser Gly Ala Ile Thr
1               5

<210> SEQ ID NO 120
<211> LENGTH: 27

```
<212> TYPE: DNA
<213> ORGANISM: Artificial Sequence
<220> FEATURE:
<223> OTHER INFORMATION: HCDR2 AbM (10) (DNA)

<400> SEQUENCE: 120 gctatttttgg ctagtggtgc gatcaca                                          27

<210> SEQ ID NO 121
<211> LENGTH: 9
<212> TYPE: PRT
<213> ORGANISM: Artificial Sequence
<220> FEATURE:
<223> OTHER INFORMATION: HCDR2 AbM (11)

<400> SEQUENCE: 121

Gly Ile Ile Gly Ser Gly Gly Ile Thr
1               5

<210> SEQ ID NO 122
<211> LENGTH: 27
<212> TYPE: DNA
<213> ORGANISM: Artificial Sequence
<220> FEATURE:
<223> OTHER INFORMATION: HCDR2 AbM (11) (DNA)

<400> SEQUENCE: 122
ggtattattg gtagtggtgg tatcaca                                           27

<210> SEQ ID NO 123
<211> LENGTH: 9
<212> TYPE: PRT
<213> ORGANISM: Artificial Sequence
<220> FEATURE:
<223> OTHER INFORMATION: HCDR2 AbM (12)

<400> SEQUENCE: 123

Ala Ile Leu Gly Ser Gly Gly Ser Thr
1               5

<210> SEQ ID NO 124
<211> LENGTH: 27
<212> TYPE: DNA
<213> ORGANISM: Artificial Sequence
<220> FEATURE:
<223> OTHER INFORMATION: HCDR2 AbM (12) (DNA)

<400> SEQUENCE: 124
gctattcttg gtagtggtgg tagcaca                                           27

<210> SEQ ID NO 125
<211> LENGTH: 9
<212> TYPE: PRT
<213> ORGANISM: Artificial Sequence
<220> FEATURE:
<223> OTHER INFORMATION: HCDR2 AbM (13)

<400> SEQUENCE: 125

Ala Ile Ile Gly Ser Gly Ser Asn Thr
1               5

<210> SEQ ID NO 126
<211> LENGTH: 27
<212> TYPE: DNA
<213> ORGANISM: Artificial Sequence
<220> FEATURE:
<223> OTHER INFORMATION: HCDR2 AbM (13) (DNA)
```

<400> SEQUENCE: 126
gctattattg gtagtggtag taacaca                                27

<210> SEQ ID NO 127
<211> LENGTH: 8
<212> TYPE: PRT
<213> ORGANISM: Artificial Sequence
<220> FEATURE:
<223> OTHER INFORMATION: HCDR2 AbM (14)

<400> SEQUENCE: 127

Ala Ile Trp Ala Ser Gly Glu Gln
1               5

<210> SEQ ID NO 128
<211> LENGTH: 24
<212> TYPE: DNA
<213> ORGANISM: Artificial Sequence
<220> FEATURE:
<223> OTHER INFORMATION: HCDR2 AbM (14) (DNA)

<400> SEQUENCE: 128
gctatttggg ctagtgggga gcaa                                   24

<210> SEQ ID NO 129
<211> LENGTH: 9
<212> TYPE: PRT
<213> ORGANISM: Artificial Sequence
<220> FEATURE:
<223> OTHER INFORMATION: HCDR2 AbM (15)

<400> SEQUENCE: 129

Ala Ile Ile Gly Ser Gly Ser Ile Thr
1               5

<210> SEQ ID NO 130
<211> LENGTH: 27
<212> TYPE: DNA
<213> ORGANISM: Artificial Sequence
<220> FEATURE:
<223> OTHER INFORMATION: HCDR2 AbM (15) (DNA)

<400> SEQUENCE: 130
gctattattg gtagtggtag tatcaca                                27

<210> SEQ ID NO 131
<211> LENGTH: 9
<212> TYPE: PRT
<213> ORGANISM: Artificial Sequence
<220> FEATURE:
<223> OTHER INFORMATION: HCDR2 AbM (16)

<400> SEQUENCE: 131

Ala Ile Ile Gly Ser Gly Gly Ile Thr
1               5

<210> SEQ ID NO 132
<211> LENGTH: 27
<212> TYPE: DNA
<213> ORGANISM: Artificial Sequence
<220> FEATURE:
<223> OTHER INFORMATION: HCDR2 AbM (16) (DNA)

<400> SEQUENCE: 132
gctattattg gtagtggtgg tatcaca                                27

<210> SEQ ID NO 133
<211> LENGTH: 9
<212> TYPE: PRT
<213> ORGANISM: Artificial Sequence
<220> FEATURE:
<223> OTHER INFORMATION: HCDR2 AbM (17)

<400> SEQUENCE: 133

Ala Ile Ser Thr Asn Gly Asn Tyr Thr
1               5

<210> SEQ ID NO 134
<211> LENGTH: 27
<212> TYPE: DNA
<213> ORGANISM: Artificial Sequence
<220> FEATURE:
<223> OTHER INFORMATION: HCDR2 AbM (17) (DNA)

<400> SEQUENCE: 134
gctattagta ctaatggtaa ttataca                                        27

<210> SEQ ID NO 135
<211> LENGTH: 8
<212> TYPE: PRT
<213> ORGANISM: Artificial Sequence
<220> FEATURE:
<223> OTHER INFORMATION: HCDR3 (1)

<400> SEQUENCE: 135

Tyr Cys Ala Lys Gly Trp Phe Gly
1               5

<210> SEQ ID NO 136
<211> LENGTH: 24
<212> TYPE: DNA
<213> ORGANISM: Artificial Sequence
<220> FEATURE:
<223> OTHER INFORMATION: HCDR3 (1) (DNA 1)

<400> SEQUENCE: 136
tactgtgcga aagggtggtt tggt                                           24

<210> SEQ ID NO 137
<211> LENGTH: 8
<212> TYPE: PRT
<213> ORGANISM: Artificial Sequence
<220> FEATURE:
<223> OTHER INFORMATION: HCDR3 (2)

<400> SEQUENCE: 137

Tyr Cys Ala Lys Gly Trp Leu Gly
1               5

<210> SEQ ID NO 138
<211> LENGTH: 24
<212> TYPE: DNA
<213> ORGANISM: Artificial Sequence
<220> FEATURE:
<223> OTHER INFORMATION: HCDR3 (2) (DNA 1)

<400> SEQUENCE: 138
tactgtgcga aaggttggct gggt                                           24

<210> SEQ ID NO 139
<211> LENGTH: 8

```
<212> TYPE: PRT
<213> ORGANISM: Artificial Sequence
<220> FEATURE:
<223> OTHER INFORMATION: HCDR3 (3)

<400> SEQUENCE: 139

Tyr Cys Ala Lys Gly Trp Phe Thr
1               5

<210> SEQ ID NO 140
<211> LENGTH: 24
<212> TYPE: DNA
<213> ORGANISM: Artificial Sequence
<220> FEATURE:
<223> OTHER INFORMATION: HCDR3 (3) (DNA)

<400> SEQUENCE: 140
tactgtgcga aggttggtt tacg                                               24

<210> SEQ ID NO 141
<211> LENGTH: 8
<212> TYPE: PRT
<213> ORGANISM: Artificial Sequence
<220> FEATURE:
<223> OTHER INFORMATION: HCDR3 (4)

<400> SEQUENCE: 141

Tyr Cys Ala Lys Ala Trp Met Gly
1               5

<210> SEQ ID NO 142
<211> LENGTH: 24
<212> TYPE: DNA
<213> ORGANISM: Artificial Sequence
<220> FEATURE:
<223> OTHER INFORMATION: HCDR3 (4) (DNA)

<400> SEQUENCE: 142
tactgtgcga aagcttggat gggg                                              24

<210> SEQ ID NO 143
<211> LENGTH: 11
<212> TYPE: PRT
<213> ORGANISM: Artificial Sequence
<220> FEATURE:
<223> OTHER INFORMATION: LCDR1 (1)

<400> SEQUENCE: 143

Arg Ala Ser Gln Ser Val Thr Ser Ser Tyr Leu
1               5                   10

<210> SEQ ID NO 144
<211> LENGTH: 33
<212> TYPE: DNA
<213> ORGANISM: Artificial Sequence
<220> FEATURE:
<223> OTHER INFORMATION: LCDR1 (1) (DNA)

<400> SEQUENCE: 144
agggccagtc agagtgttac cagtagctac tta                                    33

<210> SEQ ID NO 145
<211> LENGTH: 11
<212> TYPE: PRT
<213> ORGANISM: Artificial Sequence
<220> FEATURE:
<223> OTHER INFORMATION: LCDR1 (2)
```

<400> SEQUENCE: 145

Arg Ala Ser Gln Ser Val Ser Ser Ser Tyr Leu
1               5                   10

<210> SEQ ID NO 146
<211> LENGTH: 33
<212> TYPE: DNA
<213> ORGANISM: Artificial Sequence
<220> FEATURE:
<223> OTHER INFORMATION: LCDR1 (2) (DNA)

<400> SEQUENCE: 146
agggccagtc agagtgttag cagcagctac tta                                    33

<210> SEQ ID NO 147
<211> LENGTH: 11
<212> TYPE: PRT
<213> ORGANISM: Artificial Sequence
<220> FEATURE:
<223> OTHER INFORMATION: LCDR1 (3)

<400> SEQUENCE: 147

Arg Ala Ser Gln Ser Val Ser Arg Ser Tyr Leu
1               5                   10

<210> SEQ ID NO 148
<211> LENGTH: 33
<212> TYPE: DNA
<213> ORGANISM: Artificial Sequence
<220> FEATURE:
<223> OTHER INFORMATION: LCDR1 (3) (DNA)

<400> SEQUENCE: 148
agggccagtc agagtgttag ccgcagctac tta                                    33

<210> SEQ ID NO 149
<211> LENGTH: 11
<212> TYPE: PRT
<213> ORGANISM: Artificial Sequence
<220> FEATURE:
<223> OTHER INFORMATION: LCDR1 (4)

<400> SEQUENCE: 149

Arg Ala Ser Gln Ser Val Ser Ser Asn Tyr Leu
1               5                   10

<210> SEQ ID NO 150
<211> LENGTH: 33
<212> TYPE: DNA
<213> ORGANISM: Artificial Sequence
<220> FEATURE:
<223> OTHER INFORMATION: LCDR1 (4) (DNA 1)

<400> SEQUENCE: 150
agggccagtc agagtgttag cagcaattac tta                                    33

<210> SEQ ID NO 151
<211> LENGTH: 7
<212> TYPE: PRT
<213> ORGANISM: Artificial Sequence
<220> FEATURE:
<223> OTHER INFORMATION: LCDR2 (1)

<400> SEQUENCE: 151

Asn Val Gly Ser Arg Arg Ala

<210> SEQ ID NO 152
<211> LENGTH: 21
<212> TYPE: DNA
<213> ORGANISM: Artificial Sequence
<220> FEATURE:
<223> OTHER INFORMATION: LCDR2 (1) (DNA)

<400> SEQUENCE: 152
aatgtgggct cccgtagggc c                                              21

<210> SEQ ID NO 153
<211> LENGTH: 7
<212> TYPE: PRT
<213> ORGANISM: Artificial Sequence
<220> FEATURE:
<223> OTHER INFORMATION: LCDR2 (2)

<400> SEQUENCE: 153

Tyr Gly Ala Ser Ser Arg Ala
1               5

<210> SEQ ID NO 154
<211> LENGTH: 21
<212> TYPE: DNA
<213> ORGANISM: Artificial Sequence
<220> FEATURE:
<223> OTHER INFORMATION: LCDR2 (2) (DNA)

<400> SEQUENCE: 154
tatggagcat ccagcagggc c                                              21

<210> SEQ ID NO 155
<211> LENGTH: 7
<212> TYPE: PRT
<213> ORGANISM: Artificial Sequence
<220> FEATURE:
<223> OTHER INFORMATION: LCDR2 (3)

<400> SEQUENCE: 155

Ile Gly Ala Ser Thr Arg Ala
1               5

<210> SEQ ID NO 156
<211> LENGTH: 21
<212> TYPE: DNA
<213> ORGANISM: Artificial Sequence
<220> FEATURE:
<223> OTHER INFORMATION: LCDR2 (3) (DNA)

<400> SEQUENCE: 156
attggggcct ccaccagggc c                                              21

<210> SEQ ID NO 157
<211> LENGTH: 7
<212> TYPE: PRT
<213> ORGANISM: Artificial Sequence
<220> FEATURE:
<223> OTHER INFORMATION: LCDR2 (4)

<400> SEQUENCE: 157

Tyr Gly Ala Tyr Ile Arg Ala
1               5

<210> SEQ ID NO 158

```
<211> LENGTH: 21
<212> TYPE: DNA
<213> ORGANISM: Artificial Sequence
<220> FEATURE:
<223> OTHER INFORMATION: LCDR2 (4) (DNA)

<400> SEQUENCE: 158
tatggcgcct acatcagggc c                                              21

<210> SEQ ID NO 159
<211> LENGTH: 7
<212> TYPE: PRT
<213> ORGANISM: Artificial Sequence
<220> FEATURE:
<223> OTHER INFORMATION: LCDR2 (5)

<400> SEQUENCE: 159

Gln Gly Ala Ser Ser Arg Ala
1               5

<210> SEQ ID NO 160
<211> LENGTH: 21
<212> TYPE: DNA
<213> ORGANISM: Artificial Sequence
<220> FEATURE:
<223> OTHER INFORMATION: LCDR2 (5) (DNA)

<400> SEQUENCE: 160
cagggcgcct ccagcagggc c                                              21

<210> SEQ ID NO 161
<211> LENGTH: 7
<212> TYPE: PRT
<213> ORGANISM: Artificial Sequence
<220> FEATURE:
<223> OTHER INFORMATION: LCDR2 (6)

<400> SEQUENCE: 161

Tyr Gly Ala Ser Ile Arg Ala
1               5

<210> SEQ ID NO 162
<211> LENGTH: 21
<212> TYPE: DNA
<213> ORGANISM: Artificial Sequence
<220> FEATURE:
<223> OTHER INFORMATION: LCDR2 (6) (DNA)

<400> SEQUENCE: 162
tatggtgcct ccattagggc c                                              21

<210> SEQ ID NO 163
<211> LENGTH: 9
<212> TYPE: PRT
<213> ORGANISM: Artificial Sequence
<220> FEATURE:
<223> OTHER INFORMATION: LCDR3 (1)

<400> SEQUENCE: 163

Cys Gln Gln Gly Ile Met Leu Pro Pro
1               5

<210> SEQ ID NO 164
<211> LENGTH: 27
<212> TYPE: DNA
<213> ORGANISM: Artificial Sequence
<220> FEATURE:
```

<223> OTHER INFORMATION: LCDR3 (1) (DNA)

<400> SEQUENCE: 164
tgtcagcagg gtattatgct tcccccg					27

<210> SEQ ID NO 165
<211> LENGTH: 9
<212> TYPE: PRT
<213> ORGANISM: Artificial Sequence
<220> FEATURE:
<223> OTHER INFORMATION: LCDR3 (2)

<400> SEQUENCE: 165

Cys Gln Gln Gly Gln Leu Ile Pro Pro
1               5

<210> SEQ ID NO 166
<211> LENGTH: 27
<212> TYPE: DNA
<213> ORGANISM: Artificial Sequence
<220> FEATURE:
<223> OTHER INFORMATION: LCDR3 (2) (DNA)

<400> SEQUENCE: 166
tgtcagcagg gtcagcttat tcccct					27

<210> SEQ ID NO 167
<211> LENGTH: 9
<212> TYPE: PRT
<213> ORGANISM: Artificial Sequence
<220> FEATURE:
<223> OTHER INFORMATION: LCDR3 (3)

<400> SEQUENCE: 167

Cys Gln Gln Gly Gln Val Ile Pro Pro
1               5

<210> SEQ ID NO 168
<211> LENGTH: 27
<212> TYPE: DNA
<213> ORGANISM: Artificial Sequence
<220> FEATURE:
<223> OTHER INFORMATION: LCDR3 (3) (DNA)

<400> SEQUENCE: 168
tgtcagcagg gtcaggttat tcccct					27

<210> SEQ ID NO 169
<211> LENGTH: 9
<212> TYPE: PRT
<213> ORGANISM: Artificial Sequence
<220> FEATURE:
<223> OTHER INFORMATION: LCDR3 (4)

<400> SEQUENCE: 169

Cys Gln Gln Gly Gln Gln Ile Pro Pro
1               5

<210> SEQ ID NO 170
<211> LENGTH: 27
<212> TYPE: DNA
<213> ORGANISM: Artificial Sequence
<220> FEATURE:
<223> OTHER INFORMATION: LCDR3 (4) (DNA)

<400> SEQUENCE: 170
tgtcagcagg gtcagcagat tccccct 27

<210> SEQ ID NO 171
<211> LENGTH: 9
<212> TYPE: PRT
<213> ORGANISM: Artificial Sequence
<220> FEATURE:
<223> OTHER INFORMATION: LCDR3 (5)

<400> SEQUENCE: 171

Cys Gln Gln Gly Asn Gln Ile Pro Pro
1               5

<210> SEQ ID NO 172
<211> LENGTH: 27
<212> TYPE: DNA
<213> ORGANISM: Artificial Sequence
<220> FEATURE:
<223> OTHER INFORMATION: LCDR3 (5) (DNA)

<400> SEQUENCE: 172
tgtcagcagg gtaatcagat tccccct 27

<210> SEQ ID NO 173
<211> LENGTH: 9
<212> TYPE: PRT
<213> ORGANISM: Artificial Sequence
<220> FEATURE:
<223> OTHER INFORMATION: LCDR3 (6)

<400> SEQUENCE: 173

Cys Gln Gln Gly Leu Asn Ile Pro Ser
1               5

<210> SEQ ID NO 174
<211> LENGTH: 27
<212> TYPE: DNA
<213> ORGANISM: Artificial Sequence
<220> FEATURE:
<223> OTHER INFORMATION: LCDR3 (6) (DNA)

<400> SEQUENCE: 174
tgtcagcagg gtctgaatat tccctcg 27

<210> SEQ ID NO 175
<211> LENGTH: 9
<212> TYPE: PRT
<213> ORGANISM: Artificial Sequence
<220> FEATURE:
<223> OTHER INFORMATION: LCDR3 (7)

<400> SEQUENCE: 175

Cys Gln Gln Gly His Ile Ile Pro Pro
1               5

<210> SEQ ID NO 176
<211> LENGTH: 27
<212> TYPE: DNA
<213> ORGANISM: Artificial Sequence
<220> FEATURE:
<223> OTHER INFORMATION: LCDR3 (7) (DNA)

<400> SEQUENCE: 176
tgtcagcagg gtcatattat tccccg 27

<210> SEQ ID NO 177

```
<211> LENGTH: 9
<212> TYPE: PRT
<213> ORGANISM: Artificial Sequence
<220> FEATURE:
<223> OTHER INFORMATION: LCDR3 (8)

<400> SEQUENCE: 177

Cys Gln Gln Ala Ile Met Leu Pro Pro
1               5

<210> SEQ ID NO 178
<211> LENGTH: 27
<212> TYPE: DNA
<213> ORGANISM: Artificial Sequence
<220> FEATURE:
<223> OTHER INFORMATION: LCDR3 (8) (DNA)

<400> SEQUENCE: 178
tgtcagcagg ctattatgct tcctccg                                      27

<210> SEQ ID NO 179
<211> LENGTH: 15
<212> TYPE: DNA
<213> ORGANISM: Artificial Sequence
<220> FEATURE:
<223> OTHER INFORMATION: HCDR1 Kabat (1) (DNA 2)

<400> SEQUENCE: 179
agttatgcta tgagc                                                   15

<210> SEQ ID NO 180
<211> LENGTH: 15
<212> TYPE: DNA
<213> ORGANISM: Artificial Sequence
<220> FEATURE:
<223> OTHER INFORMATION: HCDR1 Kabat (1) (DNA 3)

<400> SEQUENCE: 180
agttatgcga tgagc                                                   15

<210> SEQ ID NO 181
<211> LENGTH: 15
<212> TYPE: DNA
<213> ORGANISM: Artificial Sequence
<220> FEATURE:
<223> OTHER INFORMATION: HCDR1 Kabat (1) (DNA 4)

<400> SEQUENCE: 181
agttatgcaa tgagc                                                   15

<210> SEQ ID NO 182
<211> LENGTH: 30
<212> TYPE: DNA
<213> ORGANISM: Artificial Sequence
<220> FEATURE:
<223> OTHER INFORMATION: HCDR1 AbM (1) (DNA 2)

<400> SEQUENCE: 182
ggattcacct ttagcagtta tgctatgagc                                   30

<210> SEQ ID NO 183
<211> LENGTH: 30
<212> TYPE: DNA
<213> ORGANISM: Artificial Sequence
<220> FEATURE:
<223> OTHER INFORMATION: HCDR1 AbM (1) (DNA 3)
```

<400> SEQUENCE: 183
ggattcacct ttagcagtta tgcgatgagc                                    30

<210> SEQ ID NO 184
<211> LENGTH: 30
<212> TYPE: DNA
<213> ORGANISM: Artificial Sequence
<220> FEATURE:
<223> OTHER INFORMATION: HCDR1 AbM (1) (DNA 4)

<400> SEQUENCE: 184
ggattcacct ttagcagtta tgcaatgagc                                    30

<210> SEQ ID NO 185
<211> LENGTH: 48
<212> TYPE: DNA
<213> ORGANISM: Artificial Sequence
<220> FEATURE:
<223> OTHER INFORMATION: HCDR2 Kabat (1) (DNA 2)

<400> SEQUENCE: 185
gctattagcg gtagtggtgg tagcacatac tacgcagact ccgtgaag                48

<210> SEQ ID NO 186
<211> LENGTH: 21
<212> TYPE: DNA
<213> ORGANISM: Artificial Sequence
<220> FEATURE:
<223> OTHER INFORMATION: HCDR2 Chothia (1) (DNA 2)

<400> SEQUENCE: 186
agcggtagtg gtggtagcac a                                             21

<210> SEQ ID NO 187
<211> LENGTH: 27
<212> TYPE: DNA
<213> ORGANISM: Artificial Sequence
<220> FEATURE:
<223> OTHER INFORMATION: HCDR2 AbM (1) (DNA 2)

<400> SEQUENCE: 187
gctattagcg gtagtggtgg tagcaca                                       27

<210> SEQ ID NO 188
<211> LENGTH: 24
<212> TYPE: DNA
<213> ORGANISM: Artificial Sequence
<220> FEATURE:
<223> OTHER INFORMATION: HCDR3 (1) (DNA 2)

<400> SEQUENCE: 188
tactgtgcga aaggttggtt tggg                                          24

<210> SEQ ID NO 189
<211> LENGTH: 24
<212> TYPE: DNA
<213> ORGANISM: Artificial Sequence
<220> FEATURE:
<223> OTHER INFORMATION: HCDR3 (2) (DNA 2)

<400> SEQUENCE: 189
tactgtgcga aagggtggct gggt                                          24

<210> SEQ ID NO 190
<211> LENGTH: 24

```
<212> TYPE: DNA
<213> ORGANISM: Artificial Sequence
<220> FEATURE:
<223> OTHER INFORMATION: HCDR3 (2) (DNA 3)

<400> SEQUENCE: 190
tactgtgcga aggttggtt gggt                                            24

<210> SEQ ID NO 191
<211> LENGTH: 33
<212> TYPE: DNA
<213> ORGANISM: Artificial Sequence
<220> FEATURE:
<223> OTHER INFORMATION: LCDR1 (4) (DNA 2)

<400> SEQUENCE: 191
agggccagtc agagtgttag cagcaactac tta                                 33

<210> SEQ ID NO 192
<211> LENGTH: 33
<212> TYPE: DNA
<213> ORGANISM: Artificial Sequence
<220> FEATURE:
<223> OTHER INFORMATION: LCDR1 (4) (DNA 3)

<400> SEQUENCE: 192
agggccagtc agagtgttag cagtaactac tta                                 33

<210> SEQ ID NO 193
<211> LENGTH: 108
<212> TYPE: PRT
<213> ORGANISM: Artificial Sequence
<220> FEATURE:
<223> OTHER INFORMATION: 3F2; VL

<400> SEQUENCE: 193
```

Glu Ile Val Leu Thr Gln Ser Pro Gly Thr Leu Ser Leu Tyr Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

```
<210> SEQ ID NO 194
<211> LENGTH: 324
<212> TYPE: DNA
<213> ORGANISM: Artificial Sequence
<220> FEATURE:
<223> OTHER INFORMATION: 3F2; VL

<400> SEQUENCE: 194
gaaatcgtgt taacgcagtc tccaggcacc ctgtctttgt atccagggga aagagccacc     60
ctctcttgca gggccagtca gagtgttacc agtagcact tagcctggta ccagcagaaa    120
cctggccagg ctcccaggct cctcatcaat gtgggctccc gtagggccac tggcatccca   180
```

```
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                            324
```

<210> SEQ ID NO 195
<211> LENGTH: 108
<212> TYPE: PRT
<213> ORGANISM: Artificial Sequence
<220> FEATURE:
<223> OTHER INFORMATION: 3F2(YS); VL

<400> SEQUENCE: 195

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 196
<211> LENGTH: 324
<212> TYPE: DNA
<213> ORGANISM: Artificial Sequence
<220> FEATURE:
<223> OTHER INFORMATION: 3F2(YS); VL

<400> SEQUENCE: 196

```
gaaatcgtgt taacgcagtc tccaggcacc ctgtctttgt ctccagggga aagagccacc     60
ctctcttgca gggccagtca gagtgttacc agtagctact tagcctggta ccagcagaaa    120
cctggccagg ctcccaggct cctcatcaat gtgggctccc gtaggccac tggcatccca     180 gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                            324
```

<210> SEQ ID NO 197
<211> LENGTH: 117
<212> TYPE: PRT
<213> ORGANISM: Artificial Sequence
<220> FEATURE:
<223> OTHER INFORMATION: 3F2; VH

<400> SEQUENCE: 197

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Phe Asn Tyr Trp Gly Gln Gly Thr Leu
                100                 105                 110

Val Thr Val Ser Ser
        115

<210> SEQ ID NO 198
<211> LENGTH: 351
<212> TYPE: DNA
<213> ORGANISM: Artificial Sequence
<220> FEATURE:
<223> OTHER INFORMATION: 3F2; VH

<400> SEQUENCE: 198
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
tttggtggtt ttaactactg gggccaagga accctggtca ccgtctcgag t              351

<210> SEQ ID NO 199
<211> LENGTH: 108
<212> TYPE: PRT
<213> ORGANISM: Artificial Sequence
<220> FEATURE:
<223> OTHER INFORMATION: 3D9, VL

<400> SEQUENCE: 199

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Ile Pro
                85                  90                  95

Pro Thr Phe Gly Gln Gly Thr Lys Val Glu Ile Lys
                100                 105

<210> SEQ ID NO 200
<211> LENGTH: 324
<212> TYPE: DNA
<213> ORGANISM: Artificial Sequence
<220> FEATURE:
<223> OTHER INFORMATION: 3D9, VL

<400> SEQUENCE: 200
gaaatcgtgt taacgcagtc tccaggcacc ctgtctttgt ctccagggga aagagccacc      60

```
ctctcttgca gggccagtca gagtgttagc agcagctact tagcctggta ccagcagaaa      120
cctggccagg ctcccaggct cctcatctat ggagcatcca gcagggccac tggcatccca      180
gacaggttca gtggcagtgg atccgggaca gacttcactc tcaccatcag cagactggag      240
cctgaagatt ttgcagtgta ttactgtcag cagggtcagc ttattccccc tacgttcggc      300
caggggacca aagtggaaat caaa                                             324
```

<210> SEQ ID NO 201
<211> LENGTH: 117
<212> TYPE: PRT
<213> ORGANISM: Artificial Sequence
<220> FEATURE:
<223> OTHER INFORMATION: 3D9, VH

<400> SEQUENCE: 201

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Gly Lys Gly Leu Glu Trp Val
        35                  40                  45

Ser Ala Ile Gly Val Ser Thr Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115
```

<210> SEQ ID NO 202
<211> LENGTH: 351
<212> TYPE: DNA
<213> ORGANISM: Artificial Sequence
<220> FEATURE:
<223> OTHER INFORMATION: 3D9, VH

<400> SEQUENCE: 202

```
gaggtgcaat tgttggagtc tgggggaggc ttggtacagc ctggggggtc cctgagactc       60
tcctgtgcag cctccggatt cacctttagc agttatgcta tgagctgggt ccgccagact      120
ccagggaagg ggctggagtg ggtctcagct attggtgtta gtactggtag cacatactac      180
gcagactccg tgaagggccg gttcaccatc tccagagaca attccaagaa cacgctgtat      240
ctgcagatga acagcctgag agccgaggac acggccgtat attactgtgc gaaaggttgg      300
ctgggtcctt ttgactactg gggccaagga accctggtca ccgtctcgag t              351
```

<210> SEQ ID NO 203
<211> LENGTH: 117
<212> TYPE: PRT
<213> ORGANISM: Artificial Sequence
<220> FEATURE:
<223> OTHER INFORMATION: 3D9(TA); VH

<400> SEQUENCE: 203

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
         35                  40                  45

Ser Ala Ile Gly Val Ser Thr Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Lys Gly Trp Leu Gly Pro Phe Asp Tyr Trp Gly Gln Gly Thr Leu
            100                 105                 110

Val Thr Val Ser Ser
            115

<210> SEQ ID NO 204
<211> LENGTH: 351
<212> TYPE: DNA
<213> ORGANISM: Artificial Sequence
<220> FEATURE:
<223> OTHER INFORMATION: 3D9(TA); VH

<400> SEQUENCE: 204
gaggtgcaat tgttggagtc tgggggaggc ttggtacagc ctgggggtc cctgagactc      60 tcctgtgcag cctccggatt caccttagc agttatgcta tgagctgggt ccgccaggct     120
ccagggaagg gctggagtg gtctcagct attggtgtta gtactggtag cacatactac      180
gcagactccg tgaagggccg gttcaccatc tccagagaca attccaagaa cacgctgtat    240
ctgcagatga acagcctgag agccgaggac acggccgtat attactgtgc gaaaggttgg    300
ctgggtcctt ttgactactg gggccaagga accctggtca ccgtctcgag t             351

<210> SEQ ID NO 205
<211> LENGTH: 108
<212> TYPE: PRT
<213> ORGANISM: Artificial Sequence
<220> FEATURE:
<223> OTHER INFORMATION: 4G8; VL

<400> SEQUENCE: 205

Glu Ile Val Leu Thr Gln Ser Pro Gly Thr Leu Ser Leu Ser Pro Gly
1                5                  10                  15

Glu Arg Ala Thr Leu Ser Cys Arg Ala Ser Gln Ser Val Ser Arg Ser
         20                  25                  30

Tyr Leu Ala Trp Tyr Gln Gln Lys Pro Gly Gln Ala Pro Arg Leu Leu
         35                  40                  45

Ile Ile Gly Ala Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                   70                  75                  80

Pro Glu Asp Phe Ala Val Tyr Tyr Cys Gln Gln Gly Gln Val Ile Pro
                 85                  90                  95

Pro Thr Phe Gly Gln Gly Thr Lys Val Glu Ile Lys
            100                 105

<210> SEQ ID NO 206
<211> LENGTH: 324
<212> TYPE: DNA
```

<213> ORGANISM: Artificial Sequence
<220> FEATURE:
<223> OTHER INFORMATION: 4G8; VL

<400> SEQUENCE: 206

```
gaaatcgtgt taacgcagtc tccaggcacc ctgtctttgt ctccagggga aagagccacc    60
ctctcttgca gggccagtca gagtgttagc cgcagctact tagcctggta ccagcagaaa   120
cctggccagg ctcccaggct cctcatcatt ggggcctcca ccagggccac tggcatccca   180
gacaggttca gtggcagtgg atccgggacg gacttcactc tcaccatcag cagactggag   240
cctgaagatt ttgcagtgta ttactgtcag cagggtcagg ttattccccc tacgttcggc   300
caggggacca agtggaaaat caaa                                          324
```

<210> SEQ ID NO 207
<211> LENGTH: 117
<212> TYPE: PRT
<213> ORGANISM: Artificial Sequence
<220> FEATURE:
<223> OTHER INFORMATION: 4G8; VH

<400> SEQUENCE: 207

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Trp Leu Gly Asn Phe Asp Tyr Trp Gly Gln Gly Thr Leu
            100                 105                 110
Val Thr Val Ser Ser
        115

<210> SEQ ID NO 208
<211> LENGTH: 351
<212> TYPE: DNA
<213> ORGANISM: Artificial Sequence
<220> FEATURE:
<223> OTHER INFORMATION: 4G8; VH

<400> SEQUENCE: 208

```
gaggtgcaat tgttggagtc tgggggaggc ttggtacagc ctggggggtc cctgagactc    60
tcctgtgcag cctccggatt cacctttagc agttatgcca tgagctgggt ccgccaggct   120
ccagggaagg ggctggagtg gtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaagggtgg   300
ctgggtaatt ttgactactg ggccaagga accctggtca ccgtctcgag t            351
```

<210> SEQ ID NO 209
<211> LENGTH: 108
<212> TYPE: PRT
<213> ORGANISM: Artificial Sequence

<220> FEATURE:
<223> OTHER INFORMATION: 4B3; VL

<400> SEQUENCE: 209

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Tyr Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 210
<211> LENGTH: 324
<212> TYPE: DNA
<213> ORGANISM: Artificial Sequence
<220> FEATURE:
<223> OTHER INFORMATION: 4B3; VL

<400> SEQUENCE: 210

```
gaaatcgtgt taacgcagtc tccaggcacc ctgtctttgt ctccagggga aagagccacc    60
ctctcttgca gggccagtca gagtgttagc agcaattact tagcctggta ccagcagaaa   120
cctggccagg ctcccaggct cctcatctat ggcgcctaca tcagggccac tggcatccca   180
gacaggttca gtggcagtgg atccgggaca gacttcactc tcaccatcag cagactggag   240
cctgaagatt ttgcagtgta ttactgtcag cagggtcagg ttattccccc tacgttcggc   300
caggggacca agtggaaat caaa                                           324
```

<210> SEQ ID NO 211
<211> LENGTH: 117
<212> TYPE: PRT
<213> ORGANISM: Artificial Sequence
<220> FEATURE:
<223> OTHER INFORMATION: 4B3; VH

<400> SEQUENCE: 211

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110
```

Val Thr Val Ser Ser
    115

<210> SEQ ID NO 212
<211> LENGTH: 351
<212> TYPE: DNA
<213> ORGANISM: Artificial Sequence
<220> FEATURE:
<223> OTHER INFORMATION: 4B3; VH

<400> SEQUENCE: 212

```
gaggtgcaat tgttggagtc tgggggaggc ttggtacagc ctgggggtc cctgagactc      60
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggtgg    300
ctgggtaatt ttgactactg gggccaagga accctggtca ccgtctcgag t             351
```

<210> SEQ ID NO 213
<211> LENGTH: 108
<212> TYPE: PRT
<213> ORGANISM: Artificial Sequence
<220> FEATURE:
<223> OTHER INFORMATION: 4D6; VL

<400> SEQUENCE: 213

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Gln Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 214
<211> LENGTH: 324
<212> TYPE: DNA
<213> ORGANISM: Artificial Sequence
<220> FEATURE:
<223> OTHER INFORMATION: 4D6; VL

<400> SEQUENCE: 214

```
gaaatcgtgt taacgcagtc tccaggcacc ctgtctttgt ctccagggga aagagccacc      60
ctctcttgca gggccagtca gagtgttagc agcaactact tagcctggta ccagcagaaa    120
cctggccagg ctcccaggct cctcatccag ggcgcctcca gcagggccac tggcatccca    180
gacaggttca gtggcagtgg atccgggaca gacttcactc tcaccatcag cagactggag    240
cctgaagatt ttgcagtgta ttactgtcag cagggtcagg ttattccccc tacgttcggc    300
caggggacca aagtggaaat caaa                                            324
```

-continued

<210> SEQ ID NO 215
<211> LENGTH: 117
<212> TYPE: PRT
<213> ORGANISM: Artificial Sequence
<220> FEATURE:
<223> OTHER INFORMATION: 4D6; VH

<400> SEQUENCE: 215

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115
```

<210> SEQ ID NO 216
<211> LENGTH: 351
<212> TYPE: DNA
<213> ORGANISM: Artificial Sequence
<220> FEATURE:
<223> OTHER INFORMATION: 4D6; VH

<400> SEQUENCE: 216

```
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcagatga acagcctgag agccgaggac acggccgtat attactgtgc gaaagggtgg    300
ctgggtaatt ttgactactg gggccaagga accctggtca ccgtctcgag t             351
```

<210> SEQ ID NO 217
<211> LENGTH: 108
<212> TYPE: PRT
<213> ORGANISM: Artificial Sequence
<220> FEATURE:
<223> OTHER INFORMATION: 2C6; VL

<400> SEQUENCE: 217

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Gly Gln Gln Ile Pro
            85                  90                  95

Pro Thr Phe Gly Gln Gly Thr Lys Val Glu Ile Lys
            100                 105

<210> SEQ ID NO 218
<211> LENGTH: 324
<212> TYPE: DNA
<213> ORGANISM: Artificial Sequence
<220> FEATURE:
<223> OTHER INFORMATION: 2C6; VL

<400> SEQUENCE: 218
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag caggctggag     240
cctgaagatt ttgcagtgta ttactgtcag cagggtcagc agattccccc tacgttcggc     300
caggggacca agtggaaat caaa                                              324

<210> SEQ ID NO 219
<211> LENGTH: 117
<212> TYPE: PRT
<213> ORGANISM: Artificial Sequence
<220> FEATURE:
<223> OTHER INFORMATION: 2C6; VH

<400> SEQUENCE: 219

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Ala Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Trp Phe Gly Asn Phe Asp Tyr Trp Gly Gln Gly Thr Leu
            100                 105                 110

Val Thr Val Ser Ser
        115

<210> SEQ ID NO 220
<211> LENGTH: 351
<212> TYPE: DNA
<213> ORGANISM: Artificial Sequence
<220> FEATURE:
<223> OTHER INFORMATION: 2C6; VH

<400> SEQUENCE: 220
gaggtgcaat tgttggagtc tgggggaggc ttggtacagc ctgggggggtc cctgagactc      60 tcctgtgcag cctccggatc cacctttagc agttatgcca tgagctgggt ccgccaggct     120
ccagggaagg ggctggagtg gtctcagct attagtggga gtgctggtta catactac        180

```
gcagactccg tgaagggccg gttcaccatc tccagagaca attccaagaa cacgctgtat        240
ctgcagatga acagcctgag agccgaggac acggccgtat attactgtgc gaaaggttgg        300
tttgggaatt ttgactactg gggccaagga accctggtca ccgtctcgag t                351
```

<210> SEQ ID NO 221
<211> LENGTH: 108
<212> TYPE: PRT
<213> ORGANISM: Artificial Sequence
<220> FEATURE:
<223> OTHER INFORMATION: 5H5; VL

<400> SEQUENCE: 221

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105
```

<210> SEQ ID NO 222
<211> LENGTH: 324
<212> TYPE: DNA
<213> ORGANISM: Artificial Sequence
<220> FEATURE:
<223> OTHER INFORMATION: 5H5; VL

<400> SEQUENCE: 222

```
gaaatcgtgt taacgcagtc tccaggcacc ctgtctttgt ctccagggga aagagccacc        60
ctctcttgca gggccagtca gagtgttagc agcagctact tagcctggta ccagcagaaa        120
cctggccagg ctcccaggct cctcatctat ggagcatcca gcagggccac tggcatccca        180
gacaggttca gtggcagtgg atccgggaca gacttcactc tcaccatcag cagactggag        240
cctgaagatt ttgcagtgta ttactgtcag cagggtaatc agattccccc tacgttcggt        300
caggggacca aagtggaaat caaa                                                324
```

<210> SEQ ID NO 223
<211> LENGTH: 116
<212> TYPE: PRT
<213> ORGANISM: Artificial Sequence
<220> FEATURE:
<223> OTHER INFORMATION: 5H5; VH

<400> SEQUENCE: 223

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Arg Ser Pro Gly Lys Gly Leu Glu Trp Val
        35                  40                  45

Ser Ala Ile Ser Gly Gly Gly Arg Thr Tyr Tyr Ala Asp Ser Val Lys
```

```
                    50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Gly Trp Phe Thr Pro Phe Asp Tyr Trp Gly Gln Gly Thr Leu Val
            100                 105                 110

Thr Val Ser Ser
        115

<210> SEQ ID NO 224
<211> LENGTH: 348
<212> TYPE: DNA
<213> ORGANISM: Artificial Sequence
<220> FEATURE:
<223> OTHER INFORMATION: 5H5; VH

<400> SEQUENCE: 224
gaggtgcaat tgttggagtc tgggggaggc ttggtacagc ctggggggtc cctgagactc      60
tcctgtgcag cctccggatt cacctttagc agttatacca tgagctgggt ccgccggtct    120
ccagggaagg ggctggagtg ggtctcagct attagtggtg gtggtaggac atactacgca    180
gactccgtga agggccggtt caccatctcc agagacaatt ccaagaacac gctgtatctg    240
cagatgaaca gcctgagagc cgaggacacg gccgtatatt actgtgcgaa aggttggttt    300
acgccttttg actactgggg ccaaggaacc ctggtcaccg tctcgagt                 348

<210> SEQ ID NO 225
<211> LENGTH: 108
<212> TYPE: PRT
<213> ORGANISM: Artificial Sequence
<220> FEATURE:
<223> OTHER INFORMATION: 2C4; VL

<400> SEQUENCE: 225

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Asn
                 20                  25                  30

Tyr Leu Ala Trp Tyr Gln Gln Lys Pro Gly Gln Ala Pro Arg Leu Leu
             35                  40                  45

Ile Tyr Gly Ala Ser Ile Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Asn Gln Ile Pro
                 85                  90                  95

Pro Thr Phe Gly Gln Gly Thr Lys Val Glu Ile Lys
            100                 105

<210> SEQ ID NO 226
<211> LENGTH: 324
<212> TYPE: DNA
<213> ORGANISM: Artificial Sequence
<220> FEATURE:
<223> OTHER INFORMATION: 2C4; VL

<400> SEQUENCE: 226
gaaatcgtgt taacgcagtc tccaggcacc ctgtctttgt ctccagggga aagagccacc     60
```

```
ctctcttgca gggccagtca gagtgttagc agtaactact tagcctggta ccagcagaaa    120
cctggccagg ctcccaggct cctcatctat ggtgcctcca ttagggccac tggcatccca    180
gacaggttca gtggcagtgg atccgggaca gacttcactc tcaccatcag cagactggag    240
cctgaagatt ttgcagtgta ttactgtcag cagggtaatc agattccccc tacgttcggt    300
caggggacca agtggaaat caaa                                            324
```

```
<210> SEQ ID NO 227
<211> LENGTH: 117
<212> TYPE: PRT
<213> ORGANISM: Artificial Sequence
<220> FEATURE:
<223> OTHER INFORMATION: 2C4; VH

<400> SEQUENCE: 227

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Thr Pro Phe Asp Tyr Trp Gly Gln Gly Thr Leu
            100                 105                 110

Val Thr Val Ser Ser
        115
```

```
<210> SEQ ID NO 228
<211> LENGTH: 351
<212> TYPE: DNA
<213> ORGANISM: Artificial Sequence
<220> FEATURE:
<223> OTHER INFORMATION: 2C4; VH

<400> SEQUENCE: 228
gaggtgcaat tgttggagtc tgggggaggc ttggtacagc ctggggggtc cctgagactc    60
tcctgtgcag cctccggatt cacctttagc agttatgcca tgagctgggt ccgccaggct    120
ccagggaagg ggctggagtg ggtctcagct attagcggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggttgg    300
tttacgcctt ttgactactg gggccaagga accctggtca ccgtctcgag t             351
```

```
<210> SEQ ID NO 229
<211> LENGTH: 108
<212> TYPE: PRT
<213> ORGANISM: Artificial Sequence
<220> FEATURE:
<223> OTHER INFORMATION: 2D9; VL

<400> SEQUENCE: 229

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105

<210> SEQ ID NO 230
<211> LENGTH: 324
<212> TYPE: DNA
<213> ORGANISM: Artificial Sequence
<220> FEATURE:
<223> OTHER INFORMATION: 2D9; VL

<400> SEQUENCE: 230
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtaatc agattccccc tacgttcggt   300
caggggacca agtggaaat caaa                                           324

<210> SEQ ID NO 231
<211> LENGTH: 117
<212> TYPE: PRT
<213> ORGANISM: Artificial Sequence
<220> FEATURE:
<223> OTHER INFORMATION: 2D9; VH

<400> SEQUENCE: 231

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Thr Pro Phe Asp Tyr Trp Gly Gln Gly Thr Leu
            100                 105                 110

Val Thr Val Ser Ser
        115

<210> SEQ ID NO 232
<211> LENGTH: 351
<212> TYPE: DNA
<213> ORGANISM: Artificial Sequence

<220> FEATURE:
<223> OTHER INFORMATION: 2D9; VH

<400> SEQUENCE: 232

```
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg ggctggagtg ggtctcagct attagcggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggttgg    300
tttacgcctt ttgactactg gggccaagga accctggtca ccgtctcgag t             351
```

<210> SEQ ID NO 233
<211> LENGTH: 108
<212> TYPE: PRT
<213> ORGANISM: Artificial Sequence
<220> FEATURE:
<223> OTHER INFORMATION: 4B8; VL

<400> SEQUENCE: 233

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 234
<211> LENGTH: 324
<212> TYPE: DNA
<213> ORGANISM: Artificial Sequence
<220> FEATURE:
<223> OTHER INFORMATION: 4B8; VL

<400> SEQUENCE: 234

```
gaaatcgtgt taacgcagtc tccaggcacc ctgtctttgt ctccagggga agagccacc     60 ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtcagg ttattccccc tacgttcggc   300
caggggacca agtggaaat caaa                                           324
```

<210> SEQ ID NO 235
<211> LENGTH: 117
<212> TYPE: PRT
<213> ORGANISM: Artificial Sequence
<220> FEATURE:
<223> OTHER INFORMATION: 4B8; VH

<400> SEQUENCE: 235

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
            115

<210> SEQ ID NO 236
<211> LENGTH: 351
<212> TYPE: DNA
<213> ORGANISM: Artificial Sequence
<220> FEATURE:
<223> OTHER INFORMATION: 4B8; VH

<400> SEQUENCE: 236
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcagatga acagcctgag agccgaggac acggccgtat attactgtgc gaaagggtgg    300
ctgggtaatt ttgactactg gggccaagga accctggtca ccgtctcgag t             351

<210> SEQ ID NO 237
<211> LENGTH: 108
<212> TYPE: PRT
<213> ORGANISM: Artificial Sequence
<220> FEATURE:
<223> OTHER INFORMATION: 7A1; VL

<400> SEQUENCE: 237

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln Gln Gly Gln Gln Ile Pro
                85                  90                  95

Pro Thr Phe Gly Gln Gly Thr Lys Val Glu Ile Lys
            100                 105

<210> SEQ ID NO 238
<211> LENGTH: 324
<212> TYPE: DNA
<213> ORGANISM: Artificial Sequence
<220> FEATURE:
<223> OTHER INFORMATION: 7A1; VL

<400> SEQUENCE: 238

```
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtcagc agattccccc tacgttcggc   300
caggggacca agtggaaat caaa                                            324
```

<210> SEQ ID NO 239
<211> LENGTH: 117
<212> TYPE: PRT
<213> ORGANISM: Artificial Sequence
<220> FEATURE:
<223> OTHER INFORMATION: 7A1; VH

<400> SEQUENCE: 239

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Asn Phe Asp Tyr Trp Gly Gln Gly Thr Leu
            100                 105                 110

Val Thr Val Ser Ser
        115
```

<210> SEQ ID NO 240
<211> LENGTH: 351
<212> TYPE: DNA
<213> ORGANISM: Artificial Sequence
<220> FEATURE:
<223> OTHER INFORMATION: 7A1; VH

<400> SEQUENCE: 240

```
gaggtgcaat tgttggagtc tgggggaggc ttggtacagc ctgggggtc cctgagactc     60
tcctgtgcag cctccggatt cacctttagc agttatgcca tgagctgggt ccgccaggct   120
ccagggaagg ggctggagtg gtctcagct attagtggta gtggtggtag cacatactac    180
gcagactccg tgaagggccg gttcaccatc tccagagaca attccaagaa cacgctgtat   240
ctgcagatga acagcctgag agccgaggac acggccgtat attactgtgc gaaaggttgg   300
tttgggaatt ttgactactg gggccaagga accctggtca ccgtctcgag t            351
```

<210> SEQ ID NO 241

```
<211> LENGTH: 108
<212> TYPE: PRT
<213> ORGANISM: Artificial Sequence
<220> FEATURE:
<223> OTHER INFORMATION: 13C2; VL

<400> SEQUENCE: 241

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Ile Pro
                85                  90                  95

Pro Thr Phe Gly Gln Gly Thr Lys Val Glu Ile Lys
            100                 105

<210> SEQ ID NO 242
<211> LENGTH: 324
<212> TYPE: DNA
<213> ORGANISM: Artificial Sequence
<220> FEATURE:
<223> OTHER INFORMATION: 13C2; VL

<400> SEQUENCE: 242
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtcagc ttattccccc tacgttcggc     300
caggggacca aagtggaaat caaa                                              324

<210> SEQ ID NO 243
<211> LENGTH: 117
<212> TYPE: PRT
<213> ORGANISM: Artificial Sequence
<220> FEATURE:
<223> OTHER INFORMATION: 13C2; VH

<400> SEQUENCE: 243

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Gly Trp Leu Gly Pro Phe Asp Tyr Trp Gly Gln Gly Thr Leu
            100                 105                 110

Val Thr Val Ser Ser
        115

<210> SEQ ID NO 244
<211> LENGTH: 351
<212> TYPE: DNA
<213> ORGANISM: Artificial Sequence
<220> FEATURE:
<223> OTHER INFORMATION: 13C2; VH

<400> SEQUENCE: 244
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggttgg    300
ctgggtcctt ttgactactg gggccaagga accctggtca ccgtctcgag t             351

<210> SEQ ID NO 245
<211> LENGTH: 108
<212> TYPE: PRT
<213> ORGANISM: Artificial Sequence
<220> FEATURE:
<223> OTHER INFORMATION: 13E8; VL

<400> SEQUENCE: 245

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105

<210> SEQ ID NO 246
<211> LENGTH: 324
<212> TYPE: DNA
<213> ORGANISM: Artificial Sequence
<220> FEATURE:
<223> OTHER INFORMATION: 13E8; VL

<400> SEQUENCE: 246
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag caggggctga atattccctc gacgttcggc   300 cagggggacca aagtggaaat caaa                                              324

<210> SEQ ID NO 247
<211> LENGTH: 117
<212> TYPE: PRT
<213> ORGANISM: Artificial Sequence
<220> FEATURE:
<223> OTHER INFORMATION: 13E8; VH

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115

<210> SEQ ID NO 248
<211> LENGTH: 351
<212> TYPE: DNA
<213> ORGANISM: Artificial Sequence
<220> FEATURE:
<223> OTHER INFORMATION: 13E8; VH

<400> SEQUENCE: 248
gaggtgcaat tgttggagtc tgggggaggc ttggtacagc ctggggggtc cctgagactc    60
tcctgtgcag cctccggatt cacctttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaaggttgg   300
ttgggtccgt ttgactactg gggccaagga accctggtca ccgtctcgag t            351

<210> SEQ ID NO 249
<211> LENGTH: 108
<212> TYPE: PRT
<213> ORGANISM: Artificial Sequence
<220> FEATURE:
<223> OTHER INFORMATION: 14C10; VL

<400> SEQUENCE: 249

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly His Ile Ile Pro
                85                  90                  95

Pro Thr Phe Gly Gln Gly Thr Lys Val Glu Ile Lys
            100                 105

<210> SEQ ID NO 250
<211> LENGTH: 324
<212> TYPE: DNA
<213> ORGANISM: Artificial Sequence
<220> FEATURE:
<223> OTHER INFORMATION: 14C10; VL

<400> SEQUENCE: 250
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtcata ttattccccc gacgttcggc   300
caggggacca agtggaaat caaa                                            324

<210> SEQ ID NO 251
<211> LENGTH: 117
<212> TYPE: PRT
<213> ORGANISM: Artificial Sequence
<220> FEATURE:
<223> OTHER INFORMATION: 14C10; VH

<400> SEQUENCE: 251

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Trp Met Gly Pro Phe Asp Tyr Trp Gly Gln Gly Thr Leu
            100                 105                 110

Val Thr Val Ser Ser
        115

<210> SEQ ID NO 252
<211> LENGTH: 351
<212> TYPE: DNA
<213> ORGANISM: Artificial Sequence
<220> FEATURE:
<223> OTHER INFORMATION: 14C10; VH

<400> SEQUENCE: 252
gaggtgcaat tgttggagtc tgggggaggc ttggtacagc ctgggggtc cctgagactc     60 tcctgtgcag cctccggatt cacctttagc agttatgcca tgagctgggt ccgccaggct   120

```
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaagcttgg    300
atggggcctt ttgactactg gggccaagga accctggtca ccgtctcgag t             351
```

<210> SEQ ID NO 253
<211> LENGTH: 108
<212> TYPE: PRT
<213> ORGANISM: Artificial Sequence
<220> FEATURE:
<223> OTHER INFORMATION: 17A11; VL

<400> SEQUENCE: 253

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105
```

<210> SEQ ID NO 254
<211> LENGTH: 324
<212> TYPE: DNA
<213> ORGANISM: Artificial Sequence
<220> FEATURE:
<223> OTHER INFORMATION: 17A11; VL

<400> SEQUENCE: 254

```
gaaatcgtgt taacgcagtc tccaggcacc ctgtctttgt ctccagggga agagccacc     60 ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagggtctga atattccctc gacgttcggc    300
caggggacca agtggaaat caaa                                             324
```

<210> SEQ ID NO 255
<211> LENGTH: 117
<212> TYPE: PRT
<213> ORGANISM: Artificial Sequence
<220> FEATURE:
<223> OTHER INFORMATION: 17A11; VH

<400> SEQUENCE: 255

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
                35                  40                  45
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115

<210> SEQ ID NO 256
<211> LENGTH: 351
<212> TYPE: DNA
<213> ORGANISM: Artificial Sequence
<220> FEATURE:
<223> OTHER INFORMATION: 17A11; VH

<400> SEQUENCE: 256
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcagatga acagcctgag agccgaggac acggccgtat attactgtgc gaaaggttgg    300
ttgggtccgt ttgactactg gggccaagga accctggtca ccgtctcgag t            351

<210> SEQ ID NO 257
<211> LENGTH: 108
<212> TYPE: PRT
<213> ORGANISM: Artificial Sequence
<220> FEATURE:
<223> OTHER INFORMATION: 19G1; VL

<400> SEQUENCE: 257

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                 70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 258
<211> LENGTH: 324
<212> TYPE: DNA
<213> ORGANISM: Artificial Sequence
<220> FEATURE:
<223> OTHER INFORMATION: 19G1; VL

<400> SEQUENCE: 258
```

```
gaaatcgtgt taacgcagtc tccaggcacc ctgtctttgt ctccagggga aagagccacc    60
ctctcttgca gggccagtca gagtgttacc agtagctact tagcctggta ccagcagaaa   120
cctggccagg ctcccaggct cctcatcaat gtgggctccc gtagggccac tggcatccca   180
gacaggttca gtggcagtgg atccgggaca gacttcactc tcaccatcag cagactggag   240
cctgaagatt ttgcagtgta ttactgtcag cagggtatta tgcttccccc gacgttcggc   300
caggggacca aagtggaaat caaa                                         324
```

<210> SEQ ID NO 259
<211> LENGTH: 117
<212> TYPE: PRT
<213> ORGANISM: Artificial Sequence
<220> FEATURE:
<223> OTHER INFORMATION: 19G1; VH

<400> SEQUENCE: 259

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 260
<211> LENGTH: 351
<212> TYPE: DNA
<213> ORGANISM: Artificial Sequence
<220> FEATURE:
<223> OTHER INFORMATION: 19G1; VH

<400> SEQUENCE: 260

```
gaggtgcaat tgttggagtc tgggggaggc ttggtacagc ctgggggtc cctgagactc     60 tcctgtgcag cctccggatt caccttagc agttatgcga tgagctgggt ccgccaggct   120
ccagggaagg gctggagtg gtctcagcg attattagta gtggtggtct cacatactac   180
gcagactccg tgaagggccg gttcaccatc tccagagaca attccaagaa cacgctgtat   240
ctgcagatga acagcctgag agccgaggac acggccgtat attactgtgc gaaaggtgtg   300
tttggtggtt taactactg gggccaagga accctggtca ccgtctcgtc c            351
```

<210> SEQ ID NO 261
<211> LENGTH: 108
<212> TYPE: PRT
<213> ORGANISM: Artificial Sequence
<220> FEATURE:
<223> OTHER INFORMATION: 20G8; VL

<400> SEQUENCE: 261

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
            85                  90                  95

Pro Thr Phe Gly Gln Gly Thr Lys Val Glu Ile Lys
            100                 105
```

<210> SEQ ID NO 262
<211> LENGTH: 324
<212> TYPE: DNA
<213> ORGANISM: Artificial Sequence
<220> FEATURE:
<223> OTHER INFORMATION: 20G8; VL

<400> SEQUENCE: 262

```
gaaatcgtgt taacgcagtc tccaggcacc ctgtctttgt ctccagggga aagagccacc      60
ctctcttgca gggccagtca gagtgttacc agtagcact tagcctggta ccagcagaaa     120
cctggccagg ctcccaggct cctcatcaat gtgggctccc gtagggccac tggcatccca     180
gacaggttca gtggcagtgg atccgggaca gacttcactc tcaccatcag cagactggag     240
cctgaagatt ttgcagtgta ttactgtcag cagggtatta tgcttccccc gacgttcggc     300
caggggacca aagtggaaat caaa                                             324
```

<210> SEQ ID NO 263
<211> LENGTH: 117
<212> TYPE: PRT
<213> ORGANISM: Artificial Sequence
<220> FEATURE:
<223> OTHER INFORMATION: 20G8; VH

<400> SEQUENCE: 263

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Trp Phe Gly Phe Asn Tyr Trp Gly Gln Gly Thr Leu
            100                 105                 110

Val Thr Val Ser Ser
        115
```

<210> SEQ ID NO 264

<211> LENGTH: 351
<212> TYPE: DNA
<213> ORGANISM: Artificial Sequence
<220> FEATURE:
<223> OTHER INFORMATION: 20G8; VH

<400> SEQUENCE: 264

```
gaggtgcaat tgttggagtc tgggggaggc ttggtacagc ctggggggtc cctgagactc    60
tcctgtgcag cctccggatt cacctttagc agttatgcaa tgagctgggt ccgccaggct   120
ccagggaagg ggctggagtg ggtctcagct attattggga gtggtagtcg tacatactac   180
gcagactccg tgaagggccg gttcaccatc tccagagaca attccaagaa cacgctgtat   240
ctgcagatga acagcctgag agccgaggac acggccgtat attactgtgc gaaagggtgg   300
tttggtggtt ttaactactg gggccaagga accctggtca ccgtctcgtc c            351
```

<210> SEQ ID NO 265
<211> LENGTH: 108
<212> TYPE: PRT
<213> ORGANISM: Artificial Sequence
<220> FEATURE:
<223> OTHER INFORMATION: 4B9; VL

<400> SEQUENCE: 265

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 266
<211> LENGTH: 324
<212> TYPE: DNA
<213> ORGANISM: Artificial Sequence
<220> FEATURE:
<223> OTHER INFORMATION: 4B9; VL

<400> SEQUENCE: 266

```
gaaatcgtgt taacgcagtc tccaggcacc ctgtctttgt ctccagggga aagagccacc    60
ctctcttgca gggccagtca gagtgttacc agtagctact tagcctggta ccagcagaaa   120
cctggccagg ctcccaggct cctcatcaat gtgggctccc gtaggccac tggcatccca   180
gacaggttca gtggcagtgg atccgggaca gacttcactc tcaccatcag cagactggag   240
cctgaagatt ttgcagtgta ttactgtcag cagggtatta tgcttccccc gacgttcggc   300
caggggacca aagtggaaat caaa                                           324
```

<210> SEQ ID NO 267
<211> LENGTH: 117
<212> TYPE: PRT
<213> ORGANISM: Artificial Sequence
<220> FEATURE:

<223> OTHER INFORMATION: 4B9; VH

<400> SEQUENCE: 267

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ile Gly Ser Gly Ala Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Trp Phe Gly Gly Phe Asn Tyr Trp Gly Gln Gly Thr Leu
            100                 105                 110
Val Thr Val Ser Ser
        115
```

<210> SEQ ID NO 268
<211> LENGTH: 351
<212> TYPE: DNA
<213> ORGANISM: Artificial Sequence
<220> FEATURE:
<223> OTHER INFORMATION: 4B9; VH

<400> SEQUENCE: 268

```
gaggtgcaat tgttggagtc tgggggaggc ttggtacagc ctggggggtc cctgagactc    60
tcctgtgcag cctccggatt cacctttagc agttatgcta tgagctgggt ccgccaggct   120
ccagggaagg ggctggagtg ggtctcagct attattggta gtggtgctag cacatactac   180
gcagactccg tgaagggccg gttcaccatc tccagagaca attccaagaa cacgctgtat   240
ctgcagatga acagcctgag agccgaggac acggccgtat attactgtgc gaaagggtgg   300
tttggtggtt ttaactactg gggccaagga accctggtca ccgtctcgtc c            351
```

<210> SEQ ID NO 269
<211> LENGTH: 108
<212> TYPE: PRT
<213> ORGANISM: Artificial Sequence
<220> FEATURE:
<223> OTHER INFORMATION: 5B8; VL

<400> SEQUENCE: 269

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Thr Ser Ser
            20                  25                  30
Tyr Leu Ala Trp Tyr Gln Gln Lys Pro Gly Gln Ala Pro Arg Leu Leu
        35                  40                  45
Ile Asn Val Gly Ser Arg Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Gly Ile Met Leu Pro
                85                  90                  95
Pro Thr Phe Gly Gln Gly Thr Lys Val Glu Ile Lys
            100                 105
```

<210> SEQ ID NO 270
<211> LENGTH: 324
<212> TYPE: DNA
<213> ORGANISM: Artificial Sequence
<220> FEATURE:
<223> OTHER INFORMATION: 5B8; VL

<400> SEQUENCE: 270

```
gaaatcgtgt taacgcagtc tccaggcacc ctgtctttgt ctccagggga aagagccacc    60
ctctcttgca gggccagtca gagtgttacc agtagctact tagcctggta ccagcagaaa   120
cctggccagg ctcccaggct cctcatcaat gtgggctccc gtagggccac tggcatccca   180
gacaggttca gtggcagtgg atccgggaca gacttcactc tcaccatcag cagactggag   240
cctgaagatt ttgcagtgta ttactgtcag cagggtatta tgcttccccc gacgttcggc   300
caggggacca agtggaaat caaa                                           324
```

<210> SEQ ID NO 271
<211> LENGTH: 117
<212> TYPE: PRT
<213> ORGANISM: Artificial Sequence
<220> FEATURE:
<223> OTHER INFORMATION: 5B8; VH

<400> SEQUENCE: 271

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Trp Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 272
<211> LENGTH: 351
<212> TYPE: DNA
<213> ORGANISM: Artificial Sequence
<220> FEATURE:
<223> OTHER INFORMATION: 5B8; VH

<400> SEQUENCE: 272

```
gaggtgcaat tgttggagtc tgggggaggc ttggtacagc ctgggggtc cctgagactc      60
tcctgtgcag cctccggatt cacctttagc agttatgcta tgagctgggt ccgccaggct   120
ccagggaagg ggctggagtg ggtctcagct atttggggtg gtggtcgtag cacatactac   180
gcagactccg tgaagggccg gttcaccatc tccagagaca attccaagaa cacgctgtat   240
ctgcagatga acagcctgag agccgaggac acggccgtat attactgtgc gaaagggtgg   300
tttggtggtt ttaactactg gggccaagga acctggtca ccgtctcgtc c             351
```

<210> SEQ ID NO 273
<211> LENGTH: 108
<212> TYPE: PRT
<213> ORGANISM: Artificial Sequence
<220> FEATURE:
<223> OTHER INFORMATION: 5F1; VL

<400> SEQUENCE: 273

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 274
<211> LENGTH: 324
<212> TYPE: DNA
<213> ORGANISM: Artificial Sequence
<220> FEATURE:
<223> OTHER INFORMATION: 5F1; VL

<400> SEQUENCE: 274
gaaatcgtgt taacgcagtc tccaggcacc ctgtctttgt ctccagggga aagagccacc      60
ctctcttgca gggccagtca gagtgttacc agtagctact tagcctggta ccagcagaaa     120
cctggccagg ctcccaggct cctcatcaat gtgggctccc gtagggccac tggcatccca     180
gacaggttca gtggcagtgg atccgggaca gacttcactc tcaccatcag cagactggag     240
cctgaagatt ttgcagtgta ttactgtcag cagggtatta tgcttccccc gacgttcggc     300
caggggacca agtggaaat caaa                                               324

<210> SEQ ID NO 275
<211> LENGTH: 117
<212> TYPE: PRT
<213> ORGANISM: Artificial Sequence
<220> FEATURE:
<223> OTHER INFORMATION: 5F1; VH

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
            85                  90                  95

Ala Lys Gly Trp Phe Gly Gly Phe Asn Tyr Trp Gly Gln Gly Thr Leu
        100                 105                 110

Val Thr Val Ser Ser
        115

<210> SEQ ID NO 276
<211> LENGTH: 351
<212> TYPE: DNA
<213> ORGANISM: Artificial Sequence
<220> FEATURE:
<223> OTHER INFORMATION: 5F1; VH

<400> SEQUENCE: 276
gaggtgcaat tgttggagtc tgggggaggc ttggtacagc ctgggggtc cctgagactc        60 tcctgtgcag cctccggatt cacctttagc agttatgcta tgagctgggt ccgccaggct      120
ccagggaagg gctggagtg gtctcagct attattagta gtgggctag cacatactac        180 gcagactccg tgaagggccg gttcaccatc tccagagaca attccaagaa cacgctgtat      240
ctgcagatga acagcctgag agccgaggac acggccgtat attactgtgc gaaagggtgg      300
tttggtggtt ttaactactg gggccaagga accctggtca ccgtctcgtc c               351

<210> SEQ ID NO 277
<211> LENGTH: 108
<212> TYPE: PRT
<213> ORGANISM: Artificial Sequence
<220> FEATURE:
<223> OTHER INFORMATION: 14B3; VL

<400> SEQUENCE: 277

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 278
<211> LENGTH: 324
<212> TYPE: DNA
<213> ORGANISM: Artificial Sequence
<220> FEATURE:
<223> OTHER INFORMATION: 14B3; VL

<400> SEQUENCE: 278
gaaatcgtgt taacgcagtc tccaggcacc ctgtctttgt ctccagggga agagccacc        60 ctctcttgca gggccagtca gagtgttacc agtagctact tagcctggta ccagcagaaa     120
cctggccagg ctcccaggct cctcatcaat gtgggctccc gtaggccac tggcatccca      180 gacaggttca gtggcagtgg atccgggaca gacttcactc tcaccatcag cagactggag     240
```

```
cctgaagatt ttgcagtgta ttactgtcag cagggtatta tgcttccccc gacgttcggc    300
caggggacca aagtggaaat caaa                                            324
```

<210> SEQ ID NO 279
<211> LENGTH: 117
<212> TYPE: PRT
<213> ORGANISM: Artificial Sequence
<220> FEATURE:
<223> OTHER INFORMATION: 14B3; VH

<400> SEQUENCE: 279

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Leu Ala Ser Gly Ala Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 280
<211> LENGTH: 351
<212> TYPE: DNA
<213> ORGANISM: Artificial Sequence
<220> FEATURE:
<223> OTHER INFORMATION: 14B3; VH

<400> SEQUENCE: 280

```
gaggtgcaat tgttggagtc tgggggaggc ttggtacagc ctgggggggtc cctgagactc    60 tcctgtgcag cctccggatt cacctttagc agttatgcta tgagctgggt ccgccaggct   120
ccagggaagg ggctggagtg ggtctcagct attttggcta gtggtgcgat cacatactac   180
gcagactccg tgaagggccg gttcaccatc tccagagaca attccaagaa cacgctgtat   240
ctgcagatga acagcctgag agccgaggac acggccgtat attactgtgc gaaagggtgg   300
tttggtggtt ttaactactg gggccaagga accctggtca ccgtctcgtc c           351
```

<210> SEQ ID NO 281
<211> LENGTH: 108
<212> TYPE: PRT
<213> ORGANISM: Artificial Sequence
<220> FEATURE:
<223> OTHER INFORMATION: 16F1; VL

<400> SEQUENCE: 281

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45
```

```
Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys
            100                 105
```

<210> SEQ ID NO 282
<211> LENGTH: 324
<212> TYPE: DNA
<213> ORGANISM: Artificial Sequence
<220> FEATURE:
<223> OTHER INFORMATION: 16F1; VL

<400> SEQUENCE: 282

```
gaaatcgtgt taacgcagtc tccaggcacc ctgtctttgt ctccagggga aagagccacc      60
ctctcttgca gggccagtca gagtgttacc agtagctact tagcctggta ccagcagaaa    120
cctggccagg ctcccaggct cctcatcaat gtgggctccc gtagggccac tggcatccca    180
gacaggttca gtggcagtgg atccgggaca gacttcactc tcaccatcag cagactggag    240
cctgaagatt ttgcagtgta ttactgtcag cagggtatta tgcttccccc gacgttcggc    300
caggggacca agtggaaat caaa                                              324
```

<210> SEQ ID NO 283
<211> LENGTH: 117
<212> TYPE: PRT
<213> ORGANISM: Artificial Sequence
<220> FEATURE:
<223> OTHER INFORMATION: 16F1; VH

<400> SEQUENCE: 283

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Gly Ile Ile Gly Ser Gly Gly Ile Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Phe Gly Gly Phe Asn Tyr Trp Gly Gln Gly Thr Leu
                100                 105                 110

Val Thr Val Ser Ser
            115
```

<210> SEQ ID NO 284
<211> LENGTH: 351
<212> TYPE: DNA
<213> ORGANISM: Artificial Sequence
<220> FEATURE:
<223> OTHER INFORMATION: 16F1; VH

<400> SEQUENCE: 284

```
gaggtgcaat tgttggagtc tgggggaggc ttggtacagc ctgggggtc cctgagactc      60 tcctgtgcag cctccggatt cacctttagc agttatgcta tgagctgggt ccgccaggct    120
ccagggaagg ggctggagtg ggtctcaggt attattggta gtggtggtat cacatactac    180
gcagactccg tgaagggccg gttcaccatc tccagagaca attccaagaa cacgctgtat    240
ctgcagatga acagcctgag agccgaggac acggccgtat attactgtgc gaaaggtgg    300 tttggtggtt ttaactactg gggccaagga accctggtca ccgtctcgtc c            351
```

<210> SEQ ID NO 285
<211> LENGTH: 108
<212> TYPE: PRT
<213> ORGANISM: Artificial Sequence
<220> FEATURE:
<223> OTHER INFORMATION: 16F8; VL

<400> SEQUENCE: 285

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 286
<211> LENGTH: 324
<212> TYPE: DNA
<213> ORGANISM: Artificial Sequence
<220> FEATURE:
<223> OTHER INFORMATION: 16F8; VL

<400> SEQUENCE: 286

```
gaaatcgtgt taacgcagtc tccaggcacc ctgtctttgt ctccagggga aagagccacc    60
ctctcttgca gggccagtca gagtgttacc agtagctact tagcctggta ccagcagaaa   120
cctggccagg ctcccaggct cctcatcaat gtgggctccc gtagggccac tggcatccca   180
gacaggttca gtggcagtgg atccgggaca gacttcactc tcaccatcag cagactggag   240
cctgaagatt ttgcagtgta ttactgtcag cagggtatta tgcttccccc gacgttcggc   300
caggggacca agtggaaat caaa                                            324
```

<210> SEQ ID NO 287
<211> LENGTH: 117
<212> TYPE: PRT
<213> ORGANISM: Artificial Sequence
<220> FEATURE:
<223> OTHER INFORMATION: 16F8; VH

<400> SEQUENCE: 287

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30
Ala Met Ser Trp Val Arg Gln Ala Pro Gly Lys Gly Leu Glu Trp Val
            35                  40                  45

Ser Ala Ile Leu Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
            115

<210> SEQ ID NO 288
<211> LENGTH: 351
<212> TYPE: DNA
<213> ORGANISM: Artificial Sequence
<220> FEATURE:
<223> OTHER INFORMATION: 16F8; VH

<400> SEQUENCE: 288
gaggtgcaat tgttggagtc tgggggaggc ttggtacagc ctgggggtc cctgagactc      60 tcctgtgcag cctccggatt caccttagc agttatgcca tgagctgggt ccgccaggct    120
ccagggaagg ggctggagtg ggtctcagct attcttggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
tttggtggtt ttaactactg gggccaagga accctggtca ccgtctcgtc c             351

<210> SEQ ID NO 289
<211> LENGTH: 108
<212> TYPE: PRT
<213> ORGANISM: Artificial Sequence
<220> FEATURE:
<223> OTHER INFORMATION: O3C9; VL

<400> SEQUENCE: 289

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                 70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 290
<211> LENGTH: 324
<212> TYPE: DNA
<213> ORGANISM: Artificial Sequence
<220> FEATURE:
```

<223> OTHER INFORMATION: O3C9; VL

<400> SEQUENCE: 290

```
gaaatcgtgt taacgcagtc tccaggcacc ctgtctttgt ctccagggga aagagccacc    60
ctctcttgca gggccagtca gagtgttacc agtagctact tagcctggta ccagcagaaa   120
cctggccagg ctcccaggct cctcatcaat gtgggctccc gtagggccac tggcatccca   180
gacaggttca gtggcagtgg atccgggaca gacttcactc tcaccatcag cagactggag   240
cctgaagatt ttgcagtgta ttactgtcag cagggtatta tgcttccccc gacgttcggc   300
caggggacca agtggaaat caaa                                           324
```

<210> SEQ ID NO 291
<211> LENGTH: 117
<212> TYPE: PRT
<213> ORGANISM: Artificial Sequence
<220> FEATURE:
<223> OTHER INFORMATION: O3C9; VH

<400> SEQUENCE: 291

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ser Pro Gly Lys Gly Leu Glu Trp Val
        35                  40                  45

Ser Ala Ile Ile Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 292
<211> LENGTH: 351
<212> TYPE: DNA
<213> ORGANISM: Artificial Sequence
<220> FEATURE:
<223> OTHER INFORMATION: O3C9; VH

<400> SEQUENCE: 292

```
gaggtgcaat tgttggagtc tgggggaggc ttggtacagc ctggggggtc cctgagactc    60
tcctgtgcag cctccggatt cacctttagc agttttgcca tgagctgggt ccgtcagtct   120
ccagggaagg ggctggagtg gtctcagct attattggta gtggtagtaa cacatactac   180
gcagactccg tgaagggccg gttcaccatc tccagagaca attccaagaa cacgctgtat   240
ctgcagatga acagcctgag agccgaggac acggccgtat attactgtgc gaaagggtgg   300
tttggtggtt ttaactactg ggccaagga accctggtca ccgtctcgtc c             351
```

<210> SEQ ID NO 293
<211> LENGTH: 108
<212> TYPE: PRT
<213> ORGANISM: Artificial Sequence
<220> FEATURE:
<223> OTHER INFORMATION: O2D7; VL

<400> SEQUENCE: 293

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Thr Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile Met Leu Pro
                85                  90                  95

Pro Thr Phe Gly Gln Gly Thr Lys Val Glu Ile Lys
            100                 105

<210> SEQ ID NO 294
<211> LENGTH: 324
<212> TYPE: DNA
<213> ORGANISM: Artificial Sequence
<220> FEATURE:
<223> OTHER INFORMATION: O2D7; VL

<400> SEQUENCE: 294

```
gaaatcgtgt taacgcagtc tccaggcacc ctgtctttgt ctccagggga aagagccacc      60
ctctcttgca gggccagtca gagtgttacc agtagctact tagcctggta ccagcagaaa     120
cctggccagg ctcccaggct cctcatcaat gtgggctccc gtagggccac tggcacccca     180
gacaggttca gtggcagtgg atccgggaca gacttcactc tcaccatcag cagactggag     240
cctgaagatt ttgcagtgta ttactgtcag caggctatta tgcttcctcc gacgttcggc     300
caggggacca agtggaaat caaa                                             324
```

<210> SEQ ID NO 295
<211> LENGTH: 117
<212> TYPE: PRT
<213> ORGANISM: Artificial Sequence
<220> FEATURE:
<223> OTHER INFORMATION: O2D7; VH

<400> SEQUENCE: 295

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
            115

<210> SEQ ID NO 296
<211> LENGTH: 351
<212> TYPE: DNA
<213> ORGANISM: Artificial Sequence
<220> FEATURE:
<223> OTHER INFORMATION: O2D7; VH

<400> SEQUENCE: 296

```
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
tttggtggtt ttaactactg ggccaagga accctggtca ccgtctcgtc c              351
```

<210> SEQ ID NO 297
<211> LENGTH: 108
<212> TYPE: PRT
<213> ORGANISM: Artificial Sequence
<220> FEATURE:
<223> OTHER INFORMATION: 28H1; VL

<400> SEQUENCE: 297

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 298
<211> LENGTH: 324
<212> TYPE: DNA
<213> ORGANISM: Artificial Sequence
<220> FEATURE:
<223> OTHER INFORMATION: 28H1; VL

<400> SEQUENCE: 298

```
gaaatcgtgt taacgcagtc tccaggcacc ctgtctttgt ctccagggga aagagccacc     60
ctctcttgca gggccagtca gagtgttagc cgcagctact tagcctggta ccagcagaaa    120
cctggccagg ctcccaggct cctcatcatt ggggcctcca ccagggccac tggcatccca    180
gacaggttca gtggcagtgg atccgggaca gacttcactc tcaccatcag cagactggag    240
cctgaagatt ttgcagtgta ttactgtcag cagggtcagg ttattccccc tacgttcggc    300
caggggacca agtggaaat caaa                                             324
```

<210> SEQ ID NO 299
<211> LENGTH: 116

<212> TYPE: PRT
<213> ORGANISM: Artificial Sequence
<220> FEATURE:
<223> OTHER INFORMATION: 28H1; VH

<400> SEQUENCE: 299

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
        115

<210> SEQ ID NO 300
<211> LENGTH: 348
<212> TYPE: DNA
<213> ORGANISM: Artificial Sequence
<220> FEATURE:
<223> OTHER INFORMATION: 28H1; VH

<400> SEQUENCE: 300
gaggtgcaat tgttggagtc tgggggaggc ttggtacagc ctggggggtc cctgagactc      60
tcctgtgcag cctccggatt cacctttagc agtcatgcta tgagctgggt ccgccaggct     120
ccagggaagg ggctggagtg ggtctcagct atttgggcta gtgggagca atactacgca      180
gactccgtga aggccggtt caccatctcc agagacaatt ccaagaacac gctgtatctg      240
cagatgaaca gcctgagagc cgaggacacg gccgtatatt actgtgcgaa aggtggctg      300
ggtaattttg actactgggg ccaaggaacc ctggtcaccg tctcgagt                  348

<210> SEQ ID NO 301
<211> LENGTH: 108
<212> TYPE: PRT
<213> ORGANISM: Artificial Sequence
<220> FEATURE:
<223> OTHER INFORMATION: 22A3; VL

<400> SEQUENCE: 301

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro

```
                    85                  90                  95
Pro Thr Phe Gly Gln Gly Thr Lys Val Glu Ile Lys
            100                 105

<210> SEQ ID NO 302
<211> LENGTH: 324
<212> TYPE: DNA
<213> ORGANISM: Artificial Sequence
<220> FEATURE:
<223> OTHER INFORMATION: 22A3; VL

<400> SEQUENCE: 302
gaaatcgtgt taacgcagtc tccaggcacc ctgtctttgt ctccagggga aagagccacc      60
ctctcttgca gggccagtca gagtgttacc agtagctact tagcctggta ccagcagaaa     120
cctggccagg ctcccaggct cctcatcaat gtgggctccc gtagggccac tggcatccca     180
gacaggttca gtggcagtgg atccgggaca gacttcactc tcaccatcag cagactggag     240
cctgaagatt ttgcagtgta ttactgtcag cagggtatta tgcttccccc gacgttcggc     300
caggggacca agtggaaat caaa                                              324

<210> SEQ ID NO 303
<211> LENGTH: 117
<212> TYPE: PRT
<213> ORGANISM: Artificial Sequence
<220> FEATURE:
<223> OTHER INFORMATION: 22A3; VH

<400> SEQUENCE: 303

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 304
<211> LENGTH: 351
<212> TYPE: DNA
<213> ORGANISM: Artificial Sequence
<220> FEATURE:
<223> OTHER INFORMATION: 22A3; VH

<400> SEQUENCE: 304
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg gctggagtg gtctcagct attattggta gtggtagtat cacatactac     180
gcagactccg tgaagggccg gttcaccatc tccagagaca attccaagaa cacgctgtat     240
```
ctgcagatga acagcctgag agccgaggac acggccgtat attactgtgc gaaagggtgg 300
tttggtggtt ttaactactg gggccaagga accctggtca ccgtctcgag t 351

<210> SEQ ID NO 305
<211> LENGTH: 108
<212> TYPE: PRT
<213> ORGANISM: Artificial Sequence
<220> FEATURE:
<223> OTHER INFORMATION: 29B11; VL

<400> SEQUENCE: 305

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 306
<211> LENGTH: 324
<212> TYPE: DNA
<213> ORGANISM: Artificial Sequence
<220> FEATURE:
<223> OTHER INFORMATION: 29B11; VL

<400> SEQUENCE: 306
gaaatcgtgt taacgcagtc tccaggcacc ctgtctttgt ctccagggga aagagccacc    60
ctctcttgca gggccagtca gagtgttacc agtagctact tagcctggta ccagcagaaa   120
cctggccagg ctcccaggct cctcatcaat gtgggctccc gtagggccac tggcatccca   180
gacaggttca gtggcagtgg atccgggaca gacttcactc tcaccatcag cagactggag   240
cctgaagatt ttgcagtgta ttactgtcag cagggtatta tgcttccccc gacgttcggc   300
caggggacca agtggaaat caaa                                           324

<210> SEQ ID NO 307
<211> LENGTH: 117
<212> TYPE: PRT
<213> ORGANISM: Artificial Sequence
<220> FEATURE:
<223> OTHER INFORMATION: 29B11; VH

<400> SEQUENCE: 307

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Gly Ile Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Trp Phe Gly Gly Phe Asn Tyr Trp Gly Gln Gly Thr Leu
            100                 105                 110

Val Thr Val Ser Ser
            115

<210> SEQ ID NO 308
<211> LENGTH: 351
<212> TYPE: DNA
<213> ORGANISM: Artificial Sequence
<220> FEATURE:
<223> OTHER INFORMATION: 29B11; VH

<400> SEQUENCE: 308
gaggtgcaat tgttggagtc tgggggaggc ttggtacagc ctgggggtc cctgagactc      60 tcctgtgcag cctccggatt cacctttagc agttatgcta tgagctgggt ccgccaggct    120
ccagggaagg gctggagtg gtctcagct attattggta gtggtggtat cacatactac      180
gcagactccg tgaagggccg gttcaccatc tccagagaca attccaagaa cacgctgtat    240
ctgcagatga acagcctgag agccgaggac acggccgtat attactgtgc gaaagggtgg    300
tttggtggtt ttaactactg gggccaagga accctggtca ccgtctcgag t            351

<210> SEQ ID NO 309
<211> LENGTH: 108
<212> TYPE: PRT
<213> ORGANISM: Artificial Sequence
<220> FEATURE:
<223> OTHER INFORMATION: 23C10; VL

<400> SEQUENCE: 309

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Arg Ser
                 20                  25                  30

Tyr Leu Ala Trp Tyr Gln Gln Lys Pro Gly Gln Ala Pro Arg Leu Leu
             35                  40                  45

Ile Ile Gly Ala Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Val Ile Pro
                 85                  90                  95

Pro Thr Phe Gly Gln Gly Thr Lys Val Glu Ile Lys
            100                 105

<210> SEQ ID NO 310
<211> LENGTH: 324
<212> TYPE: DNA
<213> ORGANISM: Artificial Sequence
<220> FEATURE:
<223> OTHER INFORMATION: 23C10; VL

<400> SEQUENCE: 310
gaaatcgtgt taacgcagtc tccaggcacc ctgtctttgt ctccagggga aagagccacc    60
ctctcttgca gggccagtca gagtgttagc cgcagctact tagcctggta ccagcagaaa    120
```

```
cctggccagg ctcccaggct cctcatcatt ggggcctcca ccagggccac tggcatccca     180
gacaggttca gtggcagtgg atccgggaca gacttcactc tcaccatcag cagactggag     240
cctgaagatt ttgcagtgta ttactgtcag cagggtcagg ttattccccc tacgttcggc     300
caggggacca agtggaaat caaa                                             324
```

```
<210> SEQ ID NO 311
<211> LENGTH: 117
<212> TYPE: PRT
<213> ORGANISM: Artificial Sequence
<220> FEATURE:
<223> OTHER INFORMATION: 23C10; VH

<400> SEQUENCE: 311
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ala Ile Ser Thr Asn Gly Asn Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115

```
<210> SEQ ID NO 312
<211> LENGTH: 351
<212> TYPE: DNA
<213> ORGANISM: Artificial Sequence
<220> FEATURE:
<223> OTHER INFORMATION: 23C10; VH

<400> SEQUENCE: 312
gaggtgcaat gttggagtc tggggggaggc ttggtacagc ctgggggtc cctgagactc      60 tcctgtgcag cctccggatt cacctttagc agttctgcca tgagctgggt ccgccaggct    120
ccagggaagg ggctggagtg ggtctcagct attagtacta atggtaatta tacatactac    180
gcagactccg tgaagggccg gttcaccatc tccagagaca attccaagaa cacgctgtat    240
ctgcagatga acagcctgag agccgaggac acggccgtat attactgtgc gaaagggtgg    300
ctgggtaatt ttgactactg ggccaagga accctggtca ccgtctcgag t              351
```

```
<210> SEQ ID NO 313
<211> LENGTH: 330
<212> TYPE: PRT
<213> ORGANISM: Homo sapiens

<400> SEQUENCE: 313
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 314
<211> LENGTH: 990
<212> TYPE: DNA
<213> ORGANISM: Homo sapiens

<400> SEQUENCE: 314
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggaccct    420 gaggtcacat gcgtggtggt ggacgtgagc cacgaagacc ctgaggtcaa gttcaactgg   480
```

```
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990

<210> SEQ ID NO 315
<211> LENGTH: 107
<212> TYPE: PRT
<213> ORGANISM: Homo sapiens

<400> SEQUENCE: 315

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 316
<211> LENGTH: 321
<212> TYPE: DNA
<213> ORGANISM: Homo sapiens

<400> SEQUENCE: 316
cgtacggtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321

<210> SEQ ID NO 317
<211> LENGTH: 748
<212> TYPE: PRT
<213> ORGANISM: Artificial Sequence
<220> FEATURE:
<223> OTHER INFORMATION: Human FAP ectodomain?lys-tag?tag

<400> SEQUENCE: 317

Arg Pro Ser Arg Val His Asn Ser Glu Glu Asn Thr Met Arg Ala Leu
```

```
1               5                   10                  15
Thr Leu Lys Asp Ile Leu Asn Gly Thr Phe Ser Tyr Lys Thr Phe Phe
                20                  25                  30
Pro Asn Trp Ile Ser Gly Gln Glu Tyr Leu His Gln Ser Ala Asp Asn
                35                  40                  45
Asn Ile Val Leu Tyr Asn Ile Glu Thr Gly Gln Ser Tyr Thr Ile Leu
 50                  55                  60
Ser Asn Arg Thr Met Lys Ser Val Asn Ala Ser Asn Tyr Gly Leu Ser
 65                  70                  75                  80
Pro Asp Arg Gln Phe Val Tyr Leu Glu Ser Asp Tyr Ser Lys Leu Trp
                85                  90                  95
Arg Tyr Ser Tyr Thr Ala Thr Tyr Tyr Ile Tyr Asp Leu Ser Asn Gly
                100                 105                 110
Glu Phe Val Arg Gly Asn Glu Leu Pro Arg Pro Ile Gln Tyr Leu Cys
                115                 120                 125
Trp Ser Pro Val Gly Ser Lys Leu Ala Tyr Val Tyr Gln Asn Asn Ile
                130                 135                 140
Tyr Leu Lys Gln Arg Pro Gly Asp Pro Phe Gln Ile Thr Phe Asn
145                 150                 155                 160
Gly Arg Glu Asn Lys Ile Phe Asn Gly Ile Pro Asp Trp Val Tyr Glu
                165                 170                 175
Glu Glu Met Leu Ala Thr Lys Tyr Ala Leu Trp Trp Ser Pro Asn Gly
                180                 185                 190
Lys Phe Leu Ala Tyr Ala Glu Phe Asn Asp Thr Asp Ile Pro Val Ile
                195                 200                 205
Ala Tyr Ser Tyr Tyr Gly Asp Glu Gln Tyr Pro Arg Thr Ile Asn Ile
                210                 215                 220
Pro Tyr Pro Lys Ala Gly Ala Lys Asn Pro Val Val Arg Ile Phe Ile
225                 230                 235                 240
Ile Asp Thr Thr Tyr Pro Ala Tyr Val Gly Pro Gln Glu Val Pro Val
                245                 250                 255
Pro Ala Met Ile Ala Ser Ser Asp Tyr Tyr Phe Ser Trp Leu Thr Trp
                260                 265                 270
Val Thr Asp Glu Arg Val Cys Leu Gln Trp Leu Lys Arg Val Gln Asn
                275                 280                 285
Val Ser Val Leu Ser Ile Cys Asp Phe Arg Glu Asp Trp Gln Thr Trp
                290                 295                 300
Asp Cys Pro Lys Thr Gln Glu His Ile Glu Glu Ser Arg Thr Gly Trp
305                 310                 315                 320
Ala Gly Gly Phe Phe Val Ser Thr Pro Val Phe Ser Tyr Asp Ala Ile
                325                 330                 335
Ser Tyr Tyr Lys Ile Phe Ser Asp Lys Asp Gly Tyr Lys His Ile His
                340                 345                 350
Tyr Ile Lys Asp Thr Val Glu Asn Ala Ile Gln Ile Thr Ser Gly Lys
                355                 360                 365
Trp Glu Ala Ile Asn Ile Phe Arg Val Thr Gln Asp Ser Leu Phe Tyr
                370                 375                 380
Ser Ser Asn Glu Phe Glu Glu Tyr Pro Gly Arg Arg Asn Ile Tyr Arg
385                 390                 395                 400
Ile Ser Ile Gly Ser Tyr Pro Pro Ser Lys Lys Cys Val Thr Cys His
                405                 410                 415
Leu Arg Lys Glu Arg Cys Gln Tyr Tyr Thr Ala Ser Phe Ser Asp Tyr
                420                 425                 430
```

```
Ala Lys Tyr Tyr Ala Leu Val Cys Tyr Gly Pro Gly Ile Pro Ile Ser
            435                 440                 445

Thr Leu His Asp Gly Arg Thr Asp Gln Glu Ile Lys Ile Leu Glu Glu
            450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
            515                 520                 525

Val Asn Trp Ile Ser Tyr Leu Ala Ser Lys Glu Gly Met Val Ile Ala
            530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
            595                 600                 605

Ala Ser Gly Thr Gly Leu Phe Lys Cys Gly Ile Ala Val Ala Pro Val
            610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
            675                 680                 685

Lys Ala Leu Val Asn Ala Gln Val Asp Phe Gln Ala Met Trp Tyr Ser
            690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His His
                740                 745
```

<210> SEQ ID NO 318
<211> LENGTH: 2244
<212> TYPE: DNA
<213> ORGANISM: Artificial Sequence
<220> FEATURE:
<223> OTHER INFORMATION: Human FAP ectodomain+poly-lys-tag+his6-tag

<400> SEQUENCE: 318

```
cgcccttcaa gagttcataa ctctgaagaa aatacaatga gagcactcac actgaaggat      60
attttaaatg gaacatttct ttataaaaca ttttttccaa actggatttc aggacaagaa     120
tatcttcatc aatctgcaga taacaatata gtactttata atattgaaac aggacaatca     180
tataccattt tgagtaatag aaccatgaaa agtgtgaatg cttcaaatta cggcttatca     240
```

```
cctgatcggc aatttgtata tctagaaagt gattattcaa agctttggag atactcttac    300
acagcaacat attacatcta tgaccttagc aatggagaat ttgtaagagg aaatgagctt    360
cctcgtccaa ttcagtattt atgctggtcg cctgttggga gtaaattagc atatgtctat    420
caaaacaata tctatttgaa acaaagacca ggagatccac cttttcaaat aacatttaat    480
ggaagagaaa ataaaatatt taatggaatc ccagactggg tttatgaaga ggaaatgctt    540
gctacaaaat atgctctctg gtggtctcct aatggaaaat ttttggcata tgcggaattt    600
aatgatacgg ataccagt tattgcctat tcctattatg gcgatgaaca atatcctaga    660
acaataaata ttccataccc aaaggctgga gctaagaatc ccgttgttcg gatatttatt    720
atcgatacca cttaccctgc gtatgtaggt ccccaggaag tgcctgttcc agcaatgata    780
gcctcaagtg attattattt cagttggctc acgtgggtta ctgatgaacg agtatgtttg    840
cagtggctaa aaagagtcca gaatgtttcg gtcctgtcta tatgtgactt cagggaagac    900
tggcagacat gggattgtcc aaagacccag gagcatatag aagaaagcag aactggatgg    960
gctggtggat tctttgtttc aacaccagtt ttcagctatg atgccatttc gtactacaaa   1020
atatttagtg acaaggatgg ctacaaacat attcactata tcaaagacac tgtggaaaat   1080
gctattcaaa ttacaagtgg caagtgggag gccataaata tattcagagt aacacaggat   1140
tcactgtttt attctagcaa tgaatttgaa gaatacctg gaagaagaaa catctacaga   1200
attagcattg gaagctatcc tccaagcaag aagtgtgtta cttgccatct aaggaaagaa   1260
aggtgccaat attacacagc aagtttcagc gactacgcca agtactatgc acttgtctgc   1320
tacggcccag gcatccccat ttccaccctt catgatggac gcactgatca agaaattaaa   1380
atcctggaag aaaacaagga attggaaaat gctttgaaaa atatccagct gcctaaagag   1440
gaaattaaga aacttgaagt agatgaaatt actttatggt acaagatgat tcttcctcct   1500
caatttgaca gatcaaagaa gtatcccttg ctaattcaag tgtatggtgg tccctgcagt   1560
cagagtgtaa ggtctgtatt tgctgttaat tggatatctt atcttgcaag taaggaaggg   1620
atggtcattg ccttggtgga tggtcgagga acagctttcc aaggtgacaa actcctctat   1680
gcagtgtatc gaaagctggg tgtttatgaa gttgaagacc agattacagc tgtcagaaaa   1740
ttcatagaaa tgggtttcat tgatgaaaaa agaatagcca tatgggctg gtcctatgga   1800 ggatacgttt catcactggc ccttgcatct ggaactggtc ttttcaaatg tggtatagca   1860
gtggctccag tctccagctg ggaatattac gcgtctgtct acacagagag attcatgggt   1920
ctcccaacaa aggatgataa tcttgagcac tataagaatt caactgtgat ggcaagagca   1980
gaatatttca gaaatgtaga ctatcttctc atccacggaa cagcagatga taatgtgcac   2040
tttcaaaact cagcacagat tgctaaagct ctggttaatg cacaagtgga tttccaggca   2100
atgtggtact ctgaccagaa ccacggctta tccggcctgt ccacgaacca cttatacacc   2160
cacatgaccc acttcctaaa gcagtgtttc tctttgtcag acggcaaaaa gaaaagaaa   2220 aagggccacc accatcacca tcac                                          2244
```

<210> SEQ ID NO 319
<211> LENGTH: 749
<212> TYPE: PRT
<213> ORGANISM: Artificial Sequence
<220> FEATURE:
<223> OTHER INFORMATION: Murine FAP ectodomain+poly-lys-tag+his6-tag

<400> SEQUENCE: 319

Arg Pro Ser Arg Val Tyr Lys Pro Glu Gly Asn Thr Lys Arg Ala Leu

```
1               5                   10                  15
Thr Leu Lys Asp Ile Leu Asn Gly Thr Phe Ser Tyr Lys Thr Tyr Phe
                20                  25                  30
Pro Asn Trp Ile Ser Glu Gln Glu Tyr Leu His Gln Ser Glu Asp Asp
                35                  40                  45
Asn Ile Val Phe Tyr Asn Ile Glu Thr Arg Glu Ser Tyr Ile Ile Leu
50                  55                  60
Ser Asn Ser Thr Met Lys Ser Val Asn Ala Thr Asp Tyr Gly Leu Ser
65                  70                  75                  80
Pro Asp Arg Gln Phe Val Tyr Leu Glu Ser Asp Tyr Ser Lys Leu Trp
                85                  90                  95
Arg Tyr Ser Tyr Thr Ala Thr Tyr Tyr Ile Tyr Asp Leu Gln Asn Gly
                100                 105                 110
Glu Phe Val Arg Gly Tyr Glu Leu Pro Arg Pro Ile Gln Tyr Leu Cys
                115                 120                 125
Trp Ser Pro Val Gly Ser Lys Leu Ala Tyr Val Tyr Gln Asn Asn Ile
    130                 135                 140
Tyr Leu Lys Gln Arg Pro Gly Asp Pro Pro Phe Gln Ile Thr Tyr Thr
145                 150                 155                 160
Gly Arg Glu Asn Arg Ile Phe Asn Gly Ile Pro Asp Trp Val Tyr Glu
                165                 170                 175
Glu Glu Met Leu Ala Thr Lys Tyr Ala Leu Trp Trp Ser Pro Asp Gly
                180                 185                 190
Lys Phe Leu Ala Tyr Val Glu Phe Asn Asp Ser Asp Ile Pro Ile Ile
                195                 200                 205
Ala Tyr Ser Tyr Tyr Gly Asp Gly Gln Tyr Pro Arg Thr Ile Asn Ile
                210                 215                 220
Pro Tyr Pro Lys Ala Gly Ala Lys Asn Pro Val Val Arg Val Phe Ile
225                 230                 235                 240
Val Asp Thr Thr Tyr Pro His His Val Gly Pro Met Glu Val Pro Val
                245                 250                 255
Pro Glu Met Ile Ala Ser Ser Asp Tyr Tyr Phe Ser Trp Leu Thr Trp
                260                 265                 270
Val Ser Ser Glu Arg Val Cys Leu Gln Trp Leu Lys Arg Val Gln Asn
                275                 280                 285
Val Ser Val Leu Ser Ile Cys Asp Phe Arg Glu Asp Trp His Ala Trp
                290                 295                 300
Glu Cys Pro Lys Asn Gln Glu His Val Glu Glu Ser Arg Thr Gly Trp
305                 310                 315                 320
Ala Gly Gly Phe Phe Val Ser Thr Pro Ala Phe Ser Gln Asp Ala Thr
                325                 330                 335
Ser Tyr Tyr Lys Ile Phe Ser Asp Lys Asp Gly Tyr Lys His Ile His
                340                 345                 350
Tyr Ile Lys Asp Thr Val Glu Asn Ala Ile Gln Ile Thr Ser Gly Lys
                355                 360                 365
Trp Glu Ala Ile Tyr Ile Phe Arg Val Thr Gln Asp Ser Leu Phe Tyr
                370                 375                 380
Ser Ser Asn Glu Phe Glu Gly Tyr Pro Gly Arg Arg Asn Ile Tyr Arg
385                 390                 395                 400
Ile Ser Ile Gly Asn Ser Pro Pro Ser Lys Lys Cys Val Thr Cys His
                405                 410                 415
Leu Arg Lys Glu Arg Cys Gln Tyr Tyr Thr Ala Ser Phe Ser Tyr Lys
                420                 425                 430
```

Ala Lys Tyr Tyr Ala Leu Val Cys Tyr Gly Pro Gly Leu Pro Ile Ser
        435                 440                 445

Thr Leu His Asp Gly Arg Thr Asp Gln Glu Ile Gln Val Leu Glu Glu
        450                 455                 460

Asn Lys Glu Leu Glu Asn Ser Leu Arg Asn Ile Gln Leu Pro Lys Val
465                 470                 475                 480

Glu Ile Lys Lys Leu Lys Asp Gly Gly Leu Thr Phe Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Lys Ser Val Phe Ala
        515                 520                 525

Val Asn Trp Ile Thr Tyr Leu Ala Ser Lys Glu Gly Ile Val Ile Ala
        530                 535                 540

Leu Val Asp Gly Arg Gly Thr Ala Phe Gln Gly Asp Lys Phe Leu His
545                 550                 555                 560

Ala Val Tyr Arg Lys Leu Gly Val Tyr Glu Val Glu Asp Gln Leu Thr
                565                 570                 575

Ala Val Arg Lys Phe Ile Glu Met Gly Phe Ile Asp Glu Glu Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
        610                 615                 620

Ser Ser Trp Glu Tyr Tyr Ala Ser Ile Tyr Ser Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
        690                 695                 700

Asp Gln Asn His Gly Ile Leu Ser Gly Arg Ser Gln Asn His Leu Tyr
705                 710                 715                 720

Thr His Met Thr His Phe Leu Lys Gln Cys Phe Ser Leu Ser Asp Gly
                725                 730                 735

Lys Lys Lys Lys Lys Gly His His His His His
            740                 745

<210> SEQ ID NO 320
<211> LENGTH: 2247
<212> TYPE: DNA
<213> ORGANISM: Artificial Sequence
<220> FEATURE:
<223> OTHER INFORMATION: Murine FAP ectodomain+poly-lys-tag+his6-tag

<400> SEQUENCE: 320
cgtccctcaa gagtttacaa acctgaagga aacacaaaga gagctcttac cttgaaggat        60 atttaaatg gaacattctc atataaaaca tattttccca actggatttc agaacaagaa        120
tatcttcatc aatctgagga tgataacata gtatttata atattgaaac aagagaatca        180
tatatcattt tgagtaatag caccatgaaa agtgtgaatg ctacagatta tggtttgtca        240

```
cctgatcggc aatttgtgta tctagaaagt gattattcaa agctctggcg atattcatac      300
acagcgacat actacatcta cgaccttcag aatggggaat ttgtaagagg atacgagctc      360
cctcgtccaa ttcagtatct atgctggtcg cctgttggga gtaaattagc atatgtatat      420
caaaacaata tttatttgaa acaaagacca ggagatccac cttttcaaat aacttatact      480
ggaagagaaa atagaatatt taatggaata ccagactggg tttatgaaga ggaaatgctt      540
gccacaaaat atgctctttg gtggtctcca gatggaaaat ttttggcata tgtagaattt      600
aatgattcag atataccaat tattgcctat tcttattatg gtgatggaca gtatcctaga      660
actataaata ttccatatcc aaaggctggg gctaagaatc cggttgttcg tgttttttatt      720
gttgacacca cctaccctca ccacgtgggc ccaatggaag tgccagttcc agaaatgata      780
gcctcaagtg actattattt cagctggctc acatgggtgt ccagtgaacg agtatgcttg      840
cagtggctaa aaagagtgca gaatgtctca gtcctgtcta tatgtgattt cagggaagac      900
tggcatgcat gggaatgtcc aaagaaccag gagcatgtag aagaaagcag aacaggatgg      960
gctggtggat tctttgtttc gacaccagct tttagccagg atgccacttc ttactacaaa     1020
atatttagcg acaaggatgg ttacaaacat attcactaca tcaaagacac tgtggaaaat     1080
gctattcaaa ttacaagtgg caagtgggag gccatatata tattccgcgt aacacaggat     1140
tcactgtttt attctagcaa tgaatttgaa ggttaccctg aagaagaaa catctacaga     1200
attagcattg gaaactctcc tccgagcaag aagtgtgtta cttgccatct aaggaaagaa     1260
aggtgccaat attacacagc aagtttcagc tacaaagcca agtactatgc actcgtctgc     1320
tatgcccctg gcctccccat ttccaccctc catgatggcc gcacagacca agaaatacaa     1380
gtattagaag aaaacaaaga actggaaaat tctctgagaa atatccagct gcctaaagtg     1440
gagattaaga gctcaaaga cggggggactg actttctggt acaagatgat tctgcctcct     1500
cagtttgaca gatcaaagaa gtacccttttg ctaattcaag tgtatggtgg tccttgtagc     1560
cagagtgtta gtctgtgtt tgctgttaat tggataactt atctcgcaag taaggagggg     1620
atagtcattg ccctggtaga tggtcggggc actgctttcc aaggtgacaa attcctgcat     1680
gccgtgtatc gaaaactggg tgtatatgaa gttgaggacc agctcacagc tgtcagaaaa     1740
ttcatagaaa tgggtttcat tgatgaagaa agaatagcca tatgggctg gtcctacgga     1800
ggttatgttt catccctggc ccttgcatct ggaactggtc ttttcaaatg tggcatagca     1860
gtggctccag tctccagctg ggaatattac gcatctatct actcagagag attcatgggc     1920
ctcccaacaa aggacgacaa tctcgaacac tataaaaatt caactgtgat ggcaagagca     1980
gaatatttca gaaatgtaga ctatcttctc atccacggaa cagcagatga taatgtgcac     2040
tttcagaact cagcacagat tgctaaagct ttggttaatg cacaagtgga tttccaggcg     2100
atgtggtact ctgaccagaa ccatggtata ttatctgggc gctcccagaa tcatttatat     2160
acccacatga cgcacttcct caagcaatgc ttttctttat cagacggcaa aaagaaaaag     2220
aaaaagggcc accaccatca ccatcac                                         2247
```

<210> SEQ ID NO 321
<211> LENGTH: 748
<212> TYPE: PRT
<213> ORGANISM: Artificial Sequence
<220> FEATURE:
<223> OTHER INFORMATION: Cynomolgus FAP ectodomain+poly-lys-tag+his6-tag

<400> SEQUENCE: 321

Arg Pro Pro Arg Val His Asn Ser Glu Glu Asn Thr Met Arg Ala Leu

```
1               5                   10                  15
Thr Leu Lys Asp Ile Leu Asn Gly Thr Phe Ser Tyr Lys Thr Phe Phe
                20                  25                  30
Pro Asn Trp Ile Ser Gly Gln Glu Tyr Leu His Gln Ser Ala Asp Asn
                35                  40                  45
Asn Ile Val Leu Tyr Asn Ile Glu Thr Gly Gln Ser Tyr Thr Ile Leu
 50                  55                  60
Ser Asn Arg Thr Met Lys Ser Val Asn Ala Ser Asn Tyr Gly Leu Ser
 65                  70                  75                  80
Pro Asp Arg Gln Phe Val Tyr Leu Glu Ser Asp Tyr Ser Lys Leu Trp
                85                  90                  95
Arg Tyr Ser Tyr Thr Ala Thr Tyr Tyr Ile Tyr Asp Leu Ser Asn Gly
                100                 105                 110
Glu Phe Val Arg Gly Asn Glu Leu Pro Arg Pro Ile Gln Tyr Leu Cys
                115                 120                 125
Trp Ser Pro Val Gly Ser Lys Leu Ala Tyr Val Tyr Gln Asn Asn Ile
     130                 135                 140
Tyr Leu Lys Gln Arg Pro Gly Asp Pro Pro Phe Gln Ile Thr Phe Asn
145                 150                 155                 160
Gly Arg Glu Asn Lys Ile Phe Asn Gly Ile Pro Asp Trp Val Tyr Glu
                165                 170                 175
Glu Glu Met Leu Ala Thr Lys Tyr Ala Leu Trp Trp Ser Pro Asn Gly
                180                 185                 190
Lys Phe Leu Ala Tyr Ala Glu Phe Asn Asp Thr Asp Ile Pro Val Ile
                195                 200                 205
Ala Tyr Ser Tyr Tyr Gly Asp Glu Gln Tyr Pro Arg Thr Ile Asn Ile
                210                 215                 220
Pro Tyr Pro Lys Ala Gly Ala Lys Asn Pro Phe Val Arg Ile Phe Ile
225                 230                 235                 240
Ile Asp Thr Thr Tyr Pro Ala Tyr Val Gly Pro Gln Glu Val Pro Val
                245                 250                 255
Pro Ala Met Ile Ala Ser Ser Asp Tyr Tyr Phe Ser Trp Leu Thr Trp
                260                 265                 270
Val Thr Asp Glu Arg Val Cys Leu Gln Trp Leu Lys Arg Val Gln Asn
                275                 280                 285
Val Ser Val Leu Ser Ile Cys Asp Phe Arg Glu Asp Trp Gln Thr Trp
                290                 295                 300
Asp Cys Pro Lys Thr Gln Glu His Ile Glu Glu Ser Arg Thr Gly Trp
305                 310                 315                 320
Ala Gly Gly Phe Phe Val Ser Thr Pro Val Phe Ser Tyr Asp Ala Ile
                325                 330                 335
Ser Tyr Tyr Lys Ile Phe Ser Asp Lys Asp Gly Tyr Lys His Ile His
                340                 345                 350
Tyr Ile Lys Asp Thr Val Glu Asn Ala Ile Gln Ile Thr Ser Gly Lys
                355                 360                 365
Trp Glu Ala Ile Asn Ile Phe Arg Val Thr Gln Asp Ser Leu Phe Tyr
                370                 375                 380
Ser Ser Asn Glu Phe Glu Asp Tyr Pro Gly Arg Arg Asn Ile Tyr Arg
385                 390                 395                 400
Ile Ser Ile Gly Ser Tyr Pro Pro Ser Lys Lys Cys Val Thr Cys His
                405                 410                 415
Leu Arg Lys Glu Arg Cys Gln Tyr Tyr Thr Ala Ser Phe Ser Asp Tyr
                420                 425                 430
```

Ala Lys Tyr Tyr Ala Leu Val Cys Tyr Gly Pro Gly Ile Pro Ile Ser
        435                 440                 445

Thr Leu His Asp Gly Arg Thr Asp Gln Glu Ile Lys Ile Leu Glu Glu
        450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
        515                 520                 525

Val Asn Trp Ile Ser Tyr Leu Ala Ser Lys Glu Gly Met Val Ile Ala
        530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
        610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
        690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His
            740                 745

<210> SEQ ID NO 322
<211> LENGTH: 2247
<212> TYPE: DNA
<213> ORGANISM: Artificial Sequence
<220> FEATURE:
<223> OTHER INFORMATION: Cynomolgus FAP ectodomain+poly-lys-tag+his6-tag
      (DNA)

<400> SEQUENCE: 322
cgccctccaa gagttcataa ctctgaagaa aatacaatga gagcactcac actgaaggat      60
attttaaatg ggacattttc ttataaaaca ttttttccaa actggatttc aggacaagaa     120
tatcttcatc aatctgcaga taacaatata gtactttata atattgaaac aggacaatca     180
tataccattt tgagtaacag aaccatgaaa agtgtgaatg cttcaaatta tggcttatca     240

```
cctgatcggc aatttgtata tctagaaagt gattattcaa agctttggag atactcttac    300
acagcaacat attacatcta tgaccttagc aatggagaat ttgtaagagg aaatgagctt    360
cctcgtccaa ttcagtattt atgctggtcg cctgttggga gtaaattagc atatgtctat    420
caaaacaata tctatttgaa acaaagacca ggagatccac cttttcaaat aacatttaat    480
ggaagagaaa ataaaatatt taatggaatc ccagactggg tttatgaaga ggaaatgctt    540
gctacaaaat atgctctctg gtggtctcct aatggaaaat ttttggcata tgcggaattt    600
aatgatacag atataccagt tattgcctat cctattatg gcgatgaaca atatcccaga     660
acaataaata ttccataccc aaaggccgga gctaagaatc cttttgttcg gatatttatt    720
atcgatacca cttaccctgc gtatgtaggt ccccaggaag tgcctgttcc agcaatgata    780
gcctcaagtg attattattt cagttggctc acgtgggtta ctgatgaacg agtatgtttg    840
cagtggctaa aaagagtcca gaatgtttcg gtcttgtcta tatgtgattt cagggaagac    900
tggcagacat gggattgtcc aaagacccag gagcatatag aagaaagcag aactggatgg    960
gctggtggat tctttgtttc aacaccagtt ttcagctatg atgccatttc atactacaaa   1020
atatttagtg acaaggatgg ctacaaacat attcactata tcaaagacac tgtggaaaat   1080
gctattcaaa ttacaagtgg caagtgggag gccataaata tattcagagt aacacaggat   1140
tcactgtttt attctagcaa tgaatttgaa gattaccctg gaagaagaaa catctacaga   1200
attagcattg gaagctatcc tccaagcaag aagtgtgtta cttgccatct aaggaaagaa   1260
aggtgccaat attacacagc aagtttcagc gactacgcca agtactatgc acttgtctgc   1320
tatggcccag gcatccccat tccacccctt catgacggac gcactgatca agaaattaaa   1380
atcctggaag aaaacaagga attggaaaat gctttgaaaa atatccagct gcctaaagag   1440
gaaattaaga aacttgaagt agatgaaatt actttatggt acaagatgat tcttcctcct   1500
caatttgaca gatcaaagaa gtatcccttg ctaattcaag tgtatggtgg tccctgcagt   1560
cagagtgtaa ggtctgtatt tgctgttaat tggatatctt atcttgcaag taaggaaggg   1620
atggtcattg ccttggtgga tggtcgggga acagctttcc aaggtgacaa actcctgtat   1680
gcagtgtatc gaaagctggg tgtttatgaa gttgaagacc agattacagc tgtcagaaaa   1740
ttcatagaaa tgggttttcat tgatgaaaaa agaatagcca tgggggctg gtcctatgga   1800
ggatatgttt catcactggc ccttgcatct ggaactggtc ttttcaaatg tgggatagca   1860
gtggctccag tctccagctg gaatattac gcgtctgtct acacagagag attcatgggt   1920
ctcccaacaa aggatgataa tcttgagcac tataagaatt caactgtgat ggcaagagca   1980
gaatatttca gaaatgtaga ctatcttctc atccacggaa cagcagatga taatgtgcac   2040
tttcaaaact cagcacagat tgctaaagct ctggttaatg cacaagtgga tttccaggca   2100
atgtggtact ctgaccagaa ccacggctta tccggcctgt ccacgaacca cttatacacc   2160
cacatgaccc acttcctaaa gcagtgtttc tctttgtcag acggcaaaaa gaaaagaaa   2220
aagggccacc accatcacca tcactga                                       2247
```

<210> SEQ ID NO 323
<211> LENGTH: 19
<212> TYPE: PRT
<213> ORGANISM: Artificial Sequence
<220> FEATURE:
<223> OTHER INFORMATION: Leader Sequence 1

<400> SEQUENCE: 323

Met Asp Trp Thr Trp Arg Ile Leu Phe Leu Val Ala Ala Ala Thr Gly
1               5                   10                  15

Ala His Ser

<210> SEQ ID NO 324
<211> LENGTH: 57
<212> TYPE: DNA
<213> ORGANISM: Artificial Sequence
<220> FEATURE:
<223> OTHER INFORMATION: Leader Sequence 1 (DNA1)

<400> SEQUENCE: 324
atggactgga cctggagaat cctcttcttg gtggcagcag ccacaggagc ccactcc        57

<210> SEQ ID NO 325
<211> LENGTH: 57
<212> TYPE: DNA
<213> ORGANISM: Artificial Sequence
<220> FEATURE:
<223> OTHER INFORMATION: Leader Sequence 1 (DNA 2)

<400> SEQUENCE: 325
atggactgga cctggaggat cctcttcttg gtggcagcag ccacaggagc ccactcc        57

<210> SEQ ID NO 326
<211> LENGTH: 22
<212> TYPE: PRT
<213> ORGANISM: Artificial Sequence
<220> FEATURE:
<223> OTHER INFORMATION: Leader Sequence 2

<400> SEQUENCE: 326

Met Asp Met Arg Val Pro Ala Gln Leu Leu Gly Leu Leu Leu Leu Trp
1               5                   10                  15

Phe Pro Gly Ala Arg Cys
            20

<210> SEQ ID NO 327
<211> LENGTH: 66
<212> TYPE: DNA
<213> ORGANISM: Artificial Sequence
<220> FEATURE:
<223> OTHER INFORMATION: Leader Sequence 2 (DNA)

<400> SEQUENCE: 327
atggacatga gggtccccgc tcagctcctg ggcctcctgc tgctctggtt cccaggtgcc     60
aggtgt                                                                66

<210> SEQ ID NO 328
<211> LENGTH: 19
<212> TYPE: PRT
<213> ORGANISM: Artificial Sequence
<220> FEATURE:
<223> OTHER INFORMATION: Leader Sequence 3

<400> SEQUENCE: 328

Met Gly Trp Ser Cys Ile Ile Leu Phe Leu Val Ala Thr Ala Thr Gly
1               5                   10                  15

Val His Ser

<210> SEQ ID NO 329
<211> LENGTH: 57
<212> TYPE: DNA
<213> ORGANISM: Artificial Sequence

```
<220> FEATURE:
<223> OTHER INFORMATION: Leader Sequence 3 (DNA 1)

<400> SEQUENCE: 329
atgggatgga gctgtatcat cctcttcttg gtagcaacag ctaccggtgt gcattcc      57

<210> SEQ ID NO 330
<211> LENGTH: 57
<212> TYPE: DNA
<213> ORGANISM: Artificial Sequence
<220> FEATURE:
<223> OTHER INFORMATION: Leader Sequence 3 (DNA 1)

<400> SEQUENCE: 330
atgggctggt cctgcatcat cctgtttctg gtggctaccg ccactggagt gcattcc      57

<210> SEQ ID NO 331
<211> LENGTH: 57
<212> TYPE: DNA
<213> ORGANISM: Artificial Sequence
<220> FEATURE:
<223> OTHER INFORMATION: Leader Sequence 3 (DNA 3)

<400> SEQUENCE: 331
atgggctggt cctgcatcat cctgtttctg gtcgccacag ccaccggcgt gcactct      57

<210> SEQ ID NO 332
<211> LENGTH: 26
<212> TYPE: DNA
<213> ORGANISM: Artificial Sequence
<220> FEATURE:
<223> OTHER INFORMATION: LMB3

<400> SEQUENCE: 332
caggaaacag ctatgaccat gattac                                        26

<210> SEQ ID NO 333
<211> LENGTH: 63
<212> TYPE: DNA
<213> ORGANISM: Artificial Sequence
<220> FEATURE:
<223> OTHER INFORMATION: LibL1b_new
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 333
cactttggtc ccctggccga acgtmnnggg mnnmnnmnna ccctgctgac agtaatacac   60
tgc                                                                 63

<210> SEQ ID NO 334
<211> LENGTH: 28
<212> TYPE: DNA
<213> ORGANISM: Artificial Sequence
<220> FEATURE:
```

<223> OTHER INFORMATION: MS63

<400> SEQUENCE: 334
tttcgcacag taatatacgg ccgtgtcc                                28

<210> SEQ ID NO 335
<211> LENGTH: 25
<212> TYPE: DNA
<213> ORGANISM: Artificial Sequence
<220> FEATURE:
<223> OTHER INFORMATION: MS64

<400> SEQUENCE: 335
acgttcggcc aggggaccaa agtgg                                   25

<210> SEQ ID NO 336
<211> LENGTH: 60
<212> TYPE: DNA
<213> ORGANISM: Artificial Sequence
<220> FEATURE:
<223> OTHER INFORMATION: Lib2H
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 336
ggccgtatat tactgtgcga aannknnknn knnknnkttt gactactggg gccaaggaac    60

<210> SEQ ID NO 337
<211> LENGTH: 30
<212> TYPE: DNA
<213> ORGANISM: Artificial Sequence
<220> FEATURE:
<223> OTHER INFORMATION: fdseqlong

<400> SEQUENCE: 337
gacgttagta aatgaatttt ctgtatgagg                              30

<210> SEQ ID NO 338
<211> LENGTH: 69
<212> TYPE: DNA
<213> ORGANISM: Artificial Sequence
<220> FEATURE:
<223> OTHER INFORMATION: RJH_LIB3
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t

<400> SEQUENCE: 338
gactttggtg ccctggccaa acgtmnnggg mnnmnnaccm nnctgcaagc agtaataggt      60
ggcaaaatc                                                             69

<210> SEQ ID NO 339
<211> LENGTH: 27
<212> TYPE: DNA
<213> ORGANISM: Artificial Sequence
<220> FEATURE:
<223> OTHER INFORMATION: RJH31

<400> SEQUENCE: 339
acgtttggcc agggcaccaa agtcgag                                         27

<210> SEQ ID NO 340
<211> LENGTH: 28
<212> TYPE: DNA
<213> ORGANISM: Artificial Sequence
<220> FEATURE:
<223> OTHER INFORMATION: RJH32

<400> SEQUENCE: 340
tctcgcacag taatacacgg cggtgtcc                                        28

<210> SEQ ID NO 341
<211> LENGTH: 94
<212> TYPE: DNA
<213> ORGANISM: Artificial Sequence
<220> FEATURE:
<223> OTHER INFORMATION: LIB88_2
<220> FEATURE:
<221> NAME/KEY: misc_difference
<222> LOCATION: (29)..(55)
<223> OTHER INFORMATION: (33% GAC Asp; 26% GGT Gly; 10% GAA Glu; 9% CGT
      Arg; 7% Lys; 6% GTT Val; 5% TCT Ser; 4% CTG Leu)1 - (23% GGT Gly;
      17% TAC Tyr; 16% TCT Ser; 11% GCT Ala; 9% CGT Arg; 7% AAC Asn; 6%
      ACT Thr; 6% GTT Val; 5% CCG Pro)8
<220> FEATURE:
<221> NAME/KEY: misc_feature
<222> LOCATION: (30)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

```
<220> FEATURE:
<221> NAME/KEY: misc_feature
<222> LOCATION: (53)..(54)
<223> OTHER INFORMATION: n is a, c, g, or t

<400> SEQUENCE: 341
ggacaccgcc gtgtattact gtgcgagabn nnnbnnbnnb nnbnnbnnbn nbnnbtttga    60
ctactggggc caagggacca ccgtgaccgt ctcc                               94

<210> SEQ ID NO 342
<211> LENGTH: 60
<212> TYPE: DNA
<213> ORGANISM: Artificial Sequence
<220> FEATURE:
<223> OTHER INFORMATION: DPK22_CDR1_rand_ba_opt

<400> SEQUENCE: 342
caggtttctg ctggtaccag gctaagtagc tgctgctaac actctgactg gccctgcaag    60

<210> SEQ ID NO 343
<211> LENGTH: 25
<212> TYPE: DNA
<213> ORGANISM: Artificial Sequence
<220> FEATURE:
<223> OTHER INFORMATION: DPK22_CDR1_fo

<400> SEQUENCE: 343
ttagcctggt accagcagaa acctg                                          25

<210> SEQ ID NO 344
<211> LENGTH: 27
<212> TYPE: DNA
<213> ORGANISM: Artificial Sequence
<220> FEATURE:
<223> OTHER INFORMATION: DPK22_Ck_BsiWI_ba

<400> SEQUENCE: 344
ggtgcagcca ccgtacgttt gatttcc                                        27

<210> SEQ ID NO 345
<211> LENGTH: 59
<212> TYPE: DNA
<213> ORGANISM: Artificial Sequence
<220> FEATURE:
<223> OTHER INFORMATION: DPK22_CDR2_rand_ba

<400> SEQUENCE: 345
ctgtctggga tgccagtggc cctgctggag gcgccataga tgaggagcct gggagcctg     59

<210> SEQ ID NO 346
<211> LENGTH: 23
<212> TYPE: DNA
<213> ORGANISM: Artificial Sequence
<220> FEATURE:
<223> OTHER INFORMATION: DPK22_CDR2_fo

<400> SEQUENCE: 346
agggccactg gcatcccaga cag                                            23

<210> SEQ ID NO 347
<211> LENGTH: 26
<212> TYPE: DNA
<213> ORGANISM: Artificial Sequence
<220> FEATURE:
<223> OTHER INFORMATION: RJH53
```

```
<400> SEQUENCE: 347
catcagggcc tgagctcgcc cgtcac                                              26

<210> SEQ ID NO 348
<211> LENGTH: 52
<212> TYPE: DNA
<213> ORGANISM: Artificial Sequence
<220> FEATURE:
<223> OTHER INFORMATION: DP47_CDR1_rand_ba_opt

<400> SEQUENCE: 348
gagcctggcg gacccagctc atggcataac tgctaaaggt gaatccggag gc                 52

<210> SEQ ID NO 349
<211> LENGTH: 22
<212> TYPE: DNA
<213> ORGANISM: Artificial Sequence
<220> FEATURE:
<223> OTHER INFORMATION: DP47_CDR1_fo

<400> SEQUENCE: 349
atgagctggg tccgccaggc tc                                                  22

<210> SEQ ID NO 350
<211> LENGTH: 26
<212> TYPE: DNA
<213> ORGANISM: Artificial Sequence
<220> FEATURE:
<223> OTHER INFORMATION: MS52

<400> SEQUENCE: 350
gaagaccgat gggcctttgg tgctag                                              26

<210> SEQ ID NO 351
<211> LENGTH: 73
<212> TYPE: DNA
<213> ORGANISM: Artificial Sequence
<220> FEATURE:
<223> OTHER INFORMATION: DP47_CDR2_rand_ba

<400> SEQUENCE: 351
ccttcacgga gtctgcgtag tatgtgctac caccactacc actaatagct gagacccact         60
ccagcccctt ccc                                                            73

<210> SEQ ID NO 352
<211> LENGTH: 25
<212> TYPE: DNA
<213> ORGANISM: Artificial Sequence
<220> FEATURE:
<223> OTHER INFORMATION: DP47_CDR2_fo

<400> SEQUENCE: 352
acatactacg cagactccgt gaagg                                               25
```

ANTI-FAP ANTIBODIES AND METHODS OF USE

CROSS REFERENCE TO RELATED APPLICATIONS

This application is a divisional of U.S. patent application Ser. No. 13/205,743, filed on Aug. 9, 2011, which claims the benefit of European Patent Application No. 10172842.6, filed on Aug. 13, 2010, the disclosures of which are incorporated herein by reference in their entirety.

FIELD OF THE INVENTION

The present invention relates to antibodies specific for Fibroblast Activation Protein (FAP). In addition, the invention relates to polynucleotides encoding such antibodies, and vectors and host cells comprising such polynucleotides. The invention further relates to methods for producing the antibodies and methods of using them in the treatment of disease.

BACKGROUND

Fibroblast Activation Protein (FAP) and Anti-FAP Antibodies

Human Fibroblast Activation Protein (FAP; GenBank Accession Number AAC51668), also known as Seprase, is a 170 kDa integral membrane serine peptidase (EC 3.4.21.B28). Together with dipeptidyl peptidase IV (also known as CD26; GenBank Accession Number P27487), a closely related cell-surface enzyme, and other peptidases, FAP belongs to the dipeptidyl peptidase IV family (Yu et al., FEBS J 277, 1126-1144 (2010)). It is a homodimer containing two N-glycosylated subunits with a large C-terminal extracellular domain, in which the enzyme's catalytic domain is located (Scanlan et al., Proc Natl Acad Sci USA 91, 5657-5661 (1994)). FAP, in its glycosylated form, has both post-prolyl dipeptidyl peptidase and gelatinase activities (Sun et al., Protein Expr Purif 24, 274-281 (2002)).

Human FAP was originally identified in cultured fibroblasts using the monoclonal antibody (mAb) F19 (described in WO 93/05804, ATCC Number HB 8269). Homologues of the protein were found in several species, including mice (Niedermeyer et al., Int J Cancer 71, 383-389 (1997), Niedermeyer et al., Eur J Biochem 254, 650-654 (1998); GenBank Accession Number AAH19190). FAP has a unique tissue distribution: its expression was found to be highly upregulated on reactive stromal fibroblasts of more than 90% of all primary and metastatic epithelial tumors, including lung, colorectal, bladder, ovarian and breast carcinomas, while it is generally absent from normal adult tissues (Rettig et al., Proc Natl Acad Sci USA 85, 3110-3114 (1988); Garin-Chesa et al., Proc Natl Acad Sci USA 87, 7235-7239 (1990)). Subsequent reports showed that FAP is not only expressed in stromal fibroblasts but also in some types of malignant cells of epithelial origin, and that FAP expression directly correlates with the malignant phenotype (Jin et al., Anticancer Res 23, 3195-3198 (2003)).

Due to its expression in many common cancers and its restricted expression in normal tissues, FAP has been considered a promising antigenic target for imaging, diagnosis and therapy of a variety of carcinomas. Thus, multiple monoclonal antibodies have been raised against FAP for research, diagnostic and therapeutic purposes.

Sibrotuzumab/BIBH1, a humanized version of the F19 antibody that specifically binds to human FAP (described in WO 99/57151), and further humanized or fully human antibodies against the FAP antigen with F19 epitope specificity (described in Mersmann et al., Int J Cancer 92, 240-248 (2001); Schmidt et al., Eur J Biochem 268, 1730-1738 (2001); WO 01/68708)) were developed. The OS4 antibody is another humanized (CDR-grafted) version of the F19 antibody (Wüest et al., J Biotech 92, 159-168 (2001), while scFv 33 and scFv 36 have a different binding specificity from F19 and are cross-reactive for the human and mouse FAP protein (Brocks et al., Mol Med 7, 461-469 (2001)). More recently, other murine anti-FAP antibodies, as well as chimeric and humanized versions thereof, were developed (WO 2007/077173, Ostermann et al., Clin Cancer Res 14, 4584-4592 (2008)).

Proteases in the tumor stroma, through proteolytic degradation of extracellular matrix (ECM) components, facilitate processes such as angiogenesis and/or tumor cell migration. Moreover, the tumor stroma plays an important role in nutrient and oxygen supply of tumors, as well as in tumor invasion and metastasis. These essential functions make it not only a diagnostic but also a potential therapeutic target.

Evidence for the feasibility of the concept of tumor stroma targeting in vivo using anti-FAP antibodies was obtained in a phase I clinical study with $^{131}$iodine-labeled F19 antibody, which demonstrated specific enrichment of the antibody in the tumors and detection of metastases (Welt et al., J Clin Oncol 12, 1193-1203 (1994). Similarly, a phase I study with sibrotuzumab demonstrated specific tumor accumulation of the $^{131}$I-labeled antibody (Scott et al., Clin Cancer Res 9, 1639-1647 (2003)). An early phase II trial of unconjugated sibrotuzumab in patients with metastatic colorectal cancer, however, was discontinued due to the lack of efficacy of the antibody in inhibiting tumor progression (Hofheinz et al., Onkologie 26, 44-48 (2003)). Also a more recently developed anti-FAP antibody failed to show anti-tumor effects in vivo in unconjugated form (WO 2007/077173).

Thus, there remains a need for enhanced therapeutic approaches, including antibodies with improved efficacy, targeting FAP for the treatment of cancers.

Antibody Glycosylation

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions (Jenkins et al., Nature Biotechnol 14, 975-81 (1996)).

IgG1 type antibodies, the most commonly used antibodies in cancer immunotherapy, are glycoproteins that have a conserved N-linked glycosylation site at Asn 297 in each CH2 domain. The two complex biantennary oligosaccharides attached to Asn 297 are buried between the CH2 domains, forming extensive contacts with the polypeptide backbone, and their presence is essential for the antibody to mediate effector functions such as antibody dependent cell-mediated cytotoxicity (ADCC) (Lifely et al., Glycobiology 5, 813-822 (1995); Jefferis et al., Immunol Rev 163, 59-76 (1998); Wright and Morrison, Trends Biotechnol 15, 26-32 (1997)). Protein engineering studies have shown that FcγRs interact with the lower hinge region of the IgG CH2 domain. Lund et al., *J. Immunol.* 157:4963-69 (1996). However, FcγR binding also requires the presence of the oligosaccharides in the CH2 region. Lund et al., *J. Immunol.* 157:4963-69 (1996); Wright and Morrison, *Trends Biotech.* 15:26-31 (1997), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction between IgG1 and FcγR, and to increase ADCC activity of IgG1s.

A way to obtain large increases in the potency of monoclonal antibodies, is to enhance their natural, cell-mediated effector functions by engineering their oligosaccharide component as described in Umaña et al., Nat Biotechnol 17, 176-180 (1999) and U.S. Pat. No. 6,602,684 (WO 99/54342), the contents of which are hereby incorporated by reference in their entirety. Umaña et al. showed that overexpression of β(1,4)-N-acetylglucosaminyltransferase III (GnTIII), a glycosyltransferase catalyzing the formation of bisected oligosaccharides, in Chinese hamster ovary (CHO) cells significantly increases the in vitro ADCC activity of antibodies produced in those cells. Overexpression of GnTIII in production cell lines leads to antibodies enriched in bisected oligosaccharides, which are generally also non-fucosylated and of the hybrid type. If in addition to GnTIII, mannosidase II (ManII) is overexpressed in production cell lines, antibodies enriched in bisected, non-fucosylated oligosaccharides of the complex type are obtained (Ferrara et al., Biotechn Bioeng 93, 851-861 (2006)). Both types of antibodies show strongly enhanced ADCC, as compared to antibodies with unmodified glycans, but only antibodies in which the majority of the N-glycans are of the complex type are able to induce significant complement-dependent cytotoxicity (Ferrara et al., Biotechn Bioeng 93, 851-861 (2006)). Alterations in the composition of the Asn 297 carbohydrate or its elimination also affect binding of the antibody Fc-domain to Fcγ-receptor (FcγR) and complement C1q protein, which is important for ADCC and CDC, respectively (Umaña et al., Nat Biotechnol 17, 176-180 (1999); Davies et al., Biotechnol Bioeng 74, 288-294 (2001); Mimura et al., J Biol Chem 276, 45539-45547 (2001); Radaev et al., J Biol Chem 276, 16478-16483 (2001); Shields et al., J Biol Chem 276, 6591-6604 (2001); Shields et al., J Biol Chem 277, 26733-26740 (2002); Simmons et al., J Immunol Methods 263, 133-147 (2002)).

BRIEF SUMMARY OF THE INVENTION

The present invention provides antibodies that specifically bind to Fibroblast Activation Protein (FAP), having a high affinity and/or enhanced effector function.

In one aspect, the invention is directed to an antibody that specifically binds FAP, comprising at least one (i.e. one, two, three, four, five or six) of the complementarity determining regions (CDRs) set forth in SEQ ID NOs 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175 and 177. In one embodiment, the antibody comprises three heavy chain CDRs (i.e. HCDR1, HCDR2, and HCDR3) and/or three light chain CDRs (i.e. LCDR1, LCDR2, and LCDR3) selected from SEQ ID NOs 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175 and 177. In a more specific embodiment, the antibody comprises an antibody heavy chain variable region and/or an antibody light chain variable region, particularly both a heavy and light chain variable region, selected from the heavy and light chain variable region sequences set forth in SEQ ID NOs 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309 and 311.

In a particular embodiment, the invention is directed to an antibody that specifically binds to FAP, wherein the antibody comprises at least one heavy or light chain complementarity determining region (CDR) selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177, or a combination thereof.

In one particular embodiment, the invention is directed to an antibody which comprises a heavy chain variable region comprising (a) a heavy chain CDR1 selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, and SEQ ID NO: 33; (b) a heavy chain CDR2 selected from the group of SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, and SEQ ID NO: 133; and (c) a heavy chain CDR3 selected from the group of SEQ ID NO: 135, SEQ ID NO: 137, SEQ ID NO: 139, and SEQ ID NO: 141.

In a particular embodiment, the invention is directed to an antibody which comprises a light chain variable region comprising (a) a light chain CDR1 selected from the group of SEQ ID NO: 143, SEQ ID NO: 145, SEQ ID NO: 147, and SEQ ID NO: 149; (b) a light chain CDR2 selected from the group of SEQ ID NO: 151, SEQ ID NO: 153, SEQ ID NO: 155, SEQ ID NO: 157, SEQ ID NO: 159, and SEQ ID NO: 161; and (c) a light chain CDR3 selected from the group of SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177.

In a particular embodiment, the invention is directed to an antibody which comprises a heavy chain variable region comprising (a) a heavy chain CDR1 selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, and SEQ ID NO: 33; (b) a heavy chain CDR2 selected from the group of SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, and SEQ ID NO: 133; and (c) a heavy chain CDR3 selected from the group of SEQ ID NO: 135, SEQ ID NO: 137, SEQ ID NO: 139, and SEQ ID NO: 141; and a light chain variable region comprising (d) a light chain CDR1 selected from the group of SEQ ID NO: 143, SEQ ID NO: 145, SEQ ID NO: 147, and SEQ ID NO: 149; (e) a light chain CDR2 selected from the group of SEQ ID NO: 151, SEQ ID NO: 153, SEQ ID NO: 155, SEQ ID NO: 157, SEQ ID NO: 159, and SEQ ID NO: 161; and (f) a light chain CDR3 selected from the group of SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177. In one embodiment, the antibody comprises at least one heavy or light chain CDR which is not a CDR selected from the group of SEQ ID NO: 3, SEQ ID NO: 5, SEQ ID NO: 13, SEQ ID NO: 15, SEQ ID NO: 23, SEQ ID NO: 25, SEQ ID NO: 27, SEQ ID NO: 35, SEQ ID NO: 37, SEQ ID NO: 39, SEQ ID NO: 41, SEQ ID NO: 69, SEQ ID NO: 71, SEQ ID NO: 73, SEQ ID NO: 75, SEQ ID NO: 101, SEQ ID NO: 103, SEQ ID NO: 105, SEQ ID NO: 107, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, and SEQ ID NO: 175.

In a particular embodiment, the invention is directed to an antibody which comprises a heavy chain variable region comprising an amino acid sequence selected from the group of: SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311.

In a particular embodiment, the invention is directed to an antibody which comprises a light chain variable region comprising an amino acid sequence selected from the group of: SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309.

In a particular embodiment, the invention is directed to an antibody which comprises a heavy chain variable region comprising an amino acid sequence selected from the group of: SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311; and a light chain variable region comprising an amino acid sequence selected from the group of: SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309. In one embodiment, the antibody comprises at least one heavy or light chain variable region which does not comprise an amino acid sequence selected from the group of SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, and SEQ ID NO: 255.

In one embodiment, the antibody comprises an Fc region, particularly an IgG Fc region. In a further embodiment, the antibody is a full-length antibody, particularly an IgG class antibody. In another embodiment, the antibody comprises a human antibody constant region. In one embodiment, the antibody is human. In one embodiment, the antibody is glycoengineered to have modified oligosaccharides in the Fc region. In one embodiment the antibody has an increased proportion of non-fucosylated and/or bisected oligosaccharides in the Fc region, as compared to a non-glycoengineered antibody. In a further embodiment, the antibody has increased effector function and/or increased Fc receptor binding affinity. In a particular embodiment, the increased effector function is increased antibody-dependent cell-mediated cytotoxicity (ADCC). In another embodiment the antibody binds to FAP with a $K_D$ value of lower than about 1 µM, preferably lower than about 100 nM, most preferably lower than about 1 nM or even lower than about 0.1 nM. In one embodiment, the antibody is affinity matured. In one embodiment, the antibody binds to FAP in human tissues. In one embodiment, the antibody does not induce internalization of FAP.

In other aspects, the invention is also directed to polypeptides, polynucleotides, host cells, and expression vectors related to the antibodies. In a further aspect, the invention relates to methods of making the antibodies. In a further aspect, the invention is directed to methods of using the antibodies, particularly for the treatment of diseases characterized by expression of FAP, such as cancer.

BRIEF DESCRIPTION OF THE FIGURES

FIGS. 6A1, 6A2, 6A3, 6B1, 6B2, 6B3, 6C1, 6C2, and 6C3 show SPR-based kinetic analyses of 3F2 (FIG. 6A1, 6A2, 6A3), 4G8 (FIG. 6B1, 6B2, 6B3) and 3D9 (FIG. 6C1, 6C2, 6C3) anti-FAP antibodies binding as Fab fragments to human, mouse and cynomolgus FAP. Processed kinetic data sets are presented, smooth lines represent a global fit of the data to a 1:1 interaction model.

FIGS. 7A1, 7A2, 7A3, 7B1, 7B2, 7B3, 7C1, 7C2, and 7C3 show SPR-based kinetic analyses of 3F2 (FIG. 7A1, 7A2, 7A3), 4G8 (FIG. 7B1, 7B2, 7B3) and 3D9 (FIG. 7C1, 7C2, 7C3) anti-FAP antibodies binding as human IgG to human, mouse and cynomolgus FAP. Processed kinetic data sets are presented, smooth lines represent a global fit of the data to a 1:1 interaction model.

FIGS. 8A1, 8A2, 8B1, 8B2, 8C1, 8C2, 8D1 and 8D2 show a representative pictures of human samples of (FIG. 8A1) non-small cell lung cancer (NSCLC) immunohistochemically stained for FAP using 2F3 mouse IgG2a antibody, (FIG. 8B1) colon adenocarcinoma immunohistochemically stained for FAP using 2F3 mouse IgG2a antibody, (FIG. 8C1) colon adenocarcinoma immunohistochemically stained for FAP using 3D9 mouse IgG2a antibody, and (FIG. 8D1) colon adenocarcinoma immunohistochemically stained for FAP using 4G8 mouse IgG2a antibody. FAP is detected in the tumor stroma in all samples and by all antibodies (left panels (FIG. 8A1, FIG. 8B1, FIG. 8C1, FIG. 8D1), while no staining is observed for the isotype control antibody (right panels (FIG. 8A2, FIG. 8B2, FIG. 8C2, FIG. 8D2)).

FIGS. 9A and 9B show binding of human IgG1 anti-FAP antibodies to FAP expressed on HEK 293 cells stably transfected with human (FIG. 9A) or murine (FIG. 9B) FAP, as determined by FACS.

FIGS. 13A and 13B show expression levels of FAP on the surface of GM05389 lung fibroblasts at different time points after incubation with the anti-FAP human IgG1 antibodies 3F2 or 4G8, as determined by FACS. No significant decrease in FAP expression levels, indicating internalization of FAP, was observed. Secondary antibody alone is shown as negative control.

FIGS. 14A1, 14A2, 14A3, 14A4, 14B1, 14B2, 14B3, 14B4, 14C1, 14C2, 14C3, 14C4, 14D1, 14D2, 14D3, and 14D4 present representative immunofluorescence images showing plasma membrane staining on GM05389 lung fibroblasts obtained after binding of anti-FAP 4G8 IgG for 45 min at 4° C. (FIG. 14A1), for 20 min at 37° C. (FIG. 14B1), for 1 hour at 37° C. (FIG. 14C1) or for 6 hours at 37° C. (FIG. 14D1). The anti-CD20 antibody GA101, used as isotype control, shows background staining (FIG. 14A3, FIG. 14B3, FIG. 14C3, FIG. 14D3). EEA1 labels early endosomes (FIG. 14A2, FIG. 14B2, FIG. 14C2, FIG. 14D2;

GA101 isotype control is shown in FIG. 14A4, FIG. 14B4, FIG. 14C4, FIG. 14D4)). Note the persistence of the FAP surface plasma membrane staining up to 6 hours after anti-FAP 4G8 antibody binding.

Figure 15A:
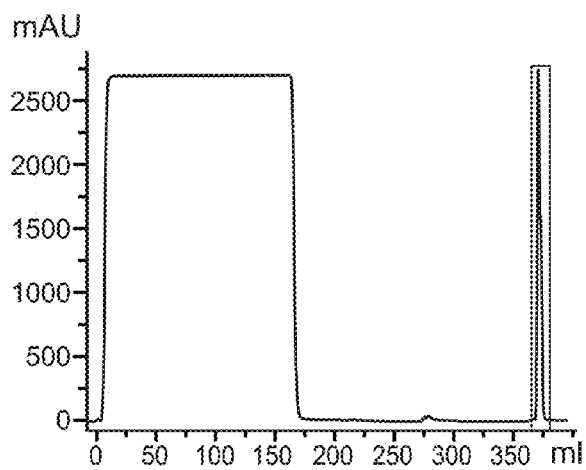
Figure 15C:
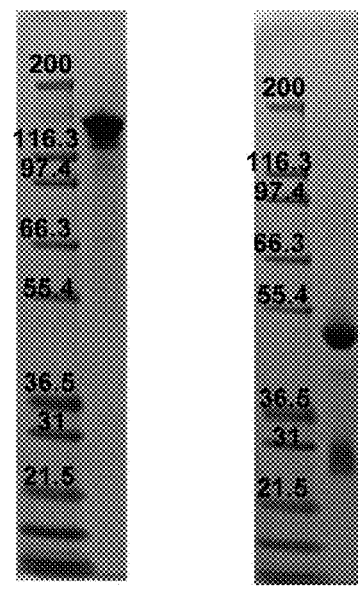
Figure 15B:
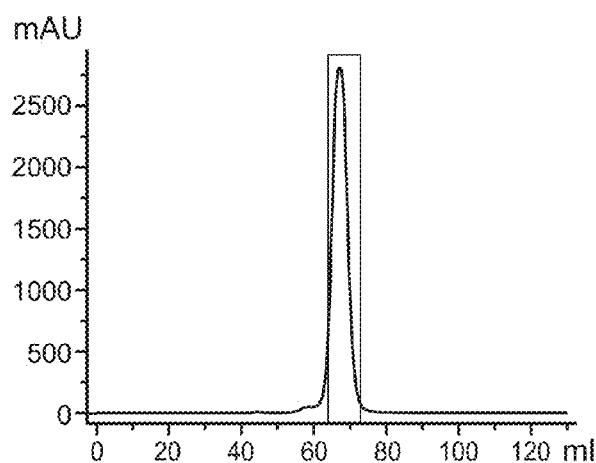
Figure 15D:
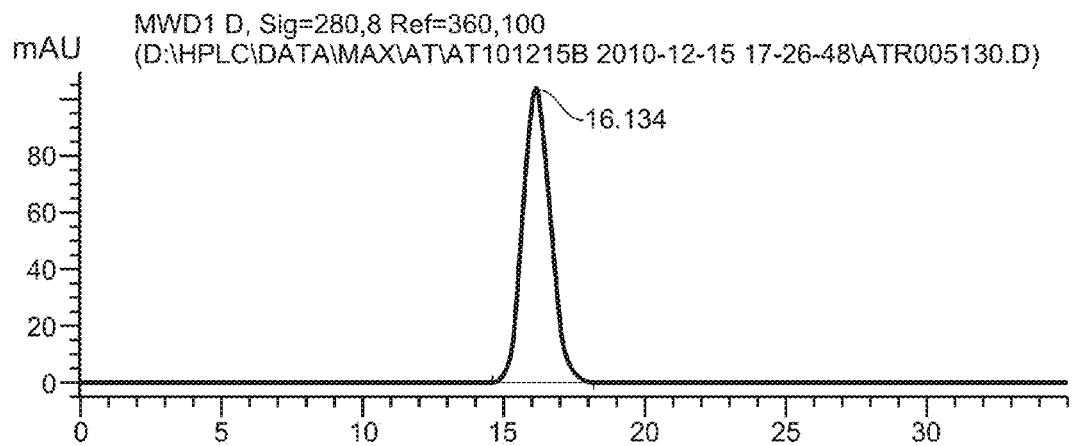

FIGS. 15A, 15B, 15C, and 15D show the purification and analysis of the wild-type 28H1 human IgG. FIG. 15A) Protein A affinity chromatography purification step. FIG. 15B) Size exclusion chromatography purification step. FIG. 15C) Analytical SDS PAGE. FIG. 15D) Analytical size exclusion chromatography. Experimental procedures are described in Example 1.

Figure 16A:
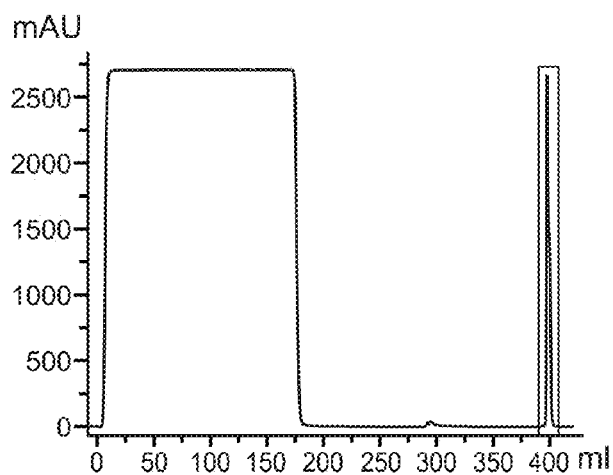
Figure 16C:
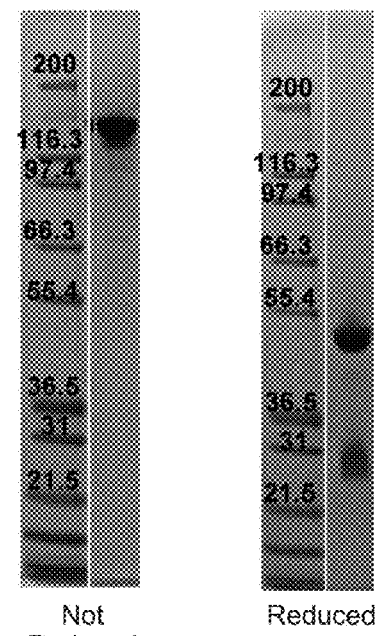
Figure 16B:
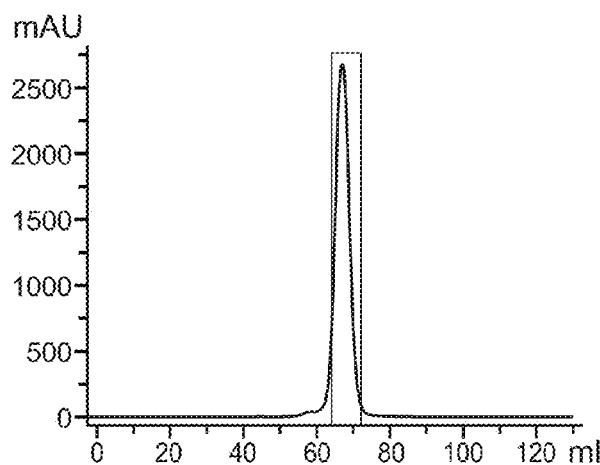
Figure 16D:
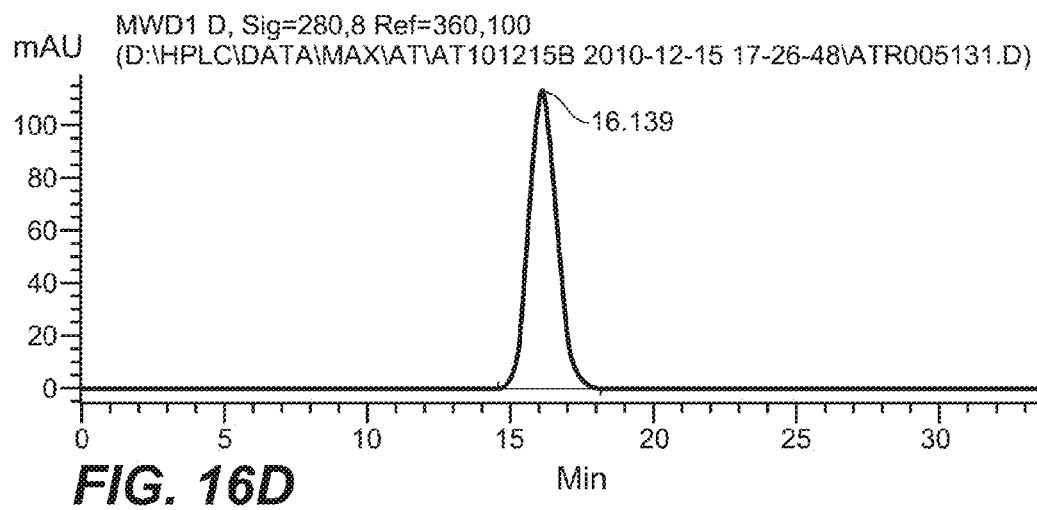

FIGS. 16A, 16B, 16C, and 16D show the purification and analysis of the glycoengineered 28H1 human IgG. FIG. 16A) Protein A affinity chromatography purification step. FIG. 16B) Size exclusion chromatography purification step. FIG. 16C) Analytical SDS PAGE. FIG. 16D) Analytical size exclusion chromatography. Experimental procedures are described in Example 1.

Figure 17A:
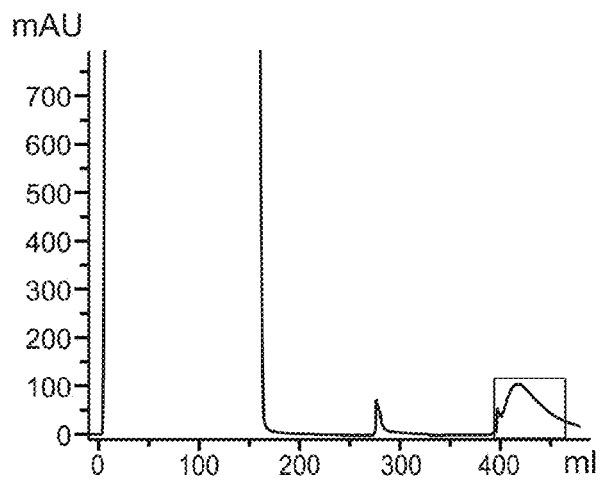
Figure 17C:
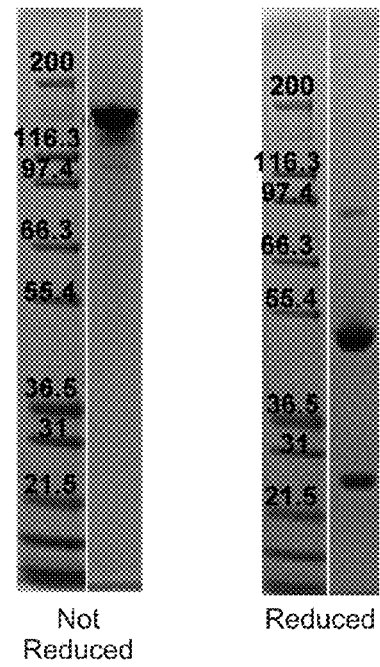
Figure 17B:
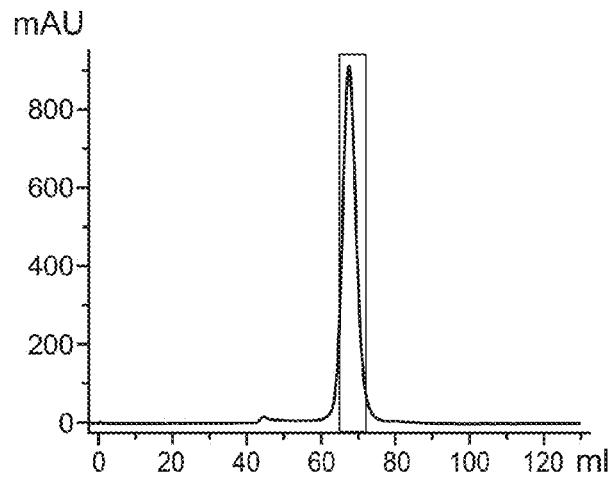
Figure 17D:
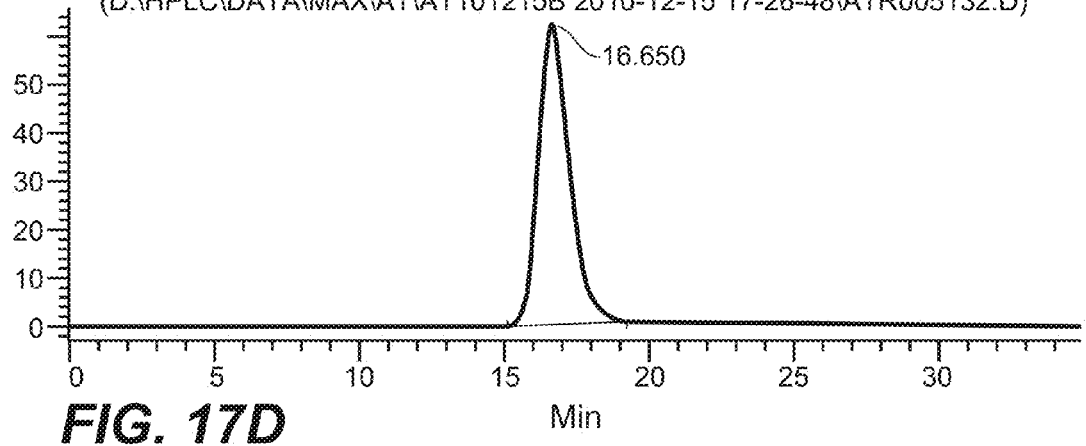

FIGS. 17A, 17B, 17C, and 17D show the purification and analysis of the wild-type 29B11 human IgG. FIG. 17A) Protein A affinity chromatography purification step. FIG. 17B) Size exclusion chromatography purification step. FIG. 17C) Analytical SDS PAGE. FIG. 17D) Analytical size exclusion chromatography. Experimental procedures are described in Example 1.

Figure 18A:
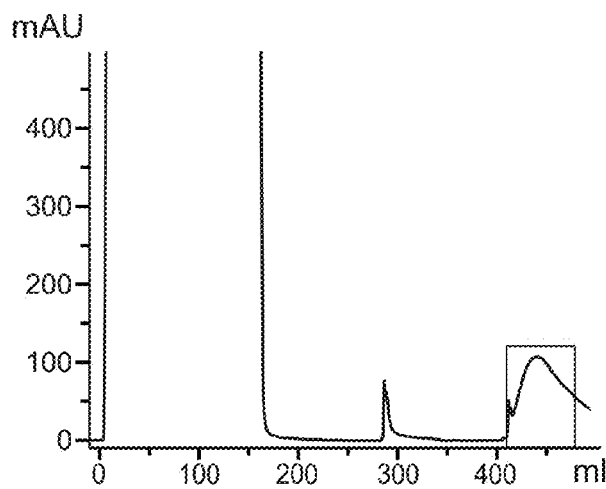
Figure 18B:
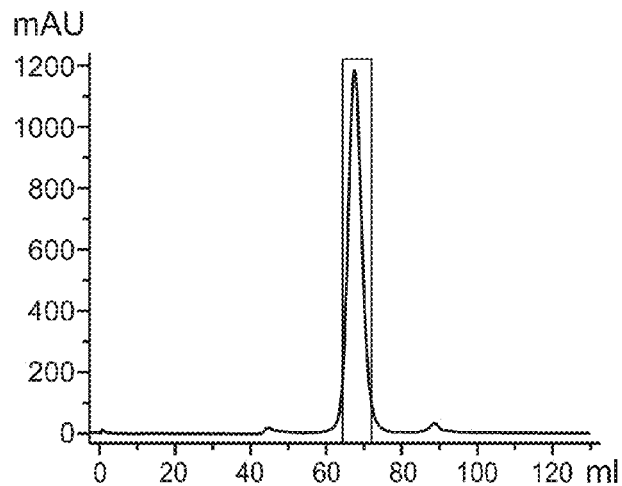
Figure 18C:
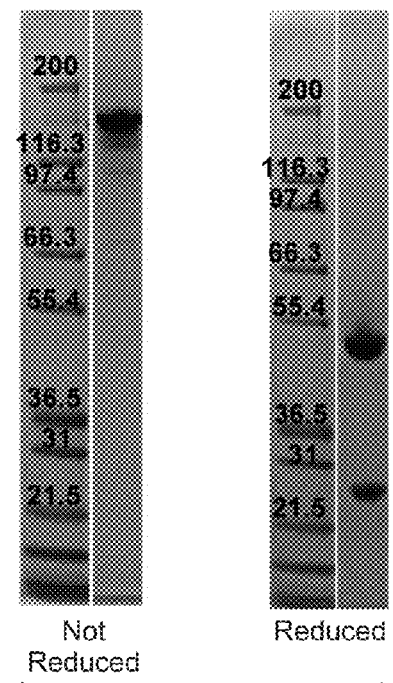
Figure 18D:
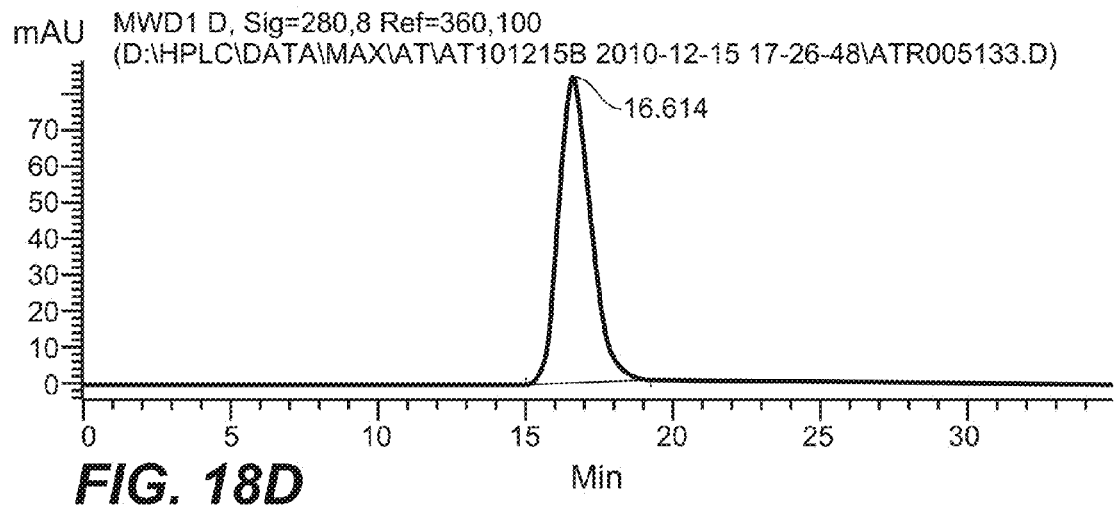

FIGS. 18A, 18B, 18C, and 18D show the purification and analysis of the glycoengineered 29B11 human IgG. FIG. 18A) Protein A affinity chromatography purification step. FIG. 18B) Size exclusion chromatography purification step. FIG. 18C) Analytical SDS PAGE. FIG. 18D) Analytical size exclusion chromatography. Experimental procedures are described in Example 1.

Figure 19A:
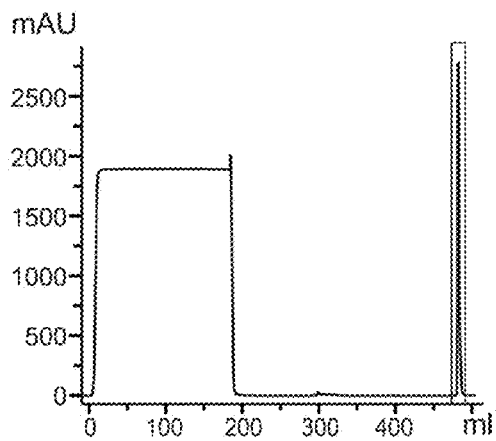
Figure 19B:
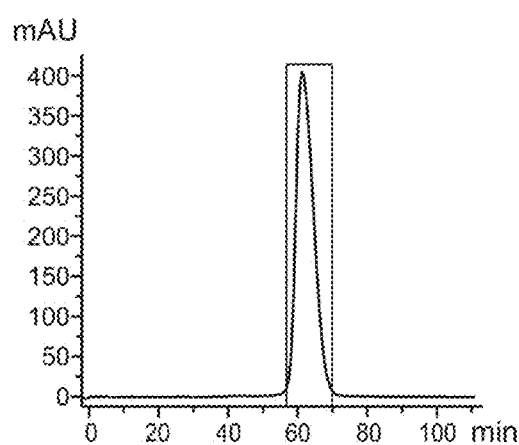
Figure 19C:
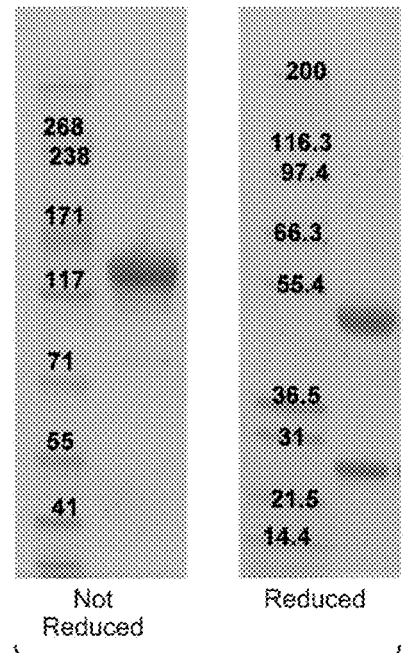
Figure 19D:
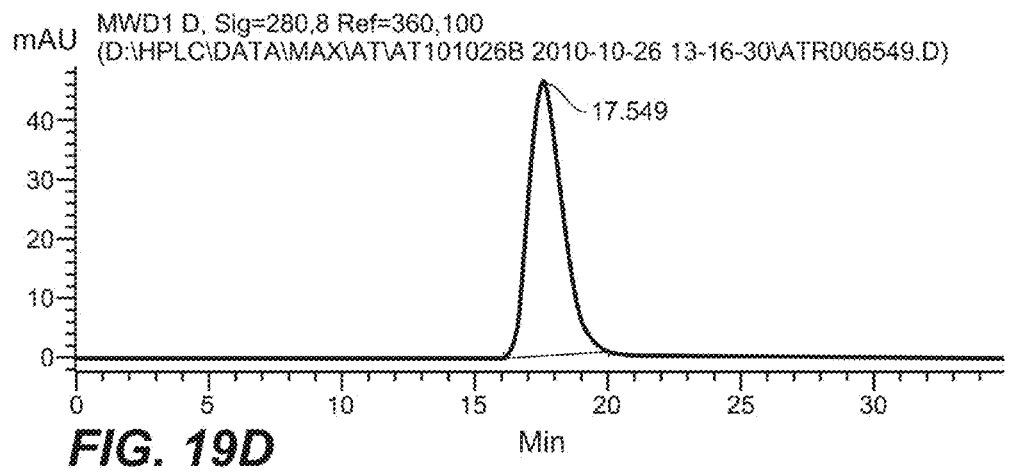

FIGS. 19A, 19B, 19C, and 19D show the purification and analysis of the wild-type 3F2 human IgG. FIG. 19A) Protein A affinity chromatography purification step. FIG. 19B) Size exclusion chromatography purification step. FIG. 19C) Analytical SDS PAGE. FIG. 19D) Analytical size exclusion chromatography. Experimental procedures are described in Example 1.

FIGS. 20A, 20B, 20C, and 20D show the purification and analysis of the glycoengineered 3F2 human IgG. FIG. 20A) Protein A affinity chromatography purification step. FIG. 20B) Size exclusion chromatography purification step. FIG. 20C) Analytical SDS PAGE. FIG. 20D) Analytical size exclusion chromatography. Experimental procedures are described in Example 1.

Figure 21A:
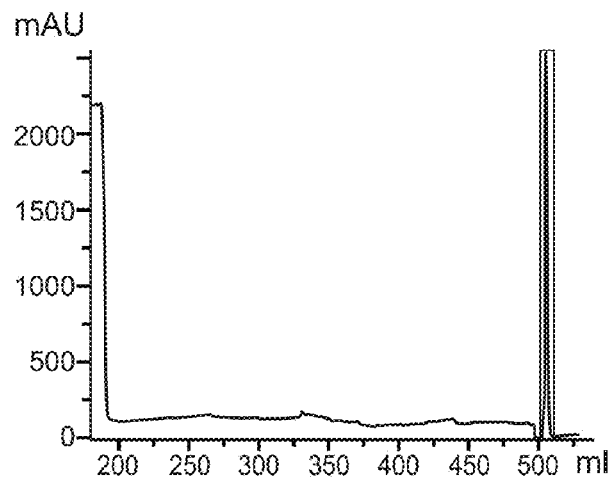
Figure 21C:
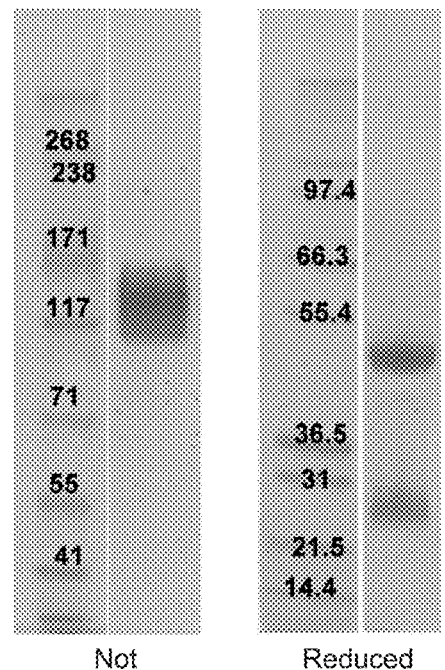
Figure 21B:
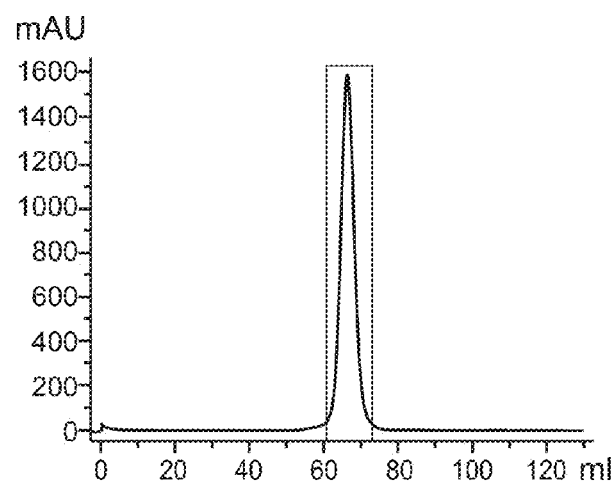
Figure 21D:
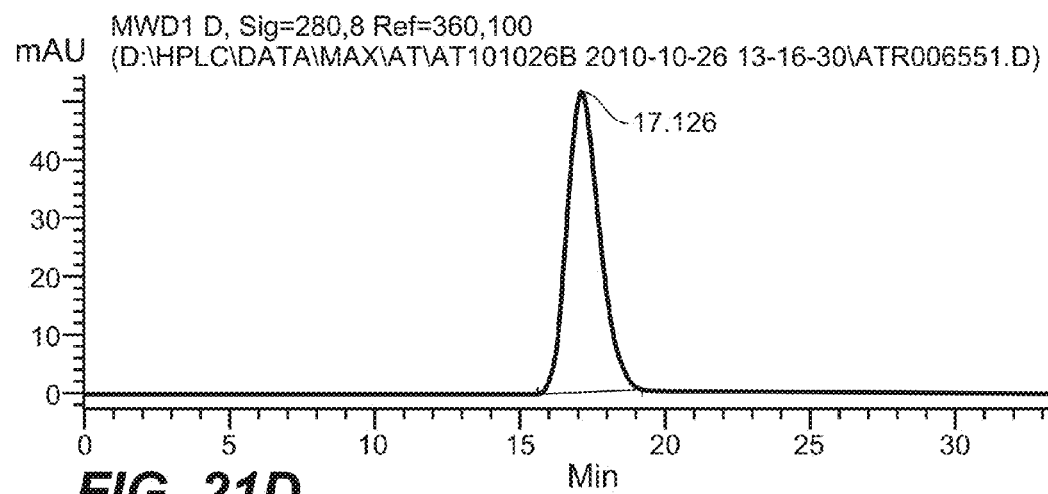

FIGS. 21A, 21B, 21C, and 21D show the purification and analysis of the wild-type 4G8 human IgG. FIG. 21A) Protein A affinity chromatography purification step. FIG. 21B) Size exclusion chromatography purification step. FIG. 21C) Analytical SDS PAGE. FIG. 21D) Analytical size exclusion chromatography. Experimental procedures are described in Example 1.

Figure 22A:
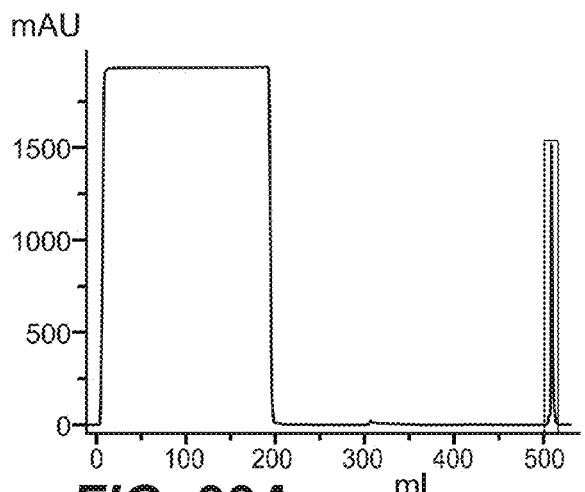
Figure 22B:
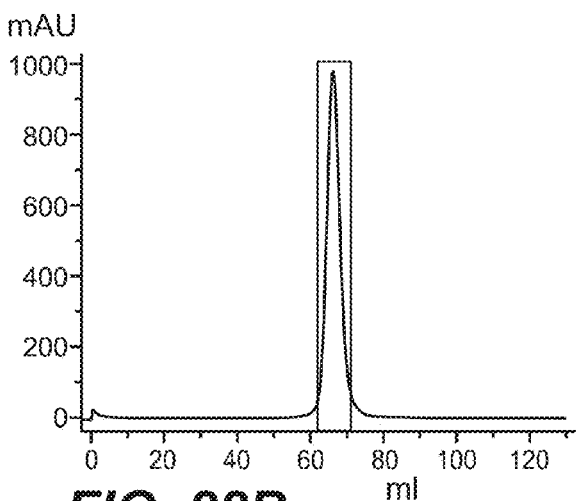
Figure 22C:
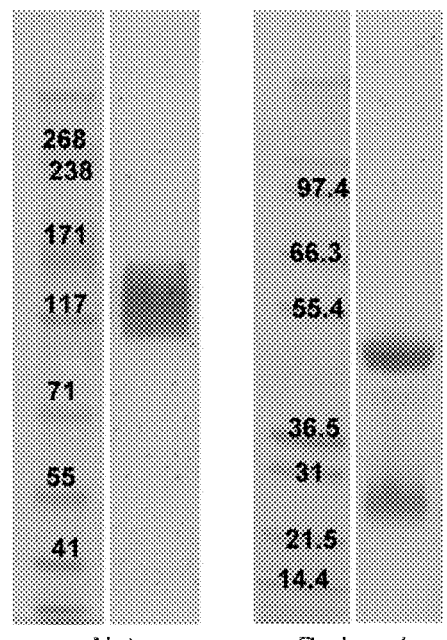
Figure 22D:
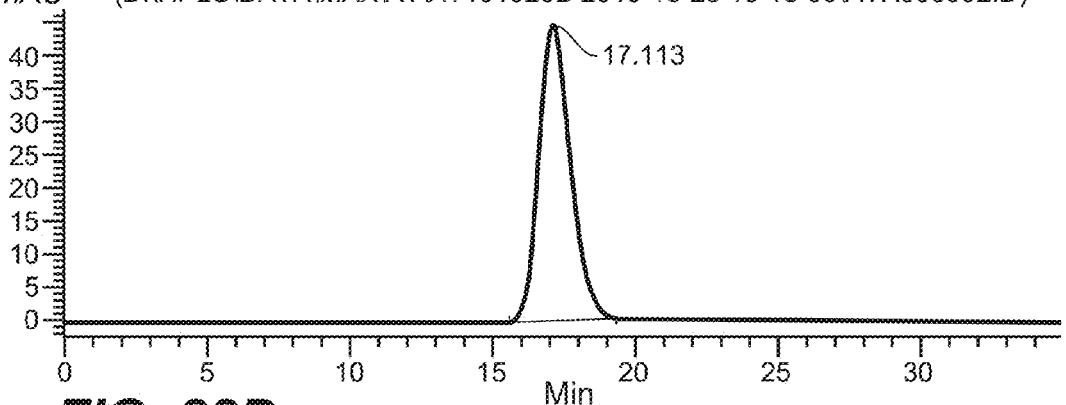

FIGS. 22A, 22B, 22C, and 22D show the purification and analysis of the glycoengineered 4G8 human IgG. FIG. 22A) Protein A affinity chromatography purification step. FIG. 22B) Size exclusion chromatography purification step. FIG. 22C) Analytical SDS PAGE. FIG. 22D) Analytical size exclusion chromatography. Experimental procedures are described in Example 1.

Figure 23:
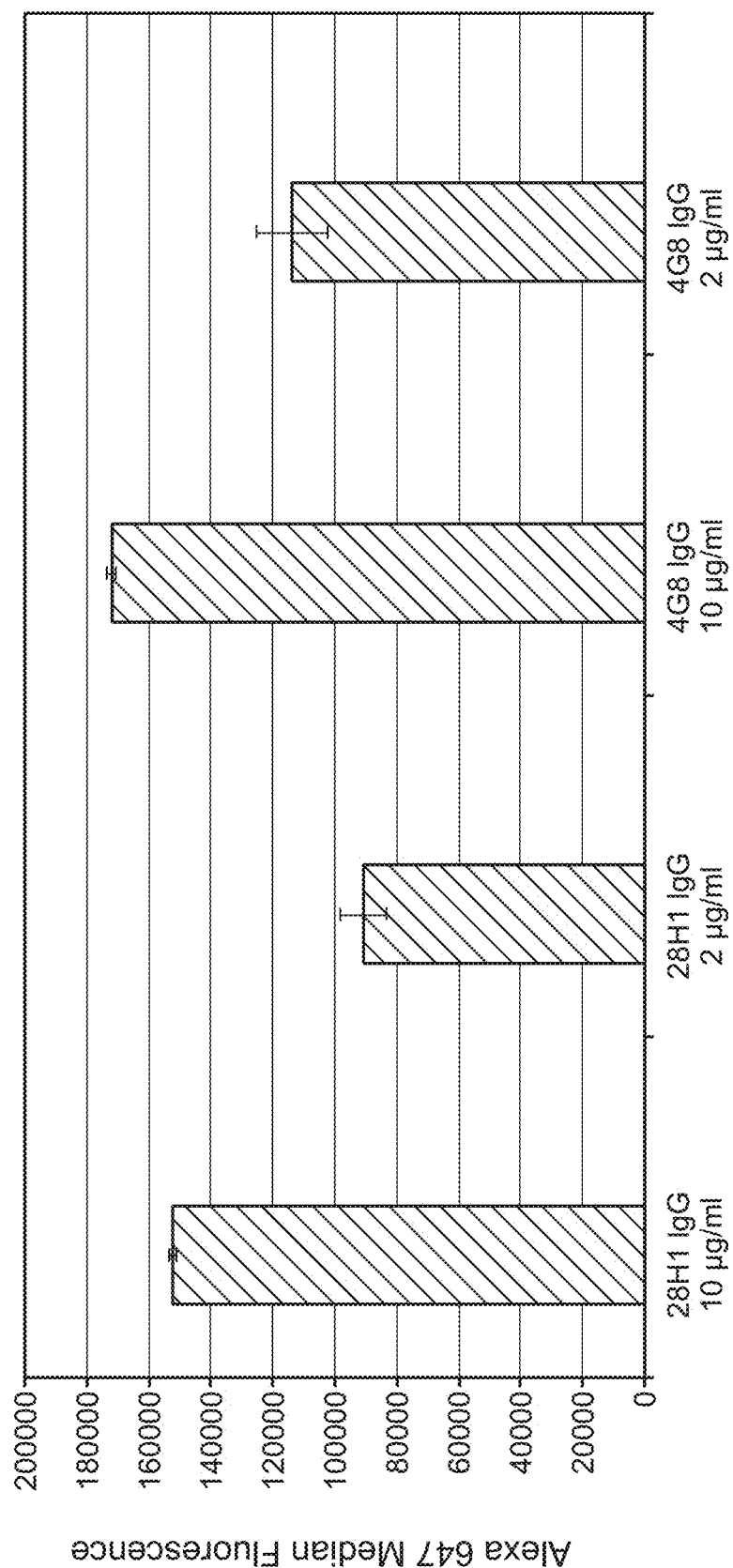

FIG. 23 shows binding of affinity matured anti-FAP antibody 28H1 to human FAP on HEK293 cells compared to binding of the parental 4G8 anti-FAP antibody.

Figure 24:
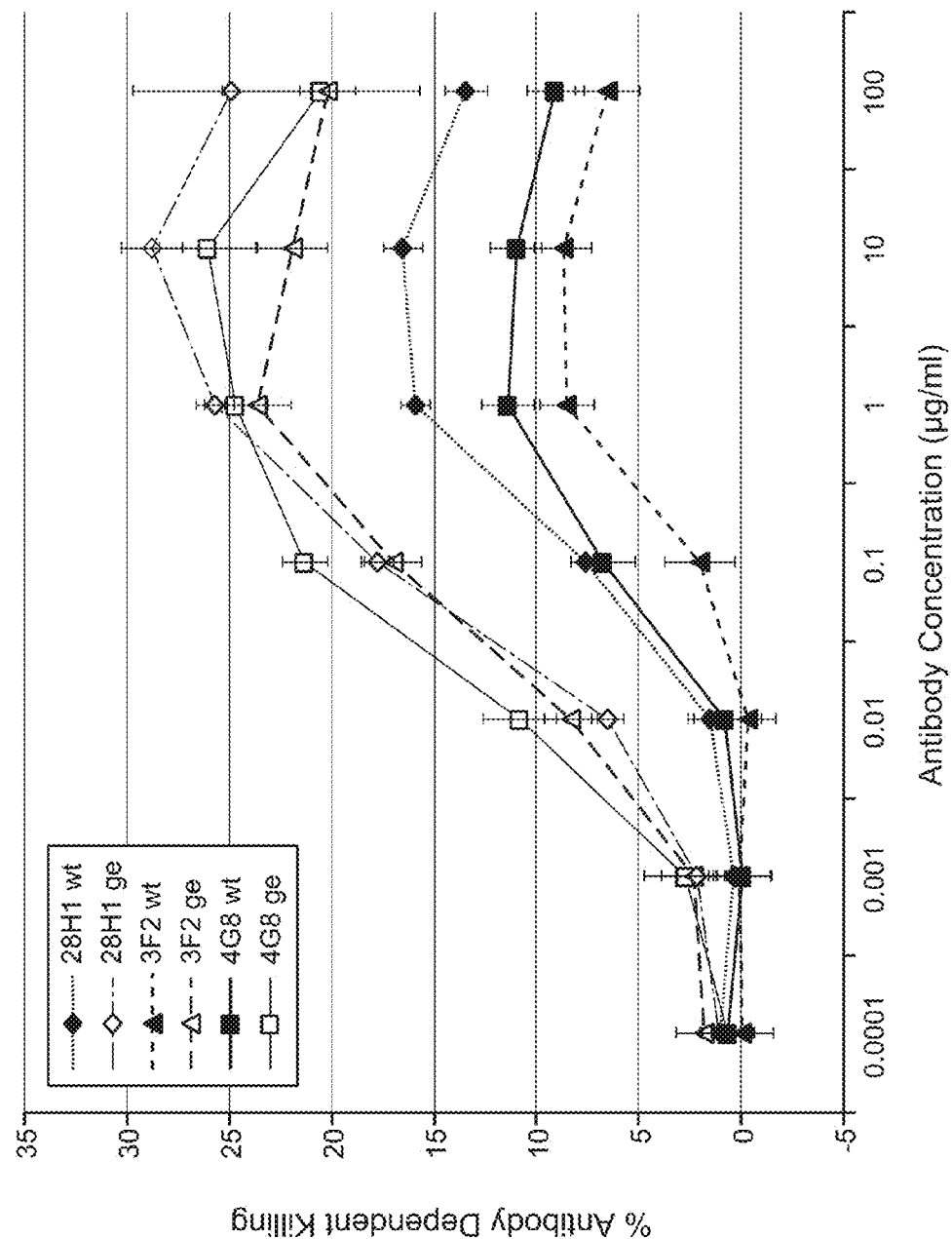

FIG. 24 shows the results of an LDH release assay to test ADCC mediated by the anti-FAP IgG antibodies 28H1 (affinity matured) and 4G8, 3F8 (parentals) as wildtype (wt) and glycoengineered (ge) versions, with HEK293-hFAP as target cells and PBMNCs as effector cells (F/F FcγRIIIa genotype).

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. Specific illustrative and exemplary embodiments for measuring binding affinity are described in the following.

An "affinity matured" antibody refers to an antibody with one or more alterations (e.g. amino acid mutations) in one or more hypervariable regions (HVRs) (e.g. CDRs), compared to a parent antibody which does not possess such alterations, such alterations resulting in an improvement in the affinity of the antibody for antigen. Typically, the affinity matured antibody binds to the same epitope as the parent antibody.

The terms "anti-FAP antibody" and "an antibody that binds to Fibroblast Activation Protein (FAP)" refer to an antibody that is capable of binding FAP with sufficient affinity such that the antibody is useful as a diagnostic and/or therapeutic agent in targeting FAP. In one embodiment, the extent of binding of an anti-FAP antibody to an unrelated, non-FAP protein is less than about 10% of the binding of the antibody to FAP as measured, e.g., by a radioimmunoassay (RIA) or flow cytometry (FACS). In one embodiment, the extent of binding of an anti-FAP antibody of the invention to DPPIV, a protein closely related to FAP (also known as CD26; GenBank Accession Number P27487), is less than about 15%, about 10% or about 5% of the binding of the antibody to FAP as measured by FACS. In certain embodiments, an antibody that binds to FAP has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-FAP antibody binds to an epitope of FAP that is conserved among FAP from different species.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity. Also included are antibody fragments having an Fc region, and fusion proteins that comprise a region equivalent to the Fc region of an immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, single-chain antibody molecules (e.g. scFv), diabodies, and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species. For chimeric antibodies, for example, the non-antigen binding components may be derived from a wide variety of species, including primates such as chimpanzees and humans. Humanized antibodies are a particularly preferred form of chimeric antibodies.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; cytokine secretion; immune-complex-mediated antigen uptake by antigen presenting cells; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

"Framework" or "FR" refers to variable domain residues other than hypervariable region (HVR) (or CDR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In one embodiment, the host cell is engineered to allow the production of an antibody with modified oligosaccharides. In certain embodiments, the host cells have been further manipulated to express increased levels of one or more polypeptides having β(1,4)-N-acetylglucosaminyltransferase III (GnTIII) activity. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

CDRs also comprise "specificity determining residues," or "SDRs," which are residues that contact antigen. SDRs are contained within regions of the CDRs called abbreviated-CDRs, or a-CDRs. In general, only one-fifth to one-third of the residues in a given CDR participate in antigen binding. The specificity-determining residues in a particular CDR can be identified by, for example, computation of interatomic contacts from three-dimensional modeling and determination of the sequence variability at a given residue position in accordance with the methods described in Padlan et al., *FASEB J.* 9(1):133-139 (1995). Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro and Fransson, *Front. Biosci.* 13:1619-1633 (2008).)

An "antibody conjugate" is an antibody conjugated to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., *J. Chromatogr. B* 848:79-87 (2007).

An "isolated" polynucleotide refers to a polynucleotide molecule that has been separated from a component of its natural environment. An isolated polynucleotide includes a polynucleotide molecule contained in cells that ordinarily contain the polynucleotide molecule, but the polynucleotide molecule is present extrachromosomally or at a chromosomal location that is different from its natural chromosomal location.

"Isolated polynucleotide encoding an anti-FAP antibody" refers to one or more polynucleotide molecules encoding antibody heavy and light chains (or fragments thereof), including such polynucleotide molecule(s) in a single vector or separate vectors, and such polynucleotide molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The light chain of an antibody may be assigned to one of two types, called kappa (κ) and lambda (λ), based on the amino acid sequence of its constant domain.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount selected from the group consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

The term "package insert" is used to refer to instructions customarily included in commercial packages of therapeutic products, that contain information about the indications, usage, dosage, administration, combination therapy, contraindications and/or warnings concerning the use of such therapeutic products.

The term "parent" antibody refers to an antibody that is used as the starting point or basis for the preparation of a variant.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Similarly, by a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide or polypeptide is at least 80%, 85%, 90%, 95%, 96%, 97%, 98% or 99% identical to a nucleotide sequence or polypeptide sequence of the present invention can be determined conventionally using known computer programs, such as the ones listed above. The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "Fibroblast Activation Protein (FAP)" as used herein, refers to any native FAP from any vertebrate source, including mammals such as primates (e.g. humans, see GenBank Accession Number AAC51668) and rodents (e.g., mice, see GenBank Accession Number AAH19190), unless otherwise indicated. The term encompasses "full-length," unprocessed FAP as well as any form of FAP that results from processing in the cell. The term also encompasses naturally occurring variants of FAP, e.g., splice variants or allelic variants. Preferably, an anti-FAP antibody of the invention binds to the extracellular domain of FAP. The amino acid sequence of exemplary human, mouse and cynomolgus monkey FAP ectodomains (with a C-terminal poly-lysine and 6× His-tag) are shown in SEQ ID NO: 317, SEQ ID NO: 319, and SEQ ID NO: 321 respectively.

As used herein, "treatment" (and grammatical variations thereof such as "treat" or "treating") refers to clinical intervention in an attempt to alter the natural course of disease of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the term "polypeptide having GnTIII activity" refers to polypeptides that are able to catalyze the addition of a N-acetylglucosamine (GlcNAc) residue in β-1-4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependence in a given activity as compared to the GnTIII (i.e., the candidate polypeptide will exhibit greater activity or not more than about 25-fold less and, preferably, not more than about tenfold less activity, and most preferably, not more than about three-fold less activity relative to the GnTIII).

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

As used herein, the term "Fc-mediated cellular cytotoxicity" includes antibody-dependent cell-mediated cytotoxicity (ADCC) and cellular cytotoxicity mediated by a soluble Fc-fusion protein containing a human Fc-region. It is an immune mechanism leading to the lysis of "targeted cells" by "human immune effector cells."

As used herein, the term "human immune effector cells" refers to a population of leukocytes that display Fc receptors on their surfaces, through which they bind to the Fc-region of antibodies or of Fc-fusion proteins and perform effector functions. Such a population may include, but is not limited to, peripheral blood mononuclear cells (PBMC) and/or natural killer (NK) cells.

As used herein, the term "targeted cells" refers to cells to which antigen binding molecules comprising an Fc region (e.g., antibodies or fragments thereof comprising an Fc region) or Fc-fusion proteins specifically bind. The antigen binding molecules or Fc fusion-proteins bind to target cells via the protein part that is N-terminal to the Fc region.

As used herein, the term "increased Fc-mediated cellular cytotoxicity" is defined as either an increase in the number of "targeted cells" that are lysed in a given time, at a given concentration of antibody or of Fc-fusion protein in the medium surrounding the target cells, by the mechanism of Fc-mediated cellular cytotoxicity defined above, and/or a reduction in the concentration of antibody or of Fc-fusion protein, in the medium surrounding the target cells, required to achieve the lysis of a given number of "targeted cells," in a given time, by the mechanism of Fc-mediated cellular cytotoxicity. The increase in Fc-mediated cellular cytotoxicity is relative to the cellular cytotoxicity mediated by the same antigen binding molecule or Fc-fusion protein produced by the same type of host cells, using the same standard production, purification, formulation and storage methods, (which are known to those skilled in the art) but that has not been produced by host cells engineered to have an altered pattern of glycosylation (e.g., to express the glycosyltransferase, GnTIII, or other glycosyltransferases) by the methods described herein.

By "antibody having increased antibody dependent cell-mediated cytotoxicity (ADCC)" is meant an antibody, as that term is defined herein, having increased ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at $5 \times 10^6$ cells/ml in RPMI cell culture medium;
   ii) the target cells are grown by standard tissue culture methods, harvested from the exponential growth phase with a viability higher than 90%, washed in RPMI cell culture medium, labeled with 100 micro-Curies of $^{51}$Cr, washed twice with cell culture medium, and resuspended in cell culture medium at a density of $10^5$ cells/ml;
   iii) 100 microliters of the final target cell suspension above are transferred to each well of a 96-well microtiter plate;
   iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
   v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
   vi) for the spontaneous release (SR) controls, 3 additional wells in the plate containing the labeled target cells, receive 50 microliters of RPMI cell culture medium instead of the antibody solution (point iv above);
   vii) the 96-well microtiter plate is then centrifuged at $50 \times g$ for 1 minute and incubated for 1 hour at 4° C.;
   viii) 50 microliters of the PBMC suspension (point i above) are added to each well to yield an effector:target cell ratio of 25:1 and the plates are placed in an incubator under 5% $CO_2$ atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER−MR)/(MR−SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

II. Compositions And Methods

Fibroblast Activation Protein (FAP) is expressed in the majority of tumors but essentially absent from healthy adult tissues, thus antibodies targeting this antigen have great therapeutic potential. The present invention provides antibodies that bind to FAP, in particular antibodies with high affinity and strong effector functions. Antibodies of the invention are useful, e.g., for the diagnosis or treatment of diseases characterized by expression of FAP, such as cancer.

A. Exemplary Anti-FAP Antibodies

The present invention provides for antibodies that specifically bind to Fibroblast Activation Protein (FAP). Particularly, the present invention provides for antibodies that specifically bind FAP, wherein said antibodies are glycoengineered to have increased effector function.

In one embodiment, an anti-FAP antibody of the invention comprises at least one (e.g. one, two, three, four, five, or six) heavy or light chain complementarity determining region (CDR) selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177, or a variant or truncated form thereof containing at least the specificity-determining residues (SDRs) for said CDR.

In one embodiment, said at least one CDR is a heavy chain CDR, particularly a heavy chain CDR3 selected from the group of SEQ ID NO: 135, SEQ ID NO: 137, SEQ ID NO: 139, and SEQ ID NO: 141. In another embodiment, the antibody comprises at least one heavy chain CDR and at least one light chain CDR, particularly a heavy chain CDR3 selected from the group of SEQ ID NO: 135, SEQ ID NO: 137, SEQ ID NO: 139, and SEQ ID NO: 141, and a light chain CDR3 selected from the group of SEQ ID NO: 163, SEQ ID NO: 165, SEQ ID NO: 167, SEQ ID NO: 169, SEQ ID NO: 171, SEQ ID NO: 173, SEQ ID NO: 175 and SEQ ID NO: 177.

In one embodiment, an antibody of the invention comprises at least one, at least two, or all three heavy chain CDR (HCDR) sequences selected from (a) HCDR1 comprising an amino acid sequence selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, and SEQ ID NO: 33; (b) HCDR2 comprising an amino acid sequence selected from the group of SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, and SEQ ID NO: 133; and (c) HCDR3 comprising an amino acid sequence selected from the group of SEQ ID NO: 135, SEQ ID NO: 137, SEQ ID NO: 139, and SEQ ID NO: 141.

In a further embodiment, the antibody comprises a heavy chain variable region comprising (a) a heavy chain CDR1 selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, and SEQ ID NO: 33; (b) a heavy chain CDR2 selected from the group of SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, and SEQ ID NO: 133; and (c) a heavy chain CDR3 selected from the group of SEQ ID NO: 135, SEQ ID NO: 137, SEQ ID NO: 139, and SEQ ID NO: 141, or variants or truncated forms thereof containing at least the SDRs for said CDRs.

In one embodiment, an antibody of the invention comprises at least one, at least two, or all three light chain CDR (LCDR) sequences selected from (a) LCDR1 comprising an amino acid sequence selected from the group of SEQ ID NO: 143, SEQ ID NO: 145, SEQ ID NO: 147, and SEQ ID NO: 149; (b) LCDR2 comprising an amino acid sequence selected from the group of SEQ ID NO: 151, SEQ ID NO: 153, SEQ ID NO: 155, SEQ ID NO: 157, SEQ ID NO: 159, and SEQ ID NO: 161; and (c) LCDR3 comprising an amino acid sequence selected from the group of SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177. In a further embodiment, the antibody comprises a light chain variable region comprising (a) a light chain CDR1 selected from the group of SEQ ID NO: 143, SEQ ID NO: 145, SEQ ID NO: 147, and SEQ ID NO: 149; (b) a light chain CDR2 selected from the group of SEQ ID NO: 151, SEQ ID NO: 153, SEQ ID NO: 155, SEQ ID NO: 157, SEQ ID NO: 159, and SEQ ID NO: 161; and (c) a light chain CDR3 selected from the group of SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177, or variants or truncated forms thereof containing at least the SDRs for said CDRs.

In a more specific embodiment, an antibody of the invention comprises a heavy chain variable region comprising a heavy chain CDR1 selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, and SEQ ID NO: 33; a heavy chain CDR2 selected from the group of SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, and SEQ ID NO: 133; and a heavy chain CDR3 selected from the group of SEQ ID NO:

135, SEQ ID NO: 137, SEQ ID NO: 139, and SEQ ID NO: 141, and a light chain variable region comprising a light chain CDR1 selected from the group of SEQ ID NO: 143, SEQ ID NO: 145, SEQ ID NO: 147, and SEQ ID NO: 149; a light chain CDR2 selected from the group of SEQ ID NO: 151, SEQ ID NO: 153, SEQ ID NO: 155, SEQ ID NO: 157, SEQ ID NO: 159, and SEQ ID NO: 161; and a light chain CDR3 selected from the group of SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177, or variants or truncated forms thereof containing at least the SDRs for said CDRs.

In another embodiment, an antibody of the invention comprises a heavy chain variable region comprising a heavy chain CDR1 selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, and SEQ ID NO: 33; a heavy chain CDR2 selected from the group of SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, and SEQ ID NO: 133; and a heavy chain CDR3 selected from the group of SEQ ID NO: 135, SEQ ID NO: 137, SEQ ID NO: 139, and SEQ ID NO: 141, and a light chain variable region comprising a light chain CDR1 selected from the group of SEQ ID NO: 143, SEQ ID NO: 145, SEQ ID NO: 147, and SEQ ID NO: 149; a light chain CDR2 selected from the group of SEQ ID NO: 151, SEQ ID NO: 153, SEQ ID NO: 155, SEQ ID NO: 157, SEQ ID NO: 159, and SEQ ID NO: 161; and a light chain CDR3 selected from the group of SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177, wherein at least one of said CDRs is selected from the group of SEQ ID NO: 7, SEQ ID NO: 9, SEQ ID NO: 11, SEQ ID NO: 17, SEQ ID NO: 19, SEQ ID NO: 21, SEQ ID NO: 29, SEQ ID NO: 31, SEQ ID NO: 33, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133 and SEQ ID NO: 177.

In another embodiment, an antibody of the invention comprises a heavy chain variable region comprising a heavy chain CDR1 selected from the group of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO:21, SEQ ID NO: 23, SEQ ID NO: 25, SEQ ID NO: 27, SEQ ID NO: 29, SEQ ID NO: 31, and SEQ ID NO: 33; a heavy chain CDR2 selected from the group of SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, and SEQ ID NO: 133; and a heavy chain CDR3 selected from the group of SEQ ID NO: 135, SEQ ID NO: 137, SEQ ID NO: 139, and SEQ ID NO: 141, and a light chain variable region comprising a light chain CDR1 selected from the group of SEQ ID NO: 143, SEQ ID NO: 145, SEQ ID NO: 147, and SEQ ID NO: 149; a light chain CDR2 selected from the group of SEQ ID NO: 151, SEQ ID NO: 153, SEQ ID NO: 155, SEQ ID NO: 157, SEQ ID NO: 159, and SEQ ID NO: 161; and a light chain CDR3 selected from the group of SEQ ID NO: 163, SEQ ID NO: 165, SEQ ID NO: 167, SEQ ID NO: 169, SEQ ID NO: 171, SEQ ID NO: 173, SEQ ID NO: 175, and SEQ ID NO: 177, wherein at least one of said CDRs is not a CDR selected from the group of SEQ ID NO: 3, SEQ ID NO: 5, SEQ ID NO: 13, SEQ ID NO: 15, SEQ ID NO: 23, SEQ ID NO: 25, SEQ ID NO: 27, SEQ ID NO: 35, SEQ ID NO: 37, SEQ ID NO: 39, SEQ ID NO: 41, SEQ ID NO: 69, SEQ ID NO: 71, SEQ ID NO: 73, SEQ ID NO: 75, SEQ ID NO: 101, SEQ ID NO: 103, SEQ ID NO: 105, SEQ ID NO: 107, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, and SEQ ID NO: 175.

In another embodiment, an antibody of the invention comprises a heavy chain variable region comprising a heavy chain CDR1 selected from the group of SEQ ID NO: 3, SEQ ID NO: 5, SEQ ID NO: 13, SEQ ID NO: 15, SEQ ID NO: 23, SEQ ID NO: 25, and SEQ ID NO: 27; a heavy chain CDR2 selected from the group of SEQ ID NO: 35, SEQ ID NO: 37, SEQ ID NO: 39, SEQ ID NO: 41, SEQ ID NO: 69, SEQ ID NO: 71, SEQ ID NO: 73, SEQ ID NO: 75, SEQ ID NO: 101, SEQ ID NO: 103, SEQ ID NO: 105, and SEQ ID NO: 107; and a heavy chain CDR3 selected from the group of SEQ ID NO: 135, SEQ ID NO: 137, SEQ ID NO: 139, and SEQ ID NO: 141, and a light chain variable region comprising a light chain CDR1 selected from the group of SEQ ID NO: 143, SEQ ID NO: 145, SEQ ID NO: 147, and SEQ ID NO: 149; a light chain CDR2 selected from the group of SEQ ID NO: 151, SEQ ID NO: 153, SEQ ID NO: 155, SEQ ID NO: 157, SEQ ID NO: 159, and SEQ ID NO: 161; and a light chain CDR3 selected from the group of SEQ ID NO: 163, SEQ ID NO: 165, SEQ ID NO: 167, SEQ ID NO: 169, SEQ ID NO: 171, SEQ ID NO: 173, and SEQ ID NO: 175, or variants or truncated forms thereof containing at least the SDRs for said CDRs.

In a specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 35, SEQ ID NO: 69, and SEQ ID NO: 101; and the heavy chain CDR3 of SEQ ID NO: 135, and a light chain variable region comprising the light chain CDR1 of SEQ ID NO: 143, the light chain CDR2 of SEQ ID NO: 151, and the light chain CDR3 of SEQ ID NO: 163. In another specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 37, SEQ ID NO: 71, and SEQ ID NO: 103; and the heavy chain CDR3 of SEQ ID NO: 137, and a light chain variable region comprising the light chain CDR1 of SEQ ID NO: 145, the light chain CDR2 of SEQ ID NO: 153, and the light chain CDR3 of SEQ ID NO: 165. In yet another specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 35, SEQ ID NO: 69, and SEQ ID NO: 101; and the heavy chain CDR3 of SEQ ID NO: 137, and a light chain variable region comprising the light chain CDR1 of SEQ ID NO: 147, the light chain CDR2 of SEQ ID NO: 155, and the light chain CDR3 of SEQ ID NO: 167. In another specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 39, SEQ ID NO: 73, and SEQ ID NO: 105; and the heavy chain CDR3 of SEQ ID NO: 135, and a light chain variable region comprising the light chain CDR1 of SEQ ID NO: 145, the light chain CDR2 of SEQ ID NO: 153, and the light chain CDR3 of SEQ ID NO: 169. In another specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 35, SEQ ID NO: 69, and SEQ ID NO: 101; and the heavy chain CDR3 of SEQ ID NO: 137, and a light chain variable region comprising the light chain CDR1 of SEQ ID NO: 149, the light chain CDR2 of SEQ ID NO: 157, and the light chain CDR3 of SEQ ID NO: 167. In another specific embodiment, an antibody of the invention comprises a heavy chain variable region comprising a heavy chain CDR1 selected from the group of SEQ ID NO: 3, SEQ ID NO: 7, SEQ ID NO: 13, SEQ ID NO: 17, SEQ ID NO: 23, and SEQ ID NO: 29; a heavy chain CDR2 selected from the group of SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 63, SEQ ID NO: 65, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 97, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 129, and SEQ ID NO: 131; and the heavy chain CDR3 of SEQ ID NO: 135, and a light chain variable region comprising the light chain CDR1 of SEQ ID NO: 143, the light chain CDR2 of SEQ ID NO: 151, and the light chain CDR3 of SEQ ID NO: 163. In a further specific embodiment, an antibody of the invention comprises a heavy chain variable region comprising a heavy chain CDR1 selected from the group of SEQ ID NO: 9, SEQ ID NO: 11, SEQ ID NO: 19, SEQ ID NO:21, SEQ ID NO: 31, and SEQ ID NO: 33; a heavy chain CDR2 selected from the group of SEQ ID NO: 61, SEQ ID NO: 67, SEQ ID NO: 95, SEQ ID NO: 99, SEQ ID NO: 127, and SEQ ID NO: 133; and the heavy chain CDR3 of SEQ ID NO: 137, and a light chain variable region comprising the light chain CDR1 of SEQ ID NO: 147, the light chain CDR2 of SEQ ID NO: 155, and the light chain CDR3 of SEQ ID NO: 167. In a further specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 35, SEQ ID NO: 69, and SEQ ID NO: 101; and the heavy chain CDR3 of SEQ ID NO: 135, and a light chain variable region comprising the light chain CDR1 of SEQ ID NO: 143, the light chain CDR2 of SEQ ID NO: 151, and the light chain CDR3 of SEQ ID NO: 177. In a further specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 43, SEQ ID NO: 77, and SEQ ID NO: 109; and the heavy chain CDR3 of SEQ ID NO: 135, and a light chain variable region comprising the light chain CDR1 of SEQ ID NO: 143, the light chain CDR2 of SEQ ID NO: 151, and the light chain CDR3 of SEQ ID NO: 163. In a further specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 45, SEQ ID NO: 79, and SEQ ID NO: 111; and the heavy chain CDR3 of SEQ ID NO: 135, and a light chain variable region comprising the light chain CDR1 of SEQ ID NO: 143, the light chain CDR2 of SEQ ID NO: 151, and the light chain CDR3 of SEQ ID NO: 163. In a further specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 65, SEQ ID NO: 89, and SEQ ID NO: 131; and the heavy chain CDR3 of SEQ ID NO: 135, and a light chain variable region comprising the light chain CDR1 of SEQ ID NO: 143, the light chain CDR2 of SEQ ID NO: 151, and the light chain CDR3 of SEQ ID NO: 163. In a further specific embodiment, an antibody of the invention comprises a heavy chain variable region comprising a heavy chain CDR1 selected from the group of SEQ ID NO: 3, SEQ ID NO: 13, and SEQ ID NO: 23; a heavy chain CDR2 selected from the group of SEQ ID NO: 47, SEQ ID NO: 81, and SEQ ID NO: 113; and the heavy chain CDR3 of SEQ ID NO: 135, and a light chain variable region comprising the light chain CDR1 of SEQ ID NO: 143, the light chain CDR2 of SEQ ID NO: 151, and the light chain CDR3 of SEQ ID NO: 163. In a further specific embodiment, an antibody of the invention comprises a heavy chain variable region comprising a heavy chain CDR1 selected from the group of SEQ ID NO: 9, SEQ ID NO: 19, and SEQ ID NO: 31; a heavy chain CDR2 selected from the group of SEQ ID NO: 61, SEQ ID NO: 95, and SEQ ID NO: 127; and the heavy chain CDR3 of SEQ ID NO: 137, and a light chain variable region comprising the light chain CDR1 of SEQ ID NO: 147, the light chain CDR2 of SEQ ID NO: 155, and the light chain CDR3 of SEQ ID NO: 167.

In one embodiment, an antibody of the invention comprises a heavy chain variable region (VH) comprising an amino acid sequence having at least about 90%, 91%, 92%, 93%, 94%, 95%, 96%, 97%, 98% or 99% identity to a sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311. In one embodiment, the antibody comprises a heavy chain variable region comprising an amino acid sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311.

In certain embodiments, a VH sequence having at least 90%, 91%, 92%, 93%, 94%, 95%, 96%, 97%, 98% or 99% identity contains substitutions (e.g., conservative substitutions), insertions, or deletions relative to the reference sequence, but an anti-FAP antibody comprising that sequence retains the ability to bind to FAP. In certain embodiments, a total of 1 to 10 amino acids have been substituted, inserted and/or deleted in SEQ ID NO 197, 201, 203, 207, 211, 215, 219, 223, 227, 231, 235, 239, 243, 247, 251, 255, 259, 263, 267, 271, 275, 279, 283, 287, 291, 295, 299, 303, 307 or 311. In certain embodiments, substitutions, insertions, or deletions occur in regions outside the HVRs or CDRs (i.e., in the FRs). Optionally, an anti-FAP antibody according to the invention comprises the VH sequence in SEQ ID NO 197, 201, 203, 207, 211, 215, 219, 223, 227, 231, 235, 239, 243, 247, 251, 255, 259, 263, 267, 271, 275, 279, 283, 287, 291, 295, 299, 303, 307 or 311, including post-translational modifications of that sequence. In a particular embodiment, the VH comprises one, two or three heavy chain CDRs selected from the sequences set forth in SEQ ID NOs 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139 and 141 for the HCDR1, HCDR2 and HCDR3.

In another embodiment, an antibody of the invention comprises a light chain variable region comprising an amino acid sequence having at least about 90%, 91%, 92%, 93%, 94%, 95%, 96%, 97%, 98% or 99% identity to a sequence selected from the group of SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309. In yet another embodiment, the antibody comprises a light chain variable region comprising an amino acid sequence selected from the group of: SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309.

In certain embodiments, a VL sequence having at least 90%, 91%, 92%, 93%, 94%, 95%, 96%, 97%, 98% or 99% identity contains substitutions (e.g., conservative substitutions), insertions, or deletions relative to the reference sequence, but an anti-FAP antibody comprising that sequence retains the ability to bind to FAP. In certain embodiments, a total of 1 to 10 amino acids have been substituted, inserted and/or deleted in SEQ ID NO 193, 195, 199, 205, 209, 213, 217, 221, 225, 229, 233, 237, 241, 245, 249, 253, 257, 261, 265, 269, 273, 277, 281, 285, 289, 293, 297, 301, 305 or 309. In certain embodiments, the substitutions, insertions, or deletions occur in regions outside the HVRs or CDRs (i.e., in the FRs). Optionally, an anti-FAP antibody of the invention comprises the VL sequence in SEQ ID NO 193, 195, 199, 205, 209, 213, 217, 221, 225, 229, 233, 237, 241, 245, 249, 253, 257, 261, 265, 269, 273, 277, 281, 285, 289, 293, 297, 301, 305 or 309, including post-translational modifications of that sequence. In a particular embodiment, the VL comprises one, two or three light chain CDRs selected from sequences set forth in SEQ ID NOs 143, 145, 147, 149, 151, 153, 155, 157, 159, 161, 163, 165, 167, 169, 171, 173, 175 and 177 for the LCDR1, LCDR2 and LCDR3.

In another aspect, an anti-FAP antibody is provided, wherein the antibody comprises a VH as in any of the embodiments provided above, and a VL as in any of the embodiments provided above. In one embodiment, the antibody comprises a heavy chain variable region comprising an amino acid sequence that is at least about 90%, 91%, 92%, 93%, 94%, 95%, 96%, 97%, 98%, 99% or 100% identical to a sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, and a light chain variable region comprising an amino acid sequence that is at least about 90%, 91%, 92%, 93%, 94%, 95%, 96%, 97%, 98%, 99% or 100% identical to a sequence selected from the group of: SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309. In one embodiment, the antibody comprises the VH and VL sequences in SEQ ID NO 197, 201, 203, 207, 211, 215, 219, 223, 227, 231, 235, 239, 243, 247, 251, 255, 259, 263, 267, 271, 275, 279, 283, 287, 291, 295, 299, 303, 307 or 311, and SEQ ID NO 193, 195, 199, 205, 209, 213, 217, 221, 225, 229, 233, 237, 241, 245, 249, 253, 257, 261, 265, 269, 273, 277, 281, 285, 289, 293, 297, 301, 305 or 309, respectively, including post-translational modifications of those sequences.

In one embodiment, the antibody comprises a heavy chain variable region comprising an amino acid sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, and a light chain variable region comprising an amino acid sequence selected from the group of: SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309, wherein at least one of said variable regions does not comprise an amino acid sequence selected from the group of SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, and SEQ ID NO: 255.

In one embodiment, the antibody comprises a heavy chain variable region comprising an amino acid sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, and a light chain variable region comprising an amino acid selected from the group of: SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309, wherein at least one of said variable regions comprises an amino acid sequence selected from the group of SEQ ID NO: 259, SEQ ID NO: 263, SEQ ID NO: 267, SEQ ID NO: 271, SEQ ID NO: 275, SEQ ID NO:279, SEQ ID NO:283, SEQ ID NO: 287, SEQ ID NO: 291, SEQ ID NO: 293, SEQ ID NO: 299, SEQ ID NO: 303, SEQ ID NO: 307, and SEQ ID NO: 311.

In one embodiment, the antibody comprises a heavy chain variable region comprising an amino acid sequence that is at least about 90%, 91%, 92%, 93%, 94%, 95%, 96%, 97%, 98%, 99% or 100% identical to a sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, and SEQ ID NO: 255, and a light chain variable region comprising an amino acid sequence that is at least about 90%, 91%, 92%, 93%, 94%, 95%, 96%, 97%, 98%, 99% or 100% identical to a sequence selected from the group of: SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, and SEQ ID NO: 253.

In a specific embodiment, an antibody of the invention comprises a heavy chain variable region comprising the amino acid sequence of SEQ ID NO:197, and a light chain variable region comprising the amino acid sequence of SEQ ID NO: 193 or SEQ ID NO: 195. In another specific embodiment, an antibodies of the invention comprises a heavy chain variable region comprising the amino acid sequence of SEQ ID NO: 201 or SEQ ID NO: 203, and a light chain variable region comprising the amino acid sequence of SEQ ID NO: 199. In yet another specific embodiment an antibody of the invention comprises a heavy chain variable region comprising the amino acid sequence of SEQ ID NO: 207, and a light chain variable region comprising the amino acid sequence of SEQ ID NO: 205. In another specific embodiment, an antibodies of the invention comprises a heavy chain variable region comprising the amino acid sequence of SEQ ID NO: 211, and a light chain variable region comprising the amino acid sequence of SEQ ID NO: 209. In yet another specific embodiment an antibody of the invention comprises a heavy chain variable region comprising the amino acid sequence of SEQ ID NO: 219, and a light chain variable region comprising the amino acid sequence of SEQ ID NO: 217. In another embodiment, an antibody of the invention comprises a heavy chain variable region comprising an amino acid sequence selected from the group of SEQ ID NO: 259, SEQ ID NO: 263, SEQ ID NO: 267, SEQ ID NO: 271, SEQ ID NO: 275, SEQ ID NO:279, SEQ ID NO:283, SEQ ID NO: 287, SEQ ID NO: 291, SEQ ID NO: 299, SEQ ID NO: 303, SEQ ID NO: 307, and SEQ ID NO: 311, or a light chain variable region comprising the amino acid sequence of SEQ ID NO: 293. In a specific embodiment, the antibodies of the invention comprise a) a heavy chain variable region comprising an amino acid sequence selected from SEQ ID NO: 259, SEQ ID NO: 263, SEQ ID NO: 267, SEQ ID NO: 271, SEQ ID NO: 275, SEQ ID NO:279, SEQ ID NO:283, SEQ ID NO: 287, SEQ ID NO: 291, SEQ ID NO: 303, and SEQ ID NO: 307, and a light chain variable region comprising the amino acid sequence of SEQ ID NO: 195, or b) a heavy chain variable region comprising the amino acid sequence or SEQ ID NO: 299 or SEQ ID NO: 311, and a light chain variable region comprising the amino acid sequence of SEQ ID NO: 205, or c) a heavy chain variable region comprising the amino acid sequence or SEQ ID NO: 197, and a light chain variable region comprising the amino acid sequence of SEQ ID NO: 293. In a specific embodiment, an antibody of the invention comprises a heavy chain variable region comprising the amino acid sequence of SEQ ID NO: 259 and a light chain variable region comprising the amino acid sequence of SEQ ID NO: 195. In another specific embodiment, an antibodies of the invention comprises a heavy chain variable region comprising the amino acid sequence of SEQ ID NO: 263 and a light chain variable region comprising the amino acid sequence of SEQ ID NO: 195. In a specific embodiment, an antibody of the invention comprises a heavy chain variable region comprising the amino acid sequence of SEQ ID NO: 307 and a light chain variable region comprising the amino acid sequence of SEQ ID NO: 305. In another specific embodiment, an antibodies of the invention comprises a heavy chain variable region comprising the amino acid sequence of SEQ ID NO: 267 and a light chain variable region comprising the amino acid sequence of SEQ ID NO: 265. In yet another specific embodiment an antibody of the invention comprises a heavy chain variable region comprising the amino acid sequence of SEQ ID NO: 299, and a light chain variable region comprising the amino acid sequence of SEQ ID NO: 205. In a particular embodiment, the antibody according to any of the above embodiments additionally comprises an Fc region or a region equivalent to the Fc region of an immunoglobulin.

In one embodiment an antibody of the invention comprises an Fc region, particularly a IgG Fc region, most particularly a IgG1 Fc region.

In a particular embodiment, the antibody of the invention is a full length antibody, particularly an IgG class antibody, most particularly an IgG1 isotype antibody. In another embodiment, the antibody of the invention is an antibody fragment, selected from the group of: an scFv fragment, an Fv fragment, a Fab fragment, and a F(ab')2 fragment. In a further embodiment, the antibody of the invention is an antibody fragment having an Fc region, or a fusion protein that comprises a region equivalent to the Fc region of an immunoglobulin. In one embodiment, the antibody of the invention is a monoclonal antibody.

In one embodiment, an antibody of the invention is chimeric, more specifically humanized. In a particular embodiment, an antibody of the invention is human. In another embodiment, an antibody of the invention comprises a human constant region. In one embodiment the antibody of the invention comprises a human Fc region, particularly a human IgG Fc region, most particularly a human IgG1 Fc region.

In one embodiment, an antibody of the invention comprises a heavy chain constant region, wherein said heavy chain constant region is a human IgG constant region, particularly a human IgG1 constant region, comprising an Fc region. In a specific embodiment, the antibody comprises a heavy chain constant region comprising the amino acid sequence of SEQ ID NO: 313. In another specific embodiment an antibody of the invention comprises a light chain constant region comprising the amino acid sequence of SEQ ID NO: 315. In yet another specific embodiment, an antibody of the invention comprises a heavy chain constant region comprising the amino acid sequence of SEQ ID NO: 313, and a light chain constant region comprising the amino acid sequence of SEQ ID NO: 315.

In a particular embodiment, the invention provides an antibody that specifically binds to FAP, wherein said antibody comprises a) a heavy chain variable region comprising an amino acid sequence that is at least about 90%, 91%, 92%, 93%, 94%, 95%, 96%, 97%, 98%, 99% or 100% identical to a sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, or a light chain variable region comprising an amino acid sequence that is at least about 90%, 91%, 92%, 93%, 94%, 95%, 96%, 97%, 98%, 99% or 100% identical to a sequence selected from the group of SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309, or a combination thereof, and b) an Fc region or a region equivalent to the Fc region of an immunoglobulin.

In one embodiment, an antibody of the invention comprises an Fc region, wherein said Fc region is a glycoengineered Fc region. In a further embodiment, an antibody of the invention is glycoengineered to have modified oligosaccharides in the Fc region. In a specific embodiment, the antibody has an increased proportion of bisected oligosaccharides in the Fc region, compared to a non-glycoengineered antibody. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antibody are bisected. The bisected oligosaccharides may be of the hybrid or complex type.

In another specific embodiment, an antibody of the invention has an increased proportion of non-fucosylated oligosaccharides in the Fc region, compared to a non-glycoengineered antibody. In a more specific embodiment, at least about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antibody are non-fucosylated. The non-fucosylated oligosaccharides may be of the hybrid or complex type.

In a particular embodiment, an antibody of the invention has an increased proportion of bisected, non-fucosylated oligosaccharides in the Fc region, compared to a non-glycoengineered antibody. Specifically, the antibody comprises an Fc region in which at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 15%, more preferably at least about 25%, at least about 35% or at least about 50%, of the N-linked oligosaccharides are bisected, non-fucosylated. The bisected, non-fucosylated oligosaccharides may be of the hybrid or complex type.

In one embodiment, an antibody of the invention has increased effector function and/or increased Fc receptor binding affinity. Increased effector function and/or increased Fc receptor binding can result e.g. from glycoengineering and/or affinity maturation of antibodies. In one embodiment, the increased effector function and/or increased Fc receptor binding is a result of glycoengineering of the Fc region of the antibody. In another embodiment, the increased effector function and/or increased Fc receptor binding is a result of a combination of increased affinity and glycoengineering. The increased effector function can include, but is not limited to, one or more of the following: increased Fc-mediated cellular cytotoxicity (including increased antibody-dependent cell-mediated cytotoxicity (ADCC)), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a particular embodiment, the increased effector function is increased ADCC. The increased Fc receptor binding preferably is increased binding to an activating Fc receptor, most preferably FcγRIIIa.

In one embodiment, an antibody of the invention does not cause a clinically significant level of toxicity when administered to an individual in a therapeutically effective amount.

In one embodiment, an antibody of the invention is affinity matured. In a further embodiment, an antibody of the invention binds to the Fibroblast Activation Protein with a dissociation constant ($K_D$) value lower than about 1 µM to about 0.001 nM, particularly a $K_D$ value lower than about 100 nM, lower than about 10 nM, lower than about 1 nM, or lower than about 0.1 nM. In one embodiment, an antibody of the invention binds to human, mouse and cynomolgus FAP. In one embodiment, an antibody of the invention binds to human and cynomolgus FAP. In a more specific embodiment, an antibody of the invention binds to human, mouse and cynomolgus FAP with a $K_D$ value lower than about 200 nM, lower than about 100 nM, more particularly lower than about 10 nM or lower than about 1 nM, most particularly lower than 0.1 nM. $K_D$ values are determined by Surface Plasmon Resonance, using the antibodies as Fab or IgG, particularly as IgG.

In one embodiment, an anti-FAP antibody of the invention binds FAP in human tissues. In one embodiment an anti-FAP antibody of the invention is cross-reactive for human and murine FAP. In another embodiment, an antibody of the invention has no substantial cross-reactivity to other members of the dipeptidyl peptidase IV family, in particular to DPPIV/CD26. In one embodiment, an anti-FAP antibody of the invention does not induce internalization of FAP upon binding of said antibody to FAP expressed on the surface of a cell.

In a particular embodiment, the invention provides an antibody that specifically binds to FAP, wherein said antibody comprises a heavy chain variable region comprising an amino acid sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, a light chain variable region comprising an amino acid sequence selected from the group of SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309, and a human IgG Fc region, and wherein optionally said antibody is glycoengineered to have increased effector function and/or Fc receptor binding affinity. In another particular embodiment, the invention provides an antibody that specifically binds to FAP, wherein said antibody comprises a heavy chain variable region comprising an amino acid sequence selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, a light chain variable region comprising an amino acid sequence selected from the group of SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309, and a human IgG Fc region, and wherein said antibody has an increased proportion of non-fucosylated oligosaccharides and/or an increased proportion of bisected oligosaccharides in said Fc region.

In one aspect, the invention provides for an antibody that specifically bind to FAP, wherein said antibody is derived from a parent antibody comprising the heavy chain CDR1 of SEQ ID NO: 3, the heavy chain CDR2 of SEQ ID NO: 35, a heavy chain CDR3 selected from the group of SEQ ID NO: 135, SEQ ID NO: 137, SEQ ID NO: 139 and SEQ ID NO: 141, the light chain CDR1 of SEQ ID NO: 145, the light chain CDR2 of SEQ ID NO: 153 and a light chain CDR3 selected from the group of SEQ ID NO: 165, SEQ ID NO: 167, SEQ ID NO: 169, SEQ ID NO: 171, SEQ ID NO: 173 and SEQ ID NO: 175, and wherein said antibody comprises at least one amino acid substitution or deletion in at least one heavy or light chain CDR of to the parent antibody. For example, the antibody may comprise at least one, e.g. from about one to about ten (i.e., about 1, 2, 3, 4, 5, 6, 7, 8, 9, or 10), and particularly from about two to about five, substitutions in one or more hypervariable regions or CDRs (i.e., 1, 2, 3, 4, 5, or 6 hypervariable regions or CDRs) of the parent antibody. In certain embodiments, any one or more amino acids of the parent antibody as provided above are substituted or deleted at the following CDR positions:

Heavy chain CDR1 (SEQ ID NO: 3): positions 2 and 3
Heavy chain CDR2 (SEQ ID NO: 35): positions 1, 3, 4, 5, 6, 7, 8 and 9
Light chain CDR1 (SEQ ID NO: 145): positions 7, 8 and 9
Light chain CDR2 (SEQ ID NO: 153): positions 1, 2, 3, 4 and 5

Light chain CDR3 (SEQ ID NO 165, 167, 169, 171, 173, or 175): positions 4, 5, 6, and 7

In certain embodiments, the substitutions are conservative substitutions, as provided herein. In certain embodiments, any one or more of the following substitutions or deletions may be made in any combination:

Heavy chain CDR1 (SEQ ID NO: 3): Y2F, H or S, A3T
Heavy chain CDR2 (SEQ ID NO: 35): A1G, S3G, I, W or L, G4V, S, A or T, S5G or N, G6T or A, G7R, S, A, E or N, S8Y, L, R, I, N, Q, I or deleted, T9 deleted
Light chain CDR1 (SEQ ID NO: 145): S7T, S8R or S9N
Light chain CDR2 (SEQ ID NO: 153): Y1N, I or Q, G2V, A3G, S4T or Y, S5R, T or I
Light chain CDR3 (SEQ ID NO 165, 167, 169, 171, 173, or 175): G4A, Q, N, L or H5I, L, V, Q, N or I6M, I7L Additionally, the antibodies may also comprise one or more additions, deletions and/or substitutions in one or more framework regions of either the heavy or the light chain, compared to the parent antibody. In one embodiment, said at least one amino acid substitution in at least one CDR contributes to increased binding affinity of the antibody compared to its parent antibody. In another embodiment said antibody has at least about 2-fold to about 10-fold greater affinity for FAP than the parent antibody (when comparing the antibody of the invention and the parent antibody in the same format, e.g. the Fab format). Further, the antibody derived from a parent antibody may incorporate any of the features, singly or in combination, described in the preceding paragraphs in relation to the antibodies of the invention.

The present invention also provides for polynucleotides encoding antibodies that specifically bind to FAP. In one aspect, the invention is directed to an isolated polynucleotide encoding a polypeptide that forms part of an anti-FAP antibody according to the invention as described hereinbefore. In one embodiment, the isolated polynucleotide encodes an antibody heavy chain and/or an antibody light chain that forms part of an anti-FAP antibody according to the invention as described hereinbefore.

In one embodiment, the invention is directed to an isolated polynucleotide comprising a sequence encoding one or more (e.g. one, two, three, four, five, or six) of the heavy or light chain complementarity determining regions (CDRs) set forth in SEQ ID NOs 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175 and 177, or a variant or truncated form thereof containing at least the specificity-determining residues (SDRs) for said CDR. In another embodiment, the polynucleotide comprises a sequence that encodes three heavy chain CDRs (e.g., HCDR1, HCDR2, and HCDR3) or three light chain CDRs (e.g. LCDR1, LCDR2, and LCDR3) selected from SEQ ID NOs 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175 and 177, or variants or truncated forms thereof containing at least the SDRs for each of said three complementarity determining regions. In yet another embodiment, the polynucleotide comprises a sequence encoding three heavy chain CDRs (e.g., HCDR1, HCDR2, and HCDR3) and three light chain CDRs (e.g. LCDR1, LCDR2, and LCDR3) selected from SEQ ID NOs 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175 and 177. In a particular embodiment the polynucleotide encoding one or more CDRs comprises a sequence that is at least about 90%, 95%, 96%, 97%, 98%, 99%, or 100% identical to one or more of the CDR nucleotide sequences shown in SEQ ID NOs 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 179, 180, 181, 182, 183, 184, 185, 186, 187, 188, 189, 190, 191 and 192.

In a further embodiment, the polynucleotide comprises a sequence encoding a heavy chain variable region selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, and/or a sequence encoding a light chain variable region selected from the group of SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309. In a particular embodiment, the polynucleotide encoding a heavy chain and/or light chain variable region comprises a sequence selected from the group of variable region nucleotide sequences presented in SEQ ID NOs 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310 and 312, or a combination thereof.

In a specific embodiment, the polynucleotide comprises a sequence encoding a heavy chain variable region selected from the group of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, and a sequence encoding a heavy chain constant region, particularly a human heavy chain constant region. In a particular embodiment, said heavy chain constant region is a human IgG heavy chain constant region, specifically a human IgG1 heavy chain constant region, comprising an Fc region. In a specific embodiment, said heavy chain constant region comprises the sequence of SEQ ID NO: 313. In another specific embodiment, the polynucleotide comprises a sequence encoding a light chain variable region selected from the group of SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309, and a sequence encoding a light chain constant region, particularly a human light chain constant region. In a specific embodiment, said light chain constant region comprises the sequence of SEQ ID NO: 315.

In one embodiment, the invention is directed to a composition that comprises a first isolated polynucleotide encoding a polypeptide comprising an amino acid sequence that is at least about 90%, 95%, 96%, 97%, 98%, 99%, or 100% identical to a sequence selected from the group consisting of SEQ ID NO: 197, SEQ ID NO: 201, SEQ ID NO: 203, SEQ ID NO: 207, SEQ ID NO: 211, SEQ ID NO: 215, SEQ ID NO: 219, SEQ ID NO: 223, SEQ ID NO: 227, SEQ ID NO: 231, SEQ ID NO: 235, SEQ ID NO: 239, SEQ ID NO: 243, SEQ ID NO: 247, SEQ ID NO: 251, SEQ ID NO: 255, SEQ ID NO: 259, SEQ ID NO: 263, SEQ ID NO: 267, SEQ ID NO: 271, SEQ ID NO: 275, SEQ ID NO: 279, SEQ ID NO: 283, SEQ ID NO: 287, SEQ ID NO: 291, SEQ ID NO: 295, SEQ ID NO: 299, SEQ ID NO: 303, SEQ ID NO: 307, and SEQ ID NO: 311, and a second isolated polynucleotide encoding a polypeptide comprising an amino acid sequence that is at least about 90%, 95%, 96%, 97%, 98%, 99%, or 100% identical to a sequence selected from the group consisting of SEQ ID NO: 193, SEQ ID NO: 195, SEQ ID NO: 199, SEQ ID NO: 205, SEQ ID NO: 209, SEQ ID NO: 213, SEQ ID NO: 217, SEQ ID NO: 221, SEQ ID NO: 225, SEQ ID NO: 229, SEQ ID NO: 233, SEQ ID NO: 237, SEQ ID NO: 241, SEQ ID NO: 245, SEQ ID NO: 249, SEQ ID NO: 253, SEQ ID NO: 257, SEQ ID NO: 261, SEQ ID NO: 265, SEQ ID NO: 269, SEQ ID NO: 273, SEQ ID NO: 277, SEQ ID NO: 281, SEQ ID NO: 285, SEQ ID NO: 289, SEQ ID NO: 293, SEQ ID NO: 297, SEQ ID NO: 301, SEQ ID NO: 305, and SEQ ID NO: 309.

In one embodiment, the invention is directed to a composition that comprises a first isolated polynucleotide comprising a sequence that is at least about 90%, 95%, 96%, 97%, 98%, 99%, or 100% identical to a sequence selected from the group consisting of SEQ ID NO: 198, SEQ ID NO: 202, SEQ ID NO: 204, SEQ ID NO: 208, SEQ ID NO: 212, SEQ ID NO: 216, SEQ ID NO: 220, SEQ ID NO: 224, SEQ ID NO: 228, SEQ ID NO: 232, SEQ ID NO: 236, SEQ ID NO: 240, SEQ ID NO: 244, SEQ ID NO: 248, SEQ ID NO: 252, SEQ ID NO: 256, SEQ ID NO: 260, SEQ ID NO: 264, SEQ ID NO: 268, SEQ ID NO: 272, SEQ ID NO: 276, SEQ ID NO: 280, SEQ ID NO: 284, SEQ ID NO: 288, SEQ ID NO: 292, SEQ ID NO: 296, SEQ ID NO: 300, SEQ ID NO: 304, SEQ ID NO: 308, and SEQ ID NO: 312, and a second isolated polynucleotide comprising a sequence that is at least about 90%, 95%, 96%, 97%, 98%, 99%, or 100% identical to a sequence selected from the group consisting of SEQ ID NO: 194, SEQ ID NO: 196, SEQ ID NO: 200, SEQ ID NO: 206, SEQ ID NO: 210, SEQ ID NO: 214, SEQ ID NO: 218, SEQ ID NO: 222, SEQ ID NO: 226, SEQ ID NO: 230, SEQ ID NO: 234, SEQ ID NO: 238, SEQ ID NO: 242, SEQ ID NO: 246, SEQ ID NO: 250, SEQ ID NO: 254, SEQ ID NO: 258, SEQ ID NO: 262, SEQ ID NO: 266, SEQ ID NO: 270, SEQ ID NO: 274, SEQ ID NO: 278, SEQ ID NO: 282, SEQ ID NO: 286, SEQ ID NO: 290, SEQ ID NO: 294, SEQ ID NO: 298, SEQ ID NO: 302, SEQ ID NO: 306, and SEQ ID NO: 310.

In a further aspect, the invention is also directed to isolated polypeptides, encoded by any of the polynucleotides according the invention as described hereinbefore.

In a further aspect, an anti-FAP antibody according to any of the above embodiments may incorporate any of the features, singly or in combination, as described in Sections 1-6 below:

1. Antibody Affinity

In certain embodiments, an antibody provided herein has a dissociation constant ($K_D$) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$M or less, e.g. from $10^{-8}$M to $10^{-13}$M, e.g., from $10^{-9}$M to $10^{-13}$ M). Preferably, the antibodies provided herein bind to Fibroblast Activation Protein (FAP), in particular human FAP, with a $K_D$ value lower than 1 nM, as determined by Surface Plasmon Resonance (SPR).

According to one embodiment, $K_D$ is measured using surface plasmon resonance. Such an assay can be performed, for example, using a BIACORE®-T100 machine (GE Healthcare) at 25° C. with CM5 chips for antigen immobilization. Briefly, carboxymethylated dextran biosensor chips (CM5, GE Healthcare.) are activated with N-ethyl-N'-(3-dimethylaminopropyl)-carbodiimide hydrochloride (EDC) and N-hydroxysuccinimide (NHS) according to the supplier's instructions. Anti-His antibody (Penta His, Qiagen) is diluted with 10 mM sodium acetate, pH 5, to 40 µg/ml before injection at a flow rate of 10 µl/minute to achieve approximately 9000 response units (RU) of coupled protein. Following the injection of the anti-His antibody, 1 M ethanolamine is injected to block unreacted groups. Subsequently, His-tagged antigen is injected at 10 µl/min at 10 nM for 20 sec (for measurements with Fab fragments) or at 20 nM for 25 s (for measurements with IgG antibodies) and is captured via its His tag by the immobilized anti-His antibody. Protein and DNA sequences of suitable FAP antigen constructs are shown in SEQ ID NOs 317-322. For kinetics measurements, serial dilutions of antibody (two-fold dilutions, range between 6.25 nM to 200 nM for Fab fragments, or five-fold dilutions, range between 3.2 pM to 10 nM for IgG) are injected in 10 mM HEPES, 150 mM NaCl, 3 mM EDTA, 0.05% Surfactant P20, pH 7.4 at 25° C. at a flow rate of 90 µl/min. The following parameters are applied: Association time 180 s, dissociation 300 s (for Fab) or 900 s (for IgG), regeneration with 10 mM glycine pH 2 for 60 s between each cycle. Association rates ($k_{on}$) and dissociation rates ($k_{off}$) are calculated using a simple one-to-one Langmuir binding model (BIACORE® T100 Evaluation Software) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999).

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003), or Carter, *Nat. Rev. Immunol.* 6:343-357 (2006).

Single-chain Fv or scFv fragments comprise a VH domain and a VL domain as a single polypeptide chain. Typically, the VH and VL domains are joined by a linker sequence. For a review of scFv fragments, see, e.g., Plückthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90:6444-6448 (1993). Triabodies and tetrabodies are also described in Hudson et al., *Nat. Med.* 9:129-134 (2003).

A minibody is a bivalent, homodimeric scFv derivative that contains a constant region, typically the CH3 region of an immunoglobulin, preferably IgG, more preferably IgG1, as the dimerisation region. Generally, the constant region is connected to the scFv via a hinge region and/or a linker region. Examples of minibody proteins can be found in Hu et al., *Cancer Res.* 56: 3055-61 (1996).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof. In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region.

In some embodiments, some FR residues in a humanized antibody are substituted with corresponding residues from a non-human antibody (e.g., the antibody from which the HVR residues are derived), e.g., to restore or improve antibody specificity or affinity. Humanization may be achieved by various methods including, but not limited to (a) grafting the entire non-human variable domains onto human constant regions to generate chimeric antibodies, (b) grafting only the non-human (e.g., donor antibody) CDRs onto human (e.g., recipient antibody) framework and constant regions with or without retention of critical framework residues (e.g., those that are important for retaining good antigen binding affinity or antibody functions), (c) grafting only the non-human specificity-determining regions (SDRs or a-CDRs; the residues critical for the antibody-antigen interaction) onto human framework and constant regions, or (d) transplanting the entire non-human variable domains, but "cloaking" them with a human-like section by replacement of surface residues. Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Jones et al., *Nature* 321:522-525 (1986); Morrison et al., *Proc. Natl. Acad. Sci.* 81:6851-6855 (1984); Morrison and Oi, *Adv. Immunol.* 44:65-92 (1988); Verhoeyen et al., *Science* 239:1534-1536 (1988); Padlan, *Molec. Immun.* 31(3):169-217 (1994); Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas.

Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for FAP and the other is for any other antigen. In certain embodiments, bispecific antibodies may bind to two different epitopes of FAP. Bispecific antibodies may also be used to localize cytotoxic agents to cells which express FAP. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983), WO 93/08829, and Traunecker et al., *EMBO J.* 10: 3655 (1991)), and "knob-in-hole" engineering (see, e.g., U.S. Pat. No. 5,731,168).

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science* 229:81 (1985)); using leucine zippers to produce bi-specific antibodies (see, e.g., Kostelny et al., *J. Immunol.* 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (scFv) dimers (see,e.g. Gruber et al., *J. Immunol.*, 152:5368 (1994)); and preparing trispecific antibodies as described, e.g., in Tutt et al. *J. Immunol.* 147: 60 (1991). Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to FAP as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Amino acid substitutions can result in replacing one amino acid with another amino acid having similar structural and/or chemical properties, e.g., conservative amino acid replacements.

"Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, phenylalanine, tryptophan, and methionine; polar neutral amino acids include serine, threonine, cysteine, tyrosine, asparagine, and glutamine; positively charged (basic) amino acids include arginine, lysine, and histidine; and negatively charged (acidic) amino acids include aspartic acid and glutamic acid. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic). The variation allowed may be experimentally determined by systematically making insertions, deletions, or substitutions of amino acids in a polypeptide molecule using recombinant DNA techniques and assaying the resulting recombinant variants for activity.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, it may be beneficial to analyze a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In some embodiments, modifications of the oligosaccharide in an antibody of the invention may be made in order to create antibody variants with certain improved properties.

In one aspect, the present invention provides glycoforms of anti-FAP antibodies having increased effector function, including antibody-dependent cellular cytotoxicity. Glycosylation engineering of antibodies has been previously described. See, e.g., U.S. Pat. No. 6,602,684, incorporated herein by reference in its entirety. Methods of producing anti-FAP antibodies from host cells that have altered activity of genes involved in glyocsylation are also described herein in detail (see, e.g, section entitled "Recombinant Methods and Compositions" below).

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., Biochemistry 36:130-38 (1997), with a low level of terminal sialic acid and bisecting N-acetylglucosamine (GlcNAc), and a variable degree of terminal galactosylation and core fucosylation (fucose attached to a GlcNAc residue in the "stem" of the biantennary oligosaccharide structure). Some studies suggest that the minimal carbohydrate structure required for FcγR binding lies within the oligosaccharide core. Lund et al., J. Immunol. 157:4963-69 (1996).

The mouse- or hamster-derived cell lines used in industry and academia for production of antibodies normally attach the required oligosaccharide determinants to Fc sites. IgGs expressed in these cell lines lack, however, the bisecting GlcNAc found in low amounts in serum IgGs. Lifely et al., Glycobiology 318:813-22 (1995). In the N-linked glycosylation pathway, a bisecting GlcNAc is added by GnTIII. Schachter, Biochem. Cell Biol. 64:163-81 (1986).

Umaña et al. used a single, antibody-producing CHO cell line that was previously engineered to express, in an externally-regulated fashion, different levels of a cloned GnTIII enzyme gene (Umaña, P., et al., Nature Biotechnol. 17:176-180 (1999)). This approach established for the first time a rigorous correlation between expression of a glycosyltransferase (e.g., GnTIII) and the ADCC activity of the modified antibody. Thus, the invention contemplates anti-FAP antibodies, comprising an Fc region or region equivalent to an Fc region having altered glycosylation resulting from changing the expression level of a glycosyltransferase gene in the antibody-producing host cell. In a specific embodiment, the change in gene expression level is an increase in GnTIII activity. Increased GnTIII activity results in an increase in the percentage of bisected oligosaccharides, as well as a decrease in the percentage of fucosylated oligosaccharides, in the Fc region of the antibody. This antibody, or fragment thereof, has increased Fc receptor binding affinity and increased effector function.

Antibodies are provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umaña et al.); and US 2005/0123546 (Umaña et al.).

In one embodiment, the anti-FAP antibodies of the invention have an increased proportion of bisected oligosaccharides in the Fc region as a result of the modification of their oligosaccharides by the methods of the present invention. In one embodiment, the percentage of bisected N-linked oligosaccharides in the Fc region of the anti-FAP antibodies of the invention is at least about 10% to about 100%, specifically at least about 50%, more specifically, at least about 60%, at least about 70%, at least about 80%, or at least about 90-95% of the total oligosaccharides. The bisected oligosaccharides may be of the hybrid or complex type.

In another embodiment, the anti-FAP antibodies of the invention have an increased proportion of nonfucosylated oligosaccharides in the Fc region as a result of the modification of their oligosaccharides by the methods of the present invention. In one embodiment, the percentage of nonfucosylated oligosaccharides is at least about 20% to about 100%, specifically at least about 50%, at least about 60% to about 70%, and more specifically, at least about 75%. The nonfucosylated oligosaccharides may be of the hybrid or complex type.

The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described for example in WO 2008/077546. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. The relative amount of fucose is the percentage of fucose-containing structures related to all glycostructures identified in an N-Glycosidase F treated sample (e. g. complex, hybrid and high mannose structures) by MALDI-TOF MS. Such fucosylation variants may have improved ADCC function.

The glycoengineering methodology that can be used with the anti-FAP antibodies of the present invention has been described in greater detail in U.S. Pat. No. 6,602,684, U.S. Pat. Appl. Publ. No. 2004/0241817 A1, U.S. Pat. Appl. Publ. No. 2003/0175884 A1, Provisional U.S. Patent Application No. 60/441,307 and WO 2004/065540, the entire contents of each of which is incorporated herein by reference in its entirety. The anti-FAP antibodies of the present invention can alternatively be glycoengineered to have reduced fucose residues in the Fc region according to the techniques disclosed in U.S. Pat. Appl. Pub. No. 2003/0157108 (Genentech), or in EP 1 176 195 A1, WO 03/084570, WO 03/085119 and U.S. Pat. Appl. Pub. Nos. 2003/0115614, 2004/093621, 2004/110282, 2004/110704, 2004/132140, Niwa et al., J Immunol Methods 306, 151/160 (2006), U.S. Pat. No. 6,946,292 (Kyowa). Glycoengineered anti-FAP antibodies of the invention may also be produced in expression systems that produce modified glycoproteins, such as those taught in U.S. Pat. Appl. Pub. No. 60/344,169 and WO 03/056914 (GlycoFi, Inc.) or in WO 2004/057002 and WO 2004/024927 (Greenovation).

Further examples of publications related to "defucosylated" or "fucose-deficient" antibody variants include: WO 2000/61739; WO 2001/29246; US 2002/0164328; US 2004/0109865; WO 2005/035586; WO 2005/035778; W02005/053742; W02002/031140; Okazaki et al. J. Mol. Biol. 336: 1239-1249 (2004); Yamane-Ohnuki et al. Biotech. Bioeng.

87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

In a particular embodiment, the anti-FAP antibodies of the invention have an increased proportion of bisected, nonfucosylated oligosaccharides in the Fc region. The bisected, nonfucosylated oligosaccharides may be either hybrid or complex. Specifically, the methods of the present invention may be used to produce anti-FAP antibodies in which at least about 10% to about 100%, specifically at least about 15%, more specifically at least about 20% to about 25%, and more specifically at least about 30% to about 35% of the oligosaccharides in the Fc region of the antigen binding molecule are bisected, nonfucosylated. The anti-FAP antibodies of the present invention may also comprise an Fc region in which at least about 10% to about 100%, specifically at least about 15%, more specifically at least about 20% to about 25%, and more specifically at least about 30% to about 35% of the oligosaccharides in the Fc region of the antibody are bisected hybrid nonfucosylated.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Increases in ADCC or other effector functions of the anti-FAP antibodies of the present invention can also achieved by increasing affinity of the antigen binding molecule for FAP, for example by affinity maturation or other methods of improving affinity (see Tang et al., *J. Immunol.* 2007, 179:2815-2823), or by amino acid modifications in the Fc region as described below. Combinations of these approaches are also encompassed by the present invention.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998).

C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

For further examples concerning Fc region variants see also U.S. Pat. Appl. Nos. 60/439,498; 60/456,041; 60/514, 549; or WO 2004/063351 (variant Fc regions with increased binding affinity due to amino acid modification); or U.S. patent application Ser. No. 10/672,280 or WO 2004/099249 (Fc variants with altered binding to FcγR due to amino acid modification), Duncan & Winter, *Nature* 322:738-40 (1988); U.S. Pat. No. 5,648,260; U.S. Pat. No. 5,624,821; and WO 94/29351.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an antibody conjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated polynucleotide encoding an anti-FAP antibody described herein is provided. Such polynucleotide may encode an amino acid sequence comprising the VL and/or an amino acid sequence comprising the VH of the antibody (e.g., the light and/or heavy chains of the antibody). In a further embodiment, one or more vectors (e.g., cloning vectors or expression vectors) comprising such polynucleotide are provided. In a further embodiment, a host cell comprising such polynucleotide or such vector is provided. In one such embodiment, a host cell comprises (e.g., has been transformed with): (1) a vector comprising a polynucleotide that encodes an amino acid sequence comprising the VL of the antibody and an amino acid sequence comprising the VH of the antibody (e.g. a polycistronic vector), or (2) a first vector comprising a polynucleotide that encodes an amino acid sequence comprising the VL of the antibody and a second vector comprising a polynucleotide that encodes an amino acid sequence comprising the VH of the antibody. In one embodiment, the host cell is a eukaryotic cell, particularly a mammalian cell, e.g. a Chinese Hamster Ovary (CHO), a baby hamster kidney (BHK) cell or lymphoid cell (e.g., Y0, NS0, Sp20 cell). In one embodiment, a method of making an anti-FAP antibody is provided, wherein the method comprises culturing a host cell comprising a polynucleotide encoding the antibody, as provided above, under conditions suitable for expression of the antibody, and optionally recovering the antibody from the host cell (or host cell culture medium).

For recombinant production of an anti-FAP antibody, one or more polynucleotide(s) encoding an antibody, e.g., as described above, are isolated and inserted into one or more vectors for further cloning and/or expression in a host cell. Methods which are well known to those skilled in the art can be used to construct expression vectors containing the coding sequence of an anti-FAP antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989) and Ausubel et al., CURRENT PROTOCOLS IN MOLECULAR BIOLOGY, Greene Publishing Associates and Wiley Interscience, N.Y (1989).

In one embodiment, one or several polynucleotides encoding an anti-FAP antibody may be expressed under the control of a constitutive promoter or, alternatively, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different polynucleotides encoding an antibody of the present invention are comprised within the host cell system, some of them may be expressed under the control of a constitutive promoter, while others are expressed under the control of a regulated promoter.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B.K.C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006). Such expression systems are also taught in U.S. Pat. Appl. No. 60/344,169 and WO 03/056914 (methods for producing human-like glycoprotein in a non-human eukaryotic host cell).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B.K.C. Lo, ed., Humana Press, Totowa, N.J.), pp. 255-268 (2003).

Stable expression is generally preferred to transient expression because it typically achieves more reproducible results and also is more amenable to large-scale production; however, it is within the skill of one in the art to determine whether transient expression is better for a particular situation.

The present invention is further directed to a method for modifying the glycosylation profile of the anti-FAP antibodies of the present invention that are produced by a host cell, comprising expressing in said host cell one or more polynucleotide(s) encoding an anti-FAP antibody and one or more polynucleotide(s) encoding a polypeptide with a glycosyltransferase activity, or a vector comprising such polynucleotides. Generally, any type of cultured cell line, including the cell lines discussed above, can be used to generate cell lines for the production of anti-FAP antibodies with altered glycosylation pattern. Preferred cell lines include CHO cells, BHK cells, NS0 cells, SP2/0 cells, YO myeloma cells, P3X63 mouse myeloma cells, PER cells, PER.C6 cells or hybridoma cells, and other mammalian cells. Polypeptides with glycosyltransferase activity include β(1,4)-N-acetylglucosaminyltransferase III (GnTIII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). In one embodiment, a combination of polynucleotides encoding for polynucleotides with glycosyltransferase activity are expressed in the host cell (e.g., GnTIII and Man II). Likewise, the method also encompasses expression of one or more polynucleotide(s) encoding the anti-FAP antibody in a host cell in which a glycosyltransferase gene has been disrupted or otherwise deactivated (e.g., a host cell in which the activity of the gene encoding α1,6 core fucosyltransferase has been knocked out). In a particular embodiment, the anti-FAP antibodies of the present invention can be produced in a host cell that further expresses a polynucleotide encoding a polypeptide having GnTIII activity to modify the glycosylation pattern of said antibodies. In a specific embodiment, the polypeptide having GnTIII activity is a fusion polypeptide comprising the Golgi localization domain of a Golgi resident polypeptide. In another particular embodiment, the expression of the anti-FAP antibody of the present invention in a host cell that expresses a polynucleotide encoding a polypeptide having GnTIII activity results in anti-FAP antibodies with increased Fc receptor binding affinity and/or increased effector function. Accordingly, in one embodiment, the present invention is directed to a host cell comprising (a) one or more isolated polynucleotide(s) comprising a sequence encoding a polypeptide having GnTIII activity; and (b) one or more isolated polynucleotide (s) encoding an anti-FAP antibody of the present invention. In a particular embodiment, the polypeptide having GnTIII activity is a fusion polypeptide comprising the catalytic domain of GnTIII and the Golgi localization domain of a heterologous Golgi resident polypeptide. Particularly, said Golgi localization domain is the Golgi localization domain of mannosidase II. Methods for generating such fusion polypeptides and using them to produce antibodies with increased effector functions are disclosed in WO2004/065540, U.S. Provisional Pat. Appl. No. 60/495,142 and U.S. Pat. Appl. Publ. No. 2004/0241817, the entire contents of which are expressly incorporated herein by reference. In another embodiment, the host cell additionally comprises an isolated polynucleotide comprising a sequence encoding a polypeptide having mannosidase II (ManII) activity. The polynucleotide(s) encoding polypeptide(s), like the polynucleotide(s) encoding the anti-FAP antibody, may be expressed under the control of a constitutive promoter or, alternately, a regulated expression system. Such systems are well known in the art, and include the systems discussed above.

The host cells which contain the coding sequence of the anti-FAP antibody and/or the coding sequence of polypeptides having glycosyltransferase activity, and which express the biologically active gene products may be identified e.g. by DNA-DNA or DNA-RNA hybridization; the presence or absence of "marker" gene functions; assessing the level of transcription as measured by the expression of the respective mRNA transcripts in the host cell; or detection of the gene product as measured by immunoassay or by its biological activity—methods which are well known in the art. GnTIII or Man II activity can be detected e.g. by employing a lectin which binds to biosynthetis products of GnTIII or ManII, respectively. An example for such a lectin is the $E_4$-PHA lectin which binds preferentially to oligosaccharides containing bisecting GlcNAc. Biosynthesis products (i.e. specific oligosaccharide structures) of polypeptides having GnTIII or ManII activity can also be detected by mass spectrometric analysis of oligosaccharides released from glycoproteins produced by cells expressing said polypeptides. Alternatively, a functional assay which measures the increased Fc receptor binding or increased effector function mediated by antibodies produced by the cells engineered with the polynucleotide encoding a polypeptide having GnTIII activity may be used.

The present invention is also directed to a method for producing an anti-FAP antibody having modified oligosaccharides, comprising (a) culturing a host cell engineered to express at least one polynucleotide encoding a polypeptide having glycosyltransferase activity under conditions which permit the production of an anti-FAP antibody according to the present invention, wherein said polypeptide having glycosyltransferase activity is expressed in an amount sufficient to modify the oligosaccharides in the Fc region of said anti-FAP antibody produced by said host cell; and (b) isolating said anti-FAP antibody. In one embodiment, the polypeptide having glycosyltransferase activity is GnTIII. In another embodiment, there are two polypeptides having glycosyltransferase activity. In a particular embodiment, the two peptides having glycosyltransferase activity are GnTIII and ManII In another embodiment, the polypeptide having glycosyltransferase activity is a fusion polypeptide comprising the catalytic domain of GnTIII. In a more specific embodiment, the fusion polypeptide further comprises the Golgi localization domain of a Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase.

In a particular embodiment, the modified anti-FAP antibody produced by the host cell or method described above has an IgG constant region or a fragment thereof comprising the Fc region. In another particular embodiment the anti-FAP antibody is a humanized or human antibody or a fragment thereof comprising an Fc region.

The anti-FAP antibody with altered glycosylation produced by the host cell or method described above typically exhibit increased Fc receptor binding affinity and/or increased effector function as a result of the modification of the host cell (e.g., by expression of a glycosyltransferase gene). Preferably, the increased Fc receptor binding affinity is increased binding to an activating Fcγ receptor, most preferably the FcγRIIIa receptor. The increased effector function is preferably an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNCs), increased binding to monocytes, increased crosslinking of target-bound antibodies, increased direct signaling inducing apoptosis, increased dendritic cell maturation, and increased T cell priming.

C. Assays

Anti-FAP antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with another specific anti-FAP antibody for binding to FAP. In certain embodiments, such a competing antibody binds to the same epitope (e.g., a linear or a conformational epitope) that is bound by said other specific anti-FAP antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized FAP is incubated in a solution comprising a first labeled antibody that binds to FAP (e.g. the 3F2 antibody described in the Examples) and a second unlabeled antibody that is being tested for its ability to compete with the first antibody for binding to FAP. The second antibody may be present in a hybridoma supernatant. As a control, immobilized FAP is incubated in a solution comprising the first labeled antibody but not the second unlabeled antibody. After incubation under conditions permissive for binding of the first antibody to FAP, excess unbound antibody is removed, and the amount of label associated with immobilized FAP is measured. If the amount of label associated with immobilized FAP is substantially reduced in the test sample relative to the control sample, then that indicates that the second antibody is competing with the first antibody for binding to FAP. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-FAP antibodies thereof having biological activity. Biological activity may include, e.g., lysis of targeted cells, antibody-dependent cell-mediated cytotoxicity (ADCC), complement-dependent cytotoxicity (CDC), or induction of apoptosis. Antibodies having such biological activity in vivo and/or in vitro are also provided. In certain embodiments, an antibody of the invention is tested for such biological activity. Exemplary assays for testing ADCC are described hereinbefore (see under "Definitions": "antibody having increased ADCC") and in Example 11. Assays for detecting cell lysis (e.g. by measurement of LDH release) or apoptosis (e.g. using the TUNEL assay) are well known in the art. Assays for measuring ADCC or CDC are also described in WO 2004/065540 (see Example 1 therein), the entire content of which is incorporated herein by reference.

D. Antibody Conjugates

The invention also provides conjugates comprising an anti-FAP antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, in an antibody-drug conjugate (ADC) an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an antibody conjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

In another embodiment, an antibody conjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The antibody conjugates herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-FAP antibodies provided herein is useful for detecting the presence of FAP in a biological sample. The term "detecting" as used herein encompasses quantitative or qualitative detection. In certain embodiments, a biological sample comprises a cell or tissue, such as cells or tissues from brain, breast, colon, kidney, liver, lung, ovary, pancreas, prostate, skeletal muscle, skin, small intestine, stomach or uterus, including also cells or tissues tumors of these organs.

In one embodiment, an anti-FAP antibody for use in a method of diagnosis or detection is provided. In a further aspect, a method of detecting the presence of FAP in a biological sample is provided. In certain embodiments, the method comprises contacting the biological sample, optionally with a control sample, with an anti-FAP antibody as described herein under conditions permissive for binding of the anti-FAP antibody to FAP, and detecting whether a complex is formed between the anti-FAP antibody and FAP. Such method may be an in vitro or in vivo method. In one embodiment, an anti-FAP antibody is used to select subjects eligible for therapy with an anti-FAP antibody, e.g. where FAP is a biomarker for selection of patients.

Exemplary disorders that may be diagnosed using an antibody of the invention include disorders associated with the expression of FAP, such as cancer and certain inflammatory conditions. In one aspect, a method of diagnosing disease in a subject is provided, said method comprising administering to said subject an effective amount of a diagnostic agent, wherein said diagnostic agent comprises an anti-FAP antibody as described herein and a label, typically an imaging agent, that allows detection of a complex of said diagnostic agent and FAP.

In certain embodiments, labeled anti-FAP antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-FAP antibody as described herein are prepared by mixing such antibody having the desired degree of purity with one or more optional pharmaceutically acceptable carriers (*Remington's*

*Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, acetate and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958.

Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, if the disease to be treated is cancer, it may be desirable to further provide one or more anti-cancer agents, e.g. a chemotherapeutic agent, an inhibitor of tumor cell proliferation, or an activator of tumor cell apoptosis. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. The formulations to be used for in vivo administration are generally sterile. Sterility may be readily accomplished, e.g., by filtration through sterile filtration membranes.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application, but will typically be injectable or infusible solutions.

G. Therapeutic Methods and Compositions

Any of the anti-FAP antibodies or pharmaceutical formulations comprising the anti-FAP antibodies provided herein may be used in therapeutic methods.

The anti-FAP antibodies provided herein can be used for treating diseases characterized by FAP expression, particularly by abnormal expression (e.g. overexpression, or expression in a different pattern in the cell) of FAP compared to normal tissue of the same cell type. FAP is abnormally expressed (e.g. overexpressed) in many human tumors compared to non-tumor tissue of the same cell type. Thus, the anti-FAP antibodies provided herein are particularly useful in the prevention of tumor formation, eradication of tumors and inhibition of tumor growth or metastasis. The anti-FAP antibodies provided herein can be used to treat any tumor expressing FAP. Particular malignancies that can be treated by the anti-FAP antibodies provided herein include, for example, lung cancer, colon cancer, gastric cancer, breast cancer, head and neck cancer, skin cancer, liver cancer, kidney cancer, prostate cancer, pancreatic cancer, brain cancer, cancer of the skeletal muscle.

The anti-FAP antibodies disclosed herein can be used to inhibit tumor growth or kill tumor cells. For example, the anti-FAP antibodies can bind to FAP that is on the membrane or cell surface of cancerous cells (tumor cells or cells of the tumor stroma) and elicit, e.g., ADCC or other effector mediated killing of the cancerous cells.

The anti-FAP antibodies can alternatively be used in order to block the function of FAP, particularly by physically interfering with its binding of another compound. For example, the antigen binding molecules can be used to block the enzymatic activity of FAP (e.g. serine peptidase, gelatinase, collagenase activity), FAP mediated ECM degradation, and/or FAP mediated cell invasion or migration.

In one aspect, an anti-FAP antibody for use as a medicament is provided. In further aspects, an anti-FAP antibody for use in treating a disease characterized by expression of FAP is provided. In certain embodiments, an anti-FAP antibody for use in a method of treatment is provided. In certain embodiments, the invention provides an anti-FAP antibody for use in a method of treating an individual having a disease characterized by expression of FAP, comprising administering to the individual an effective amount of the anti-FAP antibody. In one such embodiment, the method further comprises administering to the individual an effective amount of at least one additional therapeutic agent, e.g., as described below. In further embodiments, the invention provides an anti-FAP antibody for use in inducing lysis of a cell. In certain embodiments, the invention provides an anti-FAP antibody for use in a method of inducing lysis of a cell in an individual comprising administering to the individual an effective amount of the anti FAP antibody to induce lysis of a cell. An "individual" according to any of the above embodiments is preferably a human. A "disease characterized by expression of FAP" according to any of the above embodiments is preferably cancer, most preferably a cancer selected from the group of lung cancer, colon cancer, gastric cancer, breast cancer, head and neck cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "FAP expression" according to any of the above embodiments preferably is abnormal expression, such as overexpression or expression in a different pattern in the cell, compared to normal tissue of the same cell type.

In a further aspect, the invention provides for the use of an anti-FAP antibody in the manufacture or preparation of a medicament. In one embodiment, the medicament is for treatment of a disease characterized by expression of FAP. In a further embodiment, the medicament is for use in a method of treating a disease characterized by expression of FAP comprising administering to an individual having a disease characterized by expression of FAP an effective amount of the medicament. In one such embodiment, the method further comprises administering to the individual an effective amount of at least one additional therapeutic agent, e.g., as described below. In a further embodiment, the medicament is for inducing lysis of a cell. In a further embodiment, the medicament is for use in a method of inducing lysis of a cell in an individual comprising administering to the individual an amount effective of the medicament to inducing lysis of a cell. An "individual" according to any of the above embodiments is preferably a human. A "disease characterized by expression of FAP" according to any of the above embodiments is preferably cancer, most preferably a cancer selected from the group of lung cancer, colon cancer, gastric cancer, breast cancer, head and neck cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "FAP expression" according to any of the above embodiments preferably is abnormal expression, such as overexpression or expression in a different pattern in the cell, compared to normal tissue of the same cell type.

In a further aspect, the invention provides a method for treating a disease characterized by expression of FAP. In one embodiment, the method comprises administering to an individual having such disease characterized by expression of FAP an effective amount of an anti-FAP antibody. In one such embodiment, the method further comprises administering to the individual an effective amount of at least one additional therapeutic agent, as described below. In a further embodiment, the invention provides a method for inducing lysis of a cell in an individual. In one embodiment, the method comprises administering to the individual an effective amount of an anti-FAP antibody to induce lysis of a cell. An "individual" according to any of the above embodiments may be a human. A "disease characterized by expression of FAP" according to any of the above embodiments is preferably cancer, most preferably a cancer selected from the group of lung cancer, colon cancer, gastric cancer, breast cancer, head and neck cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "FAP expression" according to any of the above embodiments preferably is abnormal expression, such as overexpression or expression in a different pattern in the cell, compared to normal tissue of the same cell type.

In a further aspect, the invention provides pharmaceutical formulations comprising any of the anti-FAP antibodies provided herein, e.g., for use in any of the above therapeutic methods. In one embodiment, a pharmaceutical formulation comprises any of the anti-FAP antibodies provided herein and one or more pharmaceutically acceptable carrier. In another embodiment, a pharmaceutical formulation comprises any of the anti-FAP antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is an anti-cancer agent, e.g. a chemotherapeutic agent, an inhibitor of tumor cell proliferation, or an activator of tumor cell apoptosis.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy. An antibody of the invention (and any additional therapeutic agent) can be administered by any suitable means, including parenteral, intrapulmonary, and intranasal, and, if desired for local treatment, intralesional administration. Parenteral administration includes intramuscular, intravenous, intraarterial, intraperitoneal, or subcutaneous administration. Intravenous administration is typically preferred. However, the intraperitoneal route is expected to be particularly useful, for example, in the treatment of colorectal tumors. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an antibody conjugate of the invention in place of or in addition to an anti-FAP antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an antibody conjugate of the invention in place of or in addition to an anti-FAP antibody.

III. EXAMPLES

The following are examples of methods and compositions of the invention. It is understood that various other embodiments may be practiced, given the general description provided above.

Example 1

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions. DNA sequences were determined by double strand sequencing. In some cases desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of the subcloned gene fragments was confirmed by DNA sequencing. Gene Segments were designed with suitable restriction sites to allow sub-cloning into the respective expression vectors.

General information regarding the nucleotide sequences of human immunoglobulin light and heavy chains is given in: Kabat, E. A. et al., (1991) Sequences of Proteins of Immunological Interest, Fifth Ed., NIH Publication No 91-3242. For expression, all constructs contained a 5'-end DNA sequence coding for a leader peptide which targets proteins for secretion in eukaryotic cells. SEQ ID NOs 323-331 give exemplary leader peptides and polynucleotide sequences encoding them.

Preparation of (Glycoengineered) Antibodies

The full antibody heavy and light chain DNA sequences have been obtained by subcloning the variable regions in frame with either the constant heavy chain or the constant light chain pre-inserted into the respective recipient mammalian expression vector. The antibody expression was driven by an MPSV promoter and the vector carries a synthetic polyA signal sequence at the 3' end of the CDS. In addition each vector contains an EBV OriP sequence.

Antibodies are produced by co-transfecting HEK293-EBNA cells with the mammalian antibody expression vectors using a calcium phosphate-transfection. Exponentially growing HEK293-EBNA cells are transfected by the calcium phosphate method. Alternatively, HEK293 cells growing in suspension are transfected by polyethylenimine. For the production of unmodified non-glycoengineered antibody, the cells are transfected only with antibody heavy and light chain expression vectors in a 1:1 ratio.

For the production of the glycoengineered antibody, the cells are co-transfected with two additional plasmids, one for a fusion GnTIII polypeptide expression (a GnT-III expression vector), and one for mannosidase II expression (a Golgi mannosidase II expression vector) at a ratio of 4:4:1:1, respectively. Cells are grown as adherent monolayer cultures in T flasks using DMEM culture medium supplemented with 10% FCS, and are transfected when they are between 50 and 80% confluent. For the transfection of a T150 flask, 15 million cells are seeded 24 hours before transfection in 25 ml DMEM culture medium supplemented with FCS (at 10% V/V final), and cells are placed at 37° C. in an incubator with a 5% CO$_2$ atmosphere overnight. For each T150 flask to be transfected, a solution of DNA, CaCl$_2$ and water is prepared by mixing 94 µg total plasmid vector DNA divided equally between the light and heavy chain expression vectors, water to a final volume of 469 µl and 469 µl of a 1M CaCl$_2$ solution. To this solution, 938 µl of a 50 mM HEPES, 280 mM NaCl, 1.5 mM Na$_2$HPO$_4$ solution at pH 7.05 are added, mixed immediately for 10 sec and left to stand at room temperature for 20 sec. The suspension is diluted with 10 ml of DMEM supplemented with 2% FCS, and added to the T150 in place of the existing medium. Then additional 13 ml of transfection medium are added. The cells are incubated at 37° C., 5% CO$_2$ for about 17 to 20 hours, then medium is replaced with 25 ml DMEM, 10% FCS. The conditioned culture medium is harvested approx. 7 days post-media exchange by centrifugation for 15 min at 210×g, the solution is sterile filtered (0.22 um filter) and sodium azide in a final concentration of 0.01% w/v is added, and kept at 4° C.

The secreted wildtype or glycoengineered a fucosylated antibodies are purified from cell culture supernatants by affinity chromatography using Protein A (HiTrap ProtA, GE Healthcare) affinity chromatography. Briefly, the column was equilibrated with 20 mM sodium phosphate, 20 mM sodium citrate pH 7.5, the cell supernatant was loaded, followed by a first wash with 20 mM sodium phosphate, 20 mM sodium citrate pH 7.5, and a second wash with 13.3 mM sodium phosphate, 20 mM sodium citrate, 500 mM sodium chloride pH 5.45. The antibodies were eluted with 20 mM sodium citrate, 100 mM sodium chloride, 100 mM glycine pH 3. In a subsequent size exclusion chromatographic step on a HiLoad Superdex 200 column (GE Healthcare) the buffer was exchanged to 25 mM potassium phosphate, 125 mM sodium chloride, 100 mM glycine solution of pH 6.7 or alternatively 140 mM sodium chloride, 20 mM histidine, pH 6.0 and the pure monomeric IgG1 antibodies were collected. If required an additional cation exchange chromatography step is included between the two standard purification steps.

The protein concentration of purified protein samples is determined by measuring the optical density (OD) at 280 nm, using the molar extinction coefficient calculated on the basis of the amino acid sequence. Purity and molecular weight of antibodies are analyzed by SDS-PAGE in the presence and absence of a reducing agent (5 mM 1,4-dithiothreitol) and staining with Coomassie (SimpleBlue™ SafeStain from Invitrogen). The NuPAGE® Pre-Cast gel system (Invitrogen, USA) is used according to the manufacturer's instruction (4-20% Tris-Glycine gels or 3-12% Bis-Tris). The aggregate content of antibody samples is analyzed using a Superdex 200 10/300GL analytical size-exclusion column (GE Healthcare, Sweden) in 2 mM MOPS, 150 mM NaCl, 0.02% NaN$_3$, pH 7.3 running buffer at 25° C. The integrity of the amino acid backbone of reduced antibody light and heavy chains is verified by NanoElectrospray Q-TOF mass spectrometry after removal of N-glycans by enzymatic treatment with Peptide-N Glycosidase F (Roche Molecular Biochemicals).

The results of the purification and analysis of the wild-type and glycoengineered 28H1, 29B11, 3F2 and 4G8 human IgG antibodies are shown in FIGS. 15A-D, 16A-D, 17A-D, 18A-D, 19A-D, 20A-D, 21A-D, and 22A-D. The yields are given in the following table:

|  | Yield [mg/L] | |
| --- | --- | --- |
|  | wild-type | glyco-engineered |
| 28H1 hu IgG | 46 | 40 |
| 29B11 hu IgG | 10 | 14 |
| 3F2 hu IgG | 144 | 7 |
| 4G8 hu IgG | 55 | 12.6 |

The oligosaccharides attached to the Fc region of the antibodies are analysed by MALDI TOF-MS as described below. Oligosaccharides are enzymatically released from the antibodies by PNGaseF digestion. The resulting digest solution containing the released oligosaccharides is either prepared directly for MALDI TOF-MS analysis or is further digested with EndoH glycosidase prior to sample preparation for MALDI TOF-MS analysis.

Analysis of Glycostructure of (Glycoengineered) Antibodies

For determination of the relative ratios of fucose- and non-fucose (a-fucose) containing oligosaccharide structures, released glycans of purified antibody material are analyzed by MALDI-Tof-mass spectrometry. The antibody sample (about 50 µg) is incubated overnight at 37° C. with 5 mU N-Glycosidase F (QAbio; PNGaseF: E-PNG01) in 2 mM Tris, pH 7.0, in order to release the oligosaccharide from the protein backbone. For deamination of glycans acetic acid to a final concentration of 150 mM is added and incubated for 1 h at 37° C. For analysis by MALDI TOF mass spectrometry, 2 µL of the sample are mixed on the MALDI target with 2 µL DHB matrix solution (2,5-dihydroxybenzoic acid [Bruker Daltonics #201346] dissolved in 50% ethanol/5 mM NaCl at 4 mg/ml) and analysed with MALDI TOF Mass Spectrometer Autoflex II instrument [Bruker Daltonics]. Routinely, 50-300 shots are recorded and summed up to a single experiment. The spectra obtained are evaluated by the flex analysis software (Bruker Daltonics) and masses are determined for the each of the peaks detected. Subsequently, the peaks are assigned to fucose or a-fucose (non-fucose) containing carbohydrate structures by comparing the masses calculated and the masses theoretically expected for the respective structures (e.g. complex, hybrid and oligo-or high-mannose, respectively, with and without fucose).

For determination of the ratio of hybrid structures, the antibody samples are digested with N-Glycosidase F and Endo-Glycosidase H [QAbio; EndoH: E-EH02] concomitantly. N-Glycosidase F releases all N-linked glycan structures (complex, hybrid and oligo- and high mannose structures) from the protein backbone and the Endo-Glycosidase H cleaves all the hybrid type glycans additionally between the two N-acetylglucosamine (GlcNAc) residues at the reducing end of the glycan. This digest is subsequently treated and analysed by MALDI TOF mass spectrometry in the same way as described above for the N-Glycosidase F digested sample.

By comparing the pattern from the N-Glycosidase F digest and the combined N-glycosidase F/Endo H digest, the degree of reduction of the signals of a specific carbohydrate structure is used to estimate the relative content of hybrid structures. The relative amount of each carbohydrate structure is calculated from the ratio of the peak height of an individual structure and the sum of the peak heights of all oligosaccharides detected. The amount of fucose is the percentage of fucose-containing structures related to all carbohydrate structures identified in the N-Glycosidase F treated sample (e.g. complex, hybrid and oligo- and high-mannose structures, resp.). The amount of non-fucosylation is the percentage of fucose-lacking structures related to all carbohydrates identified in the N-Glycosidase F treated sample (e.g. complex, hybrid and oligo- and high-mannose structures, resp.).

The degrees of non-fucosylation of the different wild-type and glycoengineered anti-FAP antibodies is given in the following table:

| Antibody | Non-fucosylation [%] | |
|---|---|---|
| | Wild-type | glyco-engineered |
| Hu IgG 28H1 | 10 | 40 |
| Hu IgG 29B11 | 5 | 27 |
| Hu IgG 3F2(YS) | 2.4 | 64 |
| Hu IgG 4G8 | 3.8 | 78 |

Example 2

Construction of Generic Fab-Libraries

Generic antibody libraries in the Fab-format were constructed on the basis of human germline genes using the following V-domain pairings: Vk3_20 kappa light chain with VH3_23 heavy chain for the DP47-3 library and Vk1_17 kappa light chain with VH1_69 heavy chain for the DP88-3 library. See SEQ ID NOs 1 and 2.

Both libraries were randomized in CDR3 of the light chain (L3) and CDR3 of the heavy chain (H3) and were assembled from 3 fragments per library by splicing by overlapping extension (SOE) PCR. Fragment 1 comprises the 5' end of the antibody gene including randomized L3, fragment 2 is a central constant fragment spanning from L3 to H3, whereas fragment 3 comprises randomized H3 and the 3' portion of the antibody gene.

The following primer combinations were used to generate library fragments for DP47-3 library: fragment 1 (LMB3-LibL1b_new), fragment 2 (MS63-MS64), fragment 3 (Lib2H-fdseqlong). See Table 3. The following primer combinations were used to generate library fragments for the DP88-3 library: fragment 1 (LMB3-RJH_LIB3), fragment 2 (RJH31-RJH32) and fragment 3 (LIB88_2-fdseqlong). See Table 4.

TABLE 3

| Primers Used In the DP47-3 Library | | SEQ ID NO |
|---|---|---|
| LMB3 | CAGGAAACAGCTATGACCATGATTAC | 332 |
| LibL1b_new | CACTTTGGTCCCCTGGCCGAACGTMNNGGGMNNM NNMNNACCCTGCTGACAGTAATACACTGC | 333 |
| MS63 | TTTCGCACAGTAATATACGGCCGTGTCC | 334 |
| MS64 | ACGTTCGGCCAGGGGACCAAAGTGG | 335 |
| Lib2H | GGCCGTATATTACTGTGCGAAANNKNNKNNKNNK NNKTTTGACTACTGGGGCCAAGGAAC | 336 |
| fdseqlong | GACGTTAGTAAATGAATTTTCTGTATGAGG | 337 |

TABLE 4

| Primers Used in DP88-3 Library | | SEQ ID NO |
|---|---|---|
| LMB3 | CAGGAAACAGCTATGACCATGATTAC | 332 |
| RJH_LIB3 | GACTTTGGTGCCCTGGCCAAACGT MNN GGG MNN MNN ACC MNN CTGCAAGCAGTAATAGGTGGCAAAATC | 338 |
| RJH31 | ACGTTTGGCCAGGGCACCAAAGTCGAG | 339 |
| RJH32 | TCTCGCACAGTAATACACGGCGGTGTCC | 340 |
| LIB88_2 | GGACACCGCCGTGTATTACTGTGCGAGA-[33% GAC Asp; 26% GGT Gly; 10% GAA Glu; 9% CGT Arg; 7% Lys; 6% GTT Val; 5% TCT Ser; 4% CTG Leu]1 - (23% GGT Gly; 17% TAC Tyr; 16% TCT Ser; 11% GCT Ala; 9% CGT Arg; 7% AAC Asn; 6% ACT Thr; 6% GTT Val; 5% CCG Pro)8]-TTTGACTACTGGGGCCAAGGGACCACCGTGA CCGTCTCC | 341 |
| fdseqlong | GACGTTAGTAAATGAATTTTCTGTATGAGG | 337 |

The PCR protocol for the production of library fragments included: 5 minutes of initial denaturation at 94° C.; 25 cycles of 1 minute at 94° C., 1 minute at 58° C., and 1 minute at 72° C.; and terminal elongation for 10 minutes at 72° C. For assembly PCR, equimolar ratios of the 3 fragments were used as template. The assembly PCR protocol included: 3 minutes of initial denaturation at 94° C.; and 5 cycles of 30 seconds at 94° C., 1 minute at 58° C., and 2 minutes at 72° C. At this stage, primers complementary to sequence outside fragments 1-3 were added and an additional 20 cycles were performed prior to a terminal elongation for 10 min at 72° C. After assembly of sufficient amounts of full length randomized Fab constructs, the Fab constructs were digested with NcoI/NotI for the DP47-3 library and with NcoI/NheI for the DP88-3 library alongside with similarly treated acceptor phagemid vector. For the DP47-3 library, 22.8 μg of Fab library was ligated with 16.2 μg of phagemid vector. For the DP88-3 library, 30.6 μg of Fab library was ligated with 30.6 μg of phagemid vector.

Purified ligations were used for 68 transformations for the DP47-3 library and 64 transformations for the DP88-3 library, respectively, to obtain final library sizes of $4.2 \times 10^{10}$ for DP47-3 and $3.3 \times 10^9$ for DP88-3. Phagemid particles displaying the Fab libraries were rescued and purified by PEG/NaCl purification to be used for selections.

Example 3

Selection of Anti-FAP Clones (Primary Selections)

Selections were carried out against the ectodomain of human or murine fibroblast activating protein (FAP) which were cloned upstream a poly-lysine and a 6×his-tag. See SEQ ID NOs: 317 and 319. Prior to selections, the antigens were coated into immunotubes at a concentration of either 10 μg/ml or 5 μg/ml, depending on round of selection. Selections were carried out according to the following protocol: (i) binding of ~$10^{12}$ phagemid particles of library DP47-3 to immobilized human or murine FAP for 2 hours; (ii) washing of immunotubes using 5×5 mL PBS/Tween20 and 5×5 ml PBS; (iii) elution of phage particles by addition of 1 mL 100 mM TEA (triethylamine) for 10 minutes and neutralization by the addition of 500 μL 1M Tris/HCl pH 7.4; and (iv) re-infection of log-phase E. coli TG1 cells, infection with helperphage VCSM13 and subsequent PEG/NaCl precipitation of phagemid particles to be used in subsequent selection rounds.

Selections have been carried out over three or four rounds using decreasing antigen concentrations of human FAP and in some cases using murine FAP at 5 µg/ml in the final selection round. Specific binders were defined as signals 5× higher than background and were identified by ELISA. NUNC maxisorp plates were coated with 10 µg/ml of human or murine FAP followed by addition of Fab-containing bacterial supernatants and detection of specifically binding Fabs via their Flag-tags by using an anti-Flag/HRP secondary antibody.

ELISA-positive clones were bacterially expressed as 1 mL cultures in 96-well format and supernatants were subjected to a kinetic screening experiment using BIACORE T100. $K_D$ was measured by surface plasmon resonance using a BIACORE® T100 machine (GE Healthcare) at 25° C. with anti-human F(ab')2 fragment specific capture antibody (Jackson ImmunoResearch #109-005-006) immobilized by amine coupling on CM5 chips and subsequent capture of Fabs from bacterial supernatant or from purified Fab preparations. Briefly, carboxymethylated dextran biosensor chips (CM5, GE Healthcare) were activated with N-ethyl-N'-(3-dimethylaminopropyl)-carbodiimide hydrochloride (EDC) and N-hydroxysuccinimide (NHS) according to the supplier's instructions. Anti-human F(ab')2 fragment specific capture antibody was diluted with 10 mM sodium acetate, pH 5.0 at 50 µg/ml before injection at a flow rate of 10 µl/minute to achieve approximately up to 10.000 response units (RU) of coupled capture antibody. Following the injection of the capture antibody, 1 M ethanolamine was injected to block unreacted groups. For kinetic measurements, Fabs from bacterial supernatant or purified Fabs were injected at a flow rate of 10 µl/min for 300 s and a dissociation of 300 s for capture baseline stabilization. Capture levels were in the range of 100-500 RU. In a subsequent step, human or murine FAP analyte was injected either as a single concentration or as a concentration series (depending of clone affinity in a range between 100 nM and 250 pM) diluted in HBS-EP+ (GE Healthcare, 10 mM HEPES, 150 mM NaCl, 3 mM EDTA, 0.05% Surfactant P20, pH 7.4) at 25° C. at a flow rate of 50 µl/min. Association time was 120 or 180 s, dissociation time was 300 to 600 s. The surface of the sensorchip is regenerated by injection of glycine pH 1.5 for 30 s at 90 µl/min followed by injection of NaOH for 20s at the same flow rate. Association rates ($k_{on}$) and dissociation rates ($k_{off}$) were calculated using a simple one-to-one Langmuir binding model (BIACORE® T100 Evaluation Software or Scrubber software (BioLogic)) by simultaneously fitting the association and dissociation sensorgrams. The equilibrium dissociation constant ($K_D$) was calculated as the ratio $k_{off}/k_{on}$.

Example 4

Construction of Anti-FAP Affinity Maturation Libraries

Three affinity maturation libraries were constructed on basis of pre-selected antibodies from the primary anti-FAP selections. More precisely, they were based on (i) anti-human FAP clone 2D9 (library a.m.FAP2D9) (see SEQ ID NOs: 229 and 231), (ii) anti-murine FAP clone 4B8 (library a.m.FAP4B8) (see SEQ ID NOs: 233 and 235) and (iii) cross-reactive clones 7A1, 13B2, 13C2, 13E8, 14C10 and 17A11 (library a.m.FAPpool) (see SEQ ID NOs: 237 and 239 corresponding to the variable region sequences of 7A1; SEQ ID NOs: 241 and 243 corresponding to the variable region sequences of 13C2; SEQ ID NOs: 245 and 247 corresponding to the variable region sequences of 13E8; SEQ ID NOs: 249 and 251 corresponding to the variable region sequences of 14C10; and SEQ ID NOs: 253 and 255 corresponding to the variable region sequences of 17A11).

Each of these libraries consists of two sublibraries, randomized in either CDR1 and CDR2 of the light chain (L1/L2) or CDR1 and CDR2 of the heavy chain (H1/H2), respectively. These sublibraries were pooled upon transformation. Each of these sublibraries was constructed by four subsequent steps of amplification and assembly.

For L1/L2 libraries, the amplification and assembly protocol included: (i) amplification of fragment 1 (LMB3-DPK22_CDR1_rand ba_opt) and fragment 2 (DPK22_CDR1_fo-DPK22_Ck_BsiWI_ba); (ii) assembly of fragments 1 and 2 using outer primers LMB3 and DPK22_Ck_BsiWI_ba to create the template for fragment 3; (iii) amplification of fragment 3 (LMB3-DPK22_CDR2_rand_ba) and fragment 4 (DPK22_CDR2_fo-DPK22_Ck_BsiWI_ba); and (iv) final assembly of fragments 3 and 4 using the same outer primers as above. See Table 5 for primer sequences.

TABLE 5

| Primers Used in L1/L2 Affinity Maturation Libraries for anti-FAP Affinity Maturation | | SEQ ID NO |
|---|---|---|
| LMB3 | CAGGAAACAGCTATGACCATGATTAC | 332 |
| DPK22_CDR1_rand_ba_opt | CAGGTTTCTGCTGGTACCAGGCTAAGTAGCTGCTGCTAACACTCTGACTGGCCCTGCAAG | 342 |
| DPK22_CDR1_fo | TTAGCCTGGTACCAGCAGAAACCTG | 343. |
| DPK22_Ck_BsiWI_ba | GGTGCAGCCACCGTACGTTTGATTTCC | 344 |
| DPK22_CDR2_rand_ba | CTGTCTGGGATGCCAGTGGCCCTGCTGGAG GCGCCATAGATGAGGAGCCTGGGAGCCTG | 345 |
| DPK22_CDR2_fo | AGGGCCACTGGCATCCCAGACAG | 346 |

Bold: 60% original base and 40% randomization as M
Underline: 60% original base and 40% randomization as N For H1/H2 libraries, the amplification and assembly protocol included: (i) amplification of fragment 1 (RJH53-DP47_CDR1_rand_ba_opt) and fragment 2 (DP47_CDR1_fo-MS52); (ii) assembly of fragments 1 and 2 using outer primers RJH53 and MS52 to create the template for fragment 3; (iii) amplification of fragment 3 (RJH53-DP47_CDR2_rand_ba) and fragment 4 (DP47_CDR2_fo-MS52); and (iv) final assembly of fragments 3 and 4 using the same outer primers as above. See Table 6 for primer sequences.

TABLE 6

| Primers Used in H1/H2 Affinity Maturation Libraries for anti-FAP Affinity Maturation | | SEQ ID NO |
|---|---|---|
| RJH53 | CATCAGGGCCTGAGCTCGCCCGTCAC | 347 |
| DP47_CDR1_rand_ba_opt | GAGCCTGGCGGACCCAGCTCATGGCATAACTGCTAAAGGTGAATCCGGAGGC | 348 |
| DP47_CDR1_fo | ATGAGCTGGGTCCGCCAGGCTC | 349 |
| MS52 | GAAGACCGATGGGCCTTTGGTGCTAG | 350 |

TABLE 6-continued

| Primers Used in H1/H2 Affinity Maturation Libraries for anti-FAP Affinity Maturation | SEQ ID NO |
|---|---|
| DP47_CDR2_rand_ba | CCTTCACGGAGTCTGCGTAGTATGTGCTACCACCACTACCACTAATAGCTGAGACCCACTCCAGCCCCTTCCC | 351 |
| DP47_CDR2_fo | ACATACTACGCAGACTCCGTGAAGG | 352 |

Bold: 60% original base and 40% randomization as M
Underline: 60% original base and 40% randomization as N Final assembly products have been digested with NcoI/BsiWI for L1/L2 sublibraries of a.m.FAP2D9 and a.m.FAP4B8, with MunI and NheI for H1/H2 sublibraries of a.m.FAP2D9 and a.m.FAP4B8 as well as with NcoI/BamHI for L1/L2 library of a.m.FAPpool and with BspEI/PstI for H1/H2 libraries of a.m.FAPpool, respectively, alongside with similarly treated acceptor vectors based on plasmid preparations of clones 2D9, 4B8 or an equimolar mixture of clones 7A1, 13B2, 13C2, 13E8, 14C10 and 17A11, respectively. The following amounts of digested randomized (partial) V-domains and digested acceptor vector(s) were ligated for the respective libraries (μg V-domain/m vector): a.m.FAP2D9 L1/L2 sublibrary (5.7/21.5), a.m.FAP2D9 H1/H2 sublibrary (4.1/15.5), a.m.FAP4B8 L1/L2 sublibrary (6.5/24.5), a.m.FAP4B8 H1/H2 sublibrary (5.7/21.5), a.m.FAPpool L1/L2 sublibrary (4.4/20), a.m.FAPpool H1/H2 sublibrary (3.4/15.5).

Purified ligations of L1/L2 and H1/H2 sublibraries were pooled and used for 60 transformations for each of the 3 affinity maturation libraries, to obtain final library sizes of $6.2 \times 10^9$ for a.m.FAP2D9, $9.9 \times 10^9$ for a.m.FAP4B8 and $2.2 \times 10^9$ for a.m.FAPpool.

Phagemid particles displaying these Fab libraries were rescued and purified by PEG/NaCl purification to be used for secondary selections Construction of Additional Anti-FAP Affinity Maturation Libraries (Based on Clones 3F2, 3D9, 4G8, 4B3 and 2C6)

Four additional affinity maturation libraries were constructed on the basis of pre-selected cross-reactive antibodies from the first affinity-maturation campaign of anti-FAP antibodies, namely clones 3F2, 3D9, 4G8, 4B3 and 2C6 (see SEQ ID NOs: 195 and 197 corresponding to the variable region sequences of 3F2; SEQ ID NOs: 199 and 201 corresponding to the variable region sequences of 3D9; SEQ ID NOs: 205 and 207 corresponding to the variable region sequences of 4G8; SEQ ID NOs: 209 and 211 corresponding to the variable region sequences of 4B3; SEQ ID NOs: 217 and 219 corresponding to the variable region sequences of 2C6. More precisely, the four libraries were based on 1) anti-FAP clones 3F2, 4G8 and 4B3 ($V_H$ library, randomized in CDRs 1 and 2 of variable heavy chain, i.e. H1/H2 library), 2) anti-FAP clones 3D9 and 2C6 ($V_L$ library, randomized in CDRs 1 and 2 of variable light chain, i.e. L1/L2 library), 3) anti-FAP clone 3F2 (L3 library with soft randomization in CDR3 of light chain, i.e. L3 library) and 4) anti-FAP clone 3F2 (H3 library with soft randomization in CDR3 of heavy chain, i.e. H3 library). The first two libraries were constructed exactly the same way as outlined for the first affinity-maturation campaign of anti-FAP antibodies, for the L1/L2 and H1/H2 libraries, respectively. In contrast, the L3 and H3 affinity-maturation libraries based on clone 3F2, two new primers were used to introduce soft randomization in L3 (AM_3F2_DPK22_L3_ba:

CACTTTGGTCCCCTGGCCGAACGT C<u>G</u>GG<u>G</u>GAAGCA

TAATA<u>C</u>C<u>C</u>TGCTGACAGTAATACACTGC with underlined bases being 60% given base and 40% mixture N (mixture of the four nucleotides A, C, G, and T)) and H3 (AM_3F2_DP47_H3_fo:

GGCCGTATATTACTGTGCG AAA <u>GGG</u> <u>TGG</u> <u>TTT</u> <u>GGT</u> <u>GGT</u>

<u>TTT</u> AAC TACTGGGGCCAAGGAAC with underlined bases being 60% given base and 40% mixture N, bases in italics being 60% given base and 40% G, as well as underlined bases in italics being 60% given base and 40% mixture K (mixture of the two nucleotides G and T)) of the parental clone. Library sizes were as follows: H1/H2 library ($1.13 \times 10^{10}$), L1/L2 library ($5.6 \times 10^9$), L3 library ($2.3 \times 10^{10}$) and H3 library ($2.64 \times 10^{10}$).

Example 5

Selection of Affinity-Matured Anti-FAP Clones

Selections were carried out against the ectodomain of human or murine fibroblast activating protein (FAP) which were cloned 5' of a poly-lysine and a 6×his-tag. See SEQ ID NOs: 317 and 319. Prior to selections, the antigens were coated into immunotubes at a concentration of either 10 μg/mL, 5 μg/mL or 0.2 μg/mL, depending on the library and round of selection. Selections were carried out according to the following protocol: (i) binding of ~$10^{12}$ phagemid particles of library a.m.FAP2D9, a.m.FAP4B8 or a.m.FAPpool to immobilized human or murine FAP for 2 hours; (ii) washing of immuno tubes using 10–20×5 mL PBS/Tween20 and 10–20×5 mL PBS (depending on library and selection round); (iii) elution of phage particles by addition of 1 mL 100 mM TEA (triethylamine) for 10 minutes and neutralization by addition of 500 μL 1M Tris/HCl pH 7.4; and (iv) re-infection of log-phase *E. coli* TG1 cells, infection with helperphage VCSM13 and subsequent PEG/NaCl precipitation of phagemid particles to be used in subsequent selection rounds.

Selections were carried out over 2 rounds and conditions were adjusted for each of the 3 libraries individually. In detail, selection parameters were: a.m.FAP2D9 (5 μg/mL human FAP and 20 washes in total for round 1, 1 μg/mL human FAP and 30 washes in total for round 2), a.m.FAP4B8 (1 μg/mL murine FAP and 30 washes in total for round 1, 0.2 μg/mL human FAP and 40 washes in total for round 2) and a.m.FAPpool (5 μg/mL human FAP and 30 washes in total for round 1, 5 μg/mL murine FAP and 30 washes in total for round 2). Specific binders were defined as signals 5× higher than background and were identified by ELISA. NUNC maxisorp plates were coated with 1 μg/mL or 0.2 μg/mL of human or murine FAP followed by addition of Fab-containing bacterial supernatants and detection of specifically binding Fabs via their Flag-tags by using an anti-Flag/HRP secondary antibody.

ELISA-positive clones were bacterially expressed as 1 ml cultures in 96-well format and supernatants were subjected to a kinetic screening experiment using BIACORE T100, as described above (see Example 3).

Additional Selection of Affinity-Matured Anti-FAP Clones

Selections were carried out against the ectodomain of human and murine fibroblast activating protein (FAP) which were cloned upstream a 6×-lysine and a 6×-his tag (see SEQ ID NOs: 317 and 319). Prior to selections, the antigens were coated into immunotubes at a concentration of either 1 μg/ml, 0.2 μg/ml or 0.02 μg/ml, depending on the library and round of selection.

Selections and ELISA-based screenings were carried out as described for the first affinity-maturation campaign of anti-FAP antibodies. Secondary screenings were carried out using a ProteOn XPR36 biosensor (Biorad), and kinetic rate constants and affinities were determined analyzing affinity-purified Fab preparations on the same instrument. $K_D$ was measured by surface plasmon resonance using a ProteOn XPR36 machine (Biorad) at 25° C. with anti-human F(ab')2 fragment specific capture antibody (Jackson ImmunoResearch #109-005-006) immobilized on GLM chips and subsequent capture of Fabs from bacterial supernatant or from purified Fab preparations. Briefly, GLM biosensor chips (Biorad) were activated for 5 min with a freshly prepared mixture of N-ethyl-N'-(3-dimethylaminopropyl)-carbodiimide hydrochloride (EDC) and N-hydroxysuccinimide (NHS). Anti-human F(ab')2 fragment specific capture antibody was diluted to 24 μg/ml with 10 mM sodium acetate, pH 5.0 before injection for 5 min to achieve approximately up to 10.000 response units (RU) of coupled capture antibody. Following the injection of the capture antibody, 1 M ethanolamine was injected for 5 min to block unreacted groups. For kinetic measurements, Fabs from bacterial supernatant were injected at a flow rate of 30 μl/min for 100 s. Capture levels were in the range of 250 RU. In a subsequent step, serial dilutions of human, murine or cynomolgus FAP analyte were injected (two-fold dilution, highest concentration 25 nM) diluted in PBS/0.005% Tween-20 at 25° C. at a flow rate of 50 μl/min. Association time was 240 s, dissociation time 600 to 1800 s. The sensorchip was regenerated by injection of 0.85% $H_3PO_4$ for 30 s at 100 μl/min followed by injection of 50 mM NaOH for 30 s at the same flow rate. Association rates ($k_{on}$) and dissociation rates ($k_{off}$) were calculated using a simple one-to-one Langmuir binding model (ProteOn manager software version 2.1) by simultaneously fitting the association and dissociation sensorgrams. The equilibrium dissociation constant ($K_D$) is calculated as the ratio $k_{off}/k_{on}$.

The following affinity-matured clones were identified: 19G1 (see SEQ ID NOs: 257 and 259), 20G8 (see SEQ ID NOs: 281 and 263), 4B9 (see SEQ ID NOs: 265 and 267), 5B8 (see SEQ ID NOs: 269 and 271), 5F1 (see SEQ ID NOs: 273 and 275), 14B3 (see SEQ ID NOs: 277 and 279), 16F1 (see SEQ ID NOs: 281 and 283), 16F8 (see SEQ ID NOs: 285 and 287), O3C9 (see SEQ ID NOs: 289 and 291), 22A3 (see SEQ ID NOs: 301 and 303) and 29B11 (see SEQ ID NOs: 305 and 307) (all these clones were selected from the H1/H2 library and are derived from parental clone 3F2), O2D7 (see SEQ ID NOs: 293 and 295) (selected from the L3 library based on parental clone 3F2), and 28H1 (see SEQ ID NOs: 297 and 299) and 23C10 (see SEQ ID NOs: 309 and 311) (these two clones were selected from the H1/H2 library and are derived from parental clone 4G8).

FIGS. 1A-F, 2A-F, 3A-F, 4A-H, and 5A-F show the Surface Plasmon Resonance sensorgrams of selected affinity matured Fabs binding to immobilized FAP and Table 7 gives the respective affinities derived. The selected Fabs span a high affinity range in the pM to nM range and are cross-reactive for human (hu) and murine (mu) FAP, as well as Cynomolgus (cyno) FAP as determined for selected clones. The affinity matured anti-FAP Fabs were converted into the Fab-IL2-Fab format and into IgG antibodies for specificity analysis. Specificity of binding was shown by lack of binding to DPPIV as close homologue of FAP, expressed on HEK293 or CHO cells (see Example 9).

TABLE 7

Summary of kinetic equilibrium constants ($K_D$) of affinity-matured anti-FAP antibodies as Fab fragments (monovalent binding).

| antibody | affinity ($K_D$) to hu FAP [pM] | affinity ($K_D$) to mu FAP [pM] | affinity ($K_D$) to cyno FAP [pM] |
|---|---|---|---|
| 19G1 | 76 | 2600 | n.d. |
| 20G8 | 69 | 2800 | n.d. |
| 4B9 | 157 | 3300 | n.d. |
| 5B8 | 690 | 3200 | n.d. |
| 5F1 | 243 | 4100 | n.d. |
| 14B3 | 377 | 3800 | n.d. |
| 16F1 | 193 | 3400 | n.d. |
| 16F8 | 301 | 3800 | n.d. |
| O3C9 | 160 | 3700 | n.d. |
| O2D7 | 619 | 8300 | n.d. |
| 28H1 | 200 | 9 | 3600 |
| 22A3 | 34 | 655 | 522 |
| 29B11 | 35 | 436 | 23 |
| 23C10 | 1600 | 125 | 990 |

Example 6

IgG Conversion of Fabs Binding FAP

The parental 3F2, 4G8 and 3D9 Fabs and the affinity matured 3F2 and 4G8 Fab derivatives have been converted into a human IgG1 format, a mouse IgG2a format and a human IgG1 format. The full antibody heavy and light chain DNA sequences were obtained either by subcloning the variable regions in frame with the respective constant heavy and the constant light chain regions pre-inserted into different recipient mammalian expression vectors or were recombined by fusing a short sequence stretch homologous to the recipient vectors insertion site. The recombination was performed according to the "In-Fusion Cloning System" from Invitrogen.

In all vectors the antibody expression is driven by an MPSV promoter and all vectors carry a synthetic polyA signal sequence at the 3' end of the CDS. In addition each vector contains an EBV OriP sequence.

Example 7

Biacore Analysis of Anti-FAP IgG antibodies

The affinity of the anti-FAP Fab fragments 3F2, 4G8 and 3D9 as well as of the human IgG1 converted anti-FAP antibodies was subsequently determined and confirmed for human, murine and Cynomolgus FAP by Surface Plasmon Resonance (SPR) analysis at 25° C. using a BIACORE® T100 machine (GE Healthcare). For this purpose, human, mouse or Cynomolgus FAP extracellular domain (SEQ ID NOs 317-322) was captured by an immobilized anti-His antibody (Penta His Qiagen 34660) and the antibodies were used as analytes. For immobilization carboxymethylated dextran biosensor chips (CM5, GE Healthcare) were activated with N-ethyl-N'-(3-dimethylaminopropyl)-carbodiimide hydrochloride (EDC) and N-hydroxysuccinimide (NHS) according to the supplier's instructions. The Penta His antibody was diluted with 10 mM sodium acetate, pH 5, to 40 μg/ml before injection at a flow rate of 10 μl/minute to achieve approximately 9000 response units (RU) of coupled protein. Following the injection of the ligand, 1 M ethanolamine was injected to block unreacted groups.

For kinetics measurements, human, mouse or Cynomolgus FAP extracellular domain was injected at 10 μl/min at 10 nM for 20 s (for Fab fragments) or at 20 nM for 25 s (for IgG) and was captured via its His tag by the immobilized penta His antibody. Serial dilutions of antibody (two-fold dilutions, range between 6.25 nM to 200 nM for Fab fragments or five-fold dilutions, range between 3.2 pM to 10 nM for IgG) were injected in HBS-EP+ (GE Healthcare, 10 mM HEPES, 150 mM NaCl, 3 mM EDTA, 0.05% Surfactant P20, pH 7.4) at 25° C. at a flow rate of 90 μl/min. The following parameters were applied: Association time 180 s, dissociation 300 s (for Fab) or 900 s (for IgG), regeneration with 10 mM glycine pH 2 for 60 s between each cycle. Association rates ($k_{on}$) and dissociation rates ($k_{off}$) were calculated using a simple one-to-one Langmuir binding model (BIACORE® T100 Evaluation Software version 1.1.1) by simultaneously fitting the association and dissociation sensorgrams (model parameters were local Rmax and RI=0). The equilibrium dissociation constant ($K_D$) was calculated as the ratio $k_{off}/k_{on}$.

The $K_D$ values of binding are given in Table 8. FIGS. 6A1-C3 shows the corresponding SPR-based kinetic analyses for Fab fragments, FIGS. 7A1-C3 for IgG antibodies.

TABLE 8

Summary of kinetic equilibrium constants ($K_D$) of 3F2, 4G8 and 3D9 anti-FAP antibodies as Fab fragments and as IgG

| Construct | Human FAP | Murine FAP | Cyno FAP |
|---|---|---|---|
| IgG 3F2 | Avidity: 39 pM | Avidity: 29 pM | Avidity: 42 pM |
| IgG 4G8 | Avidity: 51 pM | Avidity: 1 pM | Avidity: 59 pM |
| IgG 3D9 | Avidity: 93 pM | Avidity: 96 pM | Avidity: 96 pM |
| Fab fragment 3F2 | Affinity: 13 nM | Affinity: 14 nM | Affinity: 11 nM |
| Fab fragment 4G8 | Affinity: 74 nM | Affinity: 7 nM or lower | Affinity: 56 nM |
| Fab fragment 3D9 | Affinity: 133 nM | Affinity: 32 nM | Affinity: 143 nM |

Example 8

Binding of Anti-FAP Antibodies 3F2, 4G8 and 3D9 on Human Tumor Tissue Sections

We performed experiments to detect and compare the expression of FAP in fresh frozen human tumor tissues (breast cancer, colon adenocarcinomas and NSCLC tissues) using the anti-FAP antibodies clones 3F2, 4G8 and 3D9 as mouse IgG2a.

One fresh frozen tissue microarray (TMA) (AST 274), containing thirty different tumors with two spots each, was used from the Roche TRS Pathology & Tissue Biomarkers tumorbank. The TMA containing 10 invasive ductal carcinomas of the breast, 10 colorectal adenocarcinomas and 10 non-small cell lung cancers was obtained from Asterand Ltd, Royston, UK.

For the immunohistochemical (IHC) stainings, the following antibodies were used: monoclonal mouse anti-human FAP clone 3F2 (15.8 ng/ml, diluted in Ventana Antibody Diluent), monoclonal mouse anti-human FAP clone 4G8 (1000 ng/ml, diluted in Ventana Antibody Diluent), and monoclonal mouse anti-human FAP clone.3D9 (1000 ng/ml, diluted in Ventana Antibody Diluent). A polyclonal mouse IgG2a, concentration 100 μg/mL (Provider: DAKO, X0943, lot #00058066) was used as isotype control.

The stainings were performed according to standard protocols on a Ventana Benchmark XT instrument, using the Ventana Ultra-View detection kit with HRP-system for detection (containing Universal HRP Multimer, and DAB for staining) Counter-staining was done with Hematoxylin II (Ventana, Mayer's Hematoxylin) and Blueing Reagent (Ventana) for 8 min.

The TMA was analyzed semi-quantitatively and the total FAP expression (staining intensity) as well as the localization of the FAP expression in the tumor tissue was evaluated.

With all three anti-FAP antibodies, all the tumor tissue samples (breast cancer, colorectal cancer and lung cancer) that could be evaluated showed a moderate to strong staining FAP signal intensity in the stroma component of the tumor. At least 7 out of 10 samples for each tumor and antibody could be evaluated. The remaining samples could not be evaluated, because tissue cores had folding artifacts, contained only normal tissue, or were missing.

As expected, the FAP signal was invariably located in the stroma component of tumors. There was a slight difference in signal intensity between clone 3F2 and clones 3D9 and 4G8. A slightly stronger signal was seen with clones 3D9 and 4G8, the difference was minor, however.

FIGS. 8A1-D2 shows representative micrographs of human tumor tissue samples immunohistochemically stained for FAP using the anti-FAP mouse IgG2a 3F2, 3D9 or 4G8, or an isotype control antibody.

Example 9

Binding of Anti-FAP Antibodies to FAP on Cells

Binding of human IgG1 antibodies 3F2, 4B3 and 4G8 to human and murine FAP expressed on stably transfected HEK293 cells was measured by FACS. Briefly, 150.000 cells per well were incubated with the indicated concentration of the anti-FAP antibodies 3F2, 4B3 and 4G8 in a round bottom 96-well plate, incubated for 30 min at 4° C., and washed once with PBS/0.1% BSA. Bound antibody was detected with FITC-conjugated AffiniPure F(ab')2 Fragment goat anti-human F(ab')2 Specific (Jackson Immuno Research Lab #109-096-097, working solution: 1:20 diluted in PBS/0.1% BSA, freshly prepared) after incubation for 30 min at 4° C. using a FACS Cantoll (Software FACS Diva). The results are shown in FIGS. 9A and 9B. EC50 values at half-maximal binding for binding to human and murine FAP were determined and are given in Table 9.

TABLE 9

Binding of anti-FAP antibodies to FAP on cells (EC50 values).

| | EC50 values on cells [nM] | |
|---|---|---|
| | human FAP | murine FAP |
| 3F2 IgG | 4.8 | 1.0 |
| 4B3 IgG | 5.5 | 1.6 |
| 4G8 IgG | 5.0 | 1.7 |

Specificity of FAP Antibodies

In order to assess the specificity of binding of the phage display derived antibodies, binding to HEK293 cells stably expressing DPPIV (a close homologue of FAP that is expressed on healthy tissues) or HER2 was measured for the anti-FAP human IgG1 antibodies 3F2, 4B3 and 4G8.

Figure 1A:
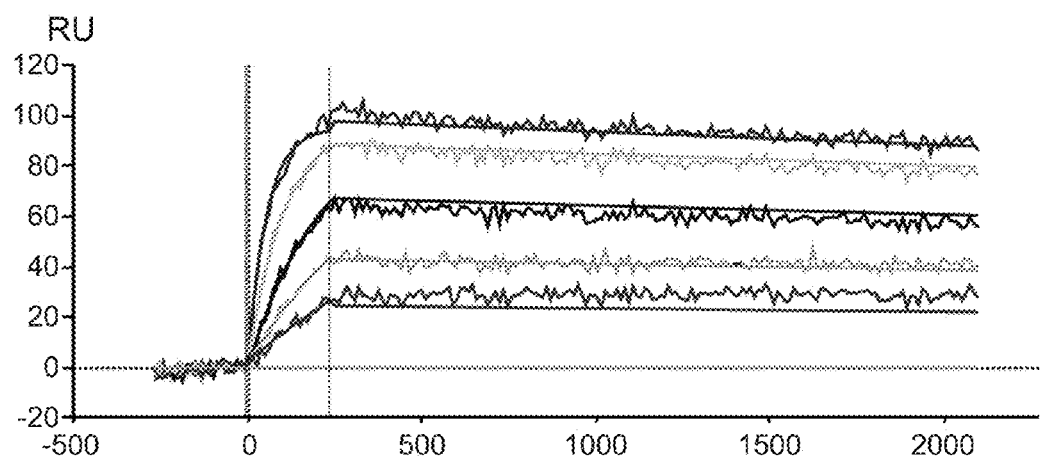
FIGS. 1A, 1B, 1C, 1D, 1E, and 1F show Surface Plasmon Resonance (SPR)-based kinetic analyses of affinity-matured anti-FAP Fab fragments. Processed kinetic data sets are presented for clone 19G1 binding to human (hu) FAP (FIG. 1A) and murine (mu) FAP (FIG. 1B), for clone 20G8 binding to hu FAP (FIG. 1C), mu FAP (FIG. 1D) and for clone 4B9 binding to hu FAP (FIG. 1E) and mu FAP (FIG. 1F). Smooth lines represent a global fit of the data to a 1:1 interaction model.
Figure 1B:
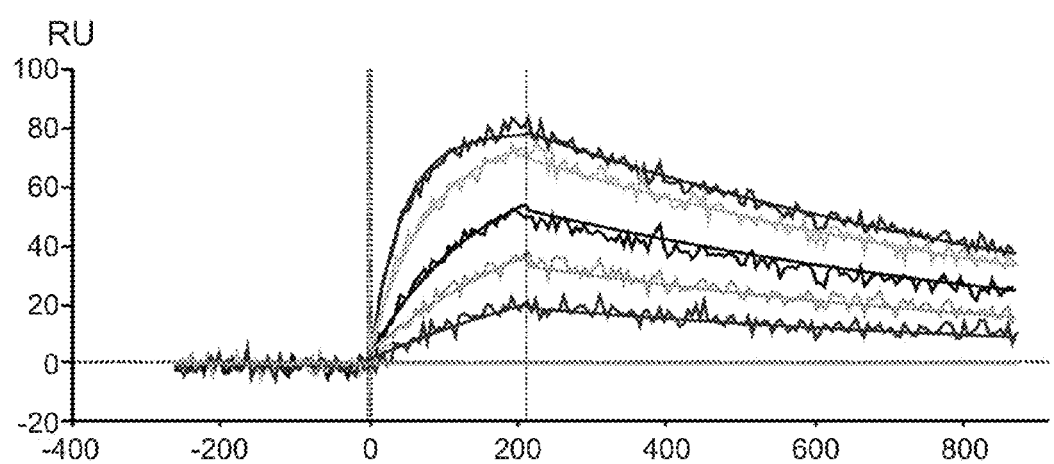
Figure 1C:
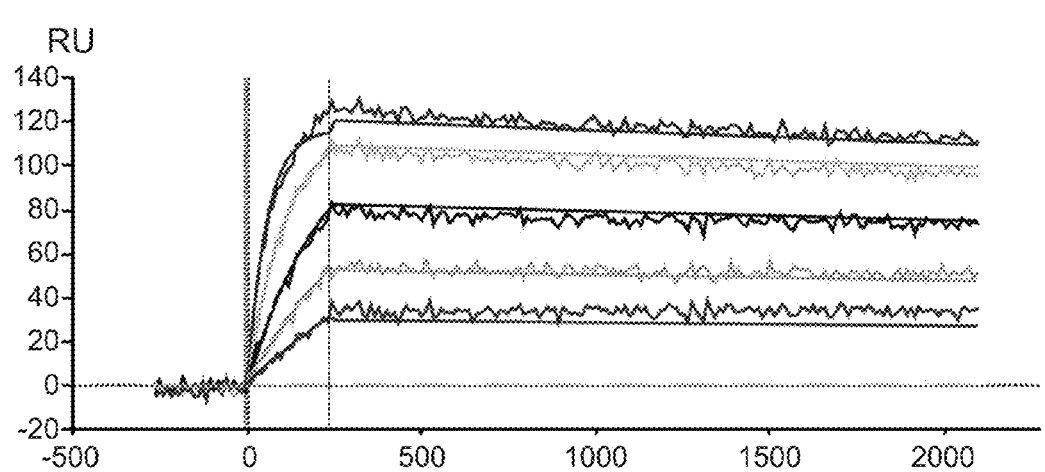
Figure 1D:
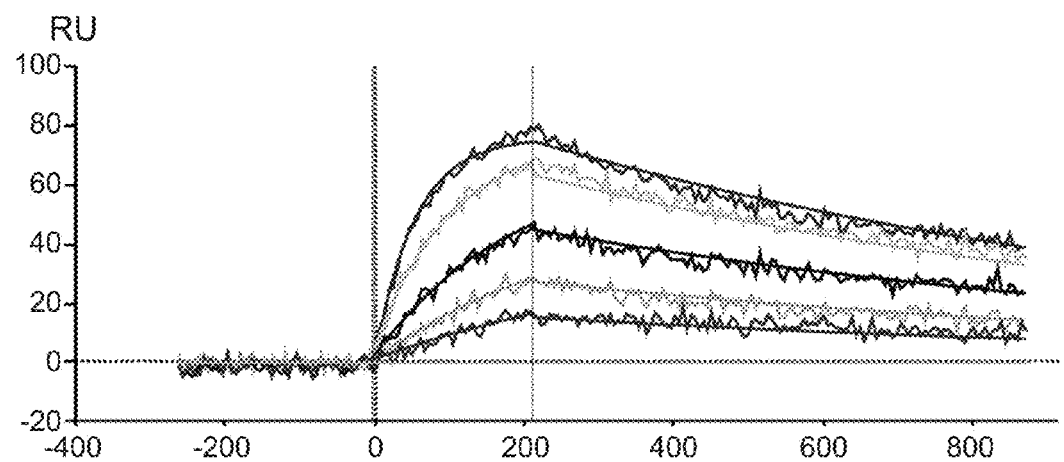
Figure 1E:
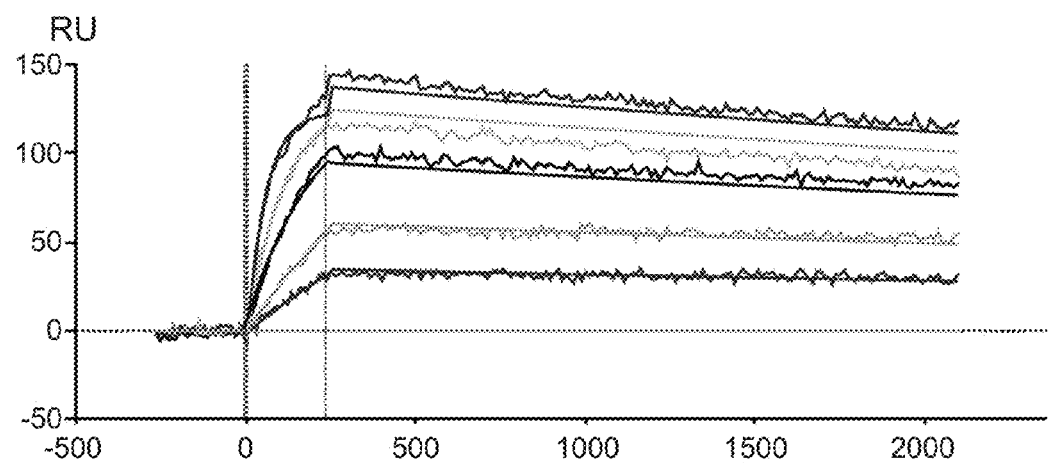
Figure 1F:
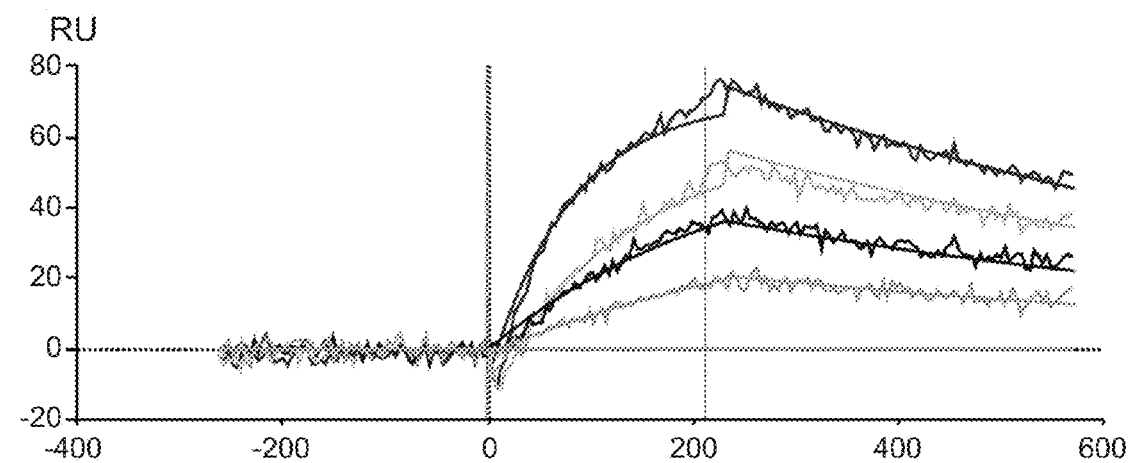
Figure 2A:
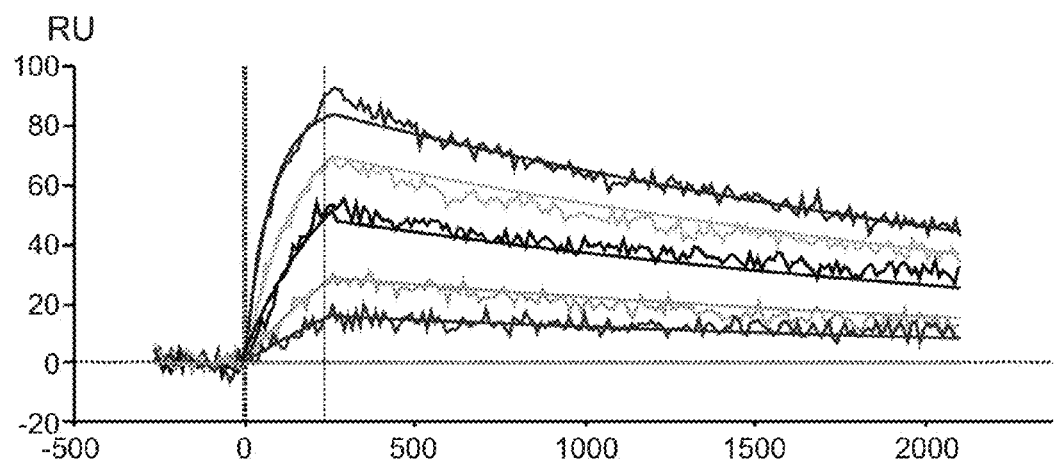
FIGS. 2A, 2B, 2C, 2D, 2E, and 2F show SPR-based kinetic analyses of affinity-matured anti-FAP Fab fragments. Processed kinetic data sets are presented for clone 5B8 binding to hu FAP (FIG. 2A) and mu FAP (FIG. 2B), for clone 5F1 binding to hu FAP (FIG. 2C), mu FAP (FIG. 2D) and for clone 14B3 binding to hu FAP (FIG. 2E) and mu FAP (FIG. 2F). Smooth lines represent a global fit of the data to a 1:1 interaction model.
Figure 2B:
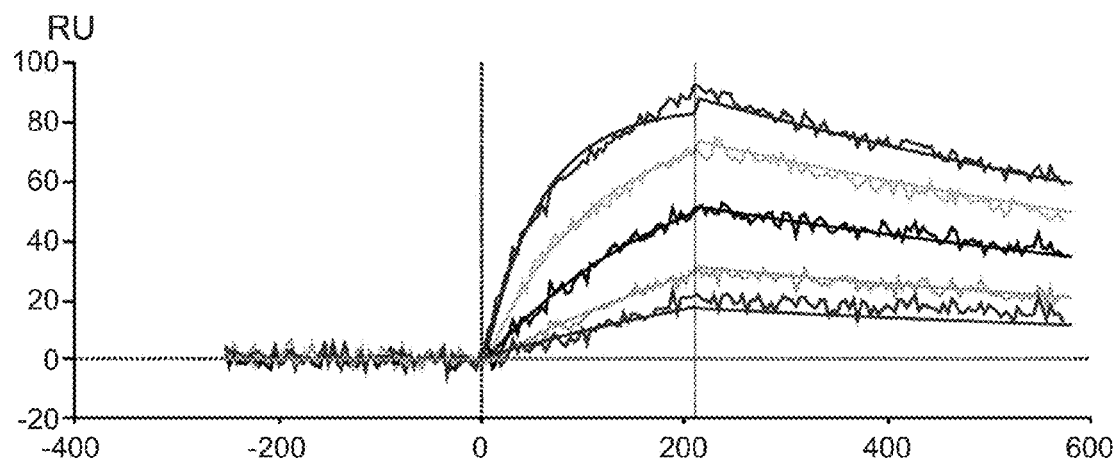
Figure 2C:
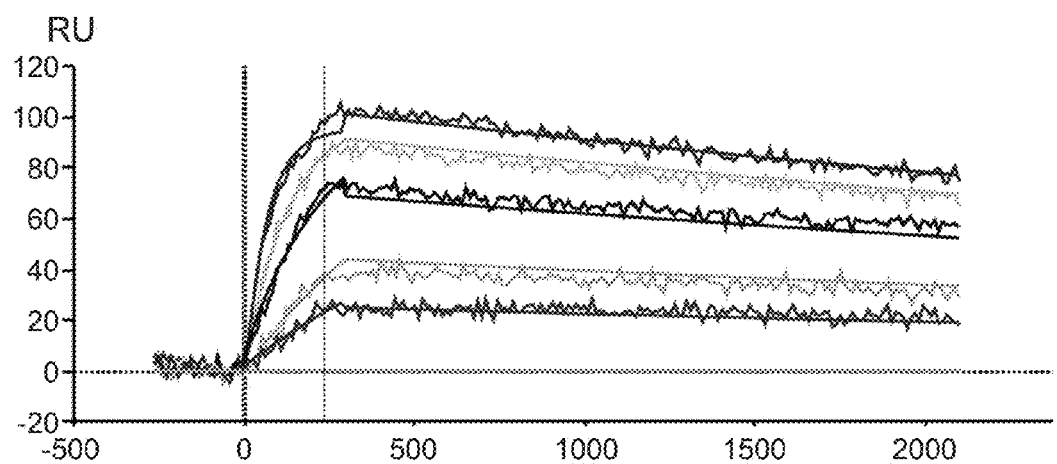
Figure 2D:
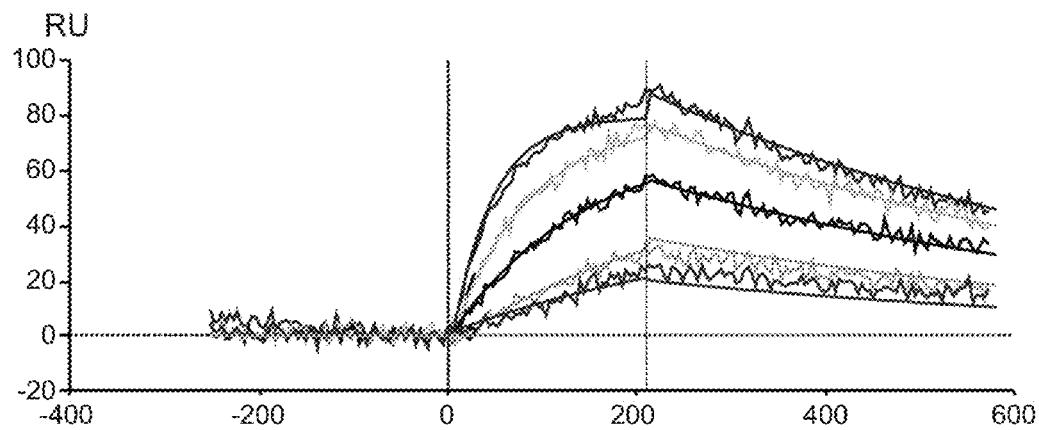
Figure 2E:
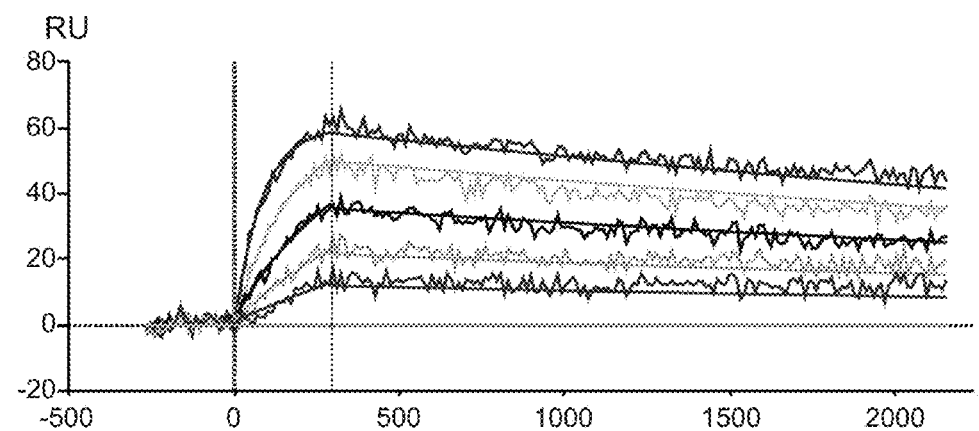
Figure 2F:
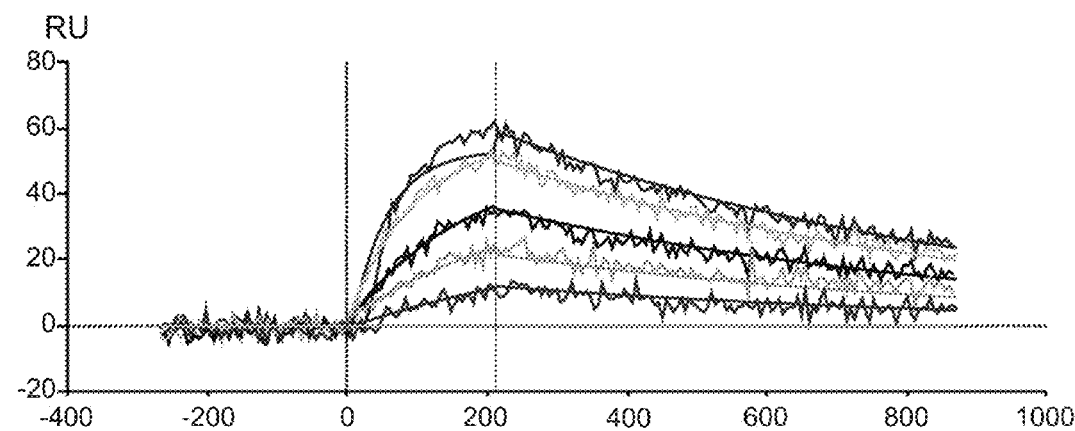
Figure 3A:
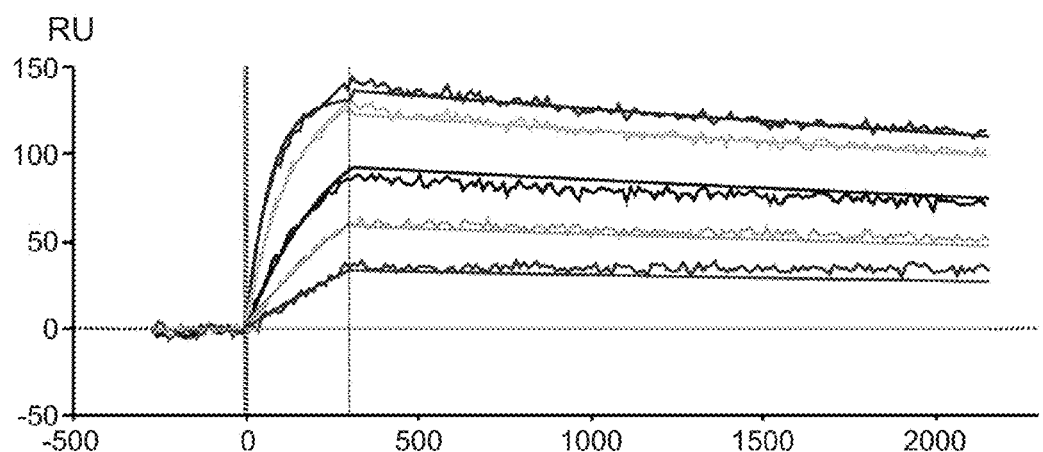
FIGS. 3A, 3B, 3C, 3D, 3E, and 3F show SPR-based kinetic analyses of affinity-matured anti-FAP Fab fragments. Processed kinetic data sets are presented for clone 16F1 binding to hu FAP (FIG. 3A) and mu FAP (FIG. 3B), for clone 16F8 binding to hu FAP (FIG. 3C), mu FAP (FIG. 3D) and for clone O3C9 binding to hu FAP (FIG. 3E) and mu FAP (FIG. 3F). Smooth lines represent a global fit of the data to a 1:1 interaction model.
Figure 3B:
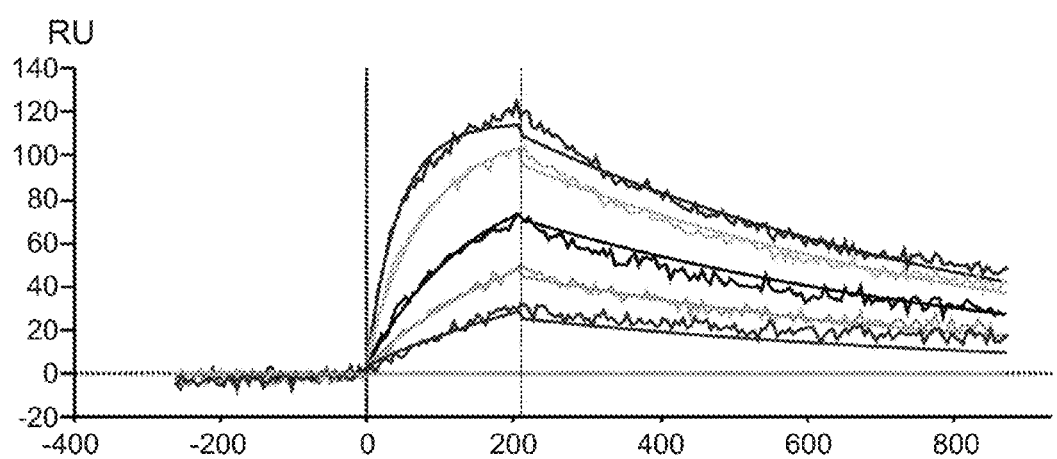
Figure 3C:
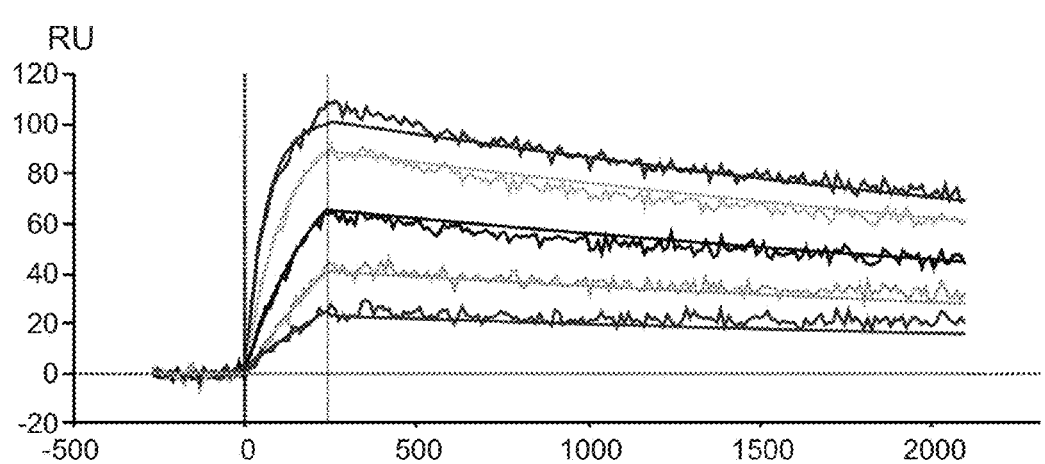
Figure 3D:
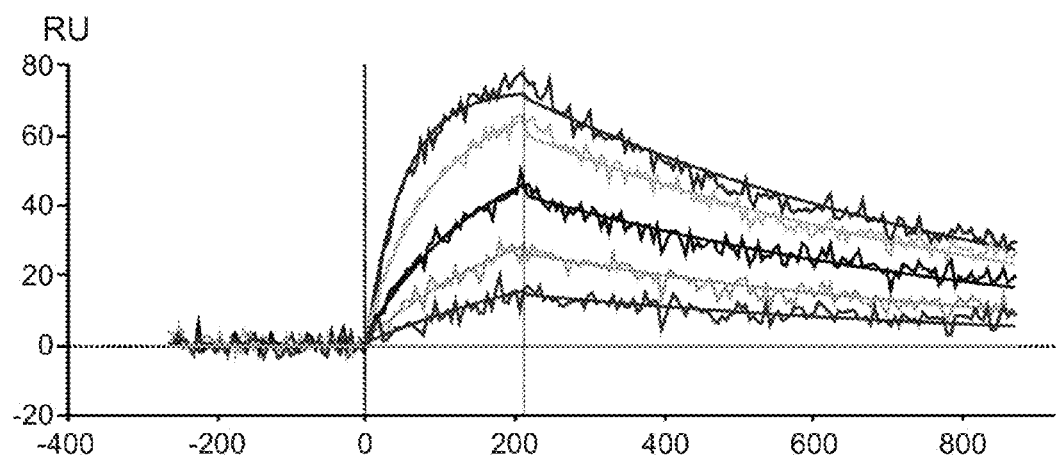
Figure 3E:
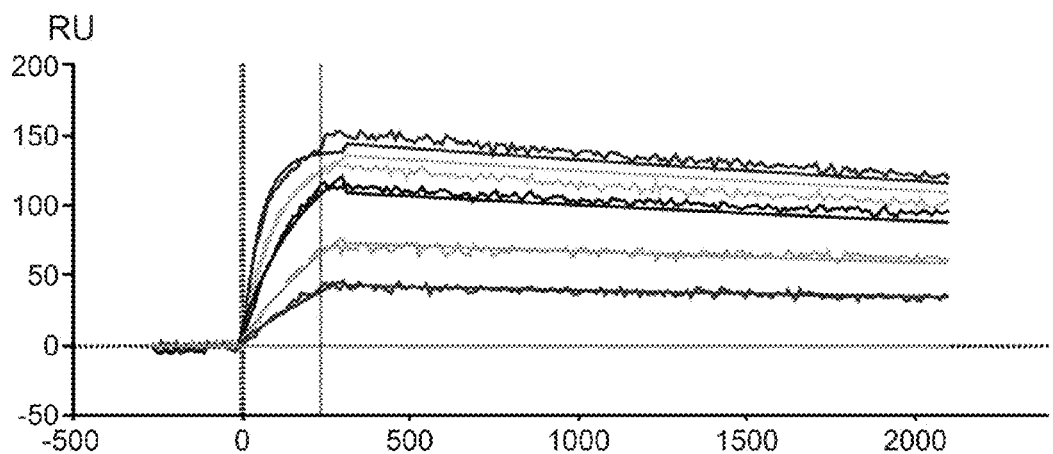
Figure 3F:
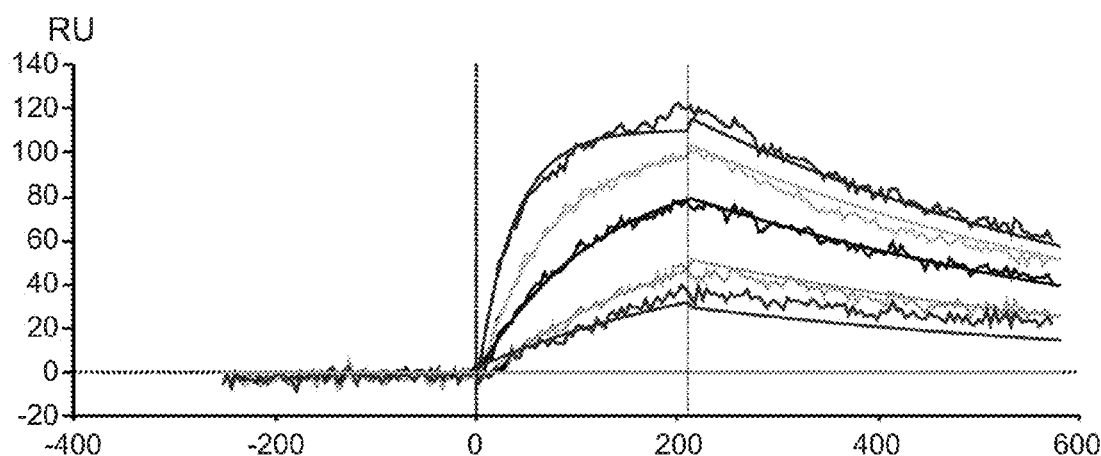
Figure 4A:
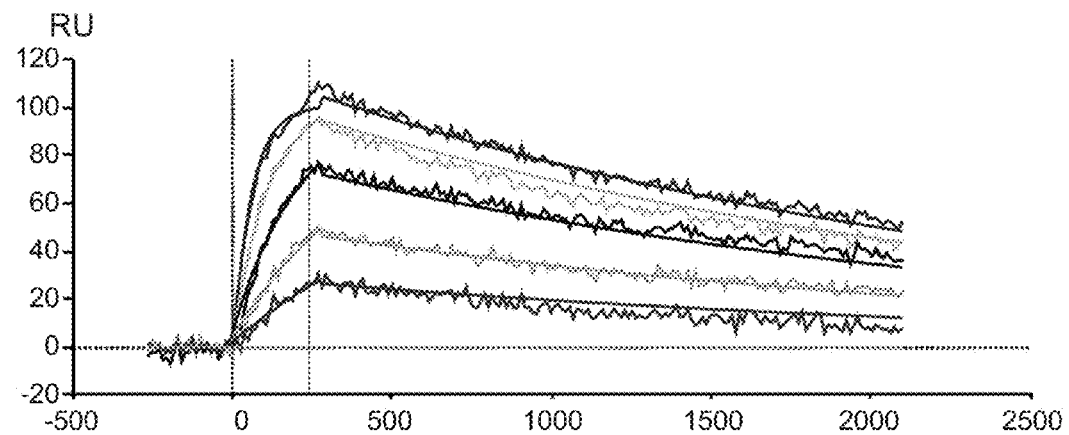
FIGS. 4A, 4B, 4C, 4D, 4E, 4F, 4G, and 4H show SPR-based kinetic analyses of affinity-matured anti-FAP Fab fragments. Processed kinetic data sets are presented for clone O2D7 binding to hu FAP (FIG. 4A) and mu FAP (FIG. 4B), for clone 28H1 binding to hu FAP (FIG. 4C), mu FAP (FIG. 4D), cyno FAP (FIG. 4E) and for clone 22A3 binding to hu FAP (FIG. 4F), mu FAP (FIG. 4G) and Cynomolgus (cyno) FAP (FIG. 4H). Smooth lines represent a global fit of the data to a 1:1 interaction model.
Figure 4B:
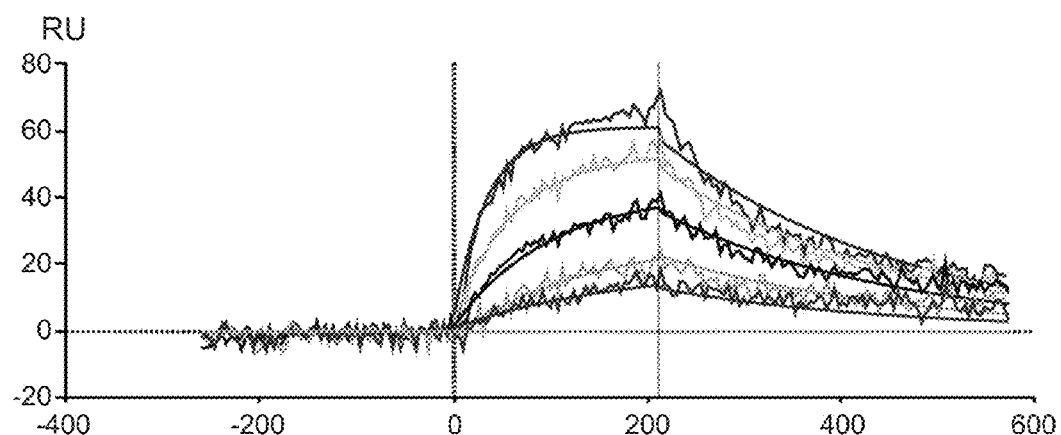
Figure 4C:
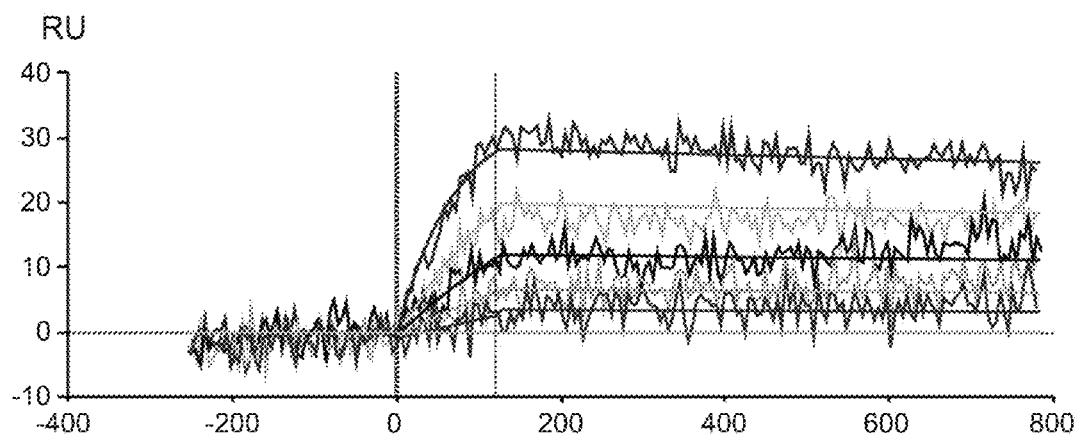
Figure 4D:
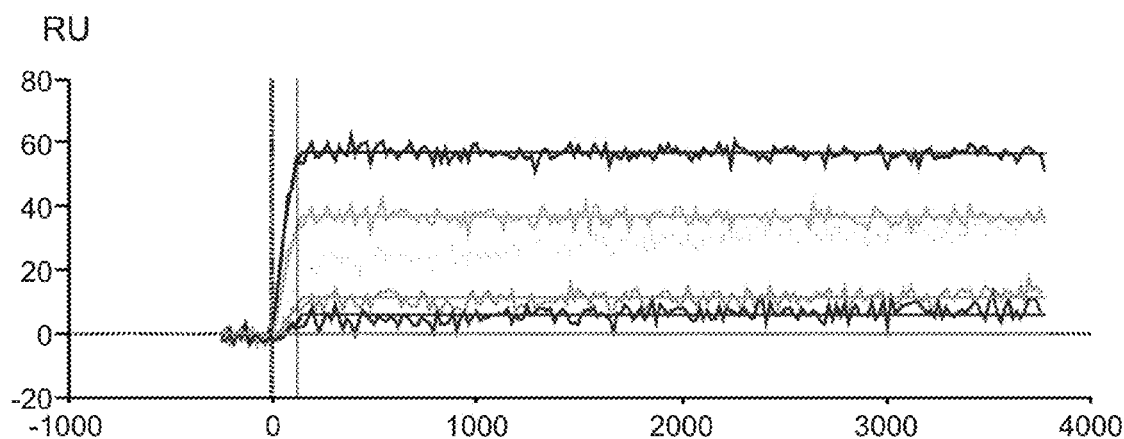
Figure 4E:
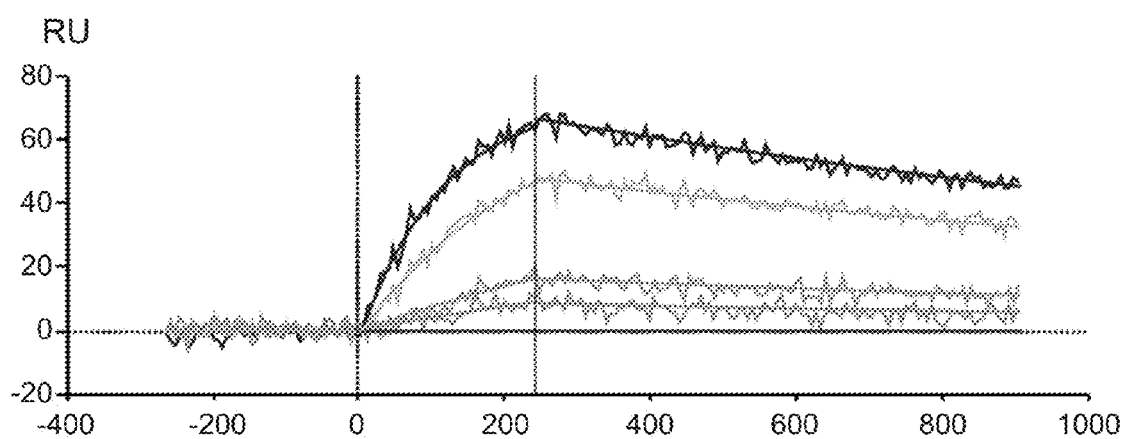
Figure 4F:
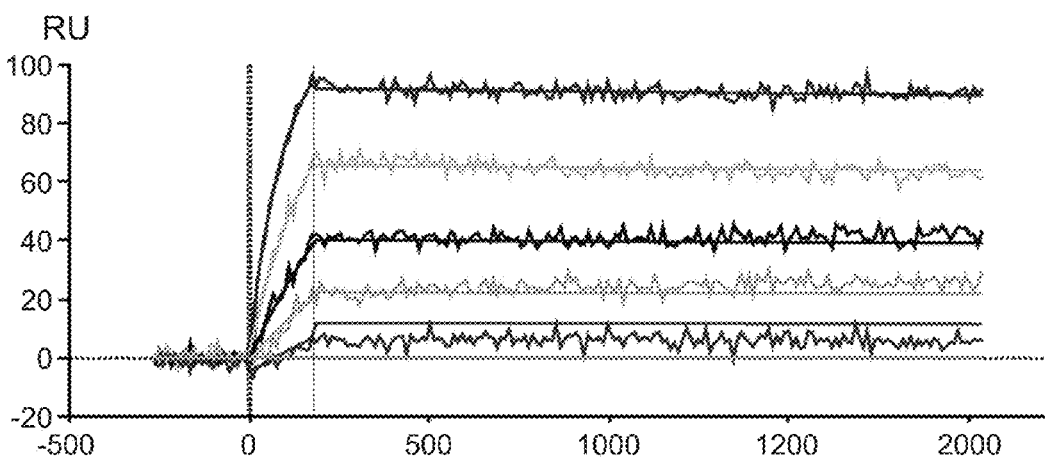
Figure 4G:
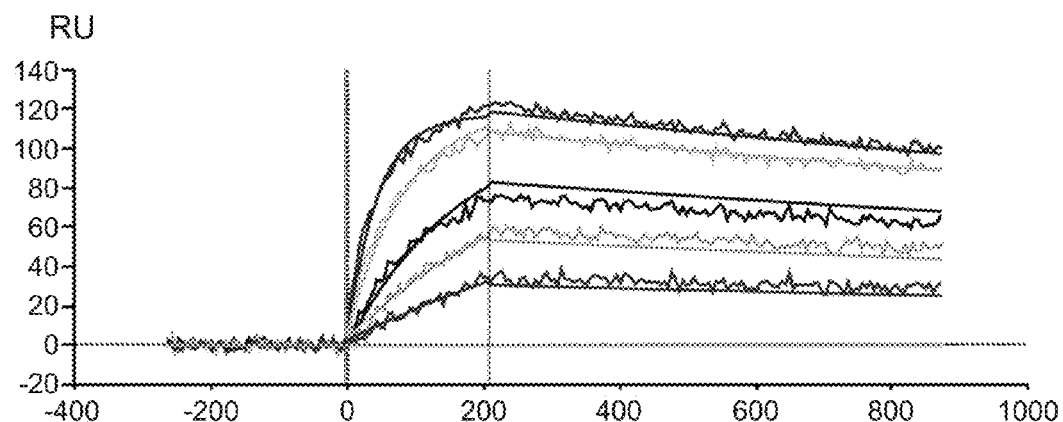
Figure 4H:
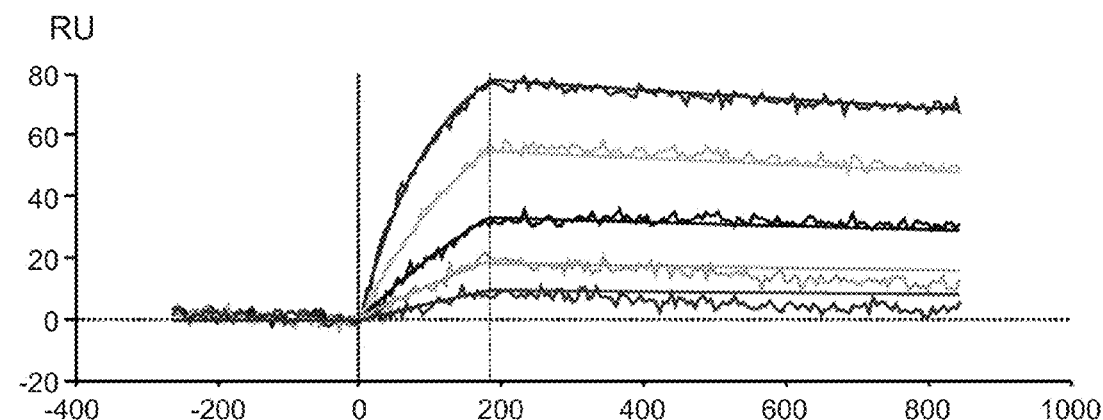
Figure 5A:
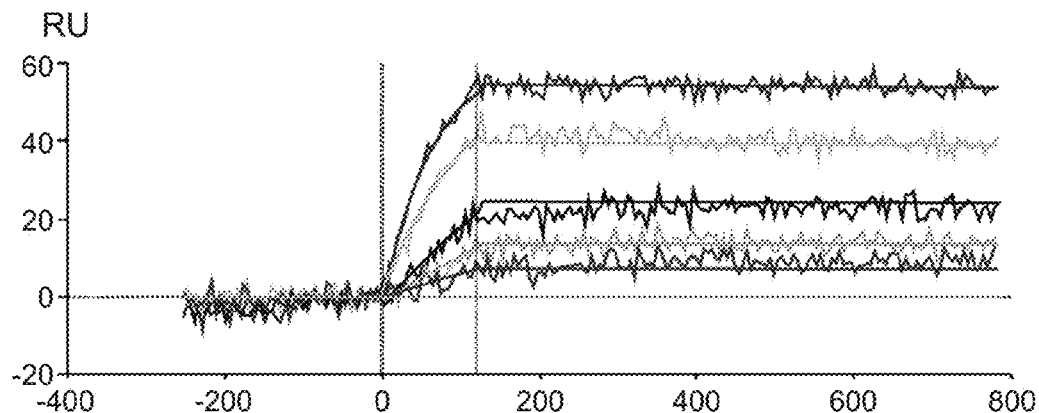
FIGS. 5A, 5B, 5C, 5D, 5E, and 5F show SPR-based kinetic analyses of affinity-matured anti-FAP Fab fragments. Processed kinetic data sets are presented for clone 29B11 binding to hu FAP (FIG. 5A), mu FAP (FIG. 5B), cyno FAP (FIG. 5C) and for clone 23C10 binding to hu FAP (FIG. 5D), mu FAP (FIG. 5E) and cyno FAP (FIG. 5F). Smooth lines represent a global fit of the data to a 1:1 interaction model.
Figure 5B:
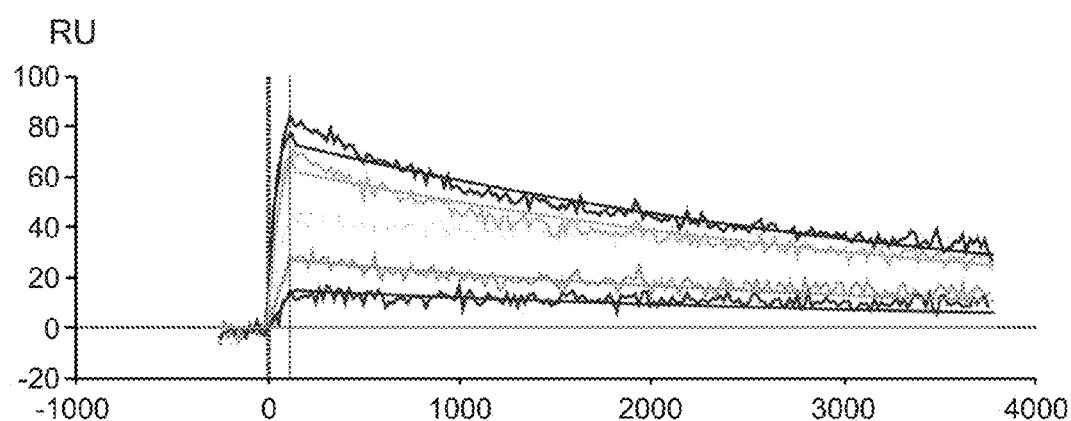
Figure 5C:
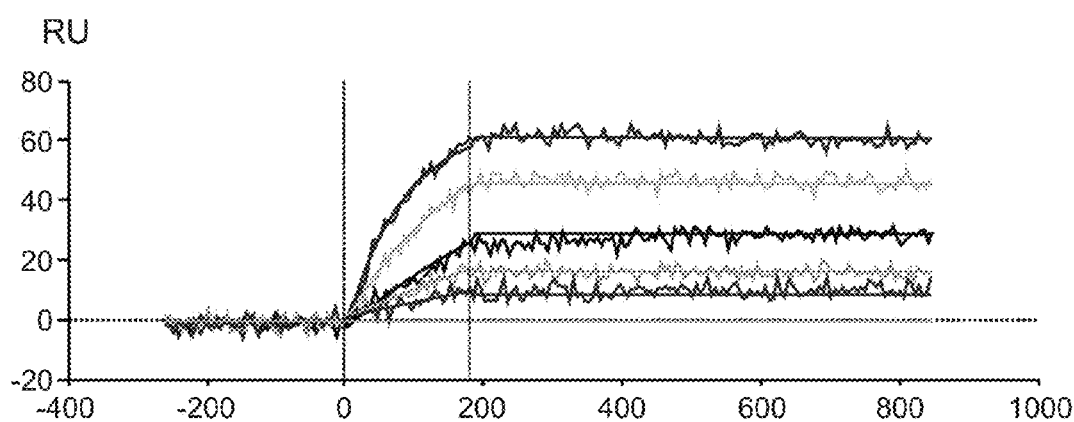
Figure 5D:
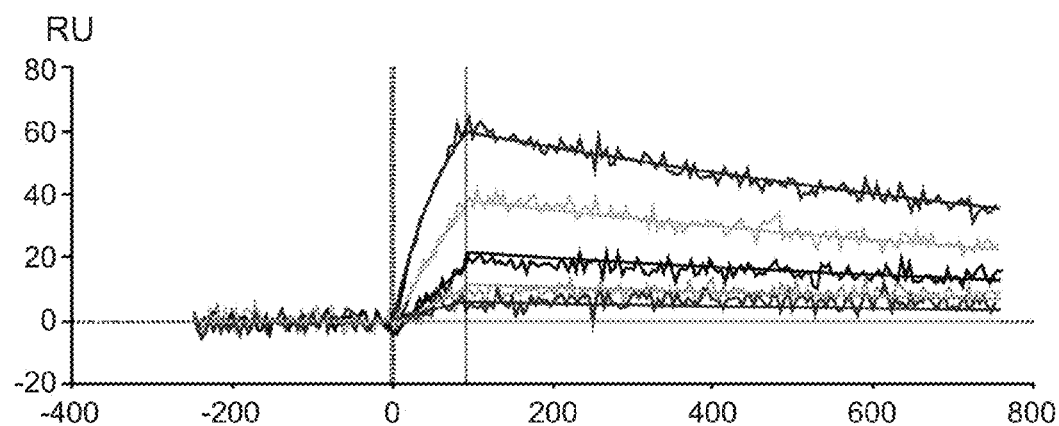
Figure 5E:
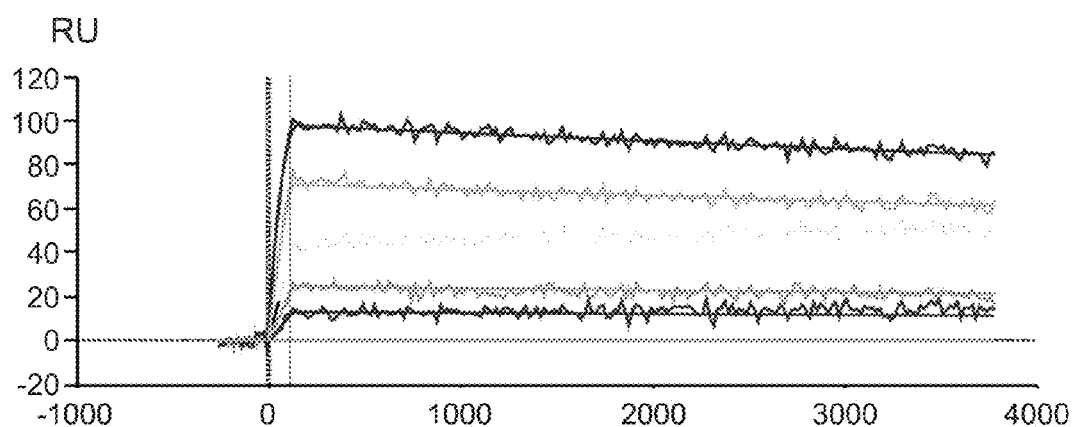
Figure 5F:
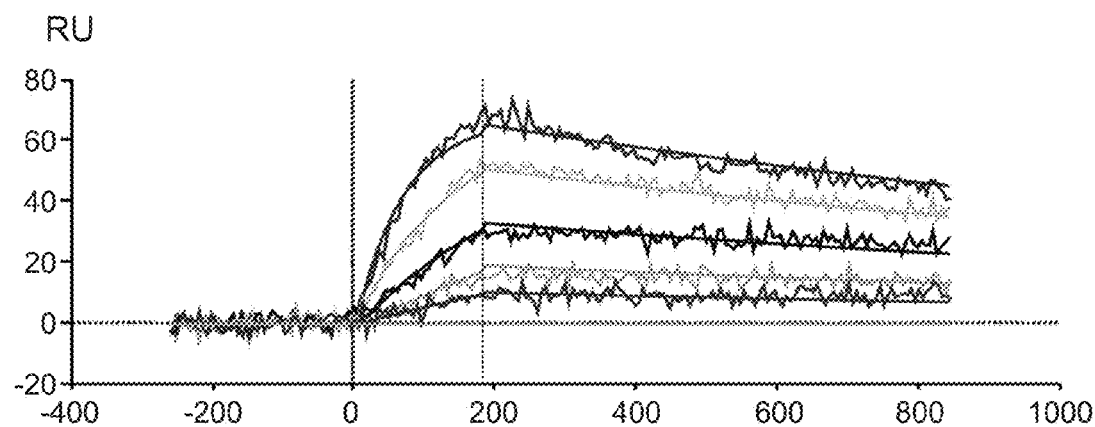
Figure 10:
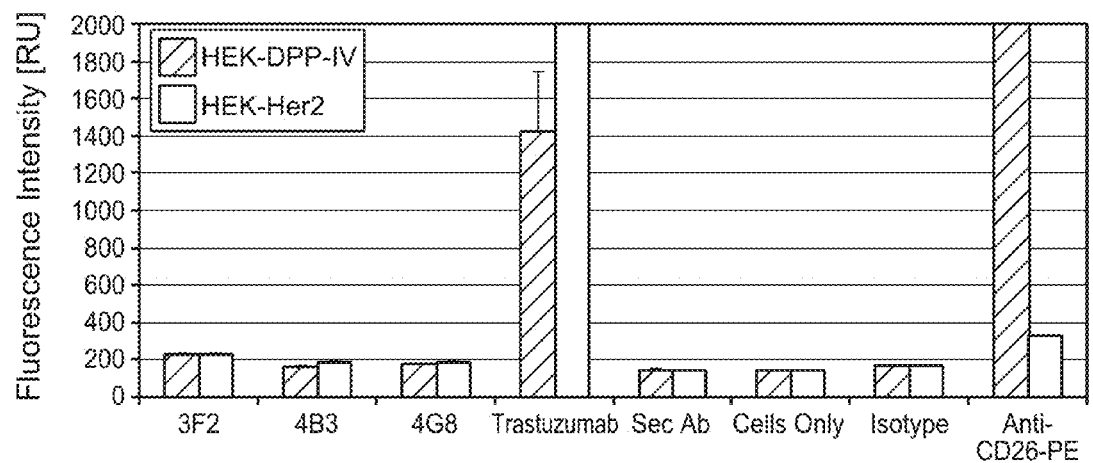
FIG. 10 shows binding of human IgG1 anti-FAP antibodies to DPPIV (CD26) or HER2 expressed on stably transfected HEK 293 cells, as determined by FACS. Anti-HER2 antibody trastuzumab and anti-CD26 antibody were used as positive controls. Secondary antibody, control IgG or no antibody at all (cells only) were used as negative controls.
Figure 11A:
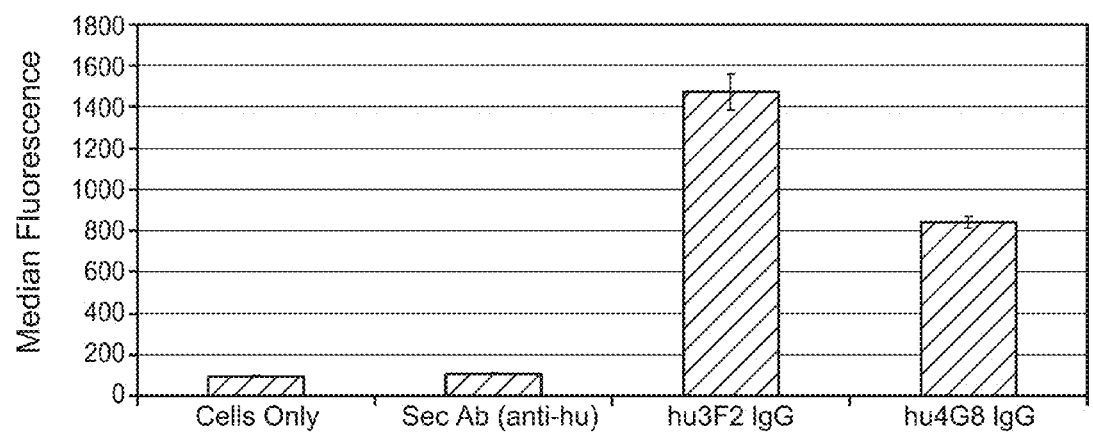
FIGS. 11A, 11B, 11C and 11D show binding of human IgG1 anti-FAP antibodies to FAP on human fibroblasts (cell line GM05389), as determined by FACS. Secondary antibody or no antibody at all were used as negative controls.
Figure 11B:
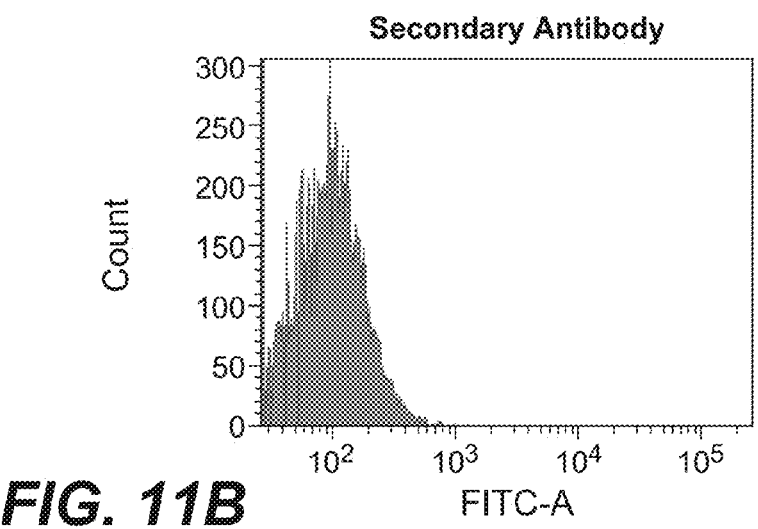
Figure 11C:
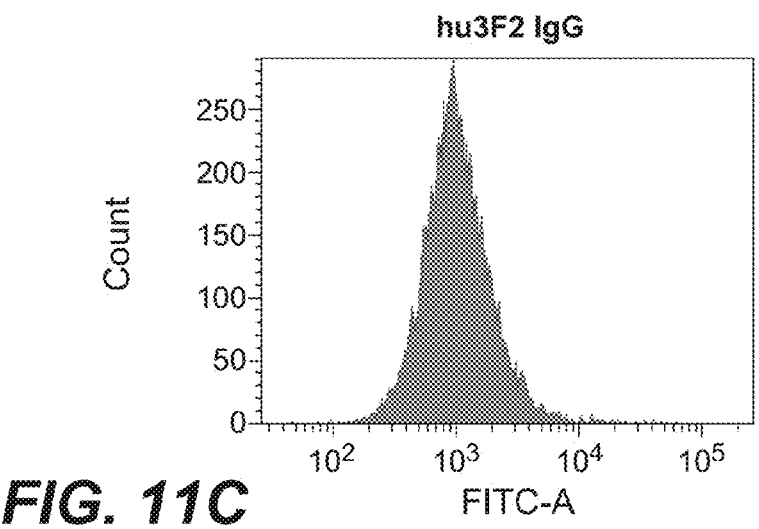
Figure 11D:
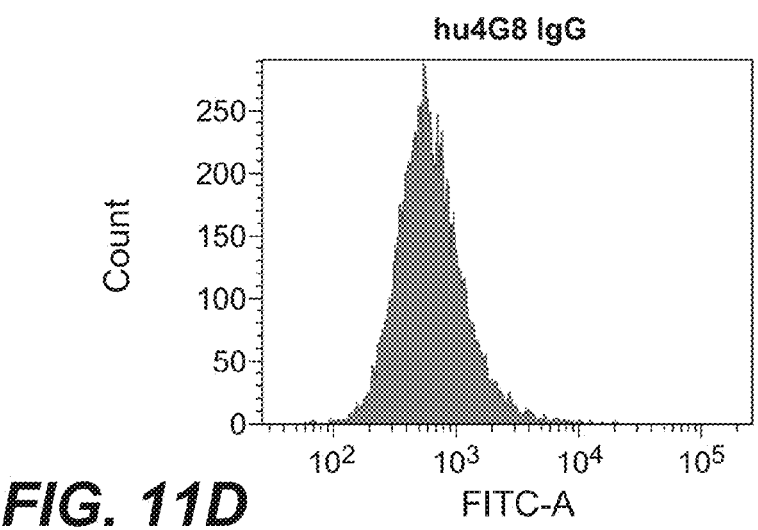

Briefly, 200.000 cells per well (HEK293-DPPIV or HEK293-HER2 as control) were incubated with 30 μg/ml of the anti-FAP antibodies 3F2, 4B3 or 4G8 in a round bottom 96-well plate, incubated for 30 min at 4° C. and washed once with PBS/0.1% BSA. Trastuzumab (anti-HER2 antibody) or a phycoerythrin (PE)-conjugated mouse anti-human anti-CD26/DPPIV antibody (CD26=DPPIV, mouse IgG1,k, BD Biosciences, #555437, clone M-A261) were used as positive controls. Bound antibody was detected with PE-conjugated AffiniPure F(ab')2 Fragment goat anti-human IgG Fcγ Specific (Jackson Immuno Research Lab #109-116-170, working solution: 1:20 diluted in PBS/0.1% BSA, freshly prepared) after incubation for 30 min at 4° C. using a FACS Cantoll (Software FACS Diva). The results of this experiment are shown in FIG. 10. None of the anti-FAP antibodies showed significant binding to DPPIV or HER2, but signals in the range of the negative controls (secondary antibody alone, isotype control antibody, or no antibody at all).

Binding of Anti-FAP Antibodies to FAP on Human Fibroblasts

Binding of human IgG1 antibodies to human FAP expressed on human fibroblast cell line GM05389 (derived from human fetal lung, National Institute of General Medical Sciences, Camden, N.J.) was measured by FACS. Briefly, 200.000 cells per well were incubated with 30 µg/ml of the anti-FAP antibodies 3F2 or 4G8 in a round bottom 96-well plate, incubated for 30 min at 4° C. and washed once with PBS/0.1% BSA. Bound antibody was detected with FITC-conjugated AffiniPure F(ab')2 Fragment goat anti-human IgG Fcγ Specific (Jackson Immuno Research Lab #109-096-098, working solution: 1:20 diluted in PBS/0.1% BSA, freshly prepared) after incubation for 30 min at 4° C. using a FACS Cantoll (Software FACS Diva). The results of this experiment are shown in FIGS. 11A-D. Both anti-FAP antibodies strongly bind to FAP expressed on human fibroblasts.

Binding of Anti-FAP Antibodies to FAP on Human Tumor Cells

Binding of human IgG1 antibodies to human FAP expressed on human fibroblasts cell line GM05389 and on stably transfected HEK293 cells was compared to FAP expression on human cancer cell lines ACHN, Colo205, MDA-MB231, MDA-MB435 and KPL4 by FACS.

Figure 12:
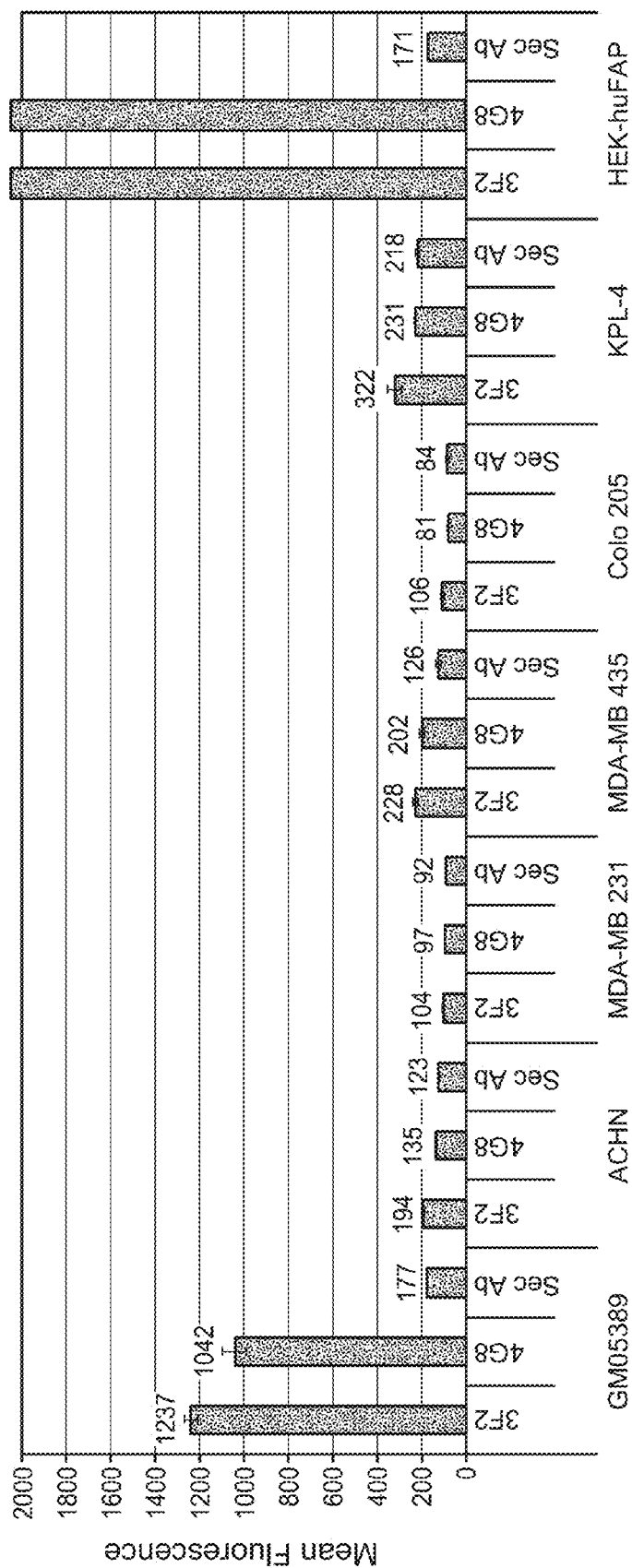
FIG. 12 shows binding of human IgG1 anti-FAP antibodies to human fibroblasts (cell line GM05389), different human tumor cell lines, or HEK 293 cells stably transfected with human FAP, as determined by FACS.

Briefly, 200.000 cells per well were incubated with 10 µg/ml of the anti-FAP antibodies 3F2 or 4G8 in a round bottom 96-well plate, incubated for 30 min at 4° C. and washed once with PBS/0.1% BSA. Bound antibody was detected with FITC-conjugated AffiniPure F(ab')2 Fragment goat anti-human F(ab')2 Specific (Jackson Immuno Research Lab #109-096-097, working solution: 1:20 diluted in PBS/0.1% BSA, freshly prepared) after incubation for 30 min at 4° C. using a FACS Cantoll (Software FACS Diva). The results of this experiment are shown in FIG. 12.

The data show that the antibodies 3F2 and 4G8 bind specifically to FAP that is strongly overexpressed on fibroblasts and stably transfected HEK293 cells; whereas only weak binding can be detected on ACHN, Colo205, MDA-MB231, MDA-MB435 and KPL4 human tumor cell lines.

Example 10

Analysis of FAP Internalization upon Binding of Anti-FAP Antibody by FACS

For several FAP antibodies known in the art it is described that they induce FAP internalization upon binding (described e.g. in Baum et al., *J Drug Target* 15, 399-406 (2007); Bauer et al., *Journal of Clinical Oncology*, 2010 ASCO Annual Meeting Proceedings (Post-Meeting Edition), vol. 28 (May 20 Supplement), abstract no. 13062 (2010); Ostermann et al., *Clin Cancer Res* 14, 4584-4592 (2008)).

Thus, we analyzed the internalization properties of our antibodies. Briefly, GM05389 cells (human lung fibroblasts,) cultured in EMEM medium +15% FCS, were detached, washed, counted, checked for viability and seeded at a density of 0.2 mio cells/well in 12 well plates. The next day, FAP antibodies 4G8 and 3F2 (FIG. 13A) or 4G8 only (FIG. 13B) were diluted to 10 µg/ml in cold medium, cells were cooled down on ice and the diluted antibodies (0.5 ml/well) or medium alone were added as indicated. Subsequently, cells were incubated for 30 min in the cold room with gentle agitation, followed by addition of 0.5 ml warm medium and further incubation of the cells at 37° C. for the indicated time periods. When the different time points were reached, cells were transferred to ice, washed once with cold PBS and incubated with 0.4 ml of the secondary antibody (Alexa Fluor 633-conjugated goat anti-human IgG, Molecular Probes #A-21091, 2 mg/ml, use 1:500) for 30 min at 4° C. Cells were then washed twice with PBS/0.1% BSA, transferred to a 96 well plate, centrifuged for 4 min at 4° C., 400×g and cell pellets were resuspended by vortexing. Cells were fixed using 100 µl 2% PFA. For FACS measurement, cells were re-suspended in 200 µl/sample PBS/0.1% BSA and measured with the plate protocol in FACS Cantoll (Software FACS Diva). The results of these experiments are presented in FIGS. 13A and B, and show that the 4G8 and 3F2 anti-FAP antibodies do not induce internalization of FAP on fibroblasts.

Analysis of FAP Internalization upon Binding of Anti-FAP Antibody by Immunofluorescence GM05389 cells (human lung fibroblasts) were grown on glass coverslips in EMEM medium+15% FCS. Before treatment, cells were washed three times with PBS and starved in EMEM medium+0.1% BSA for 2 h. The anti-FAP antibody (4G8 IgG) or an anti-CD20 antibody (GA101, used as isotype control) were diluted in cold EMEM medium to the final concentration of 10 µg/ml. After starvation, cells were cooled on ice, rinsed twice with cold PBS and incubated with the diluted antibodies (0.5 ml/well) for 45 min at 4° C. under constant agitation to allow surface binding. Cells were then washed twice with cold PBS and either fixed with cold PFA (T0, paraformaldehyde 4% in PBS pH 7.4) or further incubated at 37° C. for 20 min, 1 h, 3 h and 6 h in EMEM+10% FCS. At each time point, cells were washed twice with cold PBS and PFA-fixed for 20 min on ice. After fixation, cells were washed four times with cold PBS, permeabilized with Triton 0.03% and incubated with anti-EEA1 (early endosome marker) antibody for 45 min at room temperature in blocking buffer (PBS+10% FCS). Cells were then washed three times with PBS and incubated with fluorescently labeled secondary antibodies (donkey anti-mouse Alexa Fluor 594-conjugated antibody, and goat anti-human Alexa Fluor 488-conjugated antibody) at room temperature for further 45 min. Cells were finally washed and mounted on glass support slides using Immuno Mount mounting medium.

FIGS. 14A1-D4 presents representative immunofluorescence images showing FAP plasma membrane staining on GM05389 lung fibroblasts obtained after binding of anti-FAP 4G8 IgG for 45 min at 4° C. (A1), for 20 min at 37° C. (B1), for 1 hour at 37° C. (C1) or for 6 hours at 37° C. (D1). The anti-CD20 antibody GA101, used as isotype control, shows background staining (A3, B3, C3, D3). EEA1 labels early endosomes(A2, B2, C2, D2; GA101 isotype control is shown in A4, B4, C4, D4)). Note the persistence of the FAP surface plasma membrane staining up to 6 hours after anti-FAP 4G8 antibody binding.

Example 11

Biacore Analysis of Affinity-Matured Anti-FAP IgG Antibodies

Affinity matured anti-FAP Fab fragments derived from 3F2 and 4G8 were converted into rabbit IgG antibodies. The affinity of the affinity matured 3F2 and 4G8-based rabbit IgG1 converted anti-FAP antibodies to FAP is subsequently determined and confirmed for human, murine and Cynomolgus FAP by SPR analysis at 25° C. (Biacore). For this purpose, human, mouse or Cynomolgus FAP extracellular domain (SEQ ID NOs 317-322) is captured by an immobilized anti-His antibody (Penta His Qiagen 34660) and the antibodies are used as analytes. IgGs are diluted 1:5 from 10 nM to 3.2 pM. The following parameters are applied: Association time 180 s, dissociation 900 s, flow 90 μl/min. Regeneration with 10 mM glycine pH 2 for 60 s. The curves were fitted with the 1:1 model to get the $K_D$ values (Rmax local, RI=0).

Example 12

Binding of Affinity Matured Anti-FAP Antibodies to FAP on Cells

Binding of affinity matured human IgG1 antibody 28H1 labeled with Alexa-647 (1.89 mg/ml, 1.83 mole dye/mole protein) derived from 4G8 parental antibody to human FAP expressed on stably transfected HEK293 cells was measured by FACS. Briefly, 200.000 cells per well were incubated with the indicated concentration of 2 μg/ml and 10 μg/ml of the parental 4G8 and affinity matured 28H1 anti-FAP antibodies in a round-bottom 96-well plate, incubated for 30 min at 4° C. and washed once with PBS/0.1% BSA. Bound antibody was detected after incubation for 30 min at 4° C. using a FACS CantoII (Software FACS Diva). The data show that both antibodies bind strongly to HEK293 cells transfected with human FAP (FIG. 23).

Example 13

Binding of Affinity Matured Anti-FAP Antibodies to FAP on Human Fibroblasts

Binding of affinity matured human IgG1 antibodies derived from 3F2 to human FAP expressed on human fibroblast cell line GM05389 (derived from human fetal lung, National Institute of General Medical Sciences, Camden, N.J.) is measured by FACS. Briefly, 200.000 cells per well are incubated with 30 μg/ml of the affinity matured 3F2 anti-FAP antibody in a round-bottom 96-well plate, incubated for 30 min at 4° C. and washed once with PBS/0.1% BSA. Bound antibody is detected with FITC-conjugated AffiniPure F(ab')2 Fragment goat anti-human IgG Fcγ Specific (Jackson Immuno Research Lab #109-096-098, working solution: 1:20 diluted in PBS/0.1% BSA, freshly prepared) after incubation for 30 min at 4° C. using a FACSCantoII (Software FACS Diva). EC50 values at half-maximal binding for binding to human and murine FAP are being determined.

Example 14

Antibody-Dependent Cell-Mediated Cytotoxicity Mediated by Glycoengineered Anti-FAP IgG1 Antibodies Human IgG1 antibodies against FAP derived from 4G8 or 3F2 were glycoengineered by co-transfection with plasmids encoding for GnTIII and ManII as described in Example 1.

Subsequently, glycoengineered parental 4G8 and 3F2 and affinity matured 28H1 human IgG1 antibodies were compared in an ADCC assay for their potential to mediate superior antibody mediated cellular cytotoxicity compared to their non-glycoengineered wildtype versions.

Briefly, HEK293 cells stably transfected with human FAP as target cells were collected, washed and resuspended in culture medium, stained with freshly prepared Calcein AM (Molecular Probes) at 37° C. for 30 min, washed three times, counted and diluted to 300.000 cells/ml. This suspension was transferred to a round-bottom 96-well plate (=30.000 cells/well), the respective antibody dilution was added and incubated for 10 min to facilitate the binding of the tested antibody to the cells prior to contact with effector cells. Effector to target ratio was 25 to 1 for PBMCs. Co-incubation was performed for 4 hours. As readout the release of lactate dehydrogenase (LDH) into supernatant after disintegration of the attacked cells was determined. LDH from co-culture supernatant was collected and analyzed with a LDH detection Kit (Roche Applied Science). Substrate conversion by the LDH enzyme was measured with an ELISA absorbance reader (SoftMaxPro software, reference wavelengths: 490 nm versus 650 nm). As shown in FIG. 24 all anti-FAP antibodies tested were able to induce ADCC on HEK293-hFAP cells. The glycoengineered (ge) versions performed always better than the corresponding wildtype (wt) non-glycoengineered version.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating an individual having a disease characterized by Fibroblast Activation Protein (FAP) expression, comprising administering to the individual an effective amount of an antibody that specifically binds to FAP, wherein said antibody comprises a heavy chain variable region comprising the amino acid sequence of SEQ ID NO: 267 and a light chain variable region comprising the amino acid sequence of SEQ ID NO: 265.

2. The method of claim 1, wherein said antibody comprises an Fc region or a region equivalent to the Fc region of an immunoglobulin.

3. The method of claim 2, wherein said Fc region is an IgG Fc region.

4. The method of claim 1, wherein said antibody is a full-length IgG class antibody.

5. The method of claim 1, wherein said antibody comprises a human constant region.

6. The method of claim 1, wherein said antibody comprises a glycoengineered Fc region.

7. The method of claim 6, wherein said antibody has an increased proportion of non-fucosylated oligosaccharides in said Fc region, as compared to a non-glycoengineered antibody.

8. The method of claim 6 wherein at least 20% to 100% of the N-linked oligosaccharides in said Fc region are non-fucosylated.

9. The method of claim 6 wherein said antibody has an increased proportion of bisected oligosaccharides in said Fc region, as compared to a non-glycoengineered antibody.

10. The method of claim 6, wherein at least 20% to 100% of the N-linked oligosaccharides in said Fc region are bisected.

11. The method of claim 6, wherein at least 20% to 50% of the N-linked oligosaccharides in said Fc region are bisected, non-fucosylated.

12. The method of claim 1, wherein said antibody is in a conjugate with a cytotoxic agent.

13. The method of claim 1 further comprising administering an additional therapeutic agent to the individual.

14. The method of claim 1, wherein said disease is cancer.

15. The method of claim 14, wherein said cancer is selected from the group consisting of lung cancer, colon cancer, gastric cancer, breast cancer, head and neck cancer, skin cancer, liver cancer, kidney cancer, prostate cancer, pancreatic cancer, brain cancer, cancer of the skeletal muscle.

16. The method of claim 1, wherein said individual is a human.

17. The method of claim 1, wherein said antibody comprises a human IgG1 Fc region.

* * * * *